US011512110B2

(12) United States Patent
Teesalu et al.

(10) Patent No.: US 11,512,110 B2
(45) Date of Patent: Nov. 29, 2022

(54) TARGETED DELIVERY SYSTEM AND METHODS OF USE THEREFOR

(71) Applicant: Sanford Burnham Prebys Medical Discovery Institute, La Jolla, CA (US)

(72) Inventors: Tambet Teesalu, La Jolla, CA (US); Erkki Ruoslahti, La Jolla, CA (US); Kazuki Sugahara, La Jolla, CA (US); Shweta Sharma, La Jolla, CA (US)

(73) Assignee: SANFORD BURNHAM PREBYS MEDICAL DISCOVERY INSTITUTE, La Jolla, CA (US)

( * ) Notice: Subject to any disclaimer, the term of this patent is extended or adjusted under 35 U.S.C. 154(b) by 0 days.

(21) Appl. No.: 16/889,137

(22) Filed: Jun. 1, 2020

(65) Prior Publication Data
US 2021/0188909 A1 Jun. 24, 2021

Related U.S. Application Data

(63) Continuation of application No. 15/568,533, filed as application No. PCT/US2016/028894 on Apr. 22, 2016, now Pat. No. 10,669,311.

(60) Provisional application No. 62/151,703, filed on Apr. 23, 2015, provisional application No. 62/151,674, filed on Apr. 23, 2015.

(51) Int. Cl.
| C07K 7/06 | (2006.01) |
| A61K 47/64 | (2017.01) |
| A61K 49/18 | (2006.01) |
| A61K 47/69 | (2017.01) |
| A61K 38/00 | (2006.01) |
| G01N 33/68 | (2006.01) |

(52) U.S. Cl.
CPC ............... *C07K 7/06* (2013.01); *A61K 47/64* (2017.08); *A61K 47/6455* (2017.08); *A61K 47/6929* (2017.08); *A61K 49/1866* (2013.01); *G01N 33/6872* (2013.01); *A61K 38/00* (2013.01); *G01N 2333/4716* (2013.01)

(58) Field of Classification Search
None
See application file for complete search history.

(56) References Cited

U.S. PATENT DOCUMENTS

| 5,622,699 | A | 4/1997 | Ruoslahti et al. |
| 6,068,829 | A | 5/2000 | Ruoslahti et al. |
| 6,180,084 | B1 | 1/2001 | Ruoslahti et al. |
| 6,576,239 | B1 | 6/2003 | Ruoslahti et al. |
| 7,488,792 | B2 | 2/2009 | Ruoslahti et al. |
| 7,501,486 | B2 | 3/2009 | Ruoslahti et al. |
| 7,598,341 | B2 | 10/2009 | Ruoslahti et al. |
| 7,666,391 | B2 | 2/2010 | Ruoslahti et al. |
| 7,723,474 | B2 | 5/2010 | Ruoslahti et al. |
| 7,745,410 | B2 | 6/2010 | Ruoslahti et al. |
| 8,178,104 | B2 | 5/2012 | Ruoslahti et al. |
| 8,536,132 | B2 | 9/2013 | Ruoslahti et al. |
| 8,598,316 | B2 | 12/2013 | Hanahan et al. |
| 8,753,604 | B2 | 6/2014 | Ruoslahti et al. |
| 8,912,136 | B2 | 12/2014 | Ruoslahti et al. |
| 8,951,971 | B2 | 2/2015 | Ruoslahti et al. |
| 9,061,079 | B2 | 6/2015 | Ruoslahti et al. |
| 9,522,198 | B2 | 12/2016 | Ruoslahti et al. |
| 10,669,311 | B2 | 6/2020 | Teesalu et al. |
| 2001/0046498 | A1 | 11/2001 | Ruoslahti et al. |
| 2004/0087499 | A1 | 5/2004 | Laakkonen et al. |
| 2006/0263434 | A1 | 11/2006 | Desai et al. |
| 2009/0036349 | A1 | 2/2009 | Ruoslahti et al. |
| 2009/0226372 | A1 | 9/2009 | Ruoslahti et al. |
| 2009/0246133 | A1 | 10/2009 | Ruoslahti et al. |

(Continued)

FOREIGN PATENT DOCUMENTS

| WO | WO 00/42973 | 7/2000 |
| WO | WO 03/040693 | 5/2003 |
| WO | WO 03/087124 | 10/2003 |

OTHER PUBLICATIONS

Passonen et al. "Newp32/gC1qR Ligands for Targeted Tumor Drug Delivery," ChemBioChem 2016, 17, 570-575 (Year: 2016).*
Agemy et al. (2011) Targeted nanoparticle enhanced proapoptotic peptide as potential therapy for glioblastoma. Proc Natl Acad Sci USA 108:17450-17455.
Akerman et al. (2002) Proc Natl Acad Sci USA 99: 12617-12621.
Cai et al. (2006) Nano Lett 6: 669-676.
Corrected Notice of Allowability corresponding to Notice of Allowance corresponding to U.S. Appl. No. 15/568,533 dated Apr. 3, 2020.
Denardo et al. (2005) Clin Cancer Res 11: 7087s-7092s.
Desai et al. (2006) Clin Cancer Res 12: 1317-1324.
Hoffman et al. (2003) Cancer Cell 4: 383-391.

(Continued)

*Primary Examiner* — Christina Bradley
(74) *Attorney, Agent, or Firm* — Procopio, Cory, Hargreaves & Savitch LLP

(57) ABSTRACT

Disclosed are peptides and peptidomimetics that in some embodiments include the amino acid sequence KRGARST or (SEQ ID NO: 1), AKRGARSTA or (SEQ ID NO: 2), or CKRGARSTC (SEQ ID NO: 3). Also disclosed are conjugates and compositions that include the peptides and/or peptidomimetics, methods for directing a moiety to tumor lymphatic vasculature, methods for imaging tumor lymphatic vasculature, methods for reducing or inhibiting tumor metastasis, methods for reducing the number of tumor lymphatic vessels, methods for treating cancer, methods for treating a disease or disorder associated with a gC1q/p32 receptor biological activity, methods for detecting the presence of a gC1q/p32 receptor, methods for detecting interactions between gC1q/p32 receptors and the presently disclosed conjugates and compositions, methods for delivering the presently disclosed conjugates and compositions to gC1q/p32 receptors, methods for assessing gC1q/p32 receptor levels in cells, methods for identifying subjects having diseases associated with gC1q/p32 receptor biological activities, and methods for screening for compounds that interact with gC1q/p32 receptors.

20 Claims, 16 Drawing Sheets

Specification includes a Sequence Listing.

(56) References Cited

U.S. PATENT DOCUMENTS

| | | |
|---|---|---|
| 2010/0254914 A1 | 10/2010 | Park et al. |
| 2010/0279918 A1 | 11/2010 | Langel et al. |
| 2010/0322862 A1 | 12/2010 | Ruoslahti et al. |
| 2011/0081293 A1 | 4/2011 | Ruoslahti et al. |
| 2011/0262347 A1 | 10/2011 | Ruoslahti et al. |
| 2012/0034164 A1 | 2/2012 | Ruoslahti et al. |
| 2012/0219502 A1 | 8/2012 | Ruoslahti et al. |
| 2013/0058993 A1 | 3/2013 | Ruoslahti et al. |
| 2013/0183241 A1 | 7/2013 | Laakkonen et al. |
| 2017/0246236 A1 | 8/2017 | Agemy et al. |
| 2018/0244720 A1 | 8/2018 | Teesalu et al. |
| 2018/0303898 A1 | 10/2018 | Ruoslahti et al. |

OTHER PUBLICATIONS

Intent to Grant corresponding to European Patent Application No. 11722941.9 dated Mar. 2, 2017.
International Search Report for International Patent Application No. PCT/US2011/031785 dated Aug. 10, 2011.
Ko et al. (2009) Molecular Pharmaceutics 6(3) 971-977.
Laakkonen et al. (2002) Nat Med 8: 751-755.
Laakkonen et al. (2004) Proc Natl Acad Sci USA 101: 9381-9386.
Makela (2006) J Virol 80(13) 6603-6611.
NCBI Reference Sequence: XP 001351439.1, submitted Sep. 20, 2002 (Year: 2002).
Notice of Allowance corresponding to U.S. Appl. No. 15/568,533 dated Jan. 22, 2020.
Office Action corresponding to Canadian Patent Application No. 2,795,289 dated Apr. 16, 2014.
Office Action corresponding to Canadian Patent Application No. 2,795,289 dated Jan. 28, 2015.
Office Action corresponding to European patent application No. 11 722 941.0-1466 dated Aug. 16, 2016.
Office Action corresponding to European Patent Application No. dated Dec. 19, 2014.
Office Action corresponding to Japanese Patent Application No. 2013-503991 dated Jul. 10, 2014. (Translation).
Office Action corresponding to Japanese Patent Application No. 2013-503991 dated Nov. 25, 2014.
Office Action corresponding to U.S. Appl. No. 13/083,176 dated Jan. 3, 2014.
Office Action corresponding to U.S. Appl. No. 15/376,321 dated Dec. 21, 2018.
Office Action corresponding to U.S. Appl. No. 15/376,321 dated May 11, 2018.
Office Action corresponding to U.S. Appl. No. 15/376,321 dated Oct. 16, 2019.
Office Action corresponding to U.S. Appl. No. 15/568,533 dated May 1, 2019.
Office Action corresponding to U.S. Appl. No. 15/568,533 dated Oct. 9, 2018.
Office Action corresponding to U.S. Appl. No. 13/083,176 dated Aug. 6, 2013.
Park et al. (2008) Magnetic Iron Oxide Nanoworms for Tumor Targeting and Imaging. Adv Mater. 20(9):1630-1635.
Park et al. (2009) Systematic Surface Engineering of Magnetic Nanoworms for in vivo Tumor Targeting. Small 5(6): 694-700.
Pilch et al. (2006) Proc Natl Acad Sci USA 103: 2800-2804.
Ruoslahti (2012) Peptides as Targeting Elements and Tissue Penetration Devices for Nanoparticles. Adv. Mater. 24:3747-3756.
Senczuk et al. "Plasmodium falciparum erythrocyte membrane protein 1 functions as a ligand for P-selectin," Blood, 2001, vol. 98.
Sinek et al. (2004) Biomed Microdevices 6: 297-309.
Standley et al. (2010) Induction of Cancer Cell Death by Self-assembling Nanostructures Incorporating a Cytotoxic Peptide. Cancer Res. 70(8):3020-6.

* cited by examiner

| LIBRARY | X7 | (SEQ ID NO:) | CX7C | (SEQ ID NO:) |
|---|---|---|---|---|
| WEBLOGO CONSENSUS | LRGgRS | (197) | C_RG_Rs_C | (198) |
| INDIVIDUAL SEQUENCES | RRGGRSKLAAALE | (160) | CRRGNRSSC | (175) |
| | GRGGRSRKLAAALE | (161) | CARGARTKC | (176) |
| | GKRGGRSKLAAALE | (162) | CTRGSRSKC | (177) |
| | GRGGRSRKLAAALE | (1610) | CKRGNRSVC | (178) |
| | GRGGRSRKLAAALE | (161) | CKRGGRSAC | (179) |
| | RKRRNRA | (163) | CLSDTRKKC | (180) |
| | RTRGGRSRKLAAALE | (164) | CKRGSRSSC | (181) |
| | GRGGRSKLAAALE | (161) | CKRGSRSSC | (181) |
| | GRRGSRSKLAAALE | (165) | CQRGTRSRC | (182) |
| | GRGGSRSRKLAAALE | (161) | CTRGTRSKC | (177) |
| | RKRGGSR | (166) | CVRGGRARC | (183) |
| | RRGGRSKLAAALE | (160) | CARGKRSLC | (184) |
| | RTRGGRSKLAAALE | (164) | CKRGARSTC | (3) |
| | GRGSRSR | (167) | CKRGARSTC | (3) |
| | DEGMMNA | (168) | CTRGTRSKC | (177) |
| | GRGGRSRKLAAALE | (161) | CKRGSRSSC | (181) |
| | FRGARSR | (169) | CVRGSRSRC | (185) |
| | VRRGGRSKLAAALE | (170) | CKRGSRSSC | (181) |
| | GRRGRNSKLAAALE | (171) | CKRGGRTGC | (186) |
| | RRGARSVRGGRSRS | (172) | CARGKRSLC | (184) |
| | RGRGGRSKLAAALE | (173) | CRRGARAKC | (187) |
| | GKRGGRSKLAAALE | (174) | CQRGGRSKC | (188) |
| | | | CKRGNRSMC | (189) |

*BOLD: RGXXS/T CONSENSUS
**UNDERLINED: RXXR CendR motif

FIG. 2B

SEQUENCE LISTING

```
<160> NUMBER OF SEQ ID NOS: 199

<210> SEQ ID NO 1
<211> LENGTH: 7
<212> TYPE: PRT
<213> ORGANISM: Artificial Sequence
<220> FEATURE:
<223> OTHER INFORMATION: Artificially synthesized peptide

<400> SEQUENCE: 1

Lys Arg Gly Ala Arg Ser Thr
1               5

<210> SEQ ID NO 2
<211> LENGTH: 9
<212> TYPE: PRT
<213> ORGANISM: Artificial Sequence
<220> FEATURE:
<223> OTHER INFORMATION: Artificially synthesized peptide

<400> SEQUENCE: 2

Ala Lys Arg Gly Ala Arg Ser Thr Ala
1               5

<210> SEQ ID NO 3
<211> LENGTH: 9
<212> TYPE: PRT
<213> ORGANISM: Artificial Sequence
<220> FEATURE:
<223> OTHER INFORMATION: Artificially synthesized peptide

<400> SEQUENCE: 3

Cys Lys Arg Gly Ala Arg Ser Thr Cys
1               5

<210> SEQ ID NO 4
<211> LENGTH: 5
<212> TYPE: PRT
<213> ORGANISM: Artificial Sequence
<220> FEATURE:
<223> OTHER INFORMATION: Artificially synthesized peptide
<220> FEATURE:
<221> NAME/KEY: misc_feature
<222> LOCATION: (3)..(3)
<223> OTHER INFORMATION: Xaa can be any naturally occurring amino acid
```

```
<400> SEQUENCE: 4

Arg Gly Xaa Arg Ser
1               5

<210> SEQ ID NO 5
<211> LENGTH: 5
<212> TYPE: PRT
<213> ORGANISM: Artificial Sequence
<220> FEATURE:
<223> OTHER INFORMATION: Artificially synthesized peptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 5

Arg Gly Xaa Arg Thr
1               5

<210> SEQ ID NO 6
<211> LENGTH: 5
<212> TYPE: PRT
<213> ORGANISM: Artificial Sequence
<220> FEATURE:
<223> OTHER INFORMATION: Artificially synthesized peptide

<400> SEQUENCE: 6

Cys Gly Lys Arg Lys
1               5

<210> SEQ ID NO 7
<211> LENGTH: 9
<212> TYPE: PRT
<213> ORGANISM: Artificial Sequence
<220> FEATURE:
<223> OTHER INFORMATION: Artificially synthesized peptide

<400> SEQUENCE: 7

Cys Gly Asn Lys Arg Thr Arg Gly Cys
1               5

<210> SEQ ID NO 8
<211> LENGTH: 19
<212> TYPE: PRT
<213> ORGANISM: Artificial Sequence
<220> FEATURE:
<223> OTHER INFORMATION: Artificially synthesized peptide

<400> SEQUENCE: 8

Cys Gly Lys Arg Lys Lys Leu Ala Lys Leu Ala Lys Lys Leu Ala Lys
1               5                   10                  15

Leu Ala Lys

<210> SEQ ID NO 9
<211> LENGTH: 23
<212> TYPE: PRT
<213> ORGANISM: Artificial Sequence
<220> FEATURE:
<223> OTHER INFORMATION: Artificially synthesized peptide

<400> SEQUENCE: 9

Cys Gly Asn Lys Arg Thr Arg Gly Cys Lys Leu Ala Lys Leu Ala Lys
1               5                   10                  15

Lys Leu Ala Lys Leu Ala Lys
            20
```

```
<210> SEQ ID NO 10
<211> LENGTH: 23
<212> TYPE: PRT
<213> ORGANISM: Artificial Sequence
<220> FEATURE:
<223> OTHER INFORMATION: Artificially synthesized peptide

<400> SEQUENCE: 10

Ala Lys Arg Gly Ala Arg Ser Thr Ala Lys Leu Ala Lys Leu Ala Lys
1               5                   10                  15

Lys Leu Ala Lys Leu Ala Lys
            20

<210> SEQ ID NO 11
<211> LENGTH: 6
<212> TYPE: PRT
<213> ORGANISM: Artificial Sequence
<220> FEATURE:
<223> OTHER INFORMATION: Artificially synthesized peptide

<400> SEQUENCE: 11

Lys Leu Ala Ala Leu Glu
1               5

<210> SEQ ID NO 12
<211> LENGTH: 5
<212> TYPE: PRT
<213> ORGANISM: Artificial Sequence
<220> FEATURE:
<223> OTHER INFORMATION: Artificially synthesized peptide

<400> SEQUENCE: 12

Arg Gly Ala Arg Ser
1               5

<210> SEQ ID NO 13
<211> LENGTH: 4
<212> TYPE: PRT
<213> ORGANISM: Artificial Sequence
<220> FEATURE:
<223> OTHER INFORMATION: Artificially synthesized peptide

<400> SEQUENCE: 13

Arg Gly Arg Ser
1

<210> SEQ ID NO 14
<211> LENGTH: 7
<212> TYPE: PRT
<213> ORGANISM: Artificial Sequence
<220> FEATURE:
<223> OTHER INFORMATION: Artificially synthesized peptide

<400> SEQUENCE: 14

Arg Pro Ala Arg Pro Ala Arg
1               5

<210> SEQ ID NO 15
<211> LENGTH: 5
<212> TYPE: PRT
<213> ORGANISM: Artificial Sequence
<220> FEATURE:
<223> OTHER INFORMATION: Artificially synthesized peptide

<400> SEQUENCE: 15
```

```
Thr Gly Gly Ser Gly
1               5

<210> SEQ ID NO 16
<211> LENGTH: 4
<212> TYPE: PRT
<213> ORGANISM: Artificial Sequence
<220> FEATURE:
<223> OTHER INFORMATION: Artificially synthesized peptide

<400> SEQUENCE: 16

Gly Gly Ser Gly
1

<210> SEQ ID NO 17
<211> LENGTH: 7
<212> TYPE: PRT
<213> ORGANISM: Artificial Sequence
<220> FEATURE:
<223> OTHER INFORMATION: Artificially synthesized peptide

<400> SEQUENCE: 17

Lys Leu Ala Lys Leu Ala Lys
1               5

<210> SEQ ID NO 18
<211> LENGTH: 1163
<212> TYPE: DNA
<213> ORGANISM: Homo sapiens
<220> FEATURE:
<221> NAME/KEY: CDS
<222> LOCATION: (79)..(927)

<400> SEQUENCE: 18
ccggcggcgc ctcaggtcgc ggggcgccta ggcctgggtt gtcctttgca tctgcacgtg     60
ttcgcagtcg tttccgcg atg ctg cct ctg ctg cgc tgc gtg ccc cgt gtg    111
                    Met Leu Pro Leu Leu Arg Cys Val Pro Arg Val
                    1               5                   10 ctg ggc tcc tcc gtc gcc ggc ctc cgc gct gcc gcg ccc gcc tcg cct    159
Leu Gly Ser Ser Val Ala Gly Leu Arg Ala Ala Ala Pro Ala Ser Pro
                15                  20                  25 ttc cgg cag ctc ctg cag ccg gca ccc cgg ctg tgc acc cgg ccc ttc    207
Phe Arg Gln Leu Leu Gln Pro Ala Pro Arg Leu Cys Thr Arg Pro Phe
            30                  35                  40 ggg ctc ctc agc gtg cgc gca ggt tcc gag cgg cgg ccg ggc ctc ctg    255
Gly Leu Leu Ser Val Arg Ala Gly Ser Glu Arg Arg Pro Gly Leu Leu
        45                  50                  55 cgg cct cgc gga ccc tgc gcc tgt ggc tgt ggc tgc ggc tcg ctg cac    303
Arg Pro Arg Gly Pro Cys Ala Cys Gly Cys Gly Cys Gly Ser Leu His
60                  65                  70                  75 acc gac gga gac aaa gct ttt gtt gat ttc ctg agt gat gaa att aag    351
Thr Asp Gly Asp Lys Ala Phe Val Asp Phe Leu Ser Asp Glu Ile Lys
                80                  85                  90 gag gaa aga aaa att cag aag cat aaa acc ctc cct aag atg tct gga    399
Glu Glu Arg Lys Ile Gln Lys His Lys Thr Leu Pro Lys Met Ser Gly
            95                  100                 105 ggt tgg gag ctg gaa ctg aat ggg aca gaa gcg aaa tta gtg cgg aaa    447
Gly Trp Glu Leu Glu Leu Asn Gly Thr Glu Ala Lys Leu Val Arg Lys
        110                 115                 120 gtt gcc ggg gaa aaa atc acg gtc act ttc aac att aac aac agc atc    495
Val Ala Gly Glu Lys Ile Thr Val Thr Phe Asn Ile Asn Asn Ser Ile
    125                 130                 135 cca cca aca ttt gat ggt gag gag gaa ccc tcg caa ggg cag aag gtt    543
```

```
Pro Pro Thr Phe Asp Gly Glu Glu Pro Ser Gln Gly Gln Lys Val
140                 145                 150                 155 gaa gaa cag gag cct gaa ctg aca tca act ccc aat ttc gtg gtt gaa      591
Glu Glu Gln Glu Pro Glu Leu Thr Ser Thr Pro Asn Phe Val Val Glu
                160                 165                 170 gtt ata aag aat gat gat ggc aag aag gcc ctt gtg ttg gac tgt cat      639
Val Ile Lys Asn Asp Asp Gly Lys Lys Ala Leu Val Leu Asp Cys His
            175                 180                 185 tat cca gag gat gag gtt gga caa gaa gac gag gct gag agt gac atc      687
Tyr Pro Glu Asp Glu Val Gly Gln Glu Asp Glu Ala Glu Ser Asp Ile
        190                 195                 200 ttc tct atc agg gaa gtt agc ttt cag tcc act ggc gag tct gaa tgg      735
Phe Ser Ile Arg Glu Val Ser Phe Gln Ser Thr Gly Glu Ser Glu Trp
    205                 210                 215 aag gat act aat tat aca ctc aac aca gat tcc ttg gac tgg gcc tta      783
Lys Asp Thr Asn Tyr Thr Leu Asn Thr Asp Ser Leu Asp Trp Ala Leu
220                 225                 230                 235 tat gac cac cta atg gat ttc ctt gcc gac cga ggg gtg gac aac act      831
Tyr Asp His Leu Met Asp Phe Leu Ala Asp Arg Gly Val Asp Asn Thr
                240                 245                 250 ttt gca gat gag ctg gtg gag ctc agc aca gcc ctg gag cac cag gag      879
Phe Ala Asp Glu Leu Val Glu Leu Ser Thr Ala Leu Glu His Gln Glu
            255                 260                 265 tac att act ttt ctt gaa gac ctc aag agt ttt gtc aag agc cag tag      927
Tyr Ile Thr Phe Leu Glu Asp Leu Lys Ser Phe Val Lys Ser Gln
        270                 275                 280 agcagacaga tgctgaaagc catagtttca tggcaggctt tggccagtga acaaatccta    987
ctctgaagct agacatgtgc tttgaaatga ttatcatcct aatatcatgg gggaaaaaat   1047
accaaattta aattatatgt tttgtgttct catttattat catttttttc tgtacaaatc   1107
tattatttct agattttgt ataacatgat agacataaaa ttggtttatc tcctcc        1163
```

<210> SEQ ID NO 19
<211> LENGTH: 282
<212> TYPE: PRT
<213> ORGANISM: Homo sapiens

<400> SEQUENCE: 19

```
Met Leu Pro Leu Leu Arg Cys Val Pro Arg Val Leu Gly Ser Ser Val
1               5                   10                  15

Ala Gly Leu Arg Ala Ala Pro Ala Ser Pro Phe Arg Gln Leu Leu
                20                  25                  30

Gln Pro Ala Pro Arg Leu Cys Thr Arg Pro Phe Gly Leu Leu Ser Val
            35                  40                  45

Arg Ala Gly Ser Glu Arg Arg Pro Gly Leu Leu Arg Pro Arg Gly Pro
        50                  55                  60

Cys Ala Cys Gly Cys Gly Cys Gly Ser Leu His Thr Asp Gly Asp Lys
65                  70                  75                  80

Ala Phe Val Asp Phe Leu Ser Asp Glu Ile Lys Glu Glu Arg Lys Ile
                85                  90                  95

Gln Lys His Lys Thr Leu Pro Lys Met Ser Gly Gly Trp Glu Leu Glu
            100                 105                 110

Leu Asn Gly Thr Glu Ala Lys Leu Val Arg Lys Val Ala Gly Glu Lys
        115                 120                 125

Ile Thr Val Thr Phe Asn Ile Asn Asn Ser Ile Pro Pro Thr Phe Asp
    130                 135                 140

Gly Glu Glu Glu Pro Ser Gln Gly Gln Lys Val Glu Glu Gln Glu Pro
```

```
                145                 150                 155                 160
Glu Leu Thr Ser Thr Pro Asn Phe Val Val Glu Val Ile Lys Asn Asp
                    165                 170                 175

Asp Gly Lys Lys Ala Leu Val Leu Asp Cys His Tyr Pro Glu Asp Glu
                180                 185                 190

Val Gly Gln Glu Asp Glu Ala Glu Ser Asp Ile Phe Ser Ile Arg Glu
            195                 200                 205

Val Ser Phe Gln Ser Thr Gly Glu Ser Glu Trp Lys Asp Thr Asn Tyr
        210                 215                 220

Thr Leu Asn Thr Asp Ser Leu Asp Trp Ala Leu Tyr Asp His Leu Met
225                 230                 235                 240

Asp Phe Leu Ala Asp Arg Gly Val Asp Asn Thr Phe Ala Asp Glu Leu
                    245                 250                 255

Val Glu Leu Ser Thr Ala Leu Glu His Gln Tyr Ile Thr Phe Leu
                260                 265                 270

Glu Asp Leu Lys Ser Phe Val Lys Ser Gln
            275                 280

<210> SEQ ID NO 20
<211> LENGTH: 1408
<212> TYPE: DNA
<213> ORGANISM: Gorilla gorilla gorilla
<220> FEATURE:
<221> NAME/KEY: CDS
<222> LOCATION: (102)..(947)

<400> SEQUENCE: 20
```

| | | | | | |
|---|---|---|---|---|---|
| gcttccgggc agggggcgggg cttccggcgg cgcgtcaggt cgcggggcgc ctaggcctgg | | | | | 60 |
| gttgtccttt gcatctgcac gtgttcgcag tcgtttccgc g atg ctg cct ctg ctg | | | | | 116 |
| | | | | Met Leu Pro Leu Leu | |
| | | | | 1             5 | |

```
cgc tgc gtg ccc cgt gtg ctg ggc tcc tcc gtc gcc ggc ctc cgc gct      164
Arg Cys Val Pro Arg Val Leu Gly Ser Ser Val Ala Gly Leu Arg Ala
            10                  15                  20 gcc gcg ccc gcc tcg cct ttc cgg cag ctc ctg cag ccg gca ccc cgg      212
Ala Ala Pro Ala Ser Pro Phe Arg Gln Leu Leu Gln Pro Ala Pro Arg
        25                  30                  35 ctg tgc acc cgg ccc ttc ggg ctg ctc agc gtg cgc gca ggt tcc gag      260
Leu Cys Thr Arg Pro Phe Gly Leu Leu Ser Val Arg Ala Gly Ser Glu
    40                  45                  50 cgg cgg ccg ggc ctc ctg cgg cct cgc gga ccc tgc gcc tgt ggc tgt      308
Arg Arg Pro Gly Leu Leu Arg Pro Arg Gly Pro Cys Ala Cys Gly Cys
55                  60                  65 ggc tgc ggc tcg ctg cac acc gac gga gac aaa gct ttt gtt gat ttc      356
Gly Cys Gly Ser Leu His Thr Asp Gly Asp Lys Ala Phe Val Asp Phe
70                  75                  80                  85 ctg agt gat gaa att aag gag gaa aga aaa att cag aag cat aaa acc      404
Leu Ser Asp Glu Ile Lys Glu Glu Arg Lys Ile Gln Lys His Lys Thr
                90                  95                  100 ctc cct aag atg tct gga ggt tgg gag ctg gaa ctg aat ggg aca gaa      452
Leu Pro Lys Met Ser Gly Gly Trp Glu Leu Glu Leu Asn Gly Thr Glu
            105                 110                 115 gcg aaa tta gtg cgg aaa gtt gcc ggg gaa aaa atc act gtc act ttc      500
Ala Lys Leu Val Arg Lys Val Ala Gly Glu Lys Ile Thr Val Thr Phe
        120                 125                 130 aac att aac aac agc atc cca cca aca ttt gat ggt gag gag gaa ccc      548
Asn Ile Asn Asn Ser Ile Pro Pro Thr Phe Asp Gly Glu Glu Glu Pro
    135                 140                 145
```

| | | |
|---|---|---|
| tcg caa ggg cag aag gtt gaa gaa cag gag cct gaa ctg aca tca act<br>Ser Gln Gly Gln Lys Val Glu Glu Gln Glu Pro Glu Leu Thr Ser Thr<br>150                         155                     160                   165 | | 596 |
| ccc aat ttc gtg gtt gaa gtt ata aag aat gat ggc aag aag gcc ctt<br>Pro Asn Phe Val Val Glu Val Ile Lys Asn Asp Gly Lys Lys Ala Leu<br>                 170                     175                     180 | | 644 |
| gtg ttg gac tgt cat tat cca gag gat gag gtt gga caa gaa gac gag<br>Val Leu Asp Cys His Tyr Pro Glu Asp Glu Val Gly Gln Glu Asp Glu<br>                      185                     190                   195 | | 692 |
| gct gag agt gac atc ttc tct atc agg gaa gtt agc ttt cag tcc act<br>Ala Glu Ser Asp Ile Phe Ser Ile Arg Glu Val Ser Phe Gln Ser Thr<br>            200                     205                     210 | | 740 |
| ggc gag tct gaa tgg aag gat act aat tat aca ctc aac aca gat tcc<br>Gly Glu Ser Glu Trp Lys Asp Thr Asn Tyr Thr Leu Asn Thr Asp Ser<br>215                         220                     225 | | 788 |
| ttg gac tgg gct tta tat gac cac cta atg gat ttc ctt gct gac cga<br>Leu Asp Trp Ala Leu Tyr Asp His Leu Met Asp Phe Leu Ala Asp Arg<br>230                         235                     240                   245 | | 836 |
| ggg gtg gac aac act ttt gca gat gag ttg gtg gag ctc agc aca gcc<br>Gly Val Asp Asn Thr Phe Ala Asp Glu Leu Val Glu Leu Ser Thr Ala<br>                      250                     255                   260 | | 884 |
| ctg gag cac cag gag tac att act ttt ctt gag gac ctc aag agt ttt<br>Leu Glu His Gln Glu Tyr Ile Thr Phe Leu Glu Asp Leu Lys Ser Phe<br>            265                     270                     275 | | 932 |
| gtc aag agc cag tag agcagacaga tgctgaaagc catagtttca tggcaggctt<br>Val Lys Ser Gln<br>280 | | 987 |
| tggccagtga acaaattcta ctccgaagct agacatgtgc tttgaaatga ttatcatcct | | 1047 |
| aatatcatgg gggaaaaaat accaaattta aattatatgt tttctgctct catttattat | | 1107 |
| catttttttc tgtacaaatc tattatttct agatttttgt ataacatgat agacataaaa | | 1167 |
| ttggtttatc tcctccaagg cagtttgtct ttttctattc ctccccccttc aacctgcgtc | | 1227 |
| acaaaagacc aagaacagat gtcggaaaag ttttttttttc ttcagtattg tttaaaagtt | | 1287 |
| tcaatacaaa atacgttata aataaaaggc ttgtatgtac aaggctcctc agagggaatg | | 1347 |
| agttgtcttc aaccccatag aatgatgtga gtccaagctg gctctagagg atcacagccc | | 1407 |
| a | | 1408 |

<210> SEQ ID NO 21
<211> LENGTH: 281
<212> TYPE: PRT
<213> ORGANISM: Gorilla gorilla gorilla

<400> SEQUENCE: 21

Met Leu Pro Leu Leu Arg Cys Val Pro Arg Val Leu Gly Ser Ser Val
1               5                    10                   15

Ala Gly Leu Arg Ala Ala Ala Pro Ala Ser Pro Phe Arg Gln Leu Leu
             20                    25                   30

Gln Pro Ala Pro Arg Leu Cys Thr Arg Pro Phe Gly Leu Leu Ser Val
                 35                   40                   45

Arg Ala Gly Ser Glu Arg Arg Pro Gly Leu Leu Arg Pro Arg Gly Pro
 50                    55                    60

Cys Ala Cys Gly Cys Gly Cys Gly Ser Leu His Thr Asp Gly Asp Lys
65                   70                    75                    80

Ala Phe Val Asp Phe Leu Ser Asp Glu Ile Lys Glu Glu Arg Lys Ile
                 85                   90                   95

Gln Lys His Lys Thr Leu Pro Lys Met Ser Gly Gly Trp Glu Leu Glu

```
                100             105             110
Leu Asn Gly Thr Glu Ala Lys Leu Val Arg Lys Val Ala Gly Glu Lys
            115                 120                 125

Ile Thr Val Thr Phe Asn Ile Asn Asn Ser Ile Pro Pro Thr Phe Asp
    130                 135                 140

Gly Glu Glu Pro Ser Gln Gly Gln Lys Val Glu Gln Glu Pro
145                 150                 155                 160

Glu Leu Thr Ser Thr Pro Asn Phe Val Val Glu Val Ile Lys Asn Asp
                165                 170                 175

Gly Lys Lys Ala Leu Val Leu Asp Cys His Tyr Pro Glu Asp Glu Val
                180                 185                 190

Gly Gln Glu Asp Glu Ala Glu Ser Asp Ile Phe Ser Ile Arg Glu Val
            195                 200                 205

Ser Phe Gln Ser Thr Gly Glu Ser Glu Trp Lys Asp Thr Asn Tyr Thr
    210                 215                 220

Leu Asn Thr Asp Ser Leu Asp Trp Ala Leu Tyr Asp His Leu Met Asp
225                 230                 235                 240

Phe Leu Ala Asp Arg Gly Val Asp Asn Thr Phe Ala Asp Glu Leu Val
                245                 250                 255

Glu Leu Ser Thr Ala Leu Glu His Gln Glu Tyr Ile Thr Phe Leu Glu
            260                 265                 270

Asp Leu Lys Ser Phe Val Lys Ser Gln
            275                 280

<210> SEQ ID NO 22
<211> LENGTH: 1327
<212> TYPE: DNA
<213> ORGANISM: Pongo abelii
<220> FEATURE:
<221> NAME/KEY: CDS
<222> LOCATION: (105)..(950)

<400> SEQUENCE: 22
agcgcttccg ggcaggggcg gggcttccgg ccgcgcgtta ggtcgtgggg cacctaggtc      60
tgggtcgtcg tttgcgtctg cacgtgttcg cagtcgtttc cgcg atg ctt cct ttg     116
                                                 Met Leu Pro Leu
                                                 1 ctg cgc tgt gtg tcc cgt gtg ctg ggc tcc tcc gtc gcc cgc ctc cgc     164
Leu Arg Cys Val Ser Arg Val Leu Gly Ser Ser Val Ala Arg Leu Arg
5                   10                  15                  20 gct gcc gcg ccc gcc tcg cct ttc cgg cag ctc ctg cag ccg gcg ccc     212
Ala Ala Ala Pro Ala Ser Pro Phe Arg Gln Leu Leu Gln Pro Ala Pro
                25                  30                  35 cgg ctg tgc gcc cgg ccc ttc ggg ctg ctc agc gtg cgc gca ggt tcc     260
Arg Leu Cys Ala Arg Pro Phe Gly Leu Leu Ser Val Arg Ala Gly Ser
            40                  45                  50 gag cgg cgg ccg ggc ctc ctg cgg cct cgc gga ccc tgc gcc tgt ggc     308
Glu Arg Arg Pro Gly Leu Leu Arg Pro Arg Gly Pro Cys Ala Cys Gly
        55                  60                  65 tgt ggc tgc ggc ttg ctg cac acc gaa gga gac aaa gct ttt gtt gat     356
Cys Gly Cys Gly Leu Leu His Thr Glu Gly Asp Lys Ala Phe Val Asp
70                  75                  80 ttc ctg agt gat gaa att aag gag gaa aga aaa atc cag aag cat aaa     404
Phe Leu Ser Asp Glu Ile Lys Glu Glu Arg Lys Ile Gln Lys His Lys
85                  90                  95                  100 acc ctc cct aag atg tct gga ggt tgg gag ctg gaa ctg aat ggg aca     452
Thr Leu Pro Lys Met Ser Gly Gly Trp Glu Leu Glu Leu Asn Gly Thr
                105                 110                 115
```

```
gaa gcg aaa tta gtg cgg aaa gtt gcc ggg gaa aaa atc act gtc act    500
Glu Ala Lys Leu Val Arg Lys Val Ala Gly Glu Lys Ile Thr Val Thr
            120                 125                 130 ttc aac att aac aac agc atc cca cca aca ttt gat ggt gag gag gaa    548
Phe Asn Ile Asn Asn Ser Ile Pro Pro Thr Phe Asp Gly Glu Glu Glu
135                 140                 145 ccc tcg caa ggg cag aag gtt gaa gaa cag gag cct gaa ctg aca tca    596
Pro Ser Gln Gly Gln Lys Val Glu Glu Gln Glu Pro Glu Leu Thr Ser
    150                 155                 160 act ccc aat ttc gtg gtt gaa gtt ata aag aat gat ggc aag aag gcc    644
Thr Pro Asn Phe Val Val Glu Val Ile Lys Asn Asp Gly Lys Lys Ala
165                 170                 175                 180 ctt gtg ttg gac tgt cat tat cca gag gat gag gtt gga caa gaa gat    692
Leu Val Leu Asp Cys His Tyr Pro Glu Asp Glu Val Gly Gln Glu Asp
                185                 190                 195 gag gct gag agt gac atc ttc tct atc agg gaa gtt agc ttt cag tcc    740
Glu Ala Glu Ser Asp Ile Phe Ser Ile Arg Glu Val Ser Phe Gln Ser
            200                 205                 210 act ggc gaa tct gaa tgg aag gat act aat tat aca ctc aac acg gat    788
Thr Gly Glu Ser Glu Trp Lys Asp Thr Asn Tyr Thr Leu Asn Thr Asp
        215                 220                 225 tcc ttg gac tgg gcc tta tat gac cac cta atg gat ttc ctt gcc gac    836
Ser Leu Asp Trp Ala Leu Tyr Asp His Leu Met Asp Phe Leu Ala Asp
230                 235                 240 cga ggg gtg gac aac act ttt gca gat gag ttg gtg gag ctc agc aca    884
Arg Gly Val Asp Asn Thr Phe Ala Asp Glu Leu Val Glu Leu Ser Thr
245                 250                 255                 260 gcc ctg gag cac cag gag tac att act ttt ctt gaa gac ctc aag agt    932
Ala Leu Glu His Gln Glu Tyr Ile Thr Phe Leu Glu Asp Leu Lys Ser
                265                 270                 275 ttt gtc aag agc cag tag agcagacacg ctgaaagcca tagtttcatg            980
Phe Val Lys Ser Gln
                280 gccggctttg gccagtgaac aaatcctact ctgaagctag acatgtgctt tgaaatgatt  1040 atcatcctaa tatcatgggg gaaagatacc aagtttaaat tatatgtttt gcgctctcat  1100 ttattatcat tttttctgta cagatctatt atttctagat ttttgtataa cgcgatagac  1160 ataaaattgg tttatctcct ccaaggcagt ttgtcttttt ctattcctcc cccttcaacc  1220 tgcgtcacaa aagaccaaga acagagatgt cggaaaagtt tttttttctt cagtattgtt  1280 taaaagtttc aatacaaagt aagttataaa taaaaggctt gtatgta                1327
```

<210> SEQ ID NO 23
<211> LENGTH: 281
<212> TYPE: PRT
<213> ORGANISM: Pongo abelii

<400> SEQUENCE: 23

```
Met Leu Pro Leu Leu Arg Cys Val Ser Arg Val Leu Gly Ser Ser Val
1               5                   10                  15

Ala Arg Leu Arg Ala Ala Ala Pro Ala Ser Pro Phe Arg Gln Leu Leu
            20                  25                  30

Gln Pro Ala Pro Arg Leu Cys Ala Arg Pro Phe Gly Leu Leu Ser Val
        35                  40                  45

Arg Ala Gly Ser Glu Arg Arg Pro Gly Leu Leu Arg Pro Arg Gly Pro
    50                  55                  60

Cys Ala Cys Gly Cys Gly Cys Gly Leu Leu His Thr Glu Gly Asp Lys
65                  70                  75                  80
```

```
Ala Phe Val Asp Phe Leu Ser Asp Glu Ile Lys Glu Arg Lys Ile
             85                  90                  95

Gln Lys His Lys Thr Leu Pro Lys Met Ser Gly Gly Trp Glu Leu Glu
            100                 105                 110

Leu Asn Gly Thr Glu Ala Lys Leu Val Arg Lys Val Ala Gly Glu Lys
        115                 120                 125

Ile Thr Val Thr Phe Asn Ile Asn Asn Ser Ile Pro Pro Thr Phe Asp
130                 135                 140

Gly Glu Glu Glu Pro Ser Gln Gly Gln Lys Val Glu Glu Gln Glu Pro
145                 150                 155                 160

Glu Leu Thr Ser Thr Pro Asn Phe Val Val Glu Val Ile Lys Asn Asp
                165                 170                 175

Gly Lys Lys Ala Leu Val Leu Asp Cys His Tyr Pro Glu Asp Glu Val
            180                 185                 190

Gly Gln Glu Asp Glu Ala Glu Ser Asp Ile Phe Ser Ile Arg Glu Val
        195                 200                 205

Ser Phe Gln Ser Thr Gly Glu Ser Glu Trp Lys Asp Thr Asn Tyr Thr
    210                 215                 220

Leu Asn Thr Asp Ser Leu Asp Trp Ala Leu Tyr Asp His Leu Met Asp
225                 230                 235                 240

Phe Leu Ala Asp Arg Gly Val Asp Asn Thr Phe Ala Asp Glu Leu Val
                245                 250                 255

Glu Leu Ser Thr Ala Leu Glu His Gln Glu Tyr Ile Thr Phe Leu Glu
            260                 265                 270

Asp Leu Lys Ser Phe Val Lys Ser Gln
            275                 280

<210> SEQ ID NO 24
<211> LENGTH: 1187
<212> TYPE: DNA
<213> ORGANISM: Macaca fascicularis
<220> FEATURE:
<221> NAME/KEY: CDS
<222> LOCATION: (110)..(955)

<400> SEQUENCE: 24
cgggaagcgc ttccgggcaa gggcggggct tccggcggcg ctttaggtcg cggggtactt       60
gggcctggat tgtcctttgc atctgcacgt gttcgcagtg gattgcgcg atg cta cct      118
                                                     Met Leu Pro
                                                       1 ctg ctg cgc tgc gtg cct cgt gtg ctg ggc tcc gcc gtc ccc agc ctc        166
Leu Leu Arg Cys Val Pro Arg Val Leu Gly Ser Ala Val Pro Ser Leu
      5                  10                  15 cgc gct gcc gcg ccc gcc tcg cct ttc cgg cag ctc ctg cag ccg gcg        214
Arg Ala Ala Ala Pro Ala Ser Pro Phe Arg Gln Leu Leu Gln Pro Ala
 20                  25                  30                  35 ccc cgg ctg tgc gcc cgg ccc ttc ggg ctg ctc agc gtg cgc gca ggt        262
Pro Arg Leu Cys Ala Arg Pro Phe Gly Leu Leu Ser Val Arg Ala Gly
             40                  45                  50 tcc gag cgg cgg ccg ggc ctc ctg cgg cct cga gga ccc tgc gcc tgt        310
Ser Glu Arg Arg Pro Gly Leu Leu Arg Pro Arg Gly Pro Cys Ala Cys
         55                  60                  65 ggc tgt ggc tgc ggc ttg ctg cac act gaa gga gac aaa gct ttt gtt        358
Gly Cys Gly Cys Gly Leu Leu His Thr Glu Gly Asp Lys Ala Phe Val
     70                  75                  80 gat ttc ctg aag gat gaa att gag gag gaa aga aaa atc cag aag cat        406
Asp Phe Leu Lys Asp Glu Ile Glu Glu Glu Arg Lys Ile Gln Lys His
```

```
aaa acc ctc cct aag atg tct gga ggt tgg gag ctg gaa ctg aat ggg      454
Lys Thr Leu Pro Lys Met Ser Gly Gly Trp Glu Leu Glu Leu Asn Gly
100                 105                 110                 115 aca gaa gcg aaa tta gtg cgg aaa gtt gcc ggg gaa aaa atc att gtc      502
Thr Glu Ala Lys Leu Val Arg Lys Val Ala Gly Glu Lys Ile Ile Val
                120                 125                 130 act ttc aac att aac aac agc atc cca cca aca ttt gat ggt gag gag      550
Thr Phe Asn Ile Asn Asn Ser Ile Pro Pro Thr Phe Asp Gly Glu Glu
            135                 140                 145 gaa ccc acg caa aag cag aag gtt gaa gaa cag gag cct gaa ctg aca      598
Glu Pro Thr Gln Lys Gln Lys Val Glu Glu Gln Glu Pro Glu Leu Thr
        150                 155                 160 tca act ccc aat ttc gtg gtt gaa gtt ata aag aat gat ggc aag aag      646
Ser Thr Pro Asn Phe Val Val Glu Val Ile Lys Asn Asp Gly Lys Lys
    165                 170                 175 gcc ctt gtg ctg gac tgt cat tat cca gag gat gag gtt gga caa gaa      694
Ala Leu Val Leu Asp Cys His Tyr Pro Glu Asp Glu Val Gly Gln Glu
180                 185                 190                 195 gac gag gct gag agt gac atc ttc tct atc agg gaa gtt agc ttt cag      742
Asp Glu Ala Glu Ser Asp Ile Phe Ser Ile Arg Glu Val Ser Phe Gln
                200                 205                 210 tcc agt ggc gag tct gaa tgg aag gat act aat tac aca ctc aac aca      790
Ser Ser Gly Glu Ser Glu Trp Lys Asp Thr Asn Tyr Thr Leu Asn Thr
                215                 220                 225 gat tcc ttg gac tgg gcc tta tat gac cac cta atg gat ttc ctt gcg      838
Asp Ser Leu Asp Trp Ala Leu Tyr Asp His Leu Met Asp Phe Leu Ala
            230                 235                 240 gac cga ggg gtg gac aac act ttt gca gat gag ttg gtg gag ctc agc      886
Asp Arg Gly Val Asp Asn Thr Phe Ala Asp Glu Leu Val Glu Leu Ser
        245                 250                 255 aca gcc ctg gag cac cag gag tac att agt ttt ctt gaa gac ctc aag      934
Thr Ala Leu Glu His Gln Glu Tyr Ile Ser Phe Leu Glu Asp Leu Lys
    260                 265                 270                 275 aga ttt gtc aag agc cag tag agcagacaga cgctgaaagc cttagtttca         985
Arg Phe Val Lys Ser Gln
                280 tggcaggctc tggccagtga acaagtccta ctctgaagct agacatgtgc tttgaaatga   1045 ttatcgtcct aatatcatgg ggaaaaacac caaatttaaa ttatatgttt tgcgctctca   1105 ttatcatttt tcctgtacaa atctattatt tctagatttt tgtataacat gatagacata   1165 aaattggttt atctcctcca aa                                            1187

<210> SEQ ID NO 25
<211> LENGTH: 281
<212> TYPE: PRT
<213> ORGANISM: Macaca fascicularis

<400> SEQUENCE: 25

Met Leu Pro Leu Leu Arg Cys Val Pro Arg Val Leu Gly Ser Ala Val
1               5                   10                  15

Pro Ser Leu Arg Ala Ala Ala Pro Ala Ser Pro Phe Arg Gln Leu Leu
            20                  25                  30

Gln Pro Ala Pro Arg Leu Cys Ala Arg Pro Phe Gly Leu Leu Ser Val
        35                  40                  45

Arg Ala Gly Ser Glu Arg Arg Pro Gly Leu Leu Arg Pro Arg Gly Pro
    50                  55                  60

Cys Ala Cys Gly Cys Gly Cys Gly Leu Leu His Thr Glu Gly Asp Lys
```

```
                65                  70                  75                  80
Ala Phe Val Asp Phe Leu Lys Asp Glu Ile Glu Glu Arg Lys Ile
                    85                  90                  95
Gln Lys His Lys Thr Leu Pro Lys Met Ser Gly Gly Trp Glu Leu Glu
                100                 105                 110
Leu Asn Gly Thr Glu Ala Lys Leu Val Arg Lys Val Ala Gly Glu Lys
                115                 120                 125
Ile Ile Val Thr Phe Asn Ile Asn Asn Ser Ile Pro Pro Thr Phe Asp
    130                 135                 140
Gly Glu Glu Glu Pro Thr Gln Lys Gln Lys Val Glu Glu Gln Glu Pro
145                 150                 155                 160
Glu Leu Thr Ser Thr Pro Asn Phe Val Val Glu Val Ile Lys Asn Asp
                    165                 170                 175
Gly Lys Lys Ala Leu Val Leu Asp Cys His Tyr Pro Glu Asp Glu Val
                180                 185                 190
Gly Gln Glu Asp Glu Ala Glu Ser Asp Ile Phe Ser Ile Arg Glu Val
                195                 200                 205
Ser Phe Gln Ser Ser Gly Glu Ser Glu Trp Lys Asp Thr Asn Tyr Thr
    210                 215                 220
Leu Asn Thr Asp Ser Leu Asp Trp Ala Leu Tyr Asp His Leu Met Asp
225                 230                 235                 240
Phe Leu Ala Asp Arg Gly Val Asp Asn Thr Phe Ala Asp Glu Leu Val
                    245                 250                 255
Glu Leu Ser Thr Ala Leu Glu His Gln Glu Tyr Ile Ser Phe Leu Glu
                260                 265                 270
Asp Leu Lys Arg Phe Val Lys Ser Gln
        275                 280

<210> SEQ ID NO 26
<211> LENGTH: 1305
<212> TYPE: DNA
<213> ORGANISM: Macaca mulatta
<220> FEATURE:
<221> NAME/KEY: CDS
<222> LOCATION: (83)..(928)

<400> SEQUENCE: 26
gcttccggcg gcgctttagg tcgcggggta cttgggcctg ggttgtcctt tgcatctgca      60
cgtgttcgca gtggattgcg cg atg cta cct ctg ctg cgc tgc gtg cct cgt     112
                         Met Leu Pro Leu Leu Arg Cys Val Pro Arg
                           1               5                  10 gtg ctt ggc tcc gcc gtc ccc agc ctc cgc gct gcc gcg ccc gcc tcg     160
Val Leu Gly Ser Ala Val Pro Ser Leu Arg Ala Ala Ala Pro Ala Ser
                 15                  20                  25 cct ttc cgg cag ctc ctg cag ccg gcg ccc cgg ctg tgc gcc cgg ccc     208
Pro Phe Arg Gln Leu Leu Gln Pro Ala Pro Arg Leu Cys Ala Arg Pro
         30                  35                  40 ttc ggg ctg ctc agc gtg cgc gca ggt tcc gag cgg cgg ccg ggc ctc     256
Phe Gly Leu Leu Ser Val Arg Ala Gly Ser Glu Arg Arg Pro Gly Leu
     45                  50                  55 ctg cgg cct cga gga ccc tgc gcc tgt ggc tgt ggc tgc agc ttg ctg     304
Leu Arg Pro Arg Gly Pro Cys Ala Cys Gly Cys Gly Cys Ser Leu Leu
 60                  65                  70 cac act gaa gga gac aaa gct ttt gtt gat ttc ctg aag gat gaa att     352
His Thr Glu Gly Asp Lys Ala Phe Val Asp Phe Leu Lys Asp Glu Ile
 75                  80                  85                  90 gag gag gaa aga aaa atc cag aag cat aaa acc ctc cct aag atg tct     400
```

| | | | | | | | | | | | | | | | |
|---|---|---|---|---|---|---|---|---|---|---|---|---|---|---|---|
| Glu | Glu | Glu | Arg | Lys | Ile | Gln | Lys | His | Lys | Thr | Leu | Pro | Lys | Met | Ser |
| | | | | 95 | | | | 100 | | | | | 105 | | |

```
gga ggt tgg gag ctg gaa ctg aat ggg aca gaa gcg aaa tta gtg cgg      448
Gly Gly Trp Glu Leu Glu Leu Asn Gly Thr Glu Ala Lys Leu Val Arg
            110                 115                 120 aaa gtt gcc ggg gaa aaa atc att gtc act ttc aac att aac aac agc      496
Lys Val Ala Gly Glu Lys Ile Ile Val Thr Phe Asn Ile Asn Asn Ser
        125                 130                 135 atc cca cca aca ttt gat ggt gag gag gaa ccc acg caa aag cag aag      544
Ile Pro Pro Thr Phe Asp Gly Glu Glu Glu Pro Thr Gln Lys Gln Lys
        140                 145                 150 gtt gaa gaa cag gag cct gaa ctg aca tca act ccc aat ttc gtg gtt      592
Val Glu Glu Gln Glu Pro Glu Leu Thr Ser Thr Pro Asn Phe Val Val
155                 160                 165                 170 gaa gtt ata aag aat gat ggc aag aag gcc ctt gtg ctg gac tgt cat      640
Glu Val Ile Lys Asn Asp Gly Lys Lys Ala Leu Val Leu Asp Cys His
                175                 180                 185 tat cca gag gat gag gtt gga caa gaa gac gag gct gag agt gac atc      688
Tyr Pro Glu Asp Glu Val Gly Gln Glu Asp Glu Ala Glu Ser Asp Ile
                190                 195                 200 ttc tct atc agg gaa gtt agc ttt cag tcc agt ggc gag tct gaa tgg      736
Phe Ser Ile Arg Glu Val Ser Phe Gln Ser Ser Gly Glu Ser Glu Trp
            205                 210                 215 aag gat act aat tac aca ctc aac aca gat tcc ttg gac tgg gcc tta      784
Lys Asp Thr Asn Tyr Thr Leu Asn Thr Asp Ser Leu Asp Trp Ala Leu
220                 225                 230 tat gac cac cta atg gat ttc ctt gcg gac cga ggg gtg gac aac act      832
Tyr Asp His Leu Met Asp Phe Leu Ala Asp Arg Gly Val Asp Asn Thr
235                 240                 245                 250 ttt gca gat gag ttg gtg gag ctc agc aca gcc ctg gag cac cag gag      880
Phe Ala Asp Glu Leu Val Glu Leu Ser Thr Ala Leu Glu His Gln Glu
                255                 260                 265 tac att agt ttt ctt gaa gac ctc aag aga ttt gtc aag agc cag tag      928
Tyr Ile Ser Phe Leu Glu Asp Leu Lys Arg Phe Val Lys Ser Gln
            270                 275                 280 agcagacaga cgctgaaagc cttagtttca tggcaggctc tggccagtga acaagtccta      988
ctctgaagct agacatgtgc tttgaaatga ttatcgtcct aatatcatgg ggaaaaacac     1048
caaatttaaa ttatatgttt tgcgctctca ttatcatttt tcctgtacaa atctattatt     1108
tctagatttt tgtataacat gatagacata aaattggttt atctcctcca aagcagtgta     1168
tctattctat tcctcccgct tcaacctgcg tcacaaaaga ccaagaacag acatgtcgga     1228
aaagtttttt ttccttcagg atcggttaaa agtttcgata caaataagt tataaataaa      1288 aggcttgtat gtacaag                                                    1305

<210> SEQ ID NO 27
<211> LENGTH: 281
<212> TYPE: PRT
<213> ORGANISM: Macaca mulatta

<400> SEQUENCE: 27
```

| | | | | | | | | | | | | | | | |
|---|---|---|---|---|---|---|---|---|---|---|---|---|---|---|---|
| Met | Leu | Pro | Leu | Leu | Arg | Cys | Val | Pro | Arg | Val | Leu | Gly | Ser | Ala | Val |
| 1 | | | | 5 | | | | | 10 | | | | | 15 | |

| | | | | | | | | | | | | | | | |
|---|---|---|---|---|---|---|---|---|---|---|---|---|---|---|---|
| Pro | Ser | Leu | Arg | Ala | Ala | Ala | Pro | Ala | Ser | Pro | Phe | Arg | Gln | Leu | Leu |
| | | | 20 | | | | | 25 | | | | | 30 | | |

| | | | | | | | | | | | | | | | |
|---|---|---|---|---|---|---|---|---|---|---|---|---|---|---|---|
| Gln | Pro | Ala | Pro | Arg | Leu | Cys | Ala | Arg | Pro | Phe | Gly | Leu | Leu | Ser | Val |
| | | | 35 | | | | | 40 | | | | | 45 | | |

Arg Ala Gly Ser Glu Arg Arg Pro Gly Leu Leu Arg Pro Arg Gly Pro

```
            50                  55                  60
Cys Ala Cys Gly Cys Gly Cys Ser Leu Leu His Thr Glu Gly Asp Lys
 65                  70                  75                  80

Ala Phe Val Asp Phe Leu Lys Asp Glu Ile Glu Glu Arg Lys Ile
                 85                  90                  95

Gln Lys His Lys Thr Leu Pro Lys Met Ser Gly Gly Trp Glu Leu Glu
                100                 105                 110

Leu Asn Gly Thr Glu Ala Lys Leu Val Arg Lys Val Ala Gly Glu Lys
            115                 120                 125

Ile Ile Val Thr Phe Asn Ile Asn Asn Ser Ile Pro Pro Thr Phe Asp
        130                 135                 140

Gly Glu Glu Pro Thr Gln Lys Gln Lys Val Glu Glu Gln Glu Pro
145                 150                 155                 160

Glu Leu Thr Ser Thr Pro Asn Phe Val Val Glu Val Ile Lys Asn Asp
                165                 170                 175

Gly Lys Lys Ala Leu Val Leu Asp Cys His Tyr Pro Glu Asp Glu Val
            180                 185                 190

Gly Gln Glu Asp Glu Ala Glu Ser Asp Ile Phe Ser Ile Arg Glu Val
        195                 200                 205

Ser Phe Gln Ser Ser Gly Glu Ser Glu Trp Lys Asp Thr Asn Tyr Thr
    210                 215                 220

Leu Asn Thr Asp Ser Leu Asp Trp Ala Leu Tyr Asp His Leu Met Asp
225                 230                 235                 240

Phe Leu Ala Asp Arg Gly Val Asp Asn Thr Phe Ala Asp Glu Leu Val
                245                 250                 255

Glu Leu Ser Thr Ala Leu Glu His Gln Glu Tyr Ile Ser Phe Leu Glu
            260                 265                 270

Asp Leu Lys Arg Phe Val Lys Ser Gln
        275                 280

<210> SEQ ID NO 28
<211> LENGTH: 1187
<212> TYPE: DNA
<213> ORGANISM: Callithrix jacchus
<220> FEATURE:
<221> NAME/KEY: CDS
<222> LOCATION: (101)..(955)

<400> SEQUENCE: 28
gcttcctgac ggggcggggc ttccggcagc gggctacgtc gcggggagcc tagagttggg      60
tagtcctttg cgtctgcacg tgttcctagt cctctccgcg atg ctg cct ctg cta     115
                                              Met Leu Pro Leu Leu
                                                1               5 cgc tgc gtg ccc cgt gta ctg ggc tcc tcc gtt gcc ggc ctc cgc gcc     163
Arg Cys Val Pro Arg Val Leu Gly Ser Ser Val Ala Gly Leu Arg Ala
                 10                  15                  20 gcg gct ccc gcc tcg cct gct tcg cca ttc cgg cag ctc ctg cag ccg     211
Ala Ala Pro Ala Ser Pro Ala Ser Pro Phe Arg Gln Leu Leu Gln Pro
             25                  30                  35 gcg ccc cag ctc tgc gcc cgg ccc ttc ggg ctg ctc agc gtg cgc gca     259
Ala Pro Gln Leu Cys Ala Arg Pro Phe Gly Leu Leu Ser Val Arg Ala
         40                  45                  50 ggt tcc gag cag cgg ccg ggc ctc ctg cgg cct cgc ggg ccc tgc gcc     307
Gly Ser Glu Gln Arg Pro Gly Leu Leu Arg Pro Arg Gly Pro Cys Ala
     55                  60                  65 tgc ggc tgt ggc tgc ggc gcg ctg cac acc gaa gga gac aaa gct ttt     355
Cys Gly Cys Gly Cys Gly Ala Leu His Thr Glu Gly Asp Lys Ala Phe
 70                  75                  80
```

```
                70                  75                  80                  85
gtt gat ttc ctg agt gat gaa att aag gag gaa aga aaa atc cag aag         403
Val Asp Phe Leu Ser Asp Glu Ile Lys Glu Glu Arg Lys Ile Gln Lys
             90                  95                 100 cat aaa acc ctc cct aag atg tct gga ggt tgg gag ctg gaa ctg aat         451
His Lys Thr Leu Pro Lys Met Ser Gly Gly Trp Glu Leu Glu Leu Asn
            105                 110                 115 ggg aca gaa gct aaa tta gtg cag aaa gtt gct ggg gaa aca atc act         499
Gly Thr Glu Ala Lys Leu Val Gln Lys Val Ala Gly Glu Thr Ile Thr
        120                 125                 130 gtc act ttc aat att aac aac agc atc cca cca aca ttt gat ggt gag         547
Val Thr Phe Asn Ile Asn Asn Ser Ile Pro Pro Thr Phe Asp Gly Glu
        135                 140                 145 gag gaa ccc tcg aaa ggg cag aag gtt gaa gaa cag gag cct gaa ttg         595
Glu Glu Pro Ser Lys Gly Gln Lys Val Glu Glu Gln Glu Pro Glu Leu
150                 155                 160                 165 aca tca act ccc aat ttc gtg gtt gaa gtt ata aag aat gat ggc aag         643
Thr Ser Thr Pro Asn Phe Val Val Glu Val Ile Lys Asn Asp Gly Lys
                170                 175                 180 aag gcc ctt gtg ctg gac tgt cat tat cca gaa gat gag gtt gga caa         691
Lys Ala Leu Val Leu Asp Cys His Tyr Pro Glu Asp Glu Val Gly Gln
            185                 190                 195 gag gat gag gct gag agt gac atc ttc tct atc agg gaa gtt agc ttt         739
Glu Asp Glu Ala Glu Ser Asp Ile Phe Ser Ile Arg Glu Val Ser Phe
        200                 205                 210 cag tcc act ggc aac tct gaa tgg aag gat act aat tac aca ctc aac         787
Gln Ser Thr Gly Asn Ser Glu Trp Lys Asp Thr Asn Tyr Thr Leu Asn
        215                 220                 225 aca gat tcc ctg gac tgg gcc ttg tat gac cac cta atg gat ttc ctt         835
Thr Asp Ser Leu Asp Trp Ala Leu Tyr Asp His Leu Met Asp Phe Leu
230                 235                 240                 245 gcg gac cga ggg gtg gac aac act ttt gca gat gag ttg gtg gag ctc         883
Ala Asp Arg Gly Val Asp Asn Thr Phe Ala Asp Glu Leu Val Glu Leu
                250                 255                 260 agc aca gcc ctg gag cac cag gag tac att act ttt ctt gaa gac ctc         931
Ser Thr Ala Leu Glu His Gln Glu Tyr Ile Thr Phe Leu Glu Asp Leu
            265                 270                 275 aaa agt ttt gtc aag agc aag tag agcagacaga cactgaaagc catagtttta       985
Lys Ser Phe Val Lys Ser Lys
            280 tggcaggctt tggccattaa acaaatccaa gtcagaagct agacacgtgc tttgaaatta     1045 ttatcctaat atcatgggaa aaaaacatca aatttaaatt atatgtttta cgctctcatt     1105 tattaccatt tttttctgta caaatctatt atttgtagat ttttgtataa cataatagac     1165 aataaaattg gtttatctcc tc                                              1187

<210> SEQ ID NO 29
<211> LENGTH: 284
<212> TYPE: PRT
<213> ORGANISM: Callithrix jacchus

<400> SEQUENCE: 29

Met Leu Pro Leu Leu Arg Cys Val Pro Arg Val Leu Gly Ser Ser Val
1               5                   10                  15

Ala Gly Leu Arg Ala Ala Ala Pro Ala Ser Pro Ala Ser Pro Phe Arg
            20                  25                  30

Gln Leu Leu Gln Pro Ala Pro Gln Leu Cys Ala Arg Pro Phe Gly Leu
        35                  40                  45
```

```
        Leu Ser Val Arg Ala Gly Ser Glu Gln Arg Pro Gly Leu Leu Arg Pro
            50                  55                  60

Arg Gly Pro Cys Ala Cys Gly Cys Gly Cys Gly Ala Leu His Thr Glu
         65                  70                  75                  80

Gly Asp Lys Ala Phe Val Asp Phe Leu Ser Asp Glu Ile Lys Glu Glu
                         85                  90                  95

Arg Lys Ile Gln Lys His Lys Thr Leu Pro Lys Met Ser Gly Gly Trp
                    100                 105                 110

Glu Leu Glu Leu Asn Gly Thr Glu Ala Lys Leu Val Gln Lys Val Ala
                    115                 120                 125

Gly Glu Thr Ile Thr Val Thr Phe Asn Ile Asn Asn Ser Ile Pro Pro
        130                 135                 140

Thr Phe Asp Gly Glu Glu Pro Ser Lys Gly Gln Lys Val Glu Glu
        145                 150                 155                 160

Gln Glu Pro Glu Leu Thr Ser Thr Pro Asn Phe Val Val Glu Val Ile
                            165                 170                 175

Lys Asn Asp Gly Lys Lys Ala Leu Val Leu Asp Cys His Tyr Pro Glu
                        180                 185                 190

Asp Glu Val Gly Gln Glu Asp Glu Ala Glu Ser Asp Ile Phe Ser Ile
                    195                 200                 205

Arg Glu Val Ser Phe Gln Ser Thr Gly Asn Ser Glu Trp Lys Asp Thr
        210                 215                 220

Asn Tyr Thr Leu Asn Thr Asp Ser Leu Asp Trp Ala Leu Tyr Asp His
        225                 230                 235                 240

Leu Met Asp Phe Leu Ala Asp Arg Gly Val Asp Asn Thr Phe Ala Asp
                        245                 250                 255

Glu Leu Val Glu Leu Ser Thr Ala Leu Glu His Gln Glu Tyr Ile Thr
                    260                 265                 270

Phe Leu Glu Asp Leu Lys Ser Phe Val Lys Ser Lys
                    275                 280

<210> SEQ ID NO 30
        <211> LENGTH: 1139
        <212> TYPE: DNA
        <213> ORGANISM: Rattus norvegicus
        <220> FEATURE:
        <221> NAME/KEY: CDS
        <222> LOCATION: (8)..(841)

<400> SEQUENCE: 30 gatgctc cct ctg ctg cgc tgc gtg ccc cgc gcc ctg ggt gcc gcc gcc      49
                Pro Leu Leu Arg Cys Val Pro Arg Ala Leu Gly Ala Ala Ala
                 1               5                  10 acg ggc ctc cga gcc tcc atc ccg gcc ccg ccg ctt cgg cat tta ctg      97
        Thr Gly Leu Arg Ala Ser Ile Pro Ala Pro Pro Leu Arg His Leu Leu
         15                  20                  25                  30 cag ccc gcg ccc cgg cca tgc ctc cgg ccc ttc ggt ttg ctc agc gta     145
        Gln Pro Ala Pro Arg Pro Cys Leu Arg Pro Phe Gly Leu Leu Ser Val
                         35                  40                  45 cga gcc ggc tcc gct cgg cgc tct ggc ctc ctg cag ccc ccg gtt ccc     193
        Arg Ala Gly Ser Ala Arg Arg Ser Gly Leu Leu Gln Pro Pro Val Pro
                     50                  55                  60 tgc gcg tgc ggc tgc ggc gct ctg cac acg gaa gga gac aag gcc ttt     241
        Cys Ala Cys Gly Cys Gly Ala Leu His Thr Glu Gly Asp Lys Ala Phe
         65                  70                  75 gtt gaa ttt ttg act gat gaa att aag gaa gaa aag aag atc cag aag     289
        Val Glu Phe Leu Thr Asp Glu Ile Lys Glu Glu Lys Lys Ile Gln Lys
         80                  85                  90
```

```
cat aag tcc ctt ccc aaa atg tct gga gat tgg gag ctg gaa gtg aac      337
His Lys Ser Leu Pro Lys Met Ser Gly Asp Trp Glu Leu Glu Val Asn
 95                 100                 105                 110 ggc acg gag gct aaa tta ttg cgc aaa gtt gcc gga gaa aag atc act      385
Gly Thr Glu Ala Lys Leu Leu Arg Lys Val Ala Gly Glu Lys Ile Thr
                115                 120                 125 gtc act ttc aac att aac aat agc atc cct cca acc ttt gat ggt gaa      433
Val Thr Phe Asn Ile Asn Asn Ser Ile Pro Pro Thr Phe Asp Gly Glu
            130                 135                 140 gag gag ccc tca cag ggg cag aag gcc gaa gag cag gag cca gaa ctg      481
Glu Glu Pro Ser Gln Gly Gln Lys Ala Glu Glu Gln Glu Pro Glu Leu
        145                 150                 155 aca tca act ccc aat ttt gtg gtt gaa gtt aca aag act gat ggc aag      529
Thr Ser Thr Pro Asn Phe Val Val Glu Val Thr Lys Thr Asp Gly Lys
    160                 165                 170 aag acc ctt gta ctg gac tgc cac tat cct gag gac gag atc gga cac      577
Lys Thr Leu Val Leu Asp Cys His Tyr Pro Glu Asp Glu Ile Gly His
175                 180                 185                 190 gaa gat gag gcc gag agt gac att ttc tct att aag gaa gtg agc ttt      625
Glu Asp Glu Ala Glu Ser Asp Ile Phe Ser Ile Lys Glu Val Ser Phe
                195                 200                 205 cag acc act ggt gac tct gag tgg agg gat aca aac tac aca ctc aac      673
Gln Thr Thr Gly Asp Ser Glu Trp Arg Asp Thr Asn Tyr Thr Leu Asn
            210                 215                 220 aca gac tcc ctg gac tgg gcc ttg tat gac cac cta atg gat ttc ctt      721
Thr Asp Ser Leu Asp Trp Ala Leu Tyr Asp His Leu Met Asp Phe Leu
        225                 230                 235 gcg gac cga ggg gtg gat aac act ttt gca gat gag ttg gtg gag ctc      769
Ala Asp Arg Gly Val Asp Asn Thr Phe Ala Asp Glu Leu Val Glu Leu
    240                 245                 250 agc aca gcc ctg gag cac cag gaa tat atc acc ttt ctt gag gac ctc      817
Ser Thr Ala Leu Glu His Gln Glu Tyr Ile Thr Phe Leu Glu Asp Leu
255                 260                 265                 270 aaa agc ttt gtc aag agt cag tag aactgtgaga ctgaaggcct caatctaaac    871
Lys Ser Phe Val Lys Ser Gln
                275 ggccagctct ggtgggcgag caaaagctgc cttgacatca caactatgct ttgaaatggc    931 tgtcatccta atatatgggg gaaagcaagt ttaaattatc gccgttacac ctccatttac    991 tattcctttg ggctcttttc ctgtacacat ctattatttg tagattttg tatgacatga   1051 tgatgaacaa taaatctgac ttcatctcct ccaggaaaaa aaaaaaaaa aaaaaaaaa    1111 aaaaaaaaaa aaaaaaaaaa aaaaaaa                                     1139

<210> SEQ ID NO 31
<211> LENGTH: 277
<212> TYPE: PRT
<213> ORGANISM: Rattus norvegicus

<400> SEQUENCE: 31

Pro Leu Leu Arg Cys Val Pro Arg Ala Leu Gly Ala Ala Ala Thr Gly
  1               5                  10                  15

Leu Arg Ala Ser Ile Pro Ala Pro Pro Leu Arg His Leu Leu Gln Pro
                 20                  25                  30

Ala Pro Arg Pro Cys Leu Arg Pro Phe Gly Leu Leu Ser Val Arg Ala
             35                  40                  45

Gly Ser Ala Arg Arg Ser Gly Leu Leu Gln Pro Pro Val Pro Cys Ala
         50                  55                  60
```

```
Cys Gly Cys Gly Ala Leu His Thr Glu Gly Asp Lys Ala Phe Val Glu
 65                  70                  75                  80

Phe Leu Thr Asp Glu Ile Lys Glu Glu Lys Lys Ile Gln Lys His Lys
                 85                  90                  95

Ser Leu Pro Lys Met Ser Gly Asp Trp Glu Leu Glu Val Asn Gly Thr
            100                 105                 110

Glu Ala Lys Leu Leu Arg Lys Val Ala Gly Glu Lys Ile Thr Val Thr
        115                 120                 125

Phe Asn Ile Asn Asn Ser Ile Pro Pro Thr Phe Asp Gly Glu Glu Glu
    130                 135                 140

Pro Ser Gln Gly Gln Lys Ala Glu Glu Gln Glu Pro Glu Leu Thr Ser
145                 150                 155                 160

Thr Pro Asn Phe Val Val Glu Val Thr Lys Thr Asp Gly Lys Lys Thr
                165                 170                 175

Leu Val Leu Asp Cys His Tyr Pro Glu Asp Glu Ile Gly His Glu Asp
            180                 185                 190

Glu Ala Glu Ser Asp Ile Phe Ser Ile Lys Glu Val Ser Phe Gln Thr
        195                 200                 205

Thr Gly Asp Ser Glu Trp Arg Asp Thr Asn Tyr Thr Leu Asn Thr Asp
    210                 215                 220

Ser Leu Asp Trp Ala Leu Tyr Asp His Leu Met Asp Phe Leu Ala Asp
225                 230                 235                 240

Arg Gly Val Asp Asn Thr Phe Ala Asp Glu Leu Val Glu Leu Ser Thr
                245                 250                 255

Ala Leu Glu His Gln Glu Tyr Ile Thr Phe Leu Glu Asp Leu Lys Ser
            260                 265                 270

Phe Val Lys Ser Gln
            275

<210> SEQ ID NO 32
<211> LENGTH: 1177
<212> TYPE: DNA
<213> ORGANISM: Mus musculus
<220> FEATURE:
<221> NAME/KEY: CDS
<222> LOCATION: (77)..(916)

<400> SEQUENCE: 32
ggggcttccg gcagcgcgcg aggtcacacg gtgccttggc ccggtcgtcc ttccctctgc      60
acgtgtccgc ccgcg atg ctc cct ctg ctg cgt tgc gtg ccc cgc gcc ctc     112
              Met Leu Pro Leu Leu Arg Cys Val Pro Arg Ala Leu
                1               5                  10 ggc gcc gcc gcc tcc ggc ctc cga acc gcc atc ccg gcc cag ccg ctt     160
Gly Ala Ala Ala Ser Gly Leu Arg Thr Ala Ile Pro Ala Gln Pro Leu
         15                  20                  25 cgg cat ctc ctg cag ccc gcg ccc cgg cca tgc ctc cgg ccc ttc ggt     208
Arg His Leu Leu Gln Pro Ala Pro Arg Pro Cys Leu Arg Pro Phe Gly
     30                  35                  40 ttg ctc agc gta cgg gcc ggc tcg gct cgg cgc tct ggc ctc ctg cag     256
Leu Leu Ser Val Arg Ala Gly Ser Ala Arg Arg Ser Gly Leu Leu Gln
 45                  50                  55                  60 ccc ccg gtt ccc tgc gcg tgc ggc tgt ggc gct ctg cac acg gaa gga     304
Pro Pro Val Pro Cys Ala Cys Gly Cys Gly Ala Leu His Thr Glu Gly
                 65                  70                  75 gac aag gcc ttc gtt gaa ttc ttg act gat gaa att aag gaa gaa aag     352
Asp Lys Ala Phe Val Glu Phe Leu Thr Asp Glu Ile Lys Glu Glu Lys
             80                  85                  90
```

| | |
|---|---|
| aag atc cag aaa cac aag tcc ctt ccc aag atg tct gga gat tgg gag<br>Lys Ile Gln Lys His Lys Ser Leu Pro Lys Met Ser Gly Asp Trp Glu<br>         95                          100                  105 | 400 |
| ctg gag gtg aac ggc acg gag gct aaa tta ttg cgc aaa gtt gcc gga<br>Leu Glu Val Asn Gly Thr Glu Ala Lys Leu Leu Arg Lys Val Ala Gly<br>        110                       115                  120 | 448 |
| gaa aag atc acg gtc act ttc aac atc aac aac agc atc cct cca aca<br>Glu Lys Ile Thr Val Thr Phe Asn Ile Asn Asn Ser Ile Pro Pro Thr<br>125                  130                   135                140 | 496 |
| ttt gat ggt gag gag gag ccc tca cag ggg cag aag gct gaa gaa cag<br>Phe Asp Gly Glu Glu Glu Pro Ser Gln Gly Gln Lys Ala Glu Glu Gln<br>                145                   150                155 | 544 |
| gag cca gaa ctg aca tca act ccc aac ttt gtg gtt gaa gtt acc aag<br>Glu Pro Glu Leu Thr Ser Thr Pro Asn Phe Val Val Glu Val Thr Lys<br>        160                       165                  170 | 592 |
| act gat ggc aag aag acc ctt gta ctg gac tgt cac tat cct gag gat<br>Thr Asp Gly Lys Lys Thr Leu Val Leu Asp Cys His Tyr Pro Glu Asp<br>                175                   180                185 | 640 |
| gag att gga cac gaa gat gag gcc gag agt gat att ttc tct atc aag<br>Glu Ile Gly His Glu Asp Glu Ala Glu Ser Asp Ile Phe Ser Ile Lys<br>        190                       195                  200 | 688 |
| gaa gtt agc ttt cag gcc act ggt gac tct gag tgg agg gat aca aac<br>Glu Val Ser Phe Gln Ala Thr Gly Asp Ser Glu Trp Arg Asp Thr Asn<br>205                  210                   215                220 | 736 |
| tat aca ctc aac aca gat tcc ctg gac tgg gcc ttg tat gac cac cta<br>Tyr Thr Leu Asn Thr Asp Ser Leu Asp Trp Ala Leu Tyr Asp His Leu<br>                225                   230                235 | 784 |
| atg gat ttc ctt gcg gac cga ggg gtg gat aac act ttt gcg gat gag<br>Met Asp Phe Leu Ala Asp Arg Gly Val Asp Asn Thr Phe Ala Asp Glu<br>        240                       245                  250 | 832 |
| ttg gtg gag ctc agc aca gcc ctg gag cac cag gaa tat atc acc ttt<br>Leu Val Glu Leu Ser Thr Ala Leu Glu His Gln Glu Tyr Ile Thr Phe<br>                255                   260                265 | 880 |
| ctt gag gac ctc aaa agc ttt gtc aag aac cag tag aactcagaga<br>Leu Glu Asp Leu Lys Ser Phe Val Lys Asn Gln<br>        270                       275 | 926 |
| ctgcgggcct taatttaaat ggcaagcttt ggccagtgaa caaaagctcc cttggcatca | 986 |
| gaattatgct tcaaaaatgg ctgtcatcct aatatatcgg ggggaagcaa gtttaaatta | 1046 |
| ctgctgttac acctccattc gctattcctt gggctttttt ttctctgtac aaatttatta | 1106 |
| tttgtagatt tttgtataac atgatgatgg acaataaatc tgactccaat aaatctccaa | 1166 |
| aaaaaaaaaa a | 1177 |

<210> SEQ ID NO 33
<211> LENGTH: 279
<212> TYPE: PRT
<213> ORGANISM: Mus musculus

<400> SEQUENCE: 33

Met Leu Pro Leu Leu Arg Cys Val Pro Arg Ala Leu Gly Ala Ala Ala
1                   5                       10                     15

Ser Gly Leu Arg Thr Ala Ile Pro Ala Gln Pro Leu Arg His Leu Leu
                 20                       25                     30

Gln Pro Ala Pro Arg Pro Cys Leu Arg Pro Phe Gly Leu Leu Ser Val
                35                      40                    45

Arg Ala Gly Ser Ala Arg Arg Ser Gly Leu Leu Gln Pro Pro Val Pro
     50                      55                     60

Cys Ala Cys Gly Cys Gly Ala Leu His Thr Glu Gly Asp Lys Ala Phe

```
                65                  70                  75                  80
Val Glu Phe Leu Thr Asp Glu Ile Lys Glu Glu Lys Lys Ile Gln Lys
                        85                  90                  95

His Lys Ser Leu Pro Lys Met Ser Gly Asp Trp Glu Leu Glu Val Asn
                100                 105                 110

Gly Thr Glu Ala Lys Leu Leu Arg Lys Val Ala Gly Glu Lys Ile Thr
                115                 120                 125

Val Thr Phe Asn Ile Asn Asn Ser Ile Pro Pro Thr Phe Asp Gly Glu
        130                 135                 140

Glu Glu Pro Ser Gln Gly Gln Lys Ala Glu Glu Gln Glu Pro Glu Leu
145                 150                 155                 160

Thr Ser Thr Pro Asn Phe Val Val Glu Val Thr Lys Thr Asp Gly Lys
                    165                 170                 175

Lys Thr Leu Val Leu Asp Cys His Tyr Pro Glu Asp Glu Ile Gly His
                180                 185                 190

Glu Asp Glu Ala Glu Ser Asp Ile Phe Ser Ile Lys Glu Val Ser Phe
            195                 200                 205

Gln Ala Thr Gly Asp Ser Glu Trp Arg Asp Thr Asn Tyr Thr Leu Asn
        210                 215                 220

Thr Asp Ser Leu Asp Trp Ala Leu Tyr Asp His Leu Met Asp Phe Leu
225                 230                 235                 240

Ala Asp Arg Gly Val Asp Asn Thr Phe Ala Asp Glu Leu Val Glu Leu
                    245                 250                 255

Ser Thr Ala Leu Glu His Gln Glu Tyr Ile Thr Phe Leu Glu Asp Leu
                260                 265                 270

Lys Ser Phe Val Lys Asn Gln
            275

<210> SEQ ID NO 34
<211> LENGTH: 1329
<212> TYPE: DNA
<213> ORGANISM: Bos taurus
<220> FEATURE:
<221> NAME/KEY: CDS
<222> LOCATION: (114)..(950)

<400> SEQUENCE: 34
gggacttccg gcggcggtcc cagatctagg gggcgcagcg acaaggagtt gtccttctga      60
gcgagagttg tatttcgaat ctgcacgtgt tcgccaccgc ctccgctgcg aaa atg      116
                                                            Met
                                                            1 ttc cag ctg ctg cgc tgc gtg ccc cgc gtc ctg ggt act gcc gtc gct      164
Phe Gln Leu Leu Arg Cys Val Pro Arg Val Leu Gly Thr Ala Val Ala
        5                   10                  15 ggt ctc cgc gcc gcc gcg ccc tcc ctg ccg cgg ctg cag ccc gcg tcc      212
Gly Leu Arg Ala Ala Ala Pro Ser Leu Pro Arg Leu Gln Pro Ala Ser
            20                  25                  30 cgg cca tgc gcc cgg ccc ttc ggg ctg ctc agc gtg cgt gcg agg tcg      260
Arg Pro Cys Ala Arg Pro Phe Gly Leu Leu Ser Val Arg Ala Arg Ser
    35                  40                  45 gtg cag ctg ccc ggc ctc ctg aag cct cgg ggg ccc tgc gct tgc ggc      308
Val Gln Leu Pro Gly Leu Leu Lys Pro Arg Gly Pro Cys Ala Cys Gly
50                  55                  60                  65 tgc ggc tgt agc gga ctg cac acc gaa gga gac aaa gct ttc gtt gac      356
Cys Gly Cys Ser Gly Leu His Thr Glu Gly Asp Lys Ala Phe Val Asp
                70                  75                  80 ttc ctc agc gat gag atc aag gag gaa aag aag ata cag aaa tat aag      404
```

```
                Phe Leu Ser Asp Glu Ile Lys Glu Lys Lys Ile Gln Lys Tyr Lys
                            85                  90                  95 tct ctc ccc aaa atg tca gga ggt tgg gaa ctg gaa gtg aat ggg acg              452
Ser Leu Pro Lys Met Ser Gly Gly Trp Glu Leu Glu Val Asn Gly Thr
            100                 105                 110 gaa gcc aaa tta gtg cgg aaa gtt gct gga gaa aag atc act gtc act              500
Glu Ala Lys Leu Val Arg Lys Val Ala Gly Glu Lys Ile Thr Val Thr
        115                 120                 125 ttc aac att aac aat agc atc cca cct gct ttc ggt ggt gag gag gaa              548
Phe Asn Ile Asn Asn Ser Ile Pro Pro Ala Phe Gly Gly Glu Glu Glu
130                 135                 140                 145 gaa ccc tcc caa ggg cag aag gct gag gag cag gag cct gaa ttg aca              596
Glu Pro Ser Gln Gly Gln Lys Ala Glu Glu Gln Glu Pro Glu Leu Thr
                150                 155                 160 tcc act ccc aat ttc gtg gtt gaa gtt aca aag gac ggc agc agc aag              644
Ser Thr Pro Asn Phe Val Val Glu Val Thr Lys Asp Gly Ser Ser Lys
            165                 170                 175 gcc ctt gtg ctg gac tgc cac tat ccg gaa gat gag att gga caa gag              692
Ala Leu Val Leu Asp Cys His Tyr Pro Glu Asp Glu Ile Gly Gln Glu
        180                 185                 190 gat gac cag agt gac att ttc tcc atc aag gaa gtg agt ttt cag gcc              740
Asp Asp Gln Ser Asp Ile Phe Ser Ile Lys Glu Val Ser Phe Gln Ala
    195                 200                 205 acc ggc gag tct gac tgg aag gac aca aat tac aca ctc aac aca gac              788
Thr Gly Glu Ser Asp Trp Lys Asp Thr Asn Tyr Thr Leu Asn Thr Asp
210                 215                 220                 225 tcc ctg gat tgg ggc tta tac gac cac cta atg gat ttc ctt gcg gac              836
Ser Leu Asp Trp Gly Leu Tyr Asp His Leu Met Asp Phe Leu Ala Asp
                230                 235                 240 cga ggg gtg gac aac act ttt gcc gat gaa ttg gtg gag ctc agc aca              884
Arg Gly Val Asp Asn Thr Phe Ala Asp Glu Leu Val Glu Leu Ser Thr
            245                 250                 255 gcc ctg gag cac cag gag tac att tct ttc ctt gaa gac ctc aaa ggt              932
Ala Leu Glu His Gln Glu Tyr Ile Ser Phe Leu Glu Asp Leu Lys Gly
        260                 265                 270 ttt gtc aaa agc aag tag agcaggcagc aaggtgctga cacctt aat                     980
Phe Val Lys Ser Lys
    275 tttatggcag gctttggcca gtgaacaaaa cctaactgaa gccagaccca catgctttga           1040 aatggttttt ttttaatcc caatatcatg gaaaatgatt cgcttttaac ttatttctgt            1100 tgtctcttat ttaccattca tttaccctct acaaacccctt tatttctgga tttttgtata          1160 acataatgat ggacaataaa atctccaagg tgaaaaaaaa aaaaaaaaa aaaaaaaaaa           1220 aaaaaaaaaa aaaaaaaaaa aaaaaaaaaa aaaaaaaaaa aaaaaaaaaa aaaaaaaaaa          1280 aaaaaaaaaa aaaaaaaaa aaaaaaaaaa aagaaaaaaa aaaaaaaag                       1329

<210> SEQ ID NO 35
<211> LENGTH: 278
<212> TYPE: PRT
<213> ORGANISM: Bos taurus

<400> SEQUENCE: 35

Met Phe Gln Leu Leu Arg Cys Val Pro Arg Val Leu Gly Thr Ala Val
1               5                   10                  15

Ala Gly Leu Arg Ala Ala Ala Pro Ser Leu Pro Arg Leu Gln Pro Ala
            20                  25                  30

Ser Arg Pro Cys Ala Arg Pro Phe Gly Leu Leu Ser Val Arg Ala Arg
        35                  40                  45
```

```
Ser Val Gln Leu Pro Gly Leu Leu Lys Pro Arg Gly Pro Cys Ala Cys
     50                  55                  60

Gly Cys Gly Cys Ser Gly Leu His Thr Glu Gly Asp Lys Ala Phe Val
 65                  70                  75                  80

Asp Phe Leu Ser Asp Glu Ile Lys Glu Lys Lys Ile Gln Lys Tyr
                 85                  90                  95

Lys Ser Leu Pro Lys Met Ser Gly Gly Trp Glu Leu Glu Val Asn Gly
                100                 105                 110

Thr Glu Ala Lys Leu Val Arg Lys Val Ala Gly Glu Lys Ile Thr Val
            115                 120                 125

Thr Phe Asn Ile Asn Asn Ser Ile Pro Pro Ala Phe Gly Gly Glu Glu
        130                 135                 140

Glu Glu Pro Ser Gln Gly Gln Lys Ala Glu Gln Glu Pro Glu Leu
145                 150                 155                 160

Thr Ser Thr Pro Asn Phe Val Val Glu Val Thr Lys Asp Gly Ser Ser
                165                 170                 175

Lys Ala Leu Val Leu Asp Cys His Tyr Pro Glu Asp Glu Ile Gly Gln
                180                 185                 190

Glu Asp Asp Gln Ser Asp Ile Phe Ser Ile Lys Glu Val Ser Phe Gln
            195                 200                 205

Ala Thr Gly Glu Ser Asp Trp Lys Asp Thr Asn Tyr Thr Leu Asn Thr
        210                 215                 220

Asp Ser Leu Asp Trp Gly Leu Tyr Asp His Leu Met Asp Phe Leu Ala
225                 230                 235                 240

Asp Arg Gly Val Asp Asn Thr Phe Ala Asp Glu Leu Val Glu Leu Ser
                245                 250                 255

Thr Ala Leu Glu His Gln Glu Tyr Ile Ser Phe Leu Glu Asp Leu Lys
                260                 265                 270

Gly Phe Val Lys Ser Lys
            275

<210> SEQ ID NO 36
<211> LENGTH: 1115
<212> TYPE: DNA
<213> ORGANISM: Felis catus
<220> FEATURE:
<221> NAME/KEY: CDS
<222> LOCATION: (48)..(866)

<400> SEQUENCE: 36
tcggccgggg tcgcccttcg cacccgcacg tgtccgccgc cgccgcg atg ctt cct      56
                                                   Met Leu Pro
                                                     1 ctg ctg cgc cgc gtg ccc cgc gcg ctg ggc tcc gcc gtc gcc ggg ctc    104
Leu Leu Arg Arg Val Pro Arg Ala Leu Gly Ser Ala Val Ala Gly Leu
      5                  10                  15 cgc gcc gcg ccc gtc ccg cca acc cgg ccg ctg ctg cag ccc gcg ccc    152
Arg Ala Ala Pro Val Pro Pro Thr Arg Pro Leu Leu Gln Pro Ala Pro
 20                  25                  30                  35 cgg ccg tgc gtg cgg cct ttc ggg ctg ttc cga gtg cgc gcc ggc ctc    200
Arg Pro Cys Val Arg Pro Phe Gly Leu Phe Arg Val Arg Ala Gly Leu
                 40                  45                  50 ctg ctc ccc cgc ggg ccc tgc agc tgc ggc tgc ggc gcg ctg cac acc    248
Leu Leu Pro Arg Gly Pro Cys Ser Cys Gly Cys Gly Ala Leu His Thr
             55                  60                  65 cag gga gac aaa gct ttc gtc gag ttc ctg aac gat gag att aag gag    296
Gln Gly Asp Lys Ala Phe Val Glu Phe Leu Asn Asp Glu Ile Lys Glu
```

```
                70                  75                  80
gag aag aag atc cag aag cac ggg tcc ctc ccc aag atg tct ggg ggc      344
Glu Lys Lys Ile Gln Lys His Gly Ser Leu Pro Lys Met Ser Gly Gly
 85                  90                  95 tgg gag ctg gaa gtg aac ggg acc gaa gcc acg tta gtg cgg aaa gtg      392
Trp Glu Leu Glu Val Asn Gly Thr Glu Ala Thr Leu Val Arg Lys Val
100                 105                 110                 115 gct gga gaa aag atc acg gtg acg ttc aac att aac aac agc atc cca      440
Ala Gly Glu Lys Ile Thr Val Thr Phe Asn Ile Asn Asn Ser Ile Pro
                120                 125                 130 cca acg ttt gct ggg gag gag gag ccc tcc cag ggg cag aag gcg gaa      488
Pro Thr Phe Ala Gly Glu Glu Glu Pro Ser Gln Gly Gln Lys Ala Glu
            135                 140                 145 gaa cag gag ccc gaa ctg acg tcc act ccc aat ttc gtg gtg gag gtt      536
Glu Gln Glu Pro Glu Leu Thr Ser Thr Pro Asn Phe Val Val Glu Val
        150                 155                 160 ata aag aac ggc ggc aag aag gcc ctg gtt ctg gac tgt cac tat ccg      584
Ile Lys Asn Gly Gly Lys Lys Ala Leu Val Leu Asp Cys His Tyr Pro
    165                 170                 175 gaa gac gag gtg ggg cag gaa gag gag gac gag agt gac atc ttc gcc      632
Glu Asp Glu Val Gly Gln Glu Glu Glu Asp Glu Ser Asp Ile Phe Ala
180                 185                 190                 195 atc aga gaa gtg agc ttt cag tcg gtt ggc gag tct gag tgg aag gac      680
Ile Arg Glu Val Ser Phe Gln Ser Val Gly Glu Ser Glu Trp Lys Asp
                200                 205                 210 acg aac tac acg ctc aac acg gac tcc ctg gac tgg gcc tta tac gac      728
Thr Asn Tyr Thr Leu Asn Thr Asp Ser Leu Asp Trp Ala Leu Tyr Asp
            215                 220                 225 cac ctg atg gac ttc ctg gcc gac cgg ggg gtg gac aac act ttc gcc      776
His Leu Met Asp Phe Leu Ala Asp Arg Gly Val Asp Asn Thr Phe Ala
        230                 235                 240 gat gag ctg gtg gag ctc agc acg gcc ctg gag cac cgg gag tac atc      824
Asp Glu Leu Val Glu Leu Ser Thr Ala Leu Glu His Arg Glu Tyr Ile
    245                 250                 255 act ttt ctc gaa gac ctg aag ggg ttc gtc aag agc cag tag             866
Thr Phe Leu Glu Asp Leu Lys Gly Phe Val Lys Ser Gln
260                 265                 270 gccagaccag agcagacgtt gaacgcctcg cgttgacggc aggctttggc caggggacag    926
gcccactctg gagctagaca cgcgtgcttg gagacggttt tcgtgctgat atcatggaaa    986
ataattcaga tttaaattat ttctgctgcc ctcttattta ctgttcgttg actcctcctc   1046
taggctcagt cgctcctgga attttgtata acagaatgac ggacaataaa attggtttcg   1106
ctcccctga                                                           1115

<210> SEQ ID NO 37
<211> LENGTH: 272
<212> TYPE: PRT
<213> ORGANISM: Felis catus

<400> SEQUENCE: 37

Met Leu Pro Leu Leu Arg Arg Val Pro Arg Ala Leu Gly Ser Ala Val
1               5                   10                  15

Ala Gly Leu Arg Ala Ala Pro Val Pro Pro Thr Arg Pro Leu Leu Gln
            20                  25                  30

Pro Ala Pro Arg Pro Cys Val Arg Pro Phe Gly Leu Phe Arg Val Arg
        35                  40                  45

Ala Gly Leu Leu Leu Pro Arg Gly Pro Cys Ser Cys Gly Cys Gly Ala
    50                  55                  60
```

| | | | | | | | | | | | | |
|---|---|---|---|---|---|---|---|---|---|---|---|---|
| Leu | His | Thr | Gln | Gly | Asp | Lys | Ala | Phe | Val | Glu | Phe | Leu | Asn | Asp | Glu |
| 65 | | | | 70 | | | | | 75 | | | | | 80 | |

| Ile | Lys | Glu | Glu | Lys | Lys | Ile | Gln | Lys | His | Gly | Ser | Leu | Pro | Lys | Met |
|---|---|---|---|---|---|---|---|---|---|---|---|---|---|---|---|
| | | | 85 | | | | | 90 | | | | | 95 | | |

| Ser | Gly | Gly | Trp | Glu | Leu | Glu | Val | Asn | Gly | Thr | Glu | Ala | Thr | Leu | Val |
|---|---|---|---|---|---|---|---|---|---|---|---|---|---|---|---|
| | | | 100 | | | | | 105 | | | | | 110 | | |

| Arg | Lys | Val | Ala | Gly | Lys | Ile | Thr | Val | Thr | Phe | Asn | Ile | Asn | Asn |
|---|---|---|---|---|---|---|---|---|---|---|---|---|---|---|
| | | 115 | | | | | 120 | | | | | 125 | | |

| Ser | Ile | Pro | Pro | Thr | Phe | Ala | Gly | Glu | Glu | Pro | Ser | Gln | Gly | Gln |
|---|---|---|---|---|---|---|---|---|---|---|---|---|---|---|
| 130 | | | | | 135 | | | | | 140 | | | | |

| Lys | Ala | Glu | Glu | Gln | Glu | Pro | Glu | Leu | Thr | Ser | Thr | Pro | Asn | Phe | Val |
|---|---|---|---|---|---|---|---|---|---|---|---|---|---|---|---|
| 145 | | | | | 150 | | | | | 155 | | | | | 160 |

| Val | Glu | Val | Ile | Lys | Asn | Gly | Gly | Lys | Lys | Ala | Leu | Val | Leu | Asp | Cys |
|---|---|---|---|---|---|---|---|---|---|---|---|---|---|---|---|
| | | | | 165 | | | | | 170 | | | | | 175 | |

| His | Tyr | Pro | Glu | Asp | Glu | Val | Gly | Gln | Glu | Glu | Glu | Asp | Glu | Ser | Asp |
|---|---|---|---|---|---|---|---|---|---|---|---|---|---|---|---|
| | | | 180 | | | | | 185 | | | | | 190 | | |

| Ile | Phe | Ala | Ile | Arg | Glu | Val | Ser | Phe | Gln | Ser | Val | Gly | Glu | Ser | Glu |
|---|---|---|---|---|---|---|---|---|---|---|---|---|---|---|---|
| | | | 195 | | | | | 200 | | | | | 205 | | |

| Trp | Lys | Asp | Thr | Asn | Tyr | Thr | Leu | Asn | Thr | Asp | Ser | Leu | Asp | Trp | Ala |
|---|---|---|---|---|---|---|---|---|---|---|---|---|---|---|---|
| | 210 | | | | | 215 | | | | | 220 | | | | |

| Leu | Tyr | Asp | His | Leu | Met | Asp | Phe | Leu | Ala | Asp | Arg | Gly | Val | Asp | Asn |
|---|---|---|---|---|---|---|---|---|---|---|---|---|---|---|---|
| 225 | | | | | 230 | | | | | 235 | | | | | 240 |

| Thr | Phe | Ala | Asp | Glu | Leu | Val | Glu | Leu | Ser | Thr | Ala | Leu | Glu | His | Arg |
|---|---|---|---|---|---|---|---|---|---|---|---|---|---|---|---|
| | | | | 245 | | | | | 250 | | | | | 255 | |

| Glu | Tyr | Ile | Thr | Phe | Leu | Glu | Asp | Leu | Lys | Gly | Phe | Val | Lys | Ser | Gln |
|---|---|---|---|---|---|---|---|---|---|---|---|---|---|---|---|
| | | | 260 | | | | | 265 | | | | | 270 | | |

<210> SEQ ID NO 38
<211> LENGTH: 1168
<212> TYPE: DNA
<213> ORGANISM: Canis lupus familiaris
<220> FEATURE:
<221> NAME/KEY: CDS
<222> LOCATION: (110)..(928)

<400> SEQUENCE: 38

```
gcactgcaca ggcgcggaag cgctcccggg gaggagcggg acttccggcg gcgcgcgagc      60
cgggatccgg gcctggttcg tccttcgcgc ccgcacgtgc gttgccgcg atg cta ccg     118
                                                    Met Leu Pro
                                                      1 ctg ctg cgc cga gtg ccc cgc gcc ctg ggc tcg gcg gtc gcc ggg ctc      166
Leu Leu Arg Arg Val Pro Arg Ala Leu Gly Ser Ala Val Ala Gly Leu
  5                  10                  15 cgc gcc gcc ccc gcc ctg ccg cct ccg acc ctg ctg cgg ccg gcg ccc      214
Arg Ala Ala Pro Ala Leu Pro Pro Pro Thr Leu Leu Arg Pro Ala Pro
 20                  25                  30                  35 cgg ccg tgc gtg cgg ccc ttc ggg ctg ctc cct gtg cgc gcg ggc ctc      262
Arg Pro Cys Val Arg Pro Phe Gly Leu Leu Pro Val Arg Ala Gly Leu
                 40                  45                  50 ctg cgc tcc cgc ggg ccc tgc ggc tgc ggc tgc ggg ggc ctg cac acc      310
Leu Arg Ser Arg Gly Pro Cys Gly Cys Gly Cys Gly Gly Leu His Thr
             55                  60                  65 cag ggg gac aaa gct ttc gtc gag ttc ctg aat gat gag att aag gag      358
Gln Gly Asp Lys Ala Phe Val Glu Phe Leu Asn Asp Glu Ile Lys Glu
         70                  75                  80 gaa aag aaa ata cag aag cac aag tcc ctc ccc aaa atg tct ggg ggc      406
Glu Lys Lys Ile Gln Lys His Lys Ser Leu Pro Lys Met Ser Gly Gly
```

| | | | | | | | | | | | | | | | | |
|---|---|---|---|---|---|---|---|---|---|---|---|---|---|---|---|---|
| | | | 85 | | | | 90 | | | | | 95 | | | | |
| tgg | gag | cta | gac | atg | aat | ggg | acg | gag | gcc | aag | tta | gtg | cgg | aaa | gta | 454 |
| Trp | Glu | Leu | Asp | Met | Asn | Gly | Thr | Glu | Ala | Lys | Leu | Val | Arg | Lys | Val | |
| 100 | | | | | 105 | | | | | 110 | | | | | 115 | |
| gct | gga | gaa | aag | atc | acc | gtc | act | ttc | aac | atc | aac | aac | agc | atc | ccg | 502 |
| Ala | Gly | Glu | Lys | Ile | Thr | Val | Thr | Phe | Asn | Ile | Asn | Asn | Ser | Ile | Pro | |
| | | | | 120 | | | | | 125 | | | | | 130 | | |
| ccg | acg | ttt | gag | ggg | gag | gag | gag | ccg | gcc | cag | ggg | cag | aag | gcg | gat | 550 |
| Pro | Thr | Phe | Glu | Gly | Glu | Glu | Glu | Pro | Ala | Gln | Gly | Gln | Lys | Ala | Asp | |
| | | | 135 | | | | | 140 | | | | | 145 | | | |
| gag | cag | gag | cct | gaa | ctg | aca | tcc | act | ccc | aac | ttc | gtg | gtg | gaa | gtc | 598 |
| Glu | Gln | Glu | Pro | Glu | Leu | Thr | Ser | Thr | Pro | Asn | Phe | Val | Val | Glu | Val | |
| | | 150 | | | | | 155 | | | | | 160 | | | | |
| atc | aag | gat | ggt | ggc | aag | agg | gct | ctg | gta | ctg | gac | tgt | cac | tac | ccg | 646 |
| Ile | Lys | Asp | Gly | Gly | Lys | Arg | Ala | Leu | Val | Leu | Asp | Cys | His | Tyr | Pro | |
| 165 | | | | | 170 | | | | | 175 | | | | | | |
| gaa | gac | gag | gtg | ggg | caa | gag | gag | gag | gat | gag | agt | gac | atc | ttc | tcc | 694 |
| Glu | Asp | Glu | Val | Gly | Gln | Glu | Glu | Glu | Asp | Glu | Ser | Asp | Ile | Phe | Ser | |
| 180 | | | | | 185 | | | | | 190 | | | | | 195 | |
| atc | agg | gag | gtg | agc | ttc | cag | gcc | gtg | ggc | gag | tcg | gag | tgg | aag | gac | 742 |
| Ile | Arg | Glu | Val | Ser | Phe | Gln | Ala | Val | Gly | Glu | Ser | Glu | Trp | Lys | Asp | |
| | | | | 200 | | | | | 205 | | | | | 210 | | |
| acg | aat | tac | acg | ctc | aac | acc | gac | tcc | ctg | gac | tgg | gcc | ctg | tat | gac | 790 |
| Thr | Asn | Tyr | Thr | Leu | Asn | Thr | Asp | Ser | Leu | Asp | Trp | Ala | Leu | Tyr | Asp | |
| | | | 215 | | | | | 220 | | | | | 225 | | | |
| cac | ctg | atg | gac | ttc | ctg | gcc | gac | cgg | ggg | gtg | gat | aac | acc | ttt | gcg | 838 |
| His | Leu | Met | Asp | Phe | Leu | Ala | Asp | Arg | Gly | Val | Asp | Asn | Thr | Phe | Ala | |
| | | 230 | | | | | 235 | | | | | 240 | | | | |
| gat | gag | ctg | gtg | gag | ctc | agc | aca | gcc | ctg | gag | cac | caa | gaa | tac | atc | 886 |
| Asp | Glu | Leu | Val | Glu | Leu | Ser | Thr | Ala | Leu | Glu | His | Gln | Glu | Tyr | Ile | |
| 245 | | | | | 250 | | | | | 255 | | | | | | |
| act | ttc | ctt | gag | gat | ctc | aaa | ggt | ttt | gtc | aag | agc | cag | tag | | | 928 |
| Thr | Phe | Leu | Glu | Asp | Leu | Lys | Gly | Phe | Val | Lys | Ser | Gln | | | | |
| 260 | | | | 265 | | | | | 270 | | | | | | | | agcagcctga cgctgagcgg ggacagatgg cgggccctgg ccagggaagg agcccgcggt 988 gaagcaggac gtgtccctgg agatggcttt cttcctgata tcatgcagaa taattcagat 1048 ttaaattatt tcctttgccc tcttaactac tcttcattta ctgcttctgt acgactctcc 1108 cactcctaga ttttttgtata acacaataac ggacaataaa actggtttat cttctcccaa 1168

<210> SEQ ID NO 39
<211> LENGTH: 272
<212> TYPE: PRT
<213> ORGANISM: Canis lupus familiaris

<400> SEQUENCE: 39

Met Leu Pro Leu Leu Arg Arg Val Pro Arg Ala Leu Gly Ser Ala Val
1               5                   10                  15

Ala Gly Leu Arg Ala Ala Pro Ala Leu Pro Pro Thr Leu Leu Arg
            20                  25                  30

Pro Ala Pro Arg Pro Cys Val Arg Pro Phe Gly Leu Leu Pro Val Arg
            35                  40                  45

Ala Gly Leu Leu Arg Ser Arg Gly Pro Cys Gly Cys Gly Cys Gly Gly
        50                  55                  60

Leu His Thr Gln Gly Asp Lys Ala Phe Val Glu Phe Leu Asn Asp Glu
65                  70                  75                  80

Ile Lys Glu Glu Lys Lys Ile Gln Lys His Lys Ser Leu Pro Lys Met
                85                  90                  95

```
Ser Gly Gly Trp Glu Leu Asp Met Asn Gly Thr Glu Ala Lys Leu Val
            100                 105                 110

Arg Lys Val Ala Gly Glu Lys Ile Thr Val Thr Phe Asn Ile Asn Asn
            115                 120                 125

Ser Ile Pro Pro Thr Phe Glu Gly Glu Glu Pro Ala Gln Gly Gln
    130                 135                 140

Lys Ala Asp Glu Gln Glu Pro Glu Leu Thr Ser Thr Pro Asn Phe Val
145                 150                 155                 160

Val Glu Val Ile Lys Asp Gly Gly Lys Arg Ala Leu Val Leu Asp Cys
                165                 170                 175

His Tyr Pro Glu Asp Glu Val Gly Gln Glu Glu Asp Glu Ser Asp
            180                 185                 190

Ile Phe Ser Ile Arg Glu Val Ser Phe Gln Ala Val Gly Glu Ser Glu
            195                 200                 205

Trp Lys Asp Thr Asn Tyr Thr Leu Asn Thr Asp Ser Leu Asp Trp Ala
    210                 215                 220

Leu Tyr Asp His Leu Met Asp Phe Leu Ala Asp Arg Gly Val Asp Asn
225                 230                 235                 240

Thr Phe Ala Asp Glu Leu Val Glu Leu Ser Thr Ala Leu Glu His Gln
                245                 250                 255

Glu Tyr Ile Thr Phe Leu Glu Asp Leu Lys Gly Phe Val Lys Ser Gln
            260                 265                 270
```

<210> SEQ ID NO 40
<211> LENGTH: 1104
<212> TYPE: DNA
<213> ORGANISM: Equus caballus
<220> FEATURE:
<221> NAME/KEY: CDS
<222> LOCATION: (1)..(861)

<400> SEQUENCE: 40

```
atg tcc tgg cct gct cag ctc cag aaa gtt cgg tta ccg gat tcg agc      48
Met Ser Trp Pro Ala Gln Leu Gln Lys Val Arg Leu Pro Asp Ser Ser
1               5                   10                  15 ccc cgg gag gct gca ccg aag gcc ccc agc aga ggg cgc agt ccc gcc      96
Pro Arg Glu Ala Ala Pro Lys Ala Pro Ser Arg Gly Arg Ser Pro Ala
                20                  25                  30 cac ggt gcc cgc gct gag gca aag cgg cgg cgc gga agc gct tac tgc     144
His Gly Ala Arg Ala Glu Ala Lys Arg Arg Arg Gly Ser Ala Tyr Cys
            35                  40                  45 ggg gct cag cta tgt gct agc gtg agc gcg gaa ttg gag cgg cgt ccc     192
Gly Ala Gln Leu Cys Ala Ser Val Ser Ala Glu Leu Glu Arg Arg Pro
        50                  55                  60 gcc tcc tgc ggc tcg cgg gcc tgg tac tgc ggc tgc ggc gcg ctg cac     240
Ala Ser Cys Gly Ser Arg Ala Trp Tyr Cys Gly Cys Gly Ala Leu His
65                  70                  75                  80 acc gag ggg gac aaa gct ttt gtt gaa ttc ctg agt gat gaa att aag     288
Thr Glu Gly Asp Lys Ala Phe Val Glu Phe Leu Ser Asp Glu Ile Lys
                85                  90                  95 gag gaa aag aag ata cag aag cat aaa tcc ctc ccc aag atg tct gga     336
Glu Glu Lys Lys Ile Gln Lys His Lys Ser Leu Pro Lys Met Ser Gly
            100                 105                 110 gga tgg gag ctg gaa gtg aat ggg aca gaa gcc aaa tta gta cgg aaa     384
Gly Trp Glu Leu Glu Val Asn Gly Thr Glu Ala Lys Leu Val Arg Lys
        115                 120                 125 gtt gct gga gaa aag atc act gtc act ttc aat att aac aac agc atc     432
Val Ala Gly Glu Lys Ile Thr Val Thr Phe Asn Ile Asn Asn Ser Ile
```

-continued

```
                    130                 135                 140
cca cca aca ttt gct ggg gag gag gag ccc tcc caa ggg cag aag gtt        480
Pro Pro Thr Phe Ala Gly Glu Glu Glu Pro Ser Gln Gly Gln Lys Val
145                 150                 155                 160 gaa gaa cag gag cct gaa ttg aca tcc act ccc aat ttc gtg gtt gaa        528
Glu Glu Gln Glu Pro Glu Leu Thr Ser Thr Pro Asn Phe Val Val Glu
                165                 170                 175 gtt ata aag aat ggc ggc aag aag gcc ctt gtg ctg gac tgt cac tat        576
Val Ile Lys Asn Gly Gly Lys Lys Ala Leu Val Leu Asp Cys His Tyr
            180                 185                 190 cca gaa gat gag gtt gga caa gag gag gag gac gag agt gac att ttc        624
Pro Glu Asp Glu Val Gly Gln Glu Glu Glu Asp Glu Ser Asp Ile Phe
        195                 200                 205 tcc atc agg gaa gtg agc ttt cag tcc aca ggc gag tct gaa tgg aag        672
Ser Ile Arg Glu Val Ser Phe Gln Ser Thr Gly Glu Ser Glu Trp Lys
    210                 215                 220 gac aca aat tac aca ctc aac acg gac tcc ttg gac tgg gcc tta tat        720
Asp Thr Asn Tyr Thr Leu Asn Thr Asp Ser Leu Asp Trp Ala Leu Tyr
225                 230                 235                 240 gac cac cta atg gat ttc ctt gcg gac cga ggg gtg gac aac act ttt        768
Asp His Leu Met Asp Phe Leu Ala Asp Arg Gly Val Asp Asn Thr Phe
                245                 250                 255 gcg gat gaa ttg gtg gag ctc agc aca gcc ctg gag cac cag gag tac        816
Ala Asp Glu Leu Val Glu Leu Ser Thr Ala Leu Glu His Gln Glu Tyr
            260                 265                 270 att act ttc ctc gaa gac ctc aaa ggt ttt gtc aag agc cag tag            861
Ile Thr Phe Leu Glu Asp Leu Lys Gly Phe Val Lys Ser Gln
        275                 280                 285 agcaggcagg gtgctgaacg ccttacttat gtggtgggct tcaggcagtg aacagaccca      921
cgccggaggc agacacacgc gctttcaaat ggttttcatc ctaatatcat ggaaaattat      981
tcaaatctaa attatttctg ttgccctctt atttactatt cattcgtttc ttctcaacag     1041
atctattatt tctagatttt tgtataatgc agtgatggac agtaaaattg gtttatcctc     1101
ctc                                                                   1104

<210> SEQ ID NO 41
<211> LENGTH: 286
<212> TYPE: PRT
<213> ORGANISM: Equus caballus

<400> SEQUENCE: 41

Met Ser Trp Pro Ala Gln Leu Gln Lys Val Arg Leu Pro Asp Ser Ser
1               5                   10                  15

Pro Arg Glu Ala Ala Pro Lys Ala Pro Ser Arg Gly Arg Ser Pro Ala
                20                  25                  30

His Gly Ala Arg Ala Glu Ala Lys Arg Arg Gly Ser Ala Tyr Cys
            35                  40                  45

Gly Ala Gln Leu Cys Ala Ser Val Ser Ala Glu Leu Glu Arg Arg Pro
        50                  55                  60

Ala Ser Cys Gly Ser Arg Ala Trp Tyr Cys Gly Cys Gly Ala Leu His
65                  70                  75                  80

Thr Glu Gly Asp Lys Ala Phe Val Glu Phe Leu Ser Asp Glu Ile Lys
                85                  90                  95

Glu Glu Lys Lys Ile Gln Lys His Lys Ser Leu Pro Lys Met Ser Gly
            100                 105                 110

Gly Trp Glu Leu Glu Val Asn Gly Thr Glu Ala Lys Leu Val Arg Lys
        115                 120                 125
```

```
Val Ala Gly Glu Lys Ile Thr Val Thr Phe Asn Ile Asn Asn Ser Ile
            130                 135                 140

Pro Pro Thr Phe Ala Gly Glu Glu Pro Ser Gln Gly Gln Lys Val
145                 150                 155                 160

Glu Glu Gln Glu Pro Glu Leu Thr Ser Thr Pro Asn Phe Val Val Glu
                    165                 170                 175

Val Ile Lys Asn Gly Lys Lys Ala Leu Val Leu Asp Cys His Tyr
            180                 185                 190

Pro Glu Asp Glu Val Gly Gln Glu Glu Asp Glu Ser Asp Ile Phe
            195                 200                 205

Ser Ile Arg Glu Val Ser Phe Gln Ser Thr Gly Glu Ser Glu Trp Lys
            210                 215                 220

Asp Thr Asn Tyr Thr Leu Asn Thr Asp Ser Leu Asp Trp Ala Leu Tyr
225                 230                 235                 240

Asp His Leu Met Asp Phe Leu Ala Asp Arg Gly Val Asp Asn Thr Phe
                    245                 250                 255

Ala Asp Glu Leu Val Glu Leu Ser Thr Ala Leu Glu His Gln Glu Tyr
                260                 265                 270

Ile Thr Phe Leu Glu Asp Leu Lys Gly Phe Val Lys Ser Gln
                275                 280                 285

<210> SEQ ID NO 42
<211> LENGTH: 14
<212> TYPE: PRT
<213> ORGANISM: Artificial Sequence
<220> FEATURE:
<223> OTHER INFORMATION: Artificially synthesized peptide
<220> FEATURE:
<221> NAME/KEY: MISC_FEATURE
<222> LOCATION: (1)..(14)
<223> OTHER INFORMATION: In some embodiments, one or more up to and
      including all 14 aminos acids are D-amino acids

<400> SEQUENCE: 42

Lys Leu Ala Lys Leu Ala Lys Lys Leu Ala Lys Leu Ala Lys
1               5                   10

<210> SEQ ID NO 43
<211> LENGTH: 14
<212> TYPE: PRT
<213> ORGANISM: Artificial Sequence
<220> FEATURE:
<223> OTHER INFORMATION: Artificially synthesized peptide

<400> SEQUENCE: 43

Lys Leu Ala Lys Lys Leu Ala Lys Leu Ala Lys Lys Leu Ala
1               5                   10

<210> SEQ ID NO 44
<211> LENGTH: 14
<212> TYPE: PRT
<213> ORGANISM: Artificial Sequence
<220> FEATURE:
<223> OTHER INFORMATION: Artificially synthesized peptide

<400> SEQUENCE: 44

Lys Ala Ala Lys Lys Ala Ala Lys Ala Lys Lys Ala Ala
1               5                   10

<210> SEQ ID NO 45
<211> LENGTH: 21
<212> TYPE: PRT
```

```
<213> ORGANISM: Artificial Sequence
<220> FEATURE:
<223> OTHER INFORMATION: Artificially synthesized peptide

<400> SEQUENCE: 45

Lys Leu Gly Lys Lys Leu Gly Lys Leu Gly Lys Lys Leu Gly Lys Leu
1               5                   10                  15

Gly Lys Lys Leu Gly
            20

<210> SEQ ID NO 46
<211> LENGTH: 9
<212> TYPE: PRT
<213> ORGANISM: Artificial Sequence
<220> FEATURE:
<223> OTHER INFORMATION: Artificially synthesized peptide

<400> SEQUENCE: 46

Cys Asn Ser Arg Leu His Leu Arg Cys
1               5

<210> SEQ ID NO 47
<211> LENGTH: 9
<212> TYPE: PRT
<213> ORGANISM: Artificial Sequence
<220> FEATURE:
<223> OTHER INFORMATION: Artificially synthesized peptide

<400> SEQUENCE: 47

Cys Glu Asn Trp Trp Gly Asp Val Cys
1               5

<210> SEQ ID NO 48
<211> LENGTH: 21
<212> TYPE: PRT
<213> ORGANISM: Artificial Sequence
<220> FEATURE:
<223> OTHER INFORMATION: Artificially synthesized peptide

<400> SEQUENCE: 48

Trp Arg Cys Val Leu Arg Glu Gly Pro Ala Gly Gly Cys Ala Trp Phe
1               5                   10                  15

Asn Arg His Arg Leu
            20

<210> SEQ ID NO 49
<211> LENGTH: 9
<212> TYPE: PRT
<213> ORGANISM: Artificial Sequence
<220> FEATURE:
<223> OTHER INFORMATION: Artificially synthesized peptide

<400> SEQUENCE: 49

Cys Leu Ser Ser Arg Leu Asp Ala Cys
1               5

<210> SEQ ID NO 50
<211> LENGTH: 8
<212> TYPE: PRT
<213> ORGANISM: Artificial Sequence
<220> FEATURE:
<223> OTHER INFORMATION: Artificially synthesized peptide

<400> SEQUENCE: 50

Cys Val Leu Arg Gly Gly Arg Cys
1               5
```

```
<210> SEQ ID NO 51
<211> LENGTH: 9
<212> TYPE: PRT
<213> ORGANISM: Artificial Sequence
<220> FEATURE:
<223> OTHER INFORMATION: Artificially synthesized peptide

<400> SEQUENCE: 51

Cys Asn Ser Arg Leu Gln Leu Arg Cys
1               5

<210> SEQ ID NO 52
<211> LENGTH: 7
<212> TYPE: PRT
<213> ORGANISM: Artificial Sequence
<220> FEATURE:
<223> OTHER INFORMATION: Artificially synthesized peptide

<400> SEQUENCE: 52

Cys Gly Val Arg Leu Gly Cys
1               5

<210> SEQ ID NO 53
<211> LENGTH: 8
<212> TYPE: PRT
<213> ORGANISM: Artificial Sequence
<220> FEATURE:
<223> OTHER INFORMATION: Artificially synthesized peptide

<400> SEQUENCE: 53

Cys Lys Asp Trp Gly Arg Ile Cys
1               5

<210> SEQ ID NO 54
<211> LENGTH: 8
<212> TYPE: PRT
<213> ORGANISM: Artificial Sequence
<220> FEATURE:
<223> OTHER INFORMATION: Artificially synthesized peptide

<400> SEQUENCE: 54

Cys Leu Asp Trp Gly Arg Ile Cys
1               5

<210> SEQ ID NO 55
<211> LENGTH: 8
<212> TYPE: PRT
<213> ORGANISM: Artificial Sequence
<220> FEATURE:
<223> OTHER INFORMATION: Artificially synthesized peptide

<400> SEQUENCE: 55

Cys Thr Arg Ile Thr Glu Ser Cys
1               5

<210> SEQ ID NO 56
<211> LENGTH: 7
<212> TYPE: PRT
<213> ORGANISM: Artificial Sequence
<220> FEATURE:
<223> OTHER INFORMATION: Artificially synthesized peptide

<400> SEQUENCE: 56

Cys Glu Thr Leu Pro Ala Cys
1               5
```

<210> SEQ ID NO 57
<211> LENGTH: 8
<212> TYPE: PRT
<213> ORGANISM: Artificial Sequence
<220> FEATURE:
<223> OTHER INFORMATION: Artificially synthesized peptide

<400> SEQUENCE: 57

Cys Arg Thr Gly Thr Leu Phe Cys
1               5

<210> SEQ ID NO 58
<211> LENGTH: 8
<212> TYPE: PRT
<213> ORGANISM: Artificial Sequence
<220> FEATURE:
<223> OTHER INFORMATION: Artificially synthesized peptide

<400> SEQUENCE: 58

Cys Gly Arg Ser Leu Asp Ala Cys
1               5

<210> SEQ ID NO 59
<211> LENGTH: 9
<212> TYPE: PRT
<213> ORGANISM: Artificial Sequence
<220> FEATURE:
<223> OTHER INFORMATION: Artificially synthesized peptide

<400> SEQUENCE: 59

Cys Arg His Trp Phe Asp Val Val Cys
1               5

<210> SEQ ID NO 60
<211> LENGTH: 8
<212> TYPE: PRT
<213> ORGANISM: Artificial Sequence
<220> FEATURE:
<223> OTHER INFORMATION: Artificially synthesized peptide

<400> SEQUENCE: 60

Cys Ala Asn Ala Gln Ser His Cys
1               5

<210> SEQ ID NO 61
<211> LENGTH: 8
<212> TYPE: PRT
<213> ORGANISM: Artificial Sequence
<220> FEATURE:
<223> OTHER INFORMATION: Artificially synthesized peptide

<400> SEQUENCE: 61

Cys Gly Asn Pro Ser Tyr Arg Cys
1               5

<210> SEQ ID NO 62
<211> LENGTH: 20
<212> TYPE: PRT
<213> ORGANISM: Artificial Sequence
<220> FEATURE:
<223> OTHER INFORMATION: Artificially synthesized peptide

<400> SEQUENCE: 62

Tyr Pro Cys Gly Gly Glu Ala Val Ala Gly Val Ser Ser Val Arg Thr
1               5                   10                  15

Met Cys Ser Glu

20

<210> SEQ ID NO 63
<211> LENGTH: 20
<212> TYPE: PRT
<213> ORGANISM: Artificial Sequence
<220> FEATURE:
<223> OTHER INFORMATION: Artificially synthesized peptide

<400> SEQUENCE: 63

Leu Asn Cys Asp Tyr Gln Gly Thr Asn Pro Ala Thr Ser Val Ser Val
1               5                   10                  15

Pro Cys Thr Val
            20

<210> SEQ ID NO 64
<211> LENGTH: 7
<212> TYPE: PRT
<213> ORGANISM: Artificial Sequence
<220> FEATURE:
<223> OTHER INFORMATION: Artificially synthesized peptide

<400> SEQUENCE: 64

Cys Leu Pro Val Ala Ser Cys
1               5

<210> SEQ ID NO 65
<211> LENGTH: 7
<212> TYPE: PRT
<213> ORGANISM: Artificial Sequence
<220> FEATURE:
<223> OTHER INFORMATION: Artificially synthesized peptide

<400> SEQUENCE: 65

Cys Gly Ala Arg Glu Met Cys
1               5

<210> SEQ ID NO 66
<211> LENGTH: 8
<212> TYPE: PRT
<213> ORGANISM: Artificial Sequence
<220> FEATURE:
<223> OTHER INFORMATION: Artificially synthesized peptide

<400> SEQUENCE: 66

Cys Lys Gly Arg Ser Ser Ala Cys
1               5

<210> SEQ ID NO 67
<211> LENGTH: 8
<212> TYPE: PRT
<213> ORGANISM: Artificial Sequence
<220> FEATURE:
<223> OTHER INFORMATION: Artificially synthesized peptide

<400> SEQUENCE: 67

Cys Trp Ala Arg Ala Gln Gly Cys
1               5

<210> SEQ ID NO 68
<211> LENGTH: 8
<212> TYPE: PRT
<213> ORGANISM: Artificial Sequence
<220> FEATURE:
<223> OTHER INFORMATION: Artificially synthesized peptide

<400> SEQUENCE: 68

```
Cys Leu Gly Arg Ser Ser Val Cys
1               5

<210> SEQ ID NO 69
<211> LENGTH: 8
<212> TYPE: PRT
<213> ORGANISM: Artificial Sequence
<220> FEATURE:
<223> OTHER INFORMATION: Artificially synthesized peptide

<400> SEQUENCE: 69

Cys Thr Ser Pro Gly Gly Ser Cys
1               5

<210> SEQ ID NO 70
<211> LENGTH: 8
<212> TYPE: PRT
<213> ORGANISM: Artificial Sequence
<220> FEATURE:
<223> OTHER INFORMATION: Artificially synthesized peptide

<400> SEQUENCE: 70

Cys Met Gly Arg Trp Arg Leu Cys
1               5

<210> SEQ ID NO 71
<211> LENGTH: 8
<212> TYPE: PRT
<213> ORGANISM: Artificial Sequence
<220> FEATURE:
<223> OTHER INFORMATION: Artificially synthesized peptide

<400> SEQUENCE: 71

Cys Val Gly Glu Cys Gly Gly Cys
1               5

<210> SEQ ID NO 72
<211> LENGTH: 7
<212> TYPE: PRT
<213> ORGANISM: Artificial Sequence
<220> FEATURE:
<223> OTHER INFORMATION: Artificially synthesized peptide

<400> SEQUENCE: 72

Cys Val Ala Trp Leu Asn Cys
1               5

<210> SEQ ID NO 73
<211> LENGTH: 7
<212> TYPE: PRT
<213> ORGANISM: Artificial Sequence
<220> FEATURE:
<223> OTHER INFORMATION: Artificially synthesized peptide

<400> SEQUENCE: 73

Cys Arg Arg Phe Gln Asp Cys
1               5

<210> SEQ ID NO 74
<211> LENGTH: 7
<212> TYPE: PRT
<213> ORGANISM: Artificial Sequence
<220> FEATURE:
<223> OTHER INFORMATION: Artificially synthesized peptide

<400> SEQUENCE: 74
```

Cys Leu Met Gly Val His Cys
1               5

<210> SEQ ID NO 75
<211> LENGTH: 8
<212> TYPE: PRT
<213> ORGANISM: Artificial Sequence
<220> FEATURE:
<223> OTHER INFORMATION: Artificially synthesized peptide

<400> SEQUENCE: 75

Cys Lys Leu Leu Ser Gly Val Cys
1               5

<210> SEQ ID NO 76
<211> LENGTH: 8
<212> TYPE: PRT
<213> ORGANISM: Artificial Sequence
<220> FEATURE:
<223> OTHER INFORMATION: Artificially synthesized peptide

<400> SEQUENCE: 76

Cys Phe Val Gly His Asp Leu Cys
1               5

<210> SEQ ID NO 77
<211> LENGTH: 7
<212> TYPE: PRT
<213> ORGANISM: Artificial Sequence
<220> FEATURE:
<223> OTHER INFORMATION: Artificially synthesized peptide

<400> SEQUENCE: 77

Cys Arg Cys Leu Asn Val Cys
1               5

<210> SEQ ID NO 78
<211> LENGTH: 7
<212> TYPE: PRT
<213> ORGANISM: Artificial Sequence
<220> FEATURE:
<223> OTHER INFORMATION: Artificially synthesized peptide

<400> SEQUENCE: 78

Cys Lys Leu Met Gly Glu Cys
1               5

<210> SEQ ID NO 79
<211> LENGTH: 9
<212> TYPE: PRT
<213> ORGANISM: Artificial Sequence
<220> FEATURE:
<223> OTHER INFORMATION: Artificially synthesized peptide

<400> SEQUENCE: 79

Cys Ala Arg Ser Lys Asn Lys Asp Cys
1               5

<210> SEQ ID NO 80
<211> LENGTH: 6
<212> TYPE: PRT
<213> ORGANISM: Artificial Sequence
<220> FEATURE:
<223> OTHER INFORMATION: Artificially synthesized peptide

<400> SEQUENCE: 80

Cys Arg Lys Asp Lys Cys

```
1               5
```

<210> SEQ ID NO 81
<211> LENGTH: 13
<212> TYPE: PRT
<213> ORGANISM: Artificial Sequence
<220> FEATURE:
<223> OTHER INFORMATION: Artificially synthesized peptide

<400> SEQUENCE: 81

```
Cys Val Ala Leu Cys Arg Glu Ala Cys Gly Glu Gly Cys
1               5                   10
```

<210> SEQ ID NO 82
<211> LENGTH: 13
<212> TYPE: PRT
<213> ORGANISM: Artificial Sequence
<220> FEATURE:
<223> OTHER INFORMATION: Artificially synthesized peptide

<400> SEQUENCE: 82

```
Cys Ser Ser Gly Cys Ser Lys Asn Cys Leu Glu Met Cys
1               5                   10
```

<210> SEQ ID NO 83
<211> LENGTH: 8
<212> TYPE: PRT
<213> ORGANISM: Artificial Sequence
<220> FEATURE:
<223> OTHER INFORMATION: Artificially synthesized peptide

<400> SEQUENCE: 83

```
Cys Ile Gly Glu Val Glu Val Cys
1               5
```

<210> SEQ ID NO 84
<211> LENGTH: 9
<212> TYPE: PRT
<213> ORGANISM: Artificial Sequence
<220> FEATURE:
<223> OTHER INFORMATION: Artificially synthesized peptide

<400> SEQUENCE: 84

```
Cys Lys Trp Ser Arg Leu His Ser Cys
1               5
```

<210> SEQ ID NO 85
<211> LENGTH: 9
<212> TYPE: PRT
<213> ORGANISM: Artificial Sequence
<220> FEATURE:
<223> OTHER INFORMATION: Artificially synthesized peptide

<400> SEQUENCE: 85

```
Cys Trp Arg Gly Asp Arg Lys Ile Cys
1               5
```

<210> SEQ ID NO 86
<211> LENGTH: 9
<212> TYPE: PRT
<213> ORGANISM: Artificial Sequence
<220> FEATURE:
<223> OTHER INFORMATION: Artificially synthesized peptide

<400> SEQUENCE: 86

```
Cys Glu Arg Val Val Gly Ser Ser Cys
1               5
```

```
<210> SEQ ID NO 87
<211> LENGTH: 9
<212> TYPE: PRT
<213> ORGANISM: Artificial Sequence
<220> FEATURE:
<223> OTHER INFORMATION: Artificially synthesized peptide

<400> SEQUENCE: 87

Cys Leu Ala Lys Glu Asn Val Val Cys
1               5

<210> SEQ ID NO 88
<211> LENGTH: 13
<212> TYPE: PRT
<213> ORGANISM: Artificial Sequence
<220> FEATURE:
<223> OTHER INFORMATION: Artificially synthesized peptide

<400> SEQUENCE: 88

Cys Gly Phe Glu Cys Val Arg Gln Cys Pro Glu Arg Cys
1               5                   10

<210> SEQ ID NO 89
<211> LENGTH: 8
<212> TYPE: PRT
<213> ORGANISM: Artificial Sequence
<220> FEATURE:
<223> OTHER INFORMATION: Artificially synthesized peptide

<400> SEQUENCE: 89

Cys Gly Phe Glu Leu Glu Thr Cys
1               5

<210> SEQ ID NO 90
<211> LENGTH: 8
<212> TYPE: PRT
<213> ORGANISM: Artificial Sequence
<220> FEATURE:
<223> OTHER INFORMATION: Artificially synthesized peptide

<400> SEQUENCE: 90

Cys Thr Leu Arg Asp Arg Asn Cys
1               5

<210> SEQ ID NO 91
<211> LENGTH: 8
<212> TYPE: PRT
<213> ORGANISM: Artificial Sequence
<220> FEATURE:
<223> OTHER INFORMATION: Artificially synthesized peptide

<400> SEQUENCE: 91

Cys Gly Lys Arg Tyr Arg Asn Cys
1               5

<210> SEQ ID NO 92
<211> LENGTH: 8
<212> TYPE: PRT
<213> ORGANISM: Artificial Sequence
<220> FEATURE:
<223> OTHER INFORMATION: Artificially synthesized peptide

<400> SEQUENCE: 92

Cys Leu Arg Pro Tyr Leu Asn Cys
1               5
```

<210> SEQ ID NO 93
<211> LENGTH: 12
<212> TYPE: PRT
<213> ORGANISM: Artificial Sequence
<220> FEATURE:
<223> OTHER INFORMATION: Artificially synthesized peptide

<400> SEQUENCE: 93

Cys Thr Val Asn Glu Ala Tyr Lys Thr Arg Met Cys
1               5                   10

<210> SEQ ID NO 94
<211> LENGTH: 12
<212> TYPE: PRT
<213> ORGANISM: Artificial Sequence
<220> FEATURE:
<223> OTHER INFORMATION: Artificially synthesized peptide

<400> SEQUENCE: 94

Cys Arg Leu Arg Ser Tyr Gly Thr Leu Ser Leu Cys
1               5                   10

<210> SEQ ID NO 95
<211> LENGTH: 12
<212> TYPE: PRT
<213> ORGANISM: Artificial Sequence
<220> FEATURE:
<223> OTHER INFORMATION: Artificially synthesized peptide

<400> SEQUENCE: 95

Cys Arg Pro Trp His Asn Gln Ala His Thr Glu Cys
1               5                   10

<210> SEQ ID NO 96
<211> LENGTH: 9
<212> TYPE: PRT
<213> ORGANISM: Artificial Sequence
<220> FEATURE:
<223> OTHER INFORMATION: Artificially synthesized peptide

<400> SEQUENCE: 96

Ser Trp Cys Glu Pro Gly Trp Cys Arg
1               5

<210> SEQ ID NO 97
<211> LENGTH: 7
<212> TYPE: PRT
<213> ORGANISM: Artificial Sequence
<220> FEATURE:
<223> OTHER INFORMATION: Artificially synthesized peptide

<400> SEQUENCE: 97

Cys Lys Ala Ala Lys Asn Lys
1               5

<210> SEQ ID NO 98
<211> LENGTH: 7
<212> TYPE: PRT
<213> ORGANISM: Artificial Sequence
<220> FEATURE:
<223> OTHER INFORMATION: Artificially synthesized peptide

<400> SEQUENCE: 98

Cys Lys Gly Ala Lys Ala Arg
1               5

-continued

```
<210> SEQ ID NO 99
<211> LENGTH: 8
<212> TYPE: PRT
<213> ORGANISM: Artificial Sequence
<220> FEATURE:
<223> OTHER INFORMATION: Artificially synthesized peptide

<400> SEQUENCE: 99

Val Gly Val Gly Glu Trp Ser Val
1               5

<210> SEQ ID NO 100
<211> LENGTH: 7
<212> TYPE: PRT
<213> ORGANISM: Artificial Sequence
<220> FEATURE:
<223> OTHER INFORMATION: Artificially synthesized peptide

<400> SEQUENCE: 100

Tyr Ser Gly Lys Trp Gly Trp
1               5

<210> SEQ ID NO 101
<211> LENGTH: 7
<212> TYPE: PRT
<213> ORGANISM: Artificial Sequence
<220> FEATURE:
<223> OTHER INFORMATION: Artificially synthesized peptide

<400> SEQUENCE: 101

Gly Leu Ser Gly Gly Arg Ser
1               5

<210> SEQ ID NO 102
<211> LENGTH: 7
<212> TYPE: PRT
<213> ORGANISM: Artificial Sequence
<220> FEATURE:
<223> OTHER INFORMATION: Artificially synthesized peptide

<400> SEQUENCE: 102

Leu Met Leu Pro Arg Ala Asp
1               5

<210> SEQ ID NO 103
<211> LENGTH: 7
<212> TYPE: PRT
<213> ORGANISM: Artificial Sequence
<220> FEATURE:
<223> OTHER INFORMATION: Artificially synthesized peptide

<400> SEQUENCE: 103

Leu Pro Arg Tyr Leu Leu Ser
1               5

<210> SEQ ID NO 104
<211> LENGTH: 9
<212> TYPE: PRT
<213> ORGANISM: Artificial Sequence
<220> FEATURE:
<223> OTHER INFORMATION: Artificially synthesized peptide

<400> SEQUENCE: 104

Cys Ser Cys Phe Arg Asp Val Cys Cys
1               5

<210> SEQ ID NO 105
```

```
<211> LENGTH: 9
<212> TYPE: PRT
<213> ORGANISM: Artificial Sequence
<220> FEATURE:
<223> OTHER INFORMATION: Artificially synthesized peptide

<400> SEQUENCE: 105

Cys Arg Asp Val Val Ser Val Ile Cys
1               5

<210> SEQ ID NO 106
<211> LENGTH: 7
<212> TYPE: PRT
<213> ORGANISM: Artificial Sequence
<220> FEATURE:
<223> OTHER INFORMATION: Artificially synthesized peptide

<400> SEQUENCE: 106

Tyr Ser Gly Lys Trp Gly Lys
1               5

<210> SEQ ID NO 107
<211> LENGTH: 8
<212> TYPE: PRT
<213> ORGANISM: Artificial Sequence
<220> FEATURE:
<223> OTHER INFORMATION: Artificially synthesized peptide

<400> SEQUENCE: 107

Gly Ile Ser Ala Leu Val Leu Ser
1               5

<210> SEQ ID NO 108
<211> LENGTH: 7
<212> TYPE: PRT
<213> ORGANISM: Artificial Sequence
<220> FEATURE:
<223> OTHER INFORMATION: Artificially synthesized peptide

<400> SEQUENCE: 108

Ser Arg Arg Gln Pro Leu Ser
1               5

<210> SEQ ID NO 109
<211> LENGTH: 7
<212> TYPE: PRT
<213> ORGANISM: Artificial Sequence
<220> FEATURE:
<223> OTHER INFORMATION: Artificially synthesized peptide

<400> SEQUENCE: 109

Met Ser Pro Gln Leu Ala Thr
1               5

<210> SEQ ID NO 110
<211> LENGTH: 7
<212> TYPE: PRT
<213> ORGANISM: Artificial Sequence
<220> FEATURE:
<223> OTHER INFORMATION: Artificially synthesized peptide

<400> SEQUENCE: 110

Met Arg Arg Asp Glu Gln Arg
1               5

<210> SEQ ID NO 111
<211> LENGTH: 7
```

```
<212> TYPE: PRT
<213> ORGANISM: Artificial Sequence
<220> FEATURE:
<223> OTHER INFORMATION: Artificially synthesized peptide

<400> SEQUENCE: 111

Gln Val Arg Arg Val Pro Glu
1               5

<210> SEQ ID NO 112
<211> LENGTH: 7
<212> TYPE: PRT
<213> ORGANISM: Artificial Sequence
<220> FEATURE:
<223> OTHER INFORMATION: Artificially synthesized peptide

<400> SEQUENCE: 112

Val Arg Arg Gly Ser Pro Gln
1               5

<210> SEQ ID NO 113
<211> LENGTH: 7
<212> TYPE: PRT
<213> ORGANISM: Artificial Sequence
<220> FEATURE:
<223> OTHER INFORMATION: Artificially synthesized peptide

<400> SEQUENCE: 113

Gly Gly Arg Gly Ser Trp Glu
1               5

<210> SEQ ID NO 114
<211> LENGTH: 7
<212> TYPE: PRT
<213> ORGANISM: Artificial Sequence
<220> FEATURE:
<223> OTHER INFORMATION: Artificially synthesized peptide

<400> SEQUENCE: 114

Phe Arg Val Arg Gly Ser Pro
1               5

<210> SEQ ID NO 115
<211> LENGTH: 7
<212> TYPE: PRT
<213> ORGANISM: Artificial Sequence
<220> FEATURE:
<223> OTHER INFORMATION: Artificially synthesized peptide

<400> SEQUENCE: 115

Arg Val Arg Gly Pro Glu Arg
1               5

<210> SEQ ID NO 116
<211> LENGTH: 7
<212> TYPE: PRT
<213> ORGANISM: Artificial Sequence
<220> FEATURE:
<223> OTHER INFORMATION: Artificially synthesized peptide

<400> SEQUENCE: 116

Val Lys Ser Val Cys Arg Thr
1               5

<210> SEQ ID NO 117
<211> LENGTH: 7
<212> TYPE: PRT
```

<213> ORGANISM: Artificial Sequence
<220> FEATURE:
<223> OTHER INFORMATION: Artificially synthesized peptide

<400> SEQUENCE: 117

Trp Arg Gln Asn Met Pro Leu
1               5

<210> SEQ ID NO 118
<211> LENGTH: 7
<212> TYPE: PRT
<213> ORGANISM: Artificial Sequence
<220> FEATURE:
<223> OTHER INFORMATION: Artificially synthesized peptide

<400> SEQUENCE: 118

Ser Arg Arg Phe Val Gly Gly
1               5

<210> SEQ ID NO 119
<211> LENGTH: 7
<212> TYPE: PRT
<213> ORGANISM: Artificial Sequence
<220> FEATURE:
<223> OTHER INFORMATION: Artificially synthesized peptide

<400> SEQUENCE: 119

Ala Leu Glu Arg Arg Ser Leu
1               5

<210> SEQ ID NO 120
<211> LENGTH: 7
<212> TYPE: PRT
<213> ORGANISM: Artificial Sequence
<220> FEATURE:
<223> OTHER INFORMATION: Artificially synthesized peptide

<400> SEQUENCE: 120

Ala Arg Arg Gly Trp Thr Leu
1               5

<210> SEQ ID NO 121
<211> LENGTH: 7
<212> TYPE: PRT
<213> ORGANISM: Artificial Sequence
<220> FEATURE:
<223> OTHER INFORMATION: Artificially synthesized peptide

<400> SEQUENCE: 121

Ser Met Ser Ile Ala Arg Leu
1               5

<210> SEQ ID NO 122
<211> LENGTH: 7
<212> TYPE: PRT
<213> ORGANISM: Artificial Sequence
<220> FEATURE:
<223> OTHER INFORMATION: Artificially synthesized peptide

<400> SEQUENCE: 122

Val Ser Phe Leu Glu Tyr Arg
1               5

<210> SEQ ID NO 123
<211> LENGTH: 7
<212> TYPE: PRT
<213> ORGANISM: Artificial Sequence

```
<220> FEATURE:
<223> OTHER INFORMATION: Artificially synthesized peptide

<400> SEQUENCE: 123

Arg Gly Arg Trp Leu Ala Leu
1               5

<210> SEQ ID NO 124
<211> LENGTH: 7
<212> TYPE: PRT
<213> ORGANISM: Artificial Sequence
<220> FEATURE:
<223> OTHER INFORMATION: Artificially synthesized peptide

<400> SEQUENCE: 124

Glu Val Arg Ser Arg Leu Ser
1               5

<210> SEQ ID NO 125
<211> LENGTH: 7
<212> TYPE: PRT
<213> ORGANISM: Artificial Sequence
<220> FEATURE:
<223> OTHER INFORMATION: Artificially synthesized peptide

<400> SEQUENCE: 125

Val Arg Ala Arg Leu Met Ser
1               5

<210> SEQ ID NO 126
<211> LENGTH: 7
<212> TYPE: PRT
<213> ORGANISM: Artificial Sequence
<220> FEATURE:
<223> OTHER INFORMATION: Artificially synthesized peptide

<400> SEQUENCE: 126

Arg Val Gly Leu Val Ala Arg
1               5

<210> SEQ ID NO 127
<211> LENGTH: 7
<212> TYPE: PRT
<213> ORGANISM: Artificial Sequence
<220> FEATURE:
<223> OTHER INFORMATION: Artificially synthesized peptide

<400> SEQUENCE: 127

Arg Val Arg Leu Val Asn Leu
1               5

<210> SEQ ID NO 128
<211> LENGTH: 5
<212> TYPE: PRT
<213> ORGANISM: Artificial Sequence
<220> FEATURE:
<223> OTHER INFORMATION: Artificially synthesized peptide

<400> SEQUENCE: 128

Cys Arg Glu Lys Ala
1               5

<210> SEQ ID NO 129
<211> LENGTH: 10
<212> TYPE: PRT
<213> ORGANISM: Artificial Sequence
<220> FEATURE:
```

<223> OTHER INFORMATION: Artificially synthesized peptide

<400> SEQUENCE: 129

Cys Gly Leu Ile Ile Gln Lys Asn Glu Cys
1               5                   10

<210> SEQ ID NO 130
<211> LENGTH: 10
<212> TYPE: PRT
<213> ORGANISM: Artificial Sequence
<220> FEATURE:
<223> OTHER INFORMATION: Artificially synthesized peptide

<400> SEQUENCE: 130

Cys Asn Ala Gly Glu Ser Ser Lys Asn Cys
1               5                   10

<210> SEQ ID NO 131
<211> LENGTH: 5
<212> TYPE: PRT
<213> ORGANISM: Artificial Sequence
<220> FEATURE:
<223> OTHER INFORMATION: Artificially synthesized peptide

<400> SEQUENCE: 131

Cys Arg Pro Pro Arg
1               5

<210> SEQ ID NO 132
<211> LENGTH: 9
<212> TYPE: PRT
<213> ORGANISM: Artificial Sequence
<220> FEATURE:
<223> OTHER INFORMATION: Artificially synthesized peptide

<400> SEQUENCE: 132

Cys Gly Arg Lys Ser Lys Thr Val Cys
1               5

<210> SEQ ID NO 133
<211> LENGTH: 6
<212> TYPE: PRT
<213> ORGANISM: Artificial Sequence
<220> FEATURE:
<223> OTHER INFORMATION: Artificially synthesized peptide

<400> SEQUENCE: 133

Cys Ala Arg Pro Ala Arg
1               5

<210> SEQ ID NO 134
<211> LENGTH: 6
<212> TYPE: PRT
<213> ORGANISM: Artificial Sequence
<220> FEATURE:
<223> OTHER INFORMATION: Artificially synthesized peptide

<400> SEQUENCE: 134

Cys Pro Lys Arg Pro Arg
1               5

<210> SEQ ID NO 135
<211> LENGTH: 6
<212> TYPE: PRT
<213> ORGANISM: Artificial Sequence
<220> FEATURE:
<223> OTHER INFORMATION: Artificially synthesized peptide

```
<400> SEQUENCE: 135

Cys Lys Arg Ala Val Arg
1               5

<210> SEQ ID NO 136
<211> LENGTH: 9
<212> TYPE: PRT
<213> ORGANISM: Artificial Sequence
<220> FEATURE:
<223> OTHER INFORMATION: Artificially synthesized peptide

<400> SEQUENCE: 136

Cys Arg Asn Ser Trp Lys Pro Asn Cys
1               5

<210> SEQ ID NO 137
<211> LENGTH: 5
<212> TYPE: PRT
<213> ORGANISM: Artificial Sequence
<220> FEATURE:
<223> OTHER INFORMATION: Artificially synthesized peptide

<400> SEQUENCE: 137

Arg Gly Ser Ser Ser
1               5

<210> SEQ ID NO 138
<211> LENGTH: 9
<212> TYPE: PRT
<213> ORGANISM: Artificial Sequence
<220> FEATURE:
<223> OTHER INFORMATION: Artificially synthesized peptide

<400> SEQUENCE: 138

Cys Arg Ser Thr Arg Ala Asn Pro Cys
1               5

<210> SEQ ID NO 139
<211> LENGTH: 9
<212> TYPE: PRT
<213> ORGANISM: Artificial Sequence
<220> FEATURE:
<223> OTHER INFORMATION: Artificially synthesized peptide

<400> SEQUENCE: 139

Cys Pro Lys Thr Arg Arg Val Pro Cys
1               5

<210> SEQ ID NO 140
<211> LENGTH: 9
<212> TYPE: PRT
<213> ORGANISM: Artificial Sequence
<220> FEATURE:
<223> OTHER INFORMATION: Artificially synthesized peptide

<400> SEQUENCE: 140

Cys Ser Gly Met Ala Arg Thr Lys Cys
1               5

<210> SEQ ID NO 141
<211> LENGTH: 7
<212> TYPE: PRT
<213> ORGANISM: Artificial Sequence
<220> FEATURE:
<223> OTHER INFORMATION: Artificially synthesized peptide
```

```
<400> SEQUENCE: 141

Gly Gly Gly Val Phe Trp Gln
1               5

<210> SEQ ID NO 142
<211> LENGTH: 7
<212> TYPE: PRT
<213> ORGANISM: Artificial Sequence
<220> FEATURE:
<223> OTHER INFORMATION: Artificially synthesized peptide

<400> SEQUENCE: 142

His Gly Arg Val Arg Pro His
1               5

<210> SEQ ID NO 143
<211> LENGTH: 7
<212> TYPE: PRT
<213> ORGANISM: Artificial Sequence
<220> FEATURE:
<223> OTHER INFORMATION: Artificially synthesized peptide

<400> SEQUENCE: 143

Val Val Leu Val Thr Ser Ser
1               5

<210> SEQ ID NO 144
<211> LENGTH: 8
<212> TYPE: PRT
<213> ORGANISM: Artificial Sequence
<220> FEATURE:
<223> OTHER INFORMATION: Artificially synthesized peptide

<400> SEQUENCE: 144

Cys Leu His Arg Gly Asn Ser Cys
1               5

<210> SEQ ID NO 145
<211> LENGTH: 12
<212> TYPE: PRT
<213> ORGANISM: Artificial Sequence
<220> FEATURE:
<223> OTHER INFORMATION: Artificially synthesized peptide

<400> SEQUENCE: 145

Cys Arg Ser Trp Asn Lys Ala Asp Asn Arg Ser Cys
1               5                   10

<210> SEQ ID NO 146
<211> LENGTH: 5
<212> TYPE: PRT
<213> ORGANISM: Artificial Sequence
<220> FEATURE:
<223> OTHER INFORMATION: Artificially synthesized peptide

<400> SEQUENCE: 146

Cys Asn Gly Arg Cys
1               5

<210> SEQ ID NO 147
<211> LENGTH: 9
<212> TYPE: PRT
<213> ORGANISM: Artificial Sequence
<220> FEATURE:
<223> OTHER INFORMATION: Artificially synthesized peptide

<400> SEQUENCE: 147
```

```
Cys Ser Arg Pro Arg Ser Glu Cys
1               5
```

<210> SEQ ID NO 148
<211> LENGTH: 9
<212> TYPE: PRT
<213> ORGANISM: Artificial Sequence
<220> FEATURE:
<223> OTHER INFORMATION: Artificially synthesized peptide

<400> SEQUENCE: 148

```
Cys Ser Arg Pro Arg Arg Ser Val Cys
1               5
```

<210> SEQ ID NO 149
<211> LENGTH: 9
<212> TYPE: PRT
<213> ORGANISM: Artificial Sequence
<220> FEATURE:
<223> OTHER INFORMATION: Artificially synthesized peptide

<400> SEQUENCE: 149

```
Cys Ser Arg Pro Arg Arg Ser Trp Cys
1               5
```

<210> SEQ ID NO 150
<211> LENGTH: 31
<212> TYPE: PRT
<213> ORGANISM: Artificial Sequence
<220> FEATURE:
<223> OTHER INFORMATION: Artificially synthesized peptide

<400> SEQUENCE: 150

```
Lys Asp Glu Pro Gln Arg Arg Ser Ala Arg Leu Ser Ala Lys Pro Ala
1               5                   10                  15

Pro Pro Lys Pro Glu Pro Lys Pro Lys Ala Pro Lys Lys
            20                  25                  30
```

<210> SEQ ID NO 151
<211> LENGTH: 10
<212> TYPE: PRT
<213> ORGANISM: Artificial Sequence
<220> FEATURE:
<223> OTHER INFORMATION: Artificially synthesized peptide

<400> SEQUENCE: 151

```
Pro Gln Arg Arg Ser Ala Arg Leu Ser Ala
1               5                   10
```

<210> SEQ ID NO 152
<211> LENGTH: 10
<212> TYPE: PRT
<213> ORGANISM: Artificial Sequence
<220> FEATURE:
<223> OTHER INFORMATION: Artificially synthesized peptide

<400> SEQUENCE: 152

```
Pro Lys Arg Arg Ser Ala Arg Leu Ser Ala
1               5                   10
```

<210> SEQ ID NO 153
<211> LENGTH: 7
<212> TYPE: PRT
<213> ORGANISM: Artificial Sequence
<220> FEATURE:
<223> OTHER INFORMATION: Artificially synthesized peptide

<400> SEQUENCE: 153

Cys Arg Gly Arg Arg Ser Thr
1               5

<210> SEQ ID NO 154
<211> LENGTH: 34
<212> TYPE: PRT
<213> ORGANISM: Artificial Sequence
<220> FEATURE:
<223> OTHER INFORMATION: Artificially synthesized peptide

<400> SEQUENCE: 154

Ala Lys Val Lys Asp Glu Pro Gln Arg Arg Ser Ala Arg Leu Ser Ala
1               5                   10                  15

Lys Pro Ala Pro Pro Lys Pro Glu Pro Lys Pro Lys Lys Ala Pro Ala
            20                  25                  30

Lys Lys

<210> SEQ ID NO 155
<211> LENGTH: 9
<212> TYPE: PRT
<213> ORGANISM: Artificial Sequence
<220> FEATURE:
<223> OTHER INFORMATION: Artificially synthesized peptide

<400> SEQUENCE: 155

Cys Asn Arg Arg Thr Lys Ala Gly Cys
1               5

<210> SEQ ID NO 156
<211> LENGTH: 6
<212> TYPE: PRT
<213> ORGANISM: Artificial Sequence
<220> FEATURE:
<223> OTHER INFORMATION: Artificially synthesized peptide

<400> SEQUENCE: 156

Cys Arg Ser Arg Lys Gly
1               5

<210> SEQ ID NO 157
<211> LENGTH: 10
<212> TYPE: PRT
<213> ORGANISM: Artificial Sequence
<220> FEATURE:
<223> OTHER INFORMATION: Artificially synthesized peptide

<400> SEQUENCE: 157

Pro Gln Arg Arg Ser Ala Arg Leu Ser Ala
1               5                   10

<210> SEQ ID NO 158
<211> LENGTH: 10
<212> TYPE: PRT
<213> ORGANISM: Artificial Sequence
<220> FEATURE:
<223> OTHER INFORMATION: Artificially synthesized peptide

<400> SEQUENCE: 158

Pro Lys Arg Arg Ser Ala Arg Leu Ser Ala
1               5                   10

<210> SEQ ID NO 159
<211> LENGTH: 9

<212> TYPE: PRT
<213> ORGANISM: Artificial Sequence
<220> FEATURE:
<223> OTHER INFORMATION: Artificially synthesized peptide

<400> SEQUENCE: 159

Cys Arg Gly Asp Lys Gly Pro Asp Cys
1               5

<210> SEQ ID NO 160
<211> LENGTH: 13
<212> TYPE: PRT
<213> ORGANISM: Artificial Sequence
<220> FEATURE:
<223> OTHER INFORMATION: Artificially synthesized peptide

<400> SEQUENCE: 160

Arg Arg Gly Gly Arg Ser Lys Leu Ala Ala Ala Leu Glu
1               5                   10

<210> SEQ ID NO 161
<211> LENGTH: 14
<212> TYPE: PRT
<213> ORGANISM: Artificial Sequence
<220> FEATURE:
<223> OTHER INFORMATION: Artificially synthesized peptide

<400> SEQUENCE: 161

Gly Arg Gly Gly Arg Ser Arg Lys Leu Ala Ala Ala Leu Glu
1               5                   10

<210> SEQ ID NO 162
<211> LENGTH: 14
<212> TYPE: PRT
<213> ORGANISM: Artificial Sequence
<220> FEATURE:
<223> OTHER INFORMATION: Artificially synthesized peptide

<400> SEQUENCE: 162

Gly Lys Arg Gly Gly Arg Ser Lys Leu Ala Ala Ala Leu Glu
1               5                   10

<210> SEQ ID NO 163
<211> LENGTH: 7
<212> TYPE: PRT
<213> ORGANISM: Artificial Sequence
<220> FEATURE:
<223> OTHER INFORMATION: Artificially synthesized peptide

<400> SEQUENCE: 163

Arg Lys Arg Arg Asn Arg Ala
1               5

<210> SEQ ID NO 164
<211> LENGTH: 14
<212> TYPE: PRT
<213> ORGANISM: Artificial Sequence
<220> FEATURE:
<223> OTHER INFORMATION: Artificially synthesized peptide

<400> SEQUENCE: 164

Arg Thr Arg Gly Gly Arg Ser Lys Leu Ala Ala Ala Leu Glu
1               5                   10

<210> SEQ ID NO 165
<211> LENGTH: 14
<212> TYPE: PRT

<213> ORGANISM: Artificial Sequence
<220> FEATURE:
<223> OTHER INFORMATION: Artificially synthesized peptide

<400> SEQUENCE: 165

Gly Arg Arg Gly Ser Arg Ser Lys Leu Ala Ala Ala Leu Glu
1               5                   10

<210> SEQ ID NO 166
<211> LENGTH: 7
<212> TYPE: PRT
<213> ORGANISM: Artificial Sequence
<220> FEATURE:
<223> OTHER INFORMATION: Artificially synthesized peptide

<400> SEQUENCE: 166

Arg Lys Arg Gly Gly Arg Ser
1               5

<210> SEQ ID NO 167
<211> LENGTH: 7
<212> TYPE: PRT
<213> ORGANISM: Artificial Sequence
<220> FEATURE:
<223> OTHER INFORMATION: Artificially synthesized peptide

<400> SEQUENCE: 167

Gly Arg Gly Ser Arg Ser Arg
1               5

<210> SEQ ID NO 168
<211> LENGTH: 7
<212> TYPE: PRT
<213> ORGANISM: Artificial Sequence
<220> FEATURE:
<223> OTHER INFORMATION: Artificially synthesized peptide

<400> SEQUENCE: 168

Asp Glu Gly Met Met Asn Ala
1               5

<210> SEQ ID NO 169
<211> LENGTH: 7
<212> TYPE: PRT
<213> ORGANISM: Artificial Sequence
<220> FEATURE:
<223> OTHER INFORMATION: Artificially synthesized peptide

<400> SEQUENCE: 169

Phe Arg Gly Ala Arg Ser Arg
1               5

<210> SEQ ID NO 170
<211> LENGTH: 14
<212> TYPE: PRT
<213> ORGANISM: Artificial Sequence
<220> FEATURE:
<223> OTHER INFORMATION: Artificially synthesized peptide

<400> SEQUENCE: 170

Val Arg Arg Gly Gly Arg Ser Lys Leu Ala Ala Ala Leu Glu
1               5                   10

<210> SEQ ID NO 171
<211> LENGTH: 14
<212> TYPE: PRT
<213> ORGANISM: Artificial Sequence

```
<220> FEATURE:
<223> OTHER INFORMATION: Artificially synthesized peptide

<400> SEQUENCE: 171

Gly Arg Arg Gly Asn Arg Ser Lys Leu Ala Ala Ala Leu Glu
1               5                   10

<210> SEQ ID NO 172
<211> LENGTH: 14
<212> TYPE: PRT
<213> ORGANISM: Artificial Sequence
<220> FEATURE:
<223> OTHER INFORMATION: Artificially synthesized peptide

<400> SEQUENCE: 172

Arg Arg Gly Ala Arg Ser Val Arg Gly Gly Arg Ser Arg Ser
1               5                   10

<210> SEQ ID NO 173
<211> LENGTH: 13
<212> TYPE: PRT
<213> ORGANISM: Artificial Sequence
<220> FEATURE:
<223> OTHER INFORMATION: Artificially synthesized peptide

<400> SEQUENCE: 173

Arg Gly Arg Gly Gly Arg Ser Lys Leu Ala Ala Leu Glu
1               5                   10

<210> SEQ ID NO 174
<211> LENGTH: 14
<212> TYPE: PRT
<213> ORGANISM: Artificial Sequence
<220> FEATURE:
<223> OTHER INFORMATION: Artificially synthesized peptide

<400> SEQUENCE: 174

Gly Lys Arg Gly Gly Arg Ser Lys Leu Ala Ala Ala Leu Glu
1               5                   10

<210> SEQ ID NO 175
<211> LENGTH: 9
<212> TYPE: PRT
<213> ORGANISM: Artificial Sequence
<220> FEATURE:
<223> OTHER INFORMATION: Artificially synthesized peptide

<400> SEQUENCE: 175

Cys Arg Arg Gly Asn Arg Ser Ser Cys
1               5

<210> SEQ ID NO 176
<211> LENGTH: 9
<212> TYPE: PRT
<213> ORGANISM: Artificial Sequence
<220> FEATURE:
<223> OTHER INFORMATION: Artificially synthesized peptide

<400> SEQUENCE: 176

Cys Ala Arg Gly Ala Arg Thr Lys Cys
1               5

<210> SEQ ID NO 177
<211> LENGTH: 9
<212> TYPE: PRT
<213> ORGANISM: Artificial Sequence
<220> FEATURE:
```

<223> OTHER INFORMATION: Artificially synthesized peptide

<400> SEQUENCE: 177

Cys Thr Arg Gly Ser Arg Ser Lys Cys
1               5

<210> SEQ ID NO 178
<211> LENGTH: 9
<212> TYPE: PRT
<213> ORGANISM: Artificial Sequence
<220> FEATURE:
<223> OTHER INFORMATION: Artificially synthesized peptide

<400> SEQUENCE: 178

Cys Lys Arg Gly Asn Arg Ser Val Cys
1               5

<210> SEQ ID NO 179
<211> LENGTH: 9
<212> TYPE: PRT
<213> ORGANISM: Artificial Sequence
<220> FEATURE:
<223> OTHER INFORMATION: Artificially synthesized peptide

<400> SEQUENCE: 179

Cys Lys Arg Gly Gly Arg Ser Ala Cys
1               5

<210> SEQ ID NO 180
<211> LENGTH: 9
<212> TYPE: PRT
<213> ORGANISM: Artificial Sequence
<220> FEATURE:
<223> OTHER INFORMATION: Artificially synthesized peptide

<400> SEQUENCE: 180

Cys Leu Ser Asp Thr Arg Lys Lys Cys
1               5

<210> SEQ ID NO 181
<211> LENGTH: 9
<212> TYPE: PRT
<213> ORGANISM: Artificial Sequence
<220> FEATURE:
<223> OTHER INFORMATION: Artificially synthesized peptide

<400> SEQUENCE: 181

Cys Lys Arg Gly Ser Arg Ser Ser Cys
1               5

<210> SEQ ID NO 182
<211> LENGTH: 9
<212> TYPE: PRT
<213> ORGANISM: Artificial Sequence
<220> FEATURE:
<223> OTHER INFORMATION: Artificially synthesized peptide

<400> SEQUENCE: 182

Cys Gln Arg Gly Thr Arg Ser Arg Cys
1               5

<210> SEQ ID NO 183
<211> LENGTH: 9
<212> TYPE: PRT
<213> ORGANISM: Artificial Sequence
<220> FEATURE:
<223> OTHER INFORMATION: Artificially synthesized peptide

<400> SEQUENCE: 183

Cys Val Arg Gly Gly Arg Ala Arg Cys
1               5

<210> SEQ ID NO 184
<211> LENGTH: 9
<212> TYPE: PRT
<213> ORGANISM: Artificial Sequence
<220> FEATURE:
<223> OTHER INFORMATION: Artificially synthesized peptide

<400> SEQUENCE: 184

Cys Ala Arg Gly Lys Arg Ser Leu Cys
1               5

<210> SEQ ID NO 185
<211> LENGTH: 9
<212> TYPE: PRT
<213> ORGANISM: Artificial Sequence
<220> FEATURE:
<223> OTHER INFORMATION: Artificially synthesized peptide

<400> SEQUENCE: 185

Cys Val Arg Gly Ser Arg Ser Arg Cys
1               5

<210> SEQ ID NO 186
<211> LENGTH: 9
<212> TYPE: PRT
<213> ORGANISM: Artificial Sequence
<220> FEATURE:
<223> OTHER INFORMATION: Artificially synthesized peptide

<400> SEQUENCE: 186

Cys Lys Arg Gly Gly Arg Thr Gly Cys
1               5

<210> SEQ ID NO 187
<211> LENGTH: 9
<212> TYPE: PRT
<213> ORGANISM: Artificial Sequence
<220> FEATURE:
<223> OTHER INFORMATION: Artificially synthesized peptide

<400> SEQUENCE: 187

Cys Arg Arg Gly Ala Arg Ala Lys Cys
1               5

<210> SEQ ID NO 188
<211> LENGTH: 9
<212> TYPE: PRT
<213> ORGANISM: Artificial Sequence
<220> FEATURE:
<223> OTHER INFORMATION: Artificially synthesized peptide

<400> SEQUENCE: 188

Cys Gln Arg Gly Gly Arg Ser Lys Cys
1               5

<210> SEQ ID NO 189
<211> LENGTH: 9
<212> TYPE: PRT
<213> ORGANISM: Artificial Sequence
<220> FEATURE:
<223> OTHER INFORMATION: Artificially synthesized peptide

```
<400> SEQUENCE: 189

Cys Lys Arg Gly Asn Arg Ser Met Cys
1               5

<210> SEQ ID NO 190
<211> LENGTH: 7
<212> TYPE: PRT
<213> ORGANISM: Artificial Sequence
<220> FEATURE:
<223> OTHER INFORMATION: Artificially synthesized peptide

<400> SEQUENCE: 190

Arg Met Arg Arg Ile Asp Arg
1               5

<210> SEQ ID NO 191
<211> LENGTH: 7
<212> TYPE: PRT
<213> ORGANISM: Artificial Sequence
<220> FEATURE:
<223> OTHER INFORMATION: Artificially synthesized peptide

<400> SEQUENCE: 191

Ser Gly Val Ser Arg Asp Arg
1               5

<210> SEQ ID NO 192
<211> LENGTH: 8
<212> TYPE: PRT
<213> ORGANISM: Artificial Sequence
<220> FEATURE:
<223> OTHER INFORMATION: Artificially synthesized peptide

<400> SEQUENCE: 192

Ser Met Asn Glu Val Arg Lys Arg
1               5

<210> SEQ ID NO 193
<211> LENGTH: 7
<212> TYPE: PRT
<213> ORGANISM: Artificial Sequence
<220> FEATURE:
<223> OTHER INFORMATION: Artificially synthesized peptide

<400> SEQUENCE: 193

Ser Arg Leu Gly Arg Met Arg
1               5

<210> SEQ ID NO 194
<211> LENGTH: 15
<212> TYPE: PRT
<213> ORGANISM: Artificial Sequence
<220> FEATURE:
<223> OTHER INFORMATION: Artificially synthesized peptide

<400> SEQUENCE: 194

Gly Gly Ser Gly Lys Arg Gly Ala Arg Ser Thr Gly Gly Ser Gly
1               5                   10                  15

<210> SEQ ID NO 195
<211> LENGTH: 14
<212> TYPE: PRT
<213> ORGANISM: Artificial Sequence
<220> FEATURE:
<223> OTHER INFORMATION: Artificially synthesized peptide

<400> SEQUENCE: 195
```

```
Gly Gly Ser Gly Arg Gly Ala Arg Ser Thr Gly Gly Ser Gly
1               5                   10

<210> SEQ ID NO 196
<211> LENGTH: 14
<212> TYPE: PRT
<213> ORGANISM: Artificial Sequence
<220> FEATURE:
<223> OTHER INFORMATION: Artificially synthesized peptide

<400> SEQUENCE: 196

Gly Gly Ser Gly Lys Arg Gly Ala Arg Ser Gly Gly Ser Gly
1               5                   10

<210> SEQ ID NO 197
<211> LENGTH: 6
<212> TYPE: PRT
<213> ORGANISM: Artificial Sequence
<220> FEATURE:
<223> OTHER INFORMATION: Artificial consensus sequence
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid

<400> SEQUENCE: 197

Xaa Arg Gly Xaa Arg Ser
1               5

<210> SEQ ID NO 198
<211> LENGTH: 9
<212> TYPE: PRT
<213> ORGANISM: Artificial Sequence
<220> FEATURE:
<223> OTHER INFORMATION: Artificial consensus sequence
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (7)..(8)
<223> OTHER INFORMATION: Xaa can be any naturally occurring amino acid

<400> SEQUENCE: 198

Cys Xaa Arg Gly Xaa Arg Xaa Xaa Cys
1               5

<210> SEQ ID NO 199
<211> LENGTH: 10
<212> TYPE: PRT
<213> ORGANISM: Artificial Sequence
<220> FEATURE:
<223> OTHER INFORMATION: Artificiall synthesized peptide

<400> SEQUENCE: 199

Cys Cys Gly Asn Lys Arg Thr Arg Gly Cys
1               5                   10
```

TARGETED DELIVERY SYSTEM AND METHODS OF USE THEREFOR

CROSS REFERENCE TO RELATED APPLICATIONS

This application is a continuation of U.S. patent application Ser. No. 15/568,533, filed Oct. 23, 2017, which is a U.S. National Stage application of PCT International Patent Application Serial No. PCT/US2016/028894, filed Apr. 22, 2016, which is based on and claims the benefit of U.S. Provisional Patent Application Ser. Nos. 62/151,674 and 62/151,703, both filed Apr. 23, 2015. The disclosure of each of these applications is incorporated herein by reference in its entirety.

STATEMENT REGARDING FEDERALLY SPONSORED RESEARCH

This invention was made with government support under grants CA183287, CA167174, CA152327, and CA121949 from the National Institutes of Health. The government has certain rights in the invention.

REFERENCE TO SEQUENCE LISTING

The Sequence Listing submitted with the instant application as a ASCII text file entitled "3101_11_CON_ST25.txt" created on Jun. 1, 2020 and having a size of 123 kilobytes is hereby incorporated by reference in its entirety.

TECHNICAL FIELD

The present invention relates generally to the fields of molecular medicine and cancer biology and, more specifically, to molecules that interact with the gC1q/p32 receptor.

BACKGROUND

The gC1q/p32 receptor is a mitochondrial chaperone protein responsible for the maintenance of certain proteins in the mitochondrial oxidative phosphorylation machinery (Fogal et al., 2010; Yagi et al., 2012). This protein is also component of the CI complex of the classical complement pathway (Sim & Reid, 1991). The biological functions of the gC1q/p32 receptor are diverse, including initiation of the complement cascade for opsonization and cytolysis, and mediation of several different functions depending on the cell types expressing the gC1q/p32 receptor. The gC1q/p32 receptor enhances FcR and CR1-mediated phagocytosis in monocytes/macrophages (Bobak et al., 1987; Bobak et al., 1988); stimulates immunoglobulin production by B cells (Young et al., 1991); activates platelets to express αIIb/β3 integrins, P-selectin, and procoagulant activity (Peerschke et al., 1993; Peerschke et al., 1994); activates tumor cytotoxicity of macrophages (Leu et al., 1990); exerts anti-proliferative effects on T cell growth (Chen et al., 1994); and serves as a receptor for the *Listeria monocytogenes* invasion protein InlB (Braun et al.,).

A 33 kilodalton (kDa) receptor, designated gC1qR/p32 (and alternatively referred to herein as p32, gC1q-R, or the gC1/p32 receptor), has been identified, cloned, and sequenced (Chen et al., 1994; Ghebrehiwet et al., 1994; Peerschke et al., 1994). The crystal structure of gC1qR/p32 has also been solved (Jiang et al., 1999). Another 60 kDa receptor, designated cC1qR, binds to the amino-terminal collagen-like region of C1q (Ghebrehiwet, 1989; Chen et al., 1994). Based on the detection of gC1qR/p32 mRNA by polymerase chain reaction (PCR) amplification and gC1qR/p32 protein expression by immunochemical methods, this receptor was found to exist on a large number of different cell types, such as but not limited to B cells, T cells, monocytes/macrophages, neutrophils, eosinophils, fibroblasts, platelets, endothelial cells, liver cells, neural cells, and smooth muscle cells. The gC1q-R protein is over-expressed in tumor cells and tumors (Rubinstein et al., 2004).

The endothelial lining of blood vessels is highly diversified. Many, and perhaps all, normal tissues impart a tissue-specific "signature" on their vasculature, and tumor vessels differ from normal vessels both in morphology and molecular composition (Ruoslahti, 2002). Tumors induce angiogenesis to support expansive growth (Hanahan & Weinberg, 2000 and many of the changes in tumor vessels are angiogenesis related (Brooks et al., 1994; Ferrara et al., 1999; Pasqualini et al., 2000; Christian et al., 2003). Moreover, tumor blood vessels have tumor type-specific and, in some stages, stage-specific characteristics; in vivo screening of phage libraries has yielded distinct sets of homing peptides selectively recognizing angiogenic signatures in two transgenic mouse models of organ-specific tumorigenesis. Homing peptides can also distinguish the angiogenic blood vessels of premalignant lesions from those of fully malignant lesions in the same tumor. Lymphatic vessels in tumors also carry specific markers that distinguish tumor lymphatics from lymphatics in normal tissues (Laakkonen et al., 2002; Laakkonen et al., 2004; Zhang et al., 2006). Tumor blood vessels and lymphatics provide important targets for tumor therapy. Destroying tumor blood vessels or preventing their growth suppresses tumor growth, whereas tumor lymphatics are not essential for tumor growth, but destroying them reduces metastasis (Saharinen et al., 2004).

The gC1qR/p32 protein is primarily a mitochondrial protein, but it is also expressed at the cell surface. Its expression is greatly increased in many cancers, particularly in breast cancer, and in atherosclerotic lesions. More importantly, the expression of p32 is specific for tumor cells and cells in atherosclerotic plaques at the level of cell surface expression, which of p32 is a characteristic of cells in these conditions, and not detectable in p32-expressing normal cells. In addition to tumor cells, a macrophage population associated with tumor lymphatics expresses high levels of total and cell-surface p32. p32 expression is primarily found in poorly vascularized, hypoxic/nutrient-deprived regions, which are not readily accessible to conventional therapies.

A peptide that binds to p32 at the cell surface and inhibits tumor growth upon systemic administration called LyP-1 has been identified. LyP-1 (CGNKRTRGC; SEQ ID NO: 7) accumulates in tumors and atherosclerotic plaques, where it primarily accumulates in activated macrophage/myeloid lineage cells (Hamzah et al., 2011). The homing of LyP-1 to these lesions is specific; LyP-1 does not accumulate in normal tissues. LyP-1 has been shown to deliver imaging agents into atherosclerotic plaques and carotid inflammatory lesions, allowing enhanced imaging of the lesions (Fogal et al., 2008; Hamzah et al., 2011). Recent data also show that LyP-1 possesses a biological activity beyond the homing and carrier functions; prolonged treatment of atherosclerotic mice with this peptide has a plaque-reducing effect.

SUMMARY

This Summary lists several embodiments of the presently disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this Summary or not. To avoid excessive repetition, this Summary does not list or suggest all possible combinations of such features.

In some embodiments, the presently disclosed subject matter provides isolated peptides or peptidomimetics. In some embodiments, the presently disclosed isolated peptides or peptidomimetics comprise the amino acid sequence KRGARST (SEQ ID NO: 1) or a peptidomimetic thereof, the amino acid sequence AKRGARSTA (SEQ ID NO: 2) or a peptidomimetic thereof, or the amino acid sequence CKRGARSTC (SEQ ID NO: 3) or a peptidomimetic thereof. In some embodiments, the presently disclosed peptide or peptidomimetic is a peptide, optionally a linear peptide. In some embodiments, the isolated peptide or peptidomimetic is conformationally constrained. In some embodiments, the isolated peptide or peptidomimetic is cyclic. The presently disclosed isolated peptides or peptidomimetics have a length of in some embodiments less than 100 residues, in some embodiments less than 50 residues, in some embodiments less than 20 residues, and in some embodiments less than 15 residues.

The presently disclosed subject matter also provides in some embodiments conjugates comprising one or more moieties linked to one or more homing molecules that selectively home to tumor lymphatic vasculature, wherein the one or more homing molecules comprise the presently disclosed isolated peptides and/or peptidomimetics. In some embodiments, the conjugates further comprise one or more additional homing molecules, which in some embodiments comprise one or more antibodies or antigen-binding fragments thereof. In some embodiments, at least one of the one or more homing molecules is a peptide, optionally a peptide comprising SEQ ID NO: 1, SEQ ID NO: 2, or SEQ ID NO: 3. The peptide or peptidomimetic portions of the conjugates have in some embodiments a length of at most 200 residues, in some embodiments a length of at most 100 residues, in some embodiments a length of at most 50 residues, in some embodiments a length of at most 20 residues, in some embodiments a length of at most 15 residues, and in some embodiments a length of at most 10 residues. In some embodiments, at least one of the the homing molecules is conformationally constrained or cyclic. In some embodiments, at least one of the the homing molecules is linear. In some embodiments, at least one of the homing molecules comprises the amino acid sequence KRGARST (SEQ ID NO: 1), AKRGARSTA (SEQ ID NO: 2), CKRGARSTC (SEQ ID NO: 3), or a conservative variant or peptidomimetic thereof. In some embodiments, at least one of the homing molecules consists of the amino acid sequence KRGARST (SEQ ID NO: 1), AKRGARSTA (SEQ ID NO: 2), CKRGARSTC (SEQ ID NO: 3), or a conservative variant or peptidomimetic thereof.

In some embodiments of the presently disclosed conjugates, the moiety comprises a therapeutic agent, which in some embodiments can be a cancer chemotherapeutic agent, a cytotoxic agent, and/or an anti-lymphangiogenic agent. In some embodiments, the moiety is a detectable agent. In some embodiments, the moiety is a phage.

The conjugates can also comprise in some embodiments at least two, ten, 20, 25, 50, 100, 500, or 1000 homing molecules that each selectively homes to tumor lymphatic vasculature, which in some embodiments each independently comprise and/or consist of the amino acid sequence KRGARST (SEQ ID NO: 1), AKRGARSTA (SEQ ID NO: 2), CKRGARSTC (SEQ ID NO: 3), or a conservative variant or peptidomimetic thereof.

The presently disclosed subject matter also provides in some embodiments methods for directing a moiety to tumor lymphatic vasculature in a subject. In some embodiments, the presently disclosed methods comprise administering to the subject a conjugate that comprises a moiety linked to a homing molecule that selectively homes to tumor lymphatic vasculature, wherein the homing molecule comprises an isolated peptide and/or peptidomimetic as disclosed herein, thereby directing the moiety to tumor lymphatic vasculature.

The presently disclosed subject matter also provides in some embodiments methods for imaging tumor lymphatic vasculature in a subject. In some embodiments, the methods comprise administering to the subject a conjugate comprising a detectable agent linked to a homing molecule that selectively homes to tumor lymphatic vasculature, wherein the homing molecule comprises a isolated peptide or peptidomimetic as disclosed herein; and detecting the conjugate, thereby imaging the tumor lymphatic vasculature.

The presently disclosed subject matter also provides in some embodiments methods for reducing the number of tumor lymphatic vessels in a subject. In some embodiments, the method comprise administering to the subject a conjugate that comprises a moiety linked to a homing molecule that selectively homes to tumor lymphatic vasculature, wherein the homing molecule comprises an isolated peptide or peptidomimetic as disclosed herein, thereby reducing the number of tumor lymphatic vessels in the subject The presently disclosed subject matter also provides in some embodiments methods for reducing or inhibiting tumor metastasis in a subject. In some embodiments, the presently disclosed methods comprise administering to the subject a conjugate that comprises a moiety linked to a homing molecule that selectively homes to tumor lymphatic vasculature, wherein the homing molecule comprises an isolated peptide or peptidomimetic as disclosed herein, thereby reducing or inhibiting tumor metastasis in the subject.

The presently disclosed subject matter also provides in some embodiments methods for treating cancer in a subject. In some embodiments, the presently disclosed methods comprise administering to the subject a conjugate which comprises a moiety linked to a homing molecule that selectively homes to tumor lymphatic vasculature, wherein the homing molecule comprises an isolated peptide or peptidomimetic as disclosed herein, and further wherein the conjugate has an anti-cancer biological activity in the tumor lymphatic vasculature of the subject.

The presently disclosed subject matter also provides in some embodiments compositions comprising a surface molecule, one or more homing molecules, and a plurality of membrane perturbing molecules, wherein the homing molecule selectively homes to tumor vasculature. In some embodiments, one or more of the homing molecules comprise the amino acid sequence KRGARST (SEQ ID NO: 1) or a conservative derivative thereof, the amino acid sequence AKRGARSTA (SEQ ID NO: 2) or a conservative derivative thereof, the amino acid sequence CKRGARSTC (SEQ ID NO: 3) or a conservative derivative thereof, or any combination thereof. In some embodiments, one or more of the membrane perturbing molecules comprise the amino acid sequence $_D$(KLAKLAK)$_2$ (SEQ ID NO: 42) or a conservative variant thereof, (KLAKLAK)$_2$ (SEQ ID NO: 42) or a conservative variant thereof, (KLAKKLA)$_2$ (SEQ ID NO: 43) or a conservative variant thereof, (KAAKKAA)$_2$ (SEQ ID NO: 44) or a conservative variant thereof, or (KLGKKLG)$_3$ (SEQ ID NO: 45) or a conservative variant thereof, or any combination thereof. In some embodiments, one or more of the membrane perturbing molecules are conjugated to one or more of the homing molecules. In some embodiments, one or more of the conjugated membrane perturbing molecules and homing molecules are covalently coupled. In some embodiments, one or more of the covalently coupled membrane perturbing molecules and homing molecules comprise fusion peptides. In some embodiments, the homing molecules are conjugated with the surface molecule. In some embodiments, one or more of the conjugated homing molecules are indirectly conjugated to the surface molecule. In some embodiments, one or more of the conjugated homing molecules are directly conjugated to the surface molecule. In some embodiments, one or more of the homing molecules are covalently coupled to the surface molecule. In some embodiments, one or more of the covalently coupled homing molecules are indirectly covalently coupled to the surface molecule. In some embodiments, one or more of the covalently coupled homing molecules are directly covalently coupled to the surface molecule. In some embodiments, the membrane perturbing molecules are conjugated with the surface molecule. In some embodiments, one or more of the conjugated membrane perturbing molecules are indirectly conjugated to the surface molecule. In some embodiments, one or more of the conjugated membrane perturbing molecules are directly conjugated to the surface molecule. In some embodiments, one or more of the membrane perturbing molecules are covalently coupled to the surface molecule. In some embodiments, one or more of the covalently coupled membrane perturbing molecules are indirectly covalently coupled to the surface molecule. In some embodiments, one or more of the covalently coupled membrane perturbing molecules are directly covalently coupled to the surface molecule. In some embodiments, one or more of the conjugated homing molecules are indirectly conjugated to the surface molecule via a linker, one or more of the conjugated membrane perturbing molecules are indirectly conjugated to the surface molecule via a linker, or both.

In some embodiments, the presently disclosed compositions further comprise a plurality of linkers. In some embodiments, at least one of the linkers comprises polyethylene glycol.

In some embodiments, the presently disclosed compositions further comprise one or more internalization elements. In some embodiments, one or more of the homing molecules comprise one or more of the internalization elements. In some embodiments, one or more of the membrane perturbing molecules comprise one or more of the internalization elements. In some embodiments, the surface molecule comprises one or more of the internalization elements not comprised in either the homing molecules or the membrane perturbing molecules.

In some embodiments, the presently disclosed compositions further comprise one or more tissue penetration elements. In some embodiments, one or more of the tissue penetration elements are comprised in an internalization element. In some embodiments, the tissue penetration element is a CendR element.

In some embodiments, the presently disclosed compositions bind inside tumor blood vessels.

In some embodiments, the presently disclosed compositions are internalized in cells.

In some embodiments, the presently disclosed composition penetrates tissue.

In some embodiments, the presently disclosed compositions reduce tumor growth.

In some embodiments of the presently disclosed compositions, the surface molecule comprises an nanoparticle, a nanoworm, an iron oxide nanoworm, an iron oxide nanoparticle, an albumin nanoparticle, a liposome, a micelle, a phospholipid, a polymer, a microparticle, and/or a fluorocarbon microbubble.

In some embodiments, the presently disclosed compositions comprise at least 100, 1000, or 10,000 homing molecules, and/or comprise at least 100, 1000, or 10,000 membrane perturbing molecules.

In some embodiments of the presently disclosed compositions, one or more of the homing molecules are modified homing molecules, which in some embodiments are methylated homing molecules, optionally wherein one or more of the methylated homing molecules comprise a methylated amino acid segment, further optionally wherein the amino acid sequence is N- or C-methylated in at least one position; and/or one or more of the membrane perturbing molecules are modified membrane perturbing molecules, which in some embodiments are methylated membrane perturbing molecules, optionally wherein one or more of the methylated membrane perturbing molecules comprise a methylated amino acid segment, further optionally wherein the amino acid sequence is N- or C-methylated in at least one position.

In some embodiments of the presently disclosed compositions, the compositions further comprise one or more moieties, which in some embodiments are are independently selected from the group consisting of a therapeutic agent, an anti-angiogenic agent, a pro-angiogenic agent, a cancer chemotherapeutic agent, a cytotoxic agent, an anti-inflammatory agent, an anti-arthritic agent, a polypeptide, a nucleic acid molecule, a small molecule, an image contrast agent, a fluorophore, fluorescein, rhodamine, a radionuclide, indium-111, technetium-99, carbon-11, and carbon-13. In some embodiments, the therapeutic agent is selected from the group consisting of iRGD, Abraxane, paclitaxel, and taxol. In some embodiments, at least one of the moieties is a detectable agent, optionally FAM.

In some embodiments, the presently disclosed subject matter provides in some embodiments a method comprising administering to a subject composition of the presently disclosed subject matter, wherein the composition selectively homes to tumor vasculature in the subject, wherein the composition is internalized into cells at the site of the tumor vasculature, optionally wherein the composition has a therapeutic effect, which in some embodiments comprises a slowing in the increase of or a reduction of tumor burden and in some embodiments comprises a slowing of the increase of or reduction of tumor size. In some embodiments, the subject has one or more sites to be targeted, wherein the composition homes to one or more of the sites to be targeted. In some embodiments, the subject has a tumor, wherein the composition has a therapeutic effect on the tumor. In some embodiments, the composition penetrates tissue, and in some embodiments the composition penetrates tumor tissue.

The presently disclosed subject matter also provides in some embodiments methods for treating a disease or disorder associated with a gC1q/p32 receptor biological activity. In some embodiments, the methods comprise identifying a subject having a disease or disorder associated with a gC1q/p32 receptor biological activity; and administering to the subject a composition comprising SEQ ID NO: 1, SEQ ID NO: 2, or SEQ ID NO: 3. In some embodiments, the subject has cancer. In some embodiments, the composition further comprises a moiety, optionally a therapeutic moiety, a diagnostic agent, and/or a nanoparticle. In some embodiments, the therapeutic moiety targets a DNA-associated process.

The presently disclosed subject matter also provides in some embodiments methods for detecting the presence of gC1q/p32 receptor. In some embodiments, the methods comprise bringing into contact a cell and a TT1 Peptide composition, wherein the TT1 Peptide composition comprises a moiety linked to a composition comprising SEQ ID NO: 1, SEQ ID NO: 2, or SEQ ID NO: 3; and detecting interaction between gC1q/p32 receptor and the TT1 Peptide composition, thereby detecting the presence of gC1q/p32 receptor. In some embodiments, the moiety is a detectable agent, a polypeptide, a nucleic acid molecule, or a small molecule. In some embodiments, the TT1 Peptide composition comprises a virus, which is in some embodiments a phage.

The presently disclosed subject matter also provides in some embodiments methods for detecting interactions between a gC1q/p32 receptor and a TT1 Peptide composition. In some embodiments, the TT1 Peptide composition comprises a moiety linked to a composition comprising SEQ ID NO: 1, SEQ ID NO: 2, or SEQ ID NO: 3. In some embodiments, the methods comprise selecting a cell for its potential to comprise a gC1q/p32 receptor; bringing into contact the TT1 Peptide composition and the cell; and detecting interaction between the gC1q/p32 receptor and the TT1 Peptide composition.

The presently disclosed subject matter also provides in some embodiments methods for delivering TT1 Peptide compositions to gC1q/p32 receptors. In some embodiments, the TT1 Peptide compositions comprise one or more moieties linked to a composition comprising SEQ ID NO: 1, SEQ ID NO: 2, or SEQ ID NO: 3. In some embodiments, the methods comprise bringing into contact the TT1 Peptide composition and a cell, thereby delivering the TT1 Peptide composition to the gC1q/p32 receptor. In some embodiments, the cell is in a subject, wherein the cell is selected for its potential to comprise a gC1q/p32 receptor by detecting the presence of gC1q/p32 receptor on another cell of the subject.

The presently disclosed subject matter also provides in some embodiments methods for delivering TT1 Peptide compositions to gC1q/p32 receptors. In some embodiments, the TT1 Peptide compositions comprise one or more moieties linked to a composition comprising SEQ ID NO: 1, SEQ ID NO: 2, or SEQ ID NO: 3. In some embodiments; the methods comprise selecting a cell for its potential to comprise a gC1q/p32 receptor; and bringing into contact the TT1 Peptide composition and the cell, thereby delivering the TT1 Peptide composition to the gC1q/p32 receptor.

The presently disclosed subject matter also provides methods for assessing gC1q/p32 receptor levels in cells of a subject. In some embodiments, the methods comprise bringing into contact a cell of the subject and a TT1 Peptide composition comprising a detectable agent linked to a composition comprising SEQ ID NO: 1, SEQ ID NO: 2, or SEQ ID NO: 3; and detecting the level of the TT1 Peptide composition interacting with gC1q/p32 receptor, thereby assessing gC1q/p32 receptor level in the cell. In some embodiments, the level of gC1q/p32 receptor in the subject is compared to a previous measurement in the same subject and/or is compared to a control level or standard level.

The presently disclosed subject matter also provides in some embodiments methods for identifying subjects having a disease or disorder associated with a gC1q/p32 receptor biological activity. In some embodiments, the methods comprise bringing into contact a cell of the subject and a TT1 Peptide composition, wherein the TT1 Peptide composition comprises a moiety linked to a composition comprising SEQ ID NO: 1, SEQ ID NO: 2, or SEQ ID NO: 3; and detecting interaction between gC1q/p32 receptor and the TT1 Peptide composition, thereby detecting the presence or level of gC1q/p32, wherein the presence or level of gC1q/p32 receptor identifies the subject as having a disease or disorder associated with a gC1q/p32 receptor biological activity. In some embodiments, the disease or disorder is cancer or inflammation. In some embodiments, the cell is a cancerous cell.

The presently disclosed subject matter also provides in some embodiments methods for screening for a compound that interacts with a gC1q/p32 receptor. In some embodiments, the methods comprise bringing into contact a test compound, a TT1 Peptide composition, and a gC1q/p32 receptor, wherein the TT1 Peptide composition comprises SEQ ID NO: 1, SEQ ID NO: 2, or SEQ ID NO: 3; and detecting unbound TT1 Peptide composition, wherein a given amount of unbound TT1 Peptide composition indicates a compound that interacts with gC1q/p32 receptor. In some embodiments, the TT1 Peptide composition further comprises a moiety linked to a composition comprising SEQ ID NO: 1, SEQ ID NO: 2, or SEQ ID NO: 3. In some embodiments, the moiety further comprises a detectable agent.

The presently disclosed subject matter also provides in some embodiments methods for treating a disease or disorder associated with a gC1q/p32 receptor biological activity. In some embodiments, the methods comprise identifying a subject having a disease or disorder associated with a gC1q/p32 receptor biological activity; and administering to the subject a composition that interacts with the gC1q/p32 receptor, wherein the composition comprises a TT1 Peptide comprising SEQ ID NO: 1, SEQ ID NO: 2, or SEQ ID NO: 3, thereby treating a disease or disorder associated with a gC1q/p32 receptor biological activity.

With respect to any of the compositions, conjugates, and methods of the presently disclosed subject matter, in some embodiments the homing molecule is linear or cyclic, and/or is a peptide or peptidomimetic. In some embodiments, the homing molecule comprises the amino acid sequence KRGARST (SEQ ID NO: 1) or a conservative variant or peptidomimetic thereof, the amino acid sequence AKRGARSTA (SEQ ID NO: 2) or a conservative variant or peptidomimetic thereof, and/or the amino acid sequence CKRGARSTC (SEQ ID NO: 3) or a conservative variant or peptidomimetic thereof. In some embodiments, the moiety is, comprises, consists essentially of, or consists of a therapeutic agent, a cancer chemotherapeutic agent, a cytotoxic agent, an anti-lymphangiogenic agent, a detectable agent, a phage, a polypeptide, a nucleic acid molecule, a small molecule, a fluorophore, fluorescein, rhodamine, a radionuclide, indium-111, technetium-99, carbon-11, carbon-13, or any combination thereof. In some embodiments, the therapeutic moiety is selected from the group consisting of a cytotoxic agent, an alkylating agent, an anti-tumor antibiotic, a sequence-selective agent, an anti-angiogenic agent, cyclophosphamide, melphalan, mitomycin C, bizelesin, cisplatin, doxorubicin, etoposide, mitoxantrone, SN-38, Et-743, actinomycin D, bleomycin, geldanamycin, chlorambucil, methotrexate, and TLK286. In some embodiments, the detectable agent is, comprises, consists essentially of, or consists of a radionuclide, which in some embodiments is selected from the group consisting of indium-111, technetium-99, carbon-11, and carbon-13. In some embodiments, the one or more of the membrane perturbing molecules comprise, consist essentially of, or consist of the amino acid sequence $_D$(KLAKLAK)$_2$ (SEQ ID NO: 42), (KLAKLAK)$_2$ (SEQ ID NO: 42) (KLAKKLA)$_2$ (SEQ ID NO: 43), (KAAKKAA)$_2$ (SEQ ID NO: 44), and/or (KLGKKLG)$_3$ (SEQ ID NO: 45), or any combination thereof. In some embodiments, one or more of the homing molecules comprise, consist essentially of, and/or consist of the amino acid sequence KRGARST (SEQ ID NO: 1), AKRGARSTA (SEQ ID NO: 2), and/or CKRGARSTC (SEQ ID NO: 3), wherein one or more of the membrane perturbing molecules comprise, consist essentially of, and/or consist of the amino acid sequence $_D$(KLAKLAK)$_2$ (SEQ ID NO: 42), wherein one or more of the conjugated homing molecules are indirectly conjugated to the surface molecule via a linker, and wherein one or more of the conjugated membrane perturbing molecules are indirectly conjugated to the surface molecule via a linker, optionally a polyethylene glycol (PEG) linker.

Thus, it is an object of the presently disclosed subject matter to provide compositions and methods for delivering active agents to subjects.

An object of the presently disclosed subject matter having been stated hereinabove, and which is achieved in whole or in part by the presently disclosed subject matter, other objects will become evident as the description proceeds when taken in connection with the accompanying drawings as best described herein below.

BRIEF DESCRIPTION OF THE FIGURES

The accompanying drawings, which are incorporated in and constitute a part of this disclosure, illustrate several embodiments of the disclosed methods and compositions, and together with the description, serve to explain the principles of the disclosed methods and compositions.

FIG. 1A is a picture of an analytical SDS-PAGE gel of 6×-His-Tagged p32 expressed in Rosetta-gami-2 cells (Novagen). FIG. 1B is a plot of a sedimentation velocity assay.

FIGS. 2A and 2B depict the results of in vitro biopanning of T7 bacteriophage libraries on immobilized p32 protein. FIG. 2A is a bar graph showing the results of two peptide libraries (CX7C and X7; C=cysteine; X=any amino acid) that were used for in vitro biopanning on immFigure lobilized p32. Binding is expressed as fold over control phage displaying polyglycine heptapeptide (G7). FIG. 2B presents WebLogo (Schneider & Stephens, 1990; Crooks et al., 2004) consensus peptide motifs (XRGXRS; SEQ ID NO: 197 and CXRGXRXXC; SEQ ID NO: 198) and representative peptide sequences recovered after two rounds of ex vivo selections. For the linear library, the KLAALE (SEQ ID NO: 11) element was encoded by the phage genomic DNA and was thus not a part of the random library. The data are representative of four (4) independent screens and binding experiments.

FIG. 2A is a plot showing that an exemplary TT1 peptide (CKRGARSTC; SEQ ID NO: 3) bound to p32 with a higher affinity than LyP-1. FIG. 2B is a plot showing that the exemplary TT1 peptide, the CendR motif of which is cryptic, showed only background binding, whereas the prototypic active CendR peptide RPARPAR (SEQ ID NO: 14; triangles) avidly bound to NRP-1. NRP-1 was used as a control protein.

BRIEF DESCRIPTION OF THE SEQUENCE LISTING

Figure 1A:
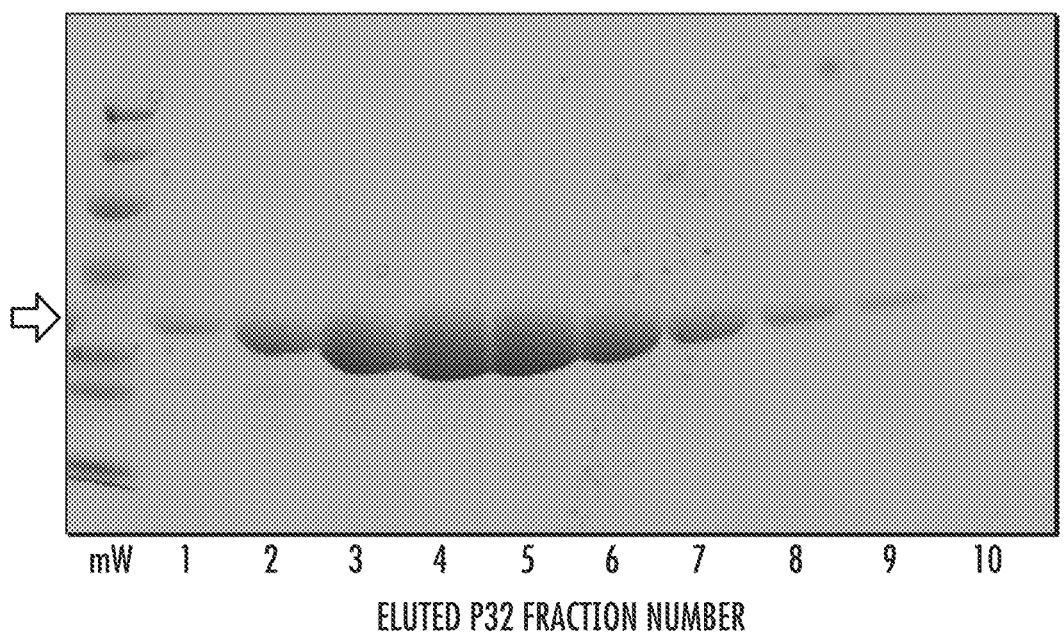
FIGS. 1A and 1B depict the results of purification and oligomerization analysis of the p32 protein.

SEQ ID NOs: 1-3 are the amino acid sequences of exemplary TT1 Peptides.

SEQ ID NOs: 4 and 5 are the amino acid sequences of a pentatpeptide motif that was highly represented in phage-displayed peptides that bound to the p32 protein.

SEQ ID NO: 6 is the amino acid sequence of an exemplary p32-binding peptide.

SEQ ID NO: 7 is the amino acid sequence of exemplary p32-binding peptide LyP-1.

SEQ ID NO: 8 is the amino acid sequence of an exemplary p32-binding peptide conjugated to a membrane-perturbing sequence.

SEQ ID NO: 9 is the amino acid sequence of an exemplary Lyp-1 Peptide-based p32-binding peptides conjugated to a membrane-perturbing sequence.

SEQ ID NO: 10 is the amino acid sequence of an exemplary TT1 Peptide-based p32-binding peptides conjugated to a membrane-perturbing sequence.

SEQ ID NO: 11 is the amino acid sequence of an element was encoded by the phage genomic DNA and was thus not a part of the random linear library.

SEQ ID NO: 12 is the amino acid sequence of a pepta-peptide core present in certain exemplary TT1 Peptides.

SEQ ID NO: 13 is the amino acid sequence present in phage clones employed in certain in vitro p32 protein binding experiments.

SEQ ID NO: 14 is the amino acid sequence of a prototypic CendR peptide that binds to NRP-1 b1b2 domain.

SEQ ID NOs: 15 and 16 are the amino acid sequences of exemplary linkers.

SEQ ID NOs: 17 and 42-45 are the amino acid sequences of exemplary membrane-perturbing peptides.

SEQ ID NOs: 18-41 are the nucleotide and amino acid sequences of exemplary p32 gene products. Within SEQ ID NOs: 18-41, the even numbered sequences are exemplary nucleotide sequences and the odd-numbered sequences are the amino acid sequences encoded by the immediately preceding SEQ ID NO.

SEQ ID NOs: 42-159 are the amino acid sequences of exemplary homing peptides.

SEQ ID NOs: 160-174 are the amino acid sequences from peptides recovered from the X7 library.

SEQ ID NOs: 175-189 are the amino acid sequences from peptides recovered from the CX7C library.

SEQ ID NOs: 190-193 are the amino acid sequences of peptides recovered from phage that were selected against the NRP-1 b1 b2 domain.

SEQ ID NOs: 194-196 are the amino acid sequences of peptides recovered from phage that were selected against the p32 protein.

SEQ ID NOs: 197 and 198 are the WebLogo consensus sequences for peptides isolated from the X7 and CX7C libraries, respectively.

SEQ ID NO: 199 is the sequence of an LyP-1 peptides with an extra cysteine added to its N-terminus.

DETAILED DESCRIPTION

The disclosed method and compositions can be understood more readily by reference to the following detailed description of exemplary embodiments, the EXAMPLES included therein, and to the Figures and their previous and following descriptions.

Before the present compounds, compositions, articles, devices, and/or methods are disclosed and described, it is to be understood that they are not limited to specific synthetic methods or specific recombinant biotechnology methods unless otherwise specified, or to particular reagents unless otherwise specified, as such may, of course, vary. It is also to be understood that the terminology used herein is for the purpose of describing particular embodiments only and is not intended to be limiting.

I. Definitions

As used in the disclosure and the appended claims, the singular forms "a," "an", and "the" include plural referents unless the context clearly dictates otherwise. Thus, for example, reference to "a pharmaceutical carrier" includes mixtures of two or more such carriers, and the like.

As used in the claims, the term "comprising", which is synonymous with "including", "containing", and "characterized by", is inclusive or open-ended and does not exclude additional, unrecited elements and/or method steps. "Comprising" is a term of art that indicates that the named elements and/or steps are present, but that other elements and/or steps can be added and still fall within the scope of the relevant subject matter.

As used herein, the phrase "consisting of" excludes any element, step, and/or ingredient not specifically recited. For example, when the phrase "consists of" appears in a clause of the body of a claim, rather than immediately following the preamble, it limits only the element set forth in that clause; other elements are not excluded from the claim as a whole.

As used herein, the phrase "consisting essentially of" limits the scope of the related disclosure or claim to the specified materials and/or steps, plus those that do not materially affect the basic and novel characteristic(s) of the disclosed and/or claimed subject matter. For example, the peptides of the presently disclosed subject matter in some embodiments can "consist essentially of" a recited amino acid sequence, which indicates that the peptide can include one or more (e.g., 1, 2, 3, 4, 5, 6, or more) N-terminal and/or C-terminal amino acids the presence of which does not materially affect the desired biological activity of the peptide. In the context of the peptides disclosed herein, in some embodiments a peptide that "consists essentially of" a particularly enumerated amino acid sequence includes only that amino acid sequence but can include one or more additional amino acids at the N- and/or C-terminus (e.g., 1, 2, 3, 4, 5, or 6 amino acids at one or both termini) provided that the presence of the additional amino acids does not significantly (e.g., by no more than ±5%, ±10%, ±15%, ±20%, ±25%, ±30%, ±35%, ±35%, ±40%, ±45%, or 50%) increase or decrease the biological activity desired for the peptide as compared to the same biological activity of the peptide lacking the additional N- and/or C-terminal amino acids.

With respect to the terms "comprising", "consisting essentially of", and "consisting of", where one of these three terms is used herein, the presently disclosed subject matter can include the use of either of the other two terms. For example, the presently disclosed subject matter relates in some embodiments to compositions comprising the amino acid sequence KRGARST (SEQ ID NO: 1). It is understood that the presently disclosed subject matter thus also encompasses peptides that in some embodiments consist essentially of the amino acid sequence KRGARST (SEQ ID NO: 1); as well as peptides that in some embodiments consist of the amino acid sequence KRGARST (SEQ ID NO: 1). Similarly, it is also understood that the methods of the presently disclosed subject matter in some embodiments comprise the steps that are disclosed herein and/or that are recited in the claims, that they in some embodiments consist essentially of the steps that are disclosed herein and/or that are recited in the claims, and that they in some embodiments consist of the steps that are disclosed herein and/or that are recited in the claim.

For all terms defined herein below, grammatical variants are also encompassed by the definitions provided. For example, the term "modulate" is defined herein, and the definition provided is understood to apply mutatis mutandis to the terms "modulating", "modulated", "modulates", "modulator", etc.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself.

For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data are provided in a number of different formats, and that these data represent endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed. Similarly, when the context allows for data values to be expressed with one or more decimal places, each and every individual value between two data values that employ the relevant number of decimal places is also disclosed. By way of example and not limitation, if 10 and 12 are disclosed, it is understood that 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, and 11.9 are also disclosed.

In this disclosure and in the claims that follow, reference will be made to a number of terms which shall be defined to have the following meanings:

The terms "optional" and "optionally" mean that the subsequently described event or circumstance might or might not occur, and that the description includes instances where said event or circumstance occurs and instances where it does not. Similarly, optional elements are either present or absent in various embodiments of the presently disclosed subject matter, and it is understood that a claim that recites one or more optional elements encompasses the situation where one, some, or all of the optional elements are either present or absent in any combination or subcombination.

The term "activity" as used herein refers to a measurable result of the interaction of molecules. Some exemplary methods of measuring these activities are provided herein.

The term "modulate" as used herein refers to the ability of a compound or composition to change an activity (in some embodiments, a biological activity) in some measurable way as compared to an appropriate control. As a result of the presence of compounds in the assays, activities can increase or decrease as compared to controls in the absence of these compounds or compositions. An increase in an activity can be at least 10%, in some embodiments at least 20%, in some embodiments at least 25%, in some embodiments at least 50%, in some embodiments at least 60%, in some embodiments at least 70%, in some embodiments at least 75%, in some embodiments at least 80%, in some embodiments at least 85%, in some embodiments at least 90%, in some embodiments at least 95%, in some embodiments at least 100%, and in some embodiments greater than 100% compared to the level of activity in the absence of the compound or composition. Similarly, a decrease in an activity can be at least 10%, in some embodiments at least 20%, in some embodiments at least 25%, in some embodiments at least 50%, in some embodiments at least 60%, in some embodiments at least 70%, in some embodiments at least 75%, in some embodiments at least 80%, in some embodiments at least 90%, in some embodiments at least 95%, and in some embodiments at least 100% compared to the level of activity in the absence of the compound or composition. A modulator (in some embodiments a compound) that increases an activity is in some embodiments referred to as an "agonist", and one that decreases, or prevents an activity is in some embodiments referred to as an "antagonist."

As used herein, the term "inhibit" refers to reducing or decreasing an activity or expression. This can be a complete inhibition of activity or expression, or a partial inhibition. In some embodiments, inhibition can be compared to a control or to a standard level. Inhibition can be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% as compared to a given control or standard level of activity or expression.

The term "monitoring" as used herein refers to any method by which an activity, including but not limited to a biological activity, can be measured.

The term "providing" as used herein in the context of reagents refers to any method of adding a compound or molecule to something known in the art. EXAMPLES of providing can include the use of pipettes, pipettors, syringes, needles, tubing, guns, etc. Providing can be manual or automated. In some embodiments, it can include transfection by any methodology or any other method for providing nucleic acids to dishes, cells, tissue, and/or cell-free systems, and can relate to in vitro or in vivo manipulations.

The term "providing" as used herein in the context of a subject or patient refers to making the subject or patient, and/or a biological sample isolated therefrom, available for treatment and/or diagnosis.

As used herein, the term "preventing" refers to administering a compound prior to the onset of clinical symptoms of a disease or conditions so as to prevent a physical manifestation of aberrations associated with the disease or condition.

The term "treating" as used herein refers to administering a compound after the onset of clinical symptoms in order to ameliorate at least one such clinical symptom or any complication resulting therefrom.

The phrase "in need of treatment" as used herein refers to a judgment made by a caregiver (e.g., physician, nurse, nurse practitioner, or individual in the case of humans; veterinarian in the case of animals, including non-human mammals) that a subject or patient requires or will benefit from a given treatment. This judgment can be made based on a variety of factors that are in the realm of a care giver's expertise, but that can include the knowledge that the subject is ill, or will be ill, as the result of a condition that is treatable by compounds of the presently disclosed subject matter.

As used herein, the term "subject" includes, but is not limited to, animals, plants, bacteria, viruses, parasites, and any other organism or entity. The subject can in some embodiments be a vertebrate, in some embodiments a mammal (e.g., a human, horse, pig, rabbit, dog, sheep, goat, non-human primate, cow, cat, guinea pig, or rodent), a fish, a bird, a reptile, or an amphibian. The subject can in some embodiments be an invertebrate, in some embodiments an arthropod (e.g., an insects or a crustacean). The term does not denote a particular age or gender. Thus, adult and newborn subjects, as well as fetuses, whether male or female, are intended to be covered. The term "patient" refers to a subject afflicted with a disease or disorder or potentially at risk for developing a disease or disorder. The term "patient" includes in some embodiments humans and in some embodiments veterinary subjects.

The terms "higher," "increases", "elevates", and "elevation" refer to increases above basal levels, e.g., as compared to a control. The terms "low", "lower", "reduces", and "reduction" refer to decreases below basal levels, e.g., as compared to a control.

Throughout the instant disclosure, various publications are referenced. The disclosures of these publications are hereby incorporated by reference in their entireties into this application in order to more fully describe the state of the art to which this pertains. The references disclosed herein are also individually and specifically incorporated by reference for the material contained in them that is discussed in the sentence in which the reference is relied upon.

It is to be understood that the disclosed method and compositions are not limited to specific synthetic methods, specific analytical techniques, or to particular reagents unless otherwise specified, and, as such, can vary. It is also to be understood that the terminology used herein is for the purpose of describing exemplary embodiments only and is not intended to be limiting.

II. Compositions and Methods of Making the Same

Disclosed are exemplary components that can be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a particular peptide is disclosed and discussed and a number of modifications that can be made to a number of molecules including the peptide are discussed, specifically contemplated is each and every combination and permutation of the peptides and the modifications that are possible, unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

II.A. TT1 and gC1qR/p32

Disclosed are compositions useful for delivering significant amounts of compounds of interest to targeted cells and tissues. The disclosed compositions are useful, for example, to deliver to targeted cells and tissues an effective amount of compounds that are excessively toxic. For example, disclosed are compositions comprising a surface molecule, one or more homing molecules, and a plurality of cargo molecules. The cargo molecules can be, for example, excessively toxic molecules. The cargo molecules can be, for example, membrane perturbing molecules. As another example, disclosed are compositions comprising a surface molecule, one or more homing molecules, and a plurality of membrane perturbing molecules. As used herein, excessively toxic compounds are compounds that too toxic when administered to a subject in unconjugated forms in what would be a therapeutically effective amount but for the toxicity.

The homing molecules can home to targets of interest, such as cells and tissues of interest. For example, the homing molecules can home to tumor vasculature. The homing molecules can selectively home to targets of interest, such as cells and tissues of interest. For example, the homing molecules can selectively home to tumor vasculature. The composition can home to one or more of the sites to be targeted. The composition can be internalized in cells. The composition can penetrate tissue. The composition can be internalized into cells at the targeted site. The composition can penetrate tissue at the targeted site. The composition can, for example be internalized into cancer cells. The composition can, for example, penetrate tumor tissue. The composition can, for example, bind inside tumor blood vessels.

Disclosed herein is the discovery that exemplary TT1 Family Peptides (including but not limited to KRGARST (SEQ ID NO: 1), AKRGARSTA (SEQ ID NO: 2), and CKRGARSTC (SEQ ID NO: 3); also referred to herein as "TT1" and/or "the TT1 Peptides") selectively interacts with the gC1q receptor (gC1qR/p32, which has been described in the literature by one of the alternative terms gC1qR and p32, and is described herein as either gC1qR, gC1q receptor, p32, or as gC1qR/p32, and which refers to the protein known in the literature as gC1qR and as p32). gC1qR/p32 is associated with tumor lymphatic vasculature, for example, the lymphatic vasculature of breast cancer tumors, squamous carcinomas, and osteosarcomas. gC1qR/p32 is also associated with inflammation (Waggoner et al., 2005, herein incorporated by reference in its entirety). Exemplary gC1qR nucleotide and amino acid sequences are presented herein below in Table 1.

TABLE 1

Exemplary gC1qR Nucleotide and Amino Acid Sequences

| Species | Nucleotide[1] | Amino Acid[1] |
|---|---|---|
| Homo sapiens | NM_001212 (SEQ ID NO: 18) | NP_001203 (SEQ ID NO: 19) |
| Gorilla gorilla gorilla | XM_004058391 (SEQ ID NO: 20) | XP_004058439 (SEQ ID NO: 21) |
| Pongo abelii | XM_002826905 (SEQ ID NO: 22) | XP_002826951 (SEQ ID NO: 23) |
| Macaca fascicularis | XM_005582637 (SEQ ID NO: 24) | XP_005582694 (SEQ ID NO: 25) |
| Macaca mulatto | XM_001100940 (SEQ ID NO: 26) | XP_001100940 (SEQ ID NO: 27) |
| Callithrix jacchus | XM_002748302 (SEQ ID NO: 28) | XP_002748348 (SEQ ID NO: 29) |
| Rattus norvegicus | NM_019259 (SEQ ID NO: 30) | NP_062132 (SEQ ID NO: 31) |
| Mus musculus | NM_007573 (SEQ ID NO: 32) | NP_031599 (SEQ ID NO: 33) |
| Bos taurus | NM_001034527 (SEQ ID NO: 34) | NP_001029699 (SEQ ID NO: 35) |
| Felis catus | XM_006939728 (SEQ ID NO: 36) | XP_006939790 (SEQ ID NO: 37) |
| Canis lupus familiaris | XM_546568 (SEQ ID NO: 38) | XP_546568 (SEQ ID NO: 39) |
| Equus caballus | XM_001918118 (SEQ ID NO: 40) | XP_001918153 (SEQ ID NO: 41) |

[1]Listed are exemplary GENBANK ® biosequence database Accession Nos.

As disclosed herein, the interaction of the exemplary TT1 Peptides of SEQ ID NOs: 1-3 and gC1qR/p32 was identified. Based on these findings, disclosed herein are TT1 Family Peptide compositions useful in diseases and disorders associated with gC1qR/p32. For example, the TT1 Family Peptide compositions disclosed herein are useful for reducing or preventing tumor metastasis in cancer patients having a primary tumor. The TT1 Family Peptide compositions can be administered, for example, to a subject having pre-metastatic breast or bone cancer or to a subject having early or late stage metastatic breast or bone cancer. TT1 Family Peptide polypeptides can also be useful, for example, for imaging tumor lymphatic vasculature, such as breast cancer or osteosarcoma lymphatic vasculature. The disclosed compositions are also useful for reducing or preventing inflammation in patients in need thereof.

Thus, disclosed herein are isolated peptides or peptidomimetic containing the pentapeptide amino acid motif RGXRS (SEQ ID NO: 4), or a peptidomimetic thereof. The presently disclosed subject matter further provides an isolated peptide or peptidomimetic containing the amino acid sequence KRGARST (SEQ ID NO: 1), the amino acid sequence AKRGARSTA (SEQ ID NO: 2), or the amino acid sequence CKRGARSTC (SEQ ID NO: 3) or a peptidomimetic thereof. Disclosed are compositions, such as those comprising a member of the TT1 Family of Peptides, that selectively interact with tumors and sites of inflammation, as well as other diseases and disorders associated with gC1qR/p32. A variety of TT1 Peptide compositions can be used in the disclosed methods. Such compositions include, without limitation, peptides as disclosed herein. The disclosed compounds, compositions, molecules, and methods can include or use the disclosed TT1 Peptide compositions in various forms, including peptides and peptidomimetics as disclosed. For convenience of expression, in many places herein the use or inclusion of peptides will be recited. It is understood that, in such cases, it is considered that TT1 Peptide compositions in various forms can also be used or included in the same or similar ways as is described in terms of peptides, and such use and inclusion is specifically contemplated and disclosed thereby.

There are multiple diseases and disorders associated with the gC1q/p32 receptor expression at the cell surface. Examples include, but are not limited to, cancer, atherosclerosis, and inflammation.

The composition comprising members of the TT1 Family of Peptides can further comprise a moiety. Examples of moieties include, but are not limited to, therapeutic or diagnostic moieties. Therapeutic moieties can include anti-angiogenic agents or cytotoxic agents. The therapeutic moiety can target a DNA-associated process. The therapeutic moiety can be selected from the group consisting of an alkylating agent, an anti-tumor antibiotic and a sequence-selective agent. Other examples of therapeutic moieties include cyclophosphamide, melphalan, mitomycin C, bizelesin, cisplatin, doxorubicin, etoposide, mitoxantrone, SN-38, Et-743, actinomycin D, bleomycin, geldanamycin, chlorambucil, methotrexate, and TLK286. The moiety can also be a nanoparticle.

Disclosed are methods of detecting the presence of gC1q/p32 receptor, the method comprising bringing into contact a cell and a TT1 Peptide composition, wherein the TT1 Peptide composition comprises a moiety linked to a composition comprising the amino acid sequence KRGARST (SEQ ID NO: 1), the amino acid sequence AKRGARSTA (SEQ ID NO: 2), or the amino acid sequence CKRGARSTC (SEQ ID NO: 3); and detecting interaction between gC1q/p32 receptor and the TT1 Peptide composition, thereby detecting the presence of gC1q/p32 receptor. The gC1q/p32 receptor can be, for example, on or in a cell. The cell can be in any context, such as in an organism, in situ, ex vivo, in culture, and/or in vitro.

The moiety can be a detectable moiety. Examples of such moieties include, but are not limited to, a polypeptide, a nucleic acid molecule, a small molecule, a fluorophore, fluorescein, rhodamine, a radionuclide, indium-111, technetium-99, carbon-11, carbon-13, or a combination thereof.

The TT1 Peptide composition being brought into contact with the cell described above can comprise a virus in one example. The TT1 Peptide composition can also comprise a phage.

By "selectively interacts with" is meant that a stated compound or material can preferentially interact with a stated target compared with non-targets. Thus, for example, in vivo, a TT1 Peptide can preferentially interact with the gC1qR/p32 as compared to non-target.

Therefore, when gC1qR/p32 is associated with a cancerous cell, or a site of inflammation, a TT1 Peptide will interact with the cancerous cell or site of inflammation preferentially, as compared to a non-cancerous cell, or a site without inflammation. Selective or preferential interaction with, for example, tumors, generally is characterized by at least a two-fold or greater localization at the cancerous site. A TT1 Peptide can be characterized by 5-fold, 10-fold, 20-fold, or more preferential localization to cancerous sites such as tumors, as compared to several or many tissue types of non-tumoral tissue, or as compared to most or all non-tumoral tissue. Thus, it is understood that, in some cases, a TT1 Peptide interacts with, in part, one or more normal organs in addition to those with gC1qR/p32 present. Selective interaction can also be referred to as targeting or homing.

As discussed above, selectively interacting with, including preferential and/or selective homing, does not mean that a TT1 Peptide does not bind to any normal and/or non-targeted areas. In some embodiments, interaction selectivity can be, for example, at least about 20-fold, at least about 30-fold, at least about 50-fold, at least about 75-fold, at least about 100-fold, at least about 150-fold, or at least about 200-fold selective for a corresponding target.

Selective interaction can be, for example, in terms of relative amounts or in terms of relative Ki over other non-target components. In some embodiments, a TT1 Peptide can have at least about a 50-fold selectivity, at least about a 100-fold selectivity, at least about a 200-fold selectivity, at least about a 300-fold selectivity, at least about a 400-fold selectivity, at least about a 500-fold selectivity, at least about a 600-fold selectivity, at least about a 700-fold selectivity, at least about an 800-fold selectivity, at least about a 1000-fold selectivity, or at least about a 1500-fold selectivity to a corresponding target. For example, a TT1 Peptide can have a Ki value against a target of in some embodiments less than about 200 nM, in some embodiments less than about 150 nM, in some embodiments less than about 100 nM, or in some embodiments less than about 75 nM. A TT1 Peptide can have a Ki value against a target of in some embodiments more than about 50 nM, in some embodiments more than about 25 nM, in some embodiments more than about 20 nM, in some embodiments more than about 15 nM, in some embodiments more than about 10 nM, in some embodiments more than about 5 nM, in some embodiments more than about 3 nM, and in some embodiments more than about 1 nM. The targeting moiety can bind its target with a dissociation constant ($k_D$) in some embodiments less than about $10^{-8}$ M, in some embodiments less than about $10^{-9}$ M, in some embodiments less than about $10^{-10}$ M, in some embodiments less than about $10^{-11}$ M, in some embodiments less than about $10^{-12}$ M, in some embodiments less than about $10^{-13}$ M, and in some embodiments less than about $10^{-14}$ M.

II.B. gC1q/p32 Receptor

It has been found that knocking down gC1qR/p32 expression in tumor cells shifted their metabolism toward glycolysis and that, surprisingly, the glycolytic phenotype was associated with impaired tumor cell survival and growth, especially under adverse growth conditions (see EXAMPLE 2 of U.S. Pat. No. 8,178,104). At the same time, tumorigenicity of the gC1qR/p32 knockdown cells was reduced. Therefore, disclosed herein are methods of targeting the gC1q/p32 receptor in order to treat gC1q/p32 receptor-related disorders and diseases, as described herein. An example of such a disease is cancer.

Also disclosed herein is a method of treating a disease in a subject associated with gC1q/p32 receptor, the method comprising administering to the subject a composition that modulates gC1q/p32 receptor expression or activity, thereby treating a disease in a subject associated with the gC1q/p32 receptor. The subject can have cancer. Expression or activity of the gC1q/p32 receptor can be inhibited. This can occur by the use of interfering nucleic acid, such as shRNA or siRNA. In some embodiments, activity of the gC1q/p32 receptor can be inhibited by a TT1 Peptide, an antibody, and/or a small molecule mimic of a TT1 Peptide. The methods of treating cancer disclosed herein can be used in conjunction with other treatment therapies as well, as described below in the section relating to moieties.

Disclosed herein are subjects having a disease associated with the gC1q/p32 receptor. By this is meant that in some embodiments the subject has either an increased level of gC1q/p32 receptor, a decreased level of gC1q/p32 receptor, or that the gC1q/p32 receptor can be targeted to treat or ameliorate the symptoms of a disease or disorder. By an "increased level of gC1q/p32 receptor" is meant that the number of gC1q/p32 receptors in the subject as a whole is increased over normal, basal, or standard levels accepted by those of skill in the art. It can also mean that the number of gC1q/p32 receptors present in a given cell is increased over a basal, normal, or standard amount. By a "decreased level of gC1q/p32 receptor" is meant that the number of gC1q/p32 receptors in the subject as a whole is deceased over normal, basal, or standard levels accepted by those of skill in the art. It can also mean that the number of gC1q/p32 receptors present in a given cell are decreased over a basal, normal, or standard amount. One of skill in the art would be able to determine gC1q/p32 levels in a subject as a whole, as well as in individual cells, using the methods disclosed herein and those known to those of skill in the art. One method of doing so involves using a composition comprising a TT1 Peptide, as disclosed herein. Diseases associated with the gC1q/p32 receptor include cancer, for example. In some embodiments, the subject has an increased level of gC1q/p32 receptor at the cell surface over normal (i.e., the same cell type in a subject that does not have the relevant disease or disorder), basal, or standard levels accepted by those of skill in the art, permitting the gC1q/p32 receptor to be targeted to treat or ameliorate the symptoms of the relevant disease or disorder.

II.C. Peptides and Peptidomimetics

Disclosed are compositions related to isolated TT1 Family Peptides comprising in some embodiments the amino acid sequence KRGARST (SEQ ID NO: 1), the amino acid sequence AKRGARSTA (SEQ ID NO: 2), or the amino acid sequence CKRGARSTC (SEQ ID NO: 3). The isolated peptides can comprise, for example, SEQ ID NO: 1, SEQ ID NO: 2, or SEQ ID NO: 3, an amino acid sequence at least about 90% identical to SEQ ID NO: 1, SEQ ID NO: 2, or SEQ ID NO: 3, or the amino acid sequence of SEQ ID NO: 1, SEQ ID NO: 2, or SEQ ID NO: 3 having one or more conservative amino acid substitutions. The peptide can be at least about 90%, 80%, 70%, or 60% identical to the amino acid sequence of SEQ ID NO: 1, SEQ ID NO: 2, or SEQ ID NO: 3. The amino acid sequence of SEQ ID NO: 1, SEQ ID NO: 2, or SEQ ID NO: 3 can have one, two, three, four, five, six, seven, eight, or nine conservative amino acid substitutions, for example. The peptide can comprise a chimera of the amino acid sequence SEQ ID NO: 1, SEQ ID NO: 2, or SEQ ID NO: 3. Such a chimera can be additive, where sequence of one sequence is added to another sequence, substitutional, where sequence of one sequence is substituted for sequence of another sequence, or a combination. As used herein in reference to a specified amino acid sequence, a "conservative variant" is a sequence in which a first amino acid is replaced by another amino acid or amino acid analog having at least one biochemical property similar to that of the first amino acid; similar properties include, for example, similar size, charge, hydrophobicity or hydrogen-bonding capacity.

The amino acid sequence can be linear, circular, or cyclic. The amino acid segment can be circularized or cyclized via any suitable linkage, for example, a disulfide bond.

The disclosed peptides can be in isolated form. As used herein in reference to the disclosed peptides, the term "isolated" means a peptide that is in a form that is relatively free from material such as contaminating polypeptides, lipids, nucleic acids, and other cellular material that normally is associated with the peptide in a cell or that is associated with the peptide in a library or in a crude preparation.

The disclosed peptides can have any suitable length. The disclosed peptides can have, for example, a relatively short length of less than six, seven, eight, nine, ten, 12, 15, 20, 25, 30, 35, 40, 45, or 50 residues. The disclosed peptides also can be useful in the context of a significantly longer sequence. Thus, the peptides can have, for example, a length of up to 75, 100, 150, 200, 250, 300, 400, 500, 1000 or 2000 residues. In some embodiments, a peptide can have a length of at least 8, 9, 10, 20, 30, 40, 50, 60, 70, 80, 90, 100, or 200 residues. In some embodiments, a peptide can have a length of 5 to 200 residues, 5 to 100 residues, 5 to 90 residues, 5 to 80 residues, 5 to 70 residues, 5 to 60 residues, 5 to 50 residues, 5 to 40 residues, 5 to 30 residues, 5 to 20 residues, 5 to 15 residues, 5 to 10 residues, 10 to 200 residues, 10 to 100 residues, 10 to 90 residues, 10 to 80 residues, 10 to 70 residues, 10 to 60 residues, 10 to 50 residues, 10 to 40 residues, 10 to 30 residues, 10 to 20 residues, 20 to 200 residues, 20 to 100 residues, 20 to 90 residues, 20 to 80 residues, 20 to 70 residues, 20 to 60 residues, 20 to 50 residues, 20 to 40 residues or 20 to 30 residues. As used herein, the term "residue" refers to an amino acid or amino acid analog.

As this specification discusses various proteins, protein sequences, peptides, peptides sequences, and amino acid sequences, it is understood that the nucleic acids that can encode those sequences are also disclosed. This would include all degenerate sequences related to a specific protein sequence, i.e., all nucleic acids having a sequence that encodes one particular protein sequence as well as all nucleic acids, including degenerate nucleic acids, encoding the disclosed variants and derivatives of the protein sequences. Thus, while each particular nucleic acid sequence may not be written out herein, it is understood that each and every sequence is in fact disclosed and described herein through the disclosed protein sequence. The disclosed peptides and proteins can be coupled to each other via peptide bonds to form fusion peptides and proteins.

The disclosed peptides and amino acid segments can be modified. As used herein, a "methylated derivative" of a protein, peptide, amino acid segment, amino acid sequence, etc. refers to a form of the protein, peptide, amino acid segment, amino acid sequence, etc. that is methylated. Unless the context indicates otherwise, reference to a methylated derivative of a protein, peptide, amino acid segment, amino acid sequence, etc. does not include any modification to the base protein, peptide, amino acid segment, amino acid sequence, etc. other than methylation. Methylated derivatives can also have other modifications, but such modifications generally will be noted. For example, conservative variants of an amino acid sequence would include conservative amino acid substitutions of the based amino acid sequence. Thus, reference to, for example, a "methylated derivative" of a specific amino acid sequence "and conservative variants thereof" would include methylated forms of the specific amino acid sequence and methylated forms of the conservative variants of the specific amino acid sequence, but not any other modifications of derivations. As another example, reference to a methylated derivative of an amino acid segment that includes amino acid substitutions would include methylated forms of the amino acid sequence of the amino acid segment and methylated forms of the amino acid sequence of the amino acid segment include amino acid substitutions.

Protein variants and derivatives are well understood by those of skill in the art and in can involve amino acid sequence modifications. For example, amino acid sequence modifications typically fall into one or more of three classes: substitutional, insertional, or deletional variants. Insertions include amino and/or carboxyl terminal fusions as well as intrasequence insertions of single or multiple amino acid residues. Insertions ordinarily will be smaller insertions than those of amino or carboxyl terminal fusions, for example, on the order of one to four residues. Immunogenic fusion protein derivatives, such as those described in the examples, are made by fusing a polypeptide sufficiently large to confer immunogenicity to the target sequence by cross-linking in vitro or by recombinant cell culture transformed with DNA encoding the fusion. Deletions are characterized by the removal of one or more amino acid residues from the protein sequence. Typically, no more than about from 2 to 6 residues are deleted at any one site within the protein molecule. These variants ordinarily are prepared by site specific mutagenesis of nucleotides in the DNA encoding the protein, thereby producing DNA encoding the variant, and thereafter expressing the DNA in recombinant cell culture. Techniques for making substitution mutations at predetermined sites in DNA having a known sequence are well known, for example M13 primer mutagenesis and PCR mutagenesis. Amino acid substitutions are typically of single residues, but can occur at a number of different locations at once; insertions usually will be on the order of about from 1 to 10 amino acid residues; and deletions will range about from 1 to 30 residues. Deletions or insertions preferably are made in adjacent pairs, i.e. a deletion of 2 residues or insertion of 2 residues. Substitutions, deletions, insertions or any combination thereof can be combined to arrive at a final construct. The mutations must not place the sequence out of reading frame and preferably will not create complementary regions that could produce secondary mRNA structure.

As used herein in reference to a specified amino acid sequence, a "conservative variant" is a sequence in which a first amino acid is replaced by another amino acid or amino acid analog having at least one biochemical property similar to that of the first amino acid; similar properties include, for example, similar size, charge, hydrophobicity or hydrogen-bonding capacity. Conservative variants are also referred to herein as "conservative amino acid substitutions," "conservative amino acid variants," "conservative substitutions," and similar phrase. A "conservative derivative" of a reference sequence refers to an amino acid sequence that differs from the reference sequences only in conservative substitutions.

As an example, a conservative variant can be a sequence in which a first uncharged polar amino acid is conservatively substituted with a second (non-identical) uncharged polar amino acid such as cysteine, serine, threonine, tyrosine, glycine, glutamine, or asparagine or an analog thereof. A conservative variant also can be a sequence in which a first basic amino acid is conservatively substituted with a second basic amino acid such as arginine, lysine, histidine, 5-hydroxylysine, N-methyllysine, or an analog thereof. Similarly, a conservative variant can be a sequence in which a first hydrophobic amino acid is conservatively substituted with a second hydrophobic amino acid such as alanine, valine, leucine, isoleucine, proline, methionine, phenylalanine, or tryptophan or an analog thereof. In the same way, a conservative variant can be a sequence in which a first acidic amino acid is conservatively substituted with a second acidic amino acid such as aspartic acid or glutamic acid or an analog thereof, a sequence in which an aromatic amino acid such as phenylalanine is conservatively substituted with a second aromatic amino acid or amino acid analog, for example, tyrosine; or a sequence in which a first relatively small amino acid such as alanine is substituted with a second relatively small amino acid or amino acid analog such as glycine or valine or an analog thereof. For example, the replacement of one amino acid residue with another that is biologically and/or chemically similar is known to those skilled in the art as a conservative substitution. For example, a conservative substitution would be replacing one hydrophobic residue for another, or one polar residue for another. The substitutions include combinations such as, for example, Gly, Ala; Val, Ile, Leu; Asp, Glu; Asn, Gln; Ser, Thr; Lys, Arg; and Phe, Tyr. Such conservatively substituted variations of each explicitly disclosed sequence are included within the mosaic polypeptides provided herein. It is understood that conservative variants of the disclosed amino acid sequences can encompass sequences containing, for example, one, two, three, four or more amino acid substitutions relative to the reference sequence, and that such variants can include naturally and non-naturally occurring amino acid analogs.

Substitutional variants are those in which at least one residue has been removed and a different residue inserted in its place. Non-limiting examples of such substitutions, referred to as conservative substitutions, can generally be made in accordance with the following Table 2.

TABLE 2

Amino Acid Substitutions

| Original Amino Acid | Conservative Substitutions |
|---|---|
| Ala | Ser |
| Arg | Lys; Gln |
| Asn | Gln; His |
| Asp | Glu |
| Cys | Ser |
| Gln | Asn; Lys |
| Glu | Asp |
| Gly | Pro |
| His | Asn; Gln |
| Ile | Leu; Val |
| Leu | Ile; Val |
| Lys | Arg; Gln |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

In some embodiments, a conservative substitution can be based on the relative similarity of the amino acid side-chain substituents. See Henikoff & Henikoff, 2000. Exemplary factors that can be considered in making conservative substitutions include side-chain hydrophobicity, hydrophilicity, charge, and size. For example, arginine, lysine, and histidine are all positively charged residues; alanine, glycine, and serine are all of similar size; and phenylalanine, tryptophan, and tyrosine all have a generally similar shape. By this analysis, arginine, lysine, and histidine; alanine, glycine, and serine; and phenylalanine, tryptophan, and tyrosine; are defined herein to be conservative substitutions.

In making conservative substitutions, the hydropathic index of amino acids can be considered. Each amino acid has been assigned a hydropathic index on the basis of its hydrophobicity and charge characteristics, these are: isoleucine (+4.5); valine (+4.2); leucine (+3.8); phenylalanine (+2.8); cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is generally understood in the art (Kyte et al., 1982). It is known that certain amino acids can be substituted for other amino acids having a similar hydropathic index or score and still retain a similar biological activity. In making changes based upon the hydropathic index, the substitution of amino acids whose hydropathic indices are in some embodiments within 2 of the original value can be made, those that are in some embodiments within 1 of the original value can be made, and those that are in some embodiments within 0.5 of the original value can be made.

It is also understood in the art that a conservative substitutions can be made effectively on the basis of hydrophilicity. U.S. Pat. No. 4,554,101 states that the greatest local average hydrophilicity of a protein, as governed by the hydrophilicity of its adjacent amino acids, correlates with its immunogenicity and antigenicity, e.g., with a biological property of the protein. It is understood that an amino acid can be substituted for another having a similar hydrophilicity value and still obtain a biologically equivalent protein.

Thus, and as detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

In making conservative substitutions based upon similar hydrophilicity values, the substitution of amino acids whose hydrophilicity values are in some embodiments within 2 of the original value can be made, those that are in some embodiments within 1 of the original value can be made, and those in some embodiments within 0.5 of the original value can be made.

Substantial changes in function or immunological identity can be made by selecting substitutions that are less conservative, i.e., selecting residues that differ more significantly in their effect on maintaining (a) the structure of the polypeptide backbone in the area of the substitution, for example as a sheet or helical conformation, (b) the charge or hydrophobicity of the molecule at the target site or (c) the bulk of the side chain. The substitutions which in general are expected to produce the greatest changes in the protein properties will be those in which (a) a hydrophilic residue, e.g., a seryl or threonyl, is substituted for (or by) a hydrophobic residue, e.g., leucyl, isoleucyl, phenylalanyl, valyl, or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine, in this case, (e) by increasing the number of sites for sulfation and/or glycosylation. These can be referred to as less conservative variants.

Peptides can have a variety of modifications. Modifications can be used to change or improve the properties of the peptides. For example, the disclosed peptides can be N-methylated, O-methylated, S-methylated, C-methylated, or a combination at one or more amino acids.

The amino and/or carboxy termini of the disclosed peptides can be modified. Amino terminus modifications include methylation (e.g., —NHCH$_3$ or —N(CH$_3$)$_2$), acetylation (e.g., with acetic acid or a halogenated derivative thereof such as α-chloroacetic acid, α-bromoacetic acid, or α-iodoacetic acid), adding a benzyloxycarbonyl (Cbz) group, or blocking the amino terminus with any blocking group containing a carboxylate functionality defined by RCOO— or sulfonyl functionality defined by R-SO2-, where R is selected from the group consisting of alkyl, aryl, heteroaryl, alkyl aryl, and the like, and similar groups. One can also incorporate a desamino acid at the N-terminus (so that there is no N-terminal amino group) to decrease susceptibility to proteases or to restrict the conformation of the peptide compound. In preferred embodiments, the N-terminus is acetylated with acetic acid or acetic anhydride.

Carboxy terminus modifications include replacing the free acid with a carboxamide group or forming a cyclic lactam at the carboxy terminus to introduce structural constraints. One can also cyclize the disclosed peptides, or incorporate a desamino or descarboxy residue at the termini of the peptide, so that there is no terminal amino or carboxyl group, to decrease susceptibility to proteases or to restrict the conformation of the peptide. C-terminal functional groups of the disclosed peptides include amide, amide lower alkyl, amide di(lower alkyl), lower alkoxy, hydroxy, and carboxy, and the lower ester derivatives thereof, and the pharmaceutically acceptable salts thereof.

One can replace the naturally occurring side chains of the genetically encoded amino acids (or the stereoisomeric D amino acids) with other side chains, for instance with groups such as alkyl, lower ($C_{1-6}$) alkyl, cyclic 4-, 5-, 6-, to 7-membered alkyl, amide, amide lower alkyl amide di(lower alkyl), lower alkoxy, hydroxy, carboxy and the lower ester derivatives thereof, and with 4-, 5-, 6-, to 7-membered heterocyclic. In particular, proline analogues in which the ring size of the proline residue is changed from 5 members to 4, 6, or 7 members can be employed. Cyclic groups can be saturated or unsaturated, and if unsaturated, can be aromatic or non-aromatic. Heterocyclic groups preferably contain one or more nitrogen, oxygen, and/or sulfur heteroatoms. Examples of such groups include the furazanyl, furyl, imidazolidinyl, imidazolyl, imidazolinyl, isothiazolyl, isoxazolyl, morpholinyl (e.g., morpholino), oxazolyl, piperazinyl (e.g., 1-piperazinyl), piperidyl (e.g., 1-piperidyl, piperidino), pyranyl, pyrazinyl, pyrazolidinyl, pyrazolinyl, pyrazolyl, pyridazinyl, pyridyl, pyrimidinyl, pyrrolidinyl (e.g., 1-pyrrolidinyl), pyrrolinyl, pyrrolyl, thiadiazolyl, thiazolyl, thienyl, thiomorpholinyl (e.g., thiomorpholino), and triazolyl. These heterocyclic groups can be substituted or unsubstituted. Where a group is substituted, the substituent can be alkyl, alkoxy, halogen, oxygen, or substituted or unsubstituted phenyl.

One can also readily modify peptides by phosphorylation, and other methods (e.g., as described in Hruby et al., 1990).

The disclosed peptides also serve as structural models for non-peptidic compounds with similar biological activity. Those of skill in the art recognize that a variety of techniques are available for constructing compounds with the same or similar desired biological activity as the lead peptide compound, but with more favorable activity than the lead with respect to solubility, stability, and susceptibility to hydrolysis and proteolysis (see Morgan & Gainor, 1989). These techniques include, but are not limited to, replacing the peptide backbone with a backbone composed of phosphonates, amidates, carbamates, sulfonamides, secondary amines, and N-methylamino acids.

Molecules can be produced that resemble peptides, but which are not connected via a natural peptide linkage. For example, linkages for amino acids or amino acid analogs can include —$CH_2NH$—, —$CH_2S$—, —$CH_2$—$CH_2$—, —CH═CH— (cis and trans), —$COCH_2$—, —CH(OH) $CH_2$—, and —$CHH_2SO$—. These and others can be found in Spatola, 1983a; Spatola, 1983b (general review); Morley, 1980; Hudson et al., 1979 (—$CH_2NH$—, $CH_2CH_2$—); Spatola et al., 1986 (—$CHH_2$—S); Hann, 1982 (—CH—CH—, cis and trans); Almquist et al., 1980 (—$COCH_2$—); Jennings-White et al., 1982 (—$COCH_2$—); European Patent Application Publication No. EP 0045665 (—CH(OH) $CH_2$—); Holladay et al., 1983 (—C(OH)$CH_2$—); and Hruby, 1982 (—$CH_2$—S—); each of which is incorporated herein by reference. An exemplary non-peptide linkage is —$CH_2NH$—. It is understood that peptide analogs can have more than one atom between the bond atoms, such as β-alanine, γ-aminobutyric acid, and the like.

Substitutional or deletional mutagenesis can be employed to insert sites for N-glycosylation (Asn-X-Thr/Ser) or O-glycosylation (Ser or Thr). Deletions of cysteine or other labile residues also can be desirable. Deletions or substitutions of potential proteolysis sites, e.g., Arg, can be accomplished, for example, by deleting one of the basic residues or substituting one by glutaminyl or histidyl residues.

Certain post-translational derivatizations can be the result of the action of recombinant host cells on the expressed polypeptide. Glutaminyl and asparaginyl residues are frequently post-translationally deamidated to the corresponding glutamyl and aspartyl residues. Alternatively, these residues are deamidated under mildly acidic conditions. Other post-translational modifications include hydroxylation of proline and lysine, phosphorylation of hydroxyl groups of seryl or threonyl residues, methylation of the o-amino groups of lysine, arginine, and histidine side chains (Creighton, 1983), acetylation of the N-terminal amine and, in some instances, amidation of the C-terminal carboxyl.

It is understood that one way to define the variants and derivatives of the disclosed amino acids sequences, amino acid segments, peptides, proteins, etc. herein is through defining the variants and derivatives in terms of homology/identity to specific known sequences. For example, specifically disclosed are variants of these and other amino acids sequences, amino acid segments, peptides, proteins, etc. herein disclosed which have at least, 70% or 75% or 80% or 85% or 90% or 95% homology to the stated sequence. Those of skill in the art readily understand how to determine the homology of two proteins. For example, the homology can be calculated after aligning the two sequences so that the homology is at its highest level.

Another way of calculating homology can be performed by published algorithms. Optimal alignment of sequences for comparison can be conducted by the local homology algorithm of Smith & Waterman, 1981, by the homology alignment algorithm of Needleman & Wunsch, 1970, by the search for similarity method of Pearson & Lipman, 1988, by computerized implementations of these algorithms (GAP, BESTFIT, FASTA, and TFASTA in the Wisconsin Genetics Software Package, Genetics Computer Group, 575 Science Dr., Madison, Wis., United States of America), or by inspection.

The same types of homology can be obtained for nucleic acids by for example the algorithms disclosed in Zuker, 1989; Jaeger et al., 1989a; Jaeger et al., 1989bl each of which is herein incorporated by reference for at least material related to nucleic acid alignment.

It is understood that the description of conservative variants and homology can be combined together in any combination, such as embodiments that have at least 70% homology to a particular sequence wherein the variants are conservative variants.

As this specification discusses various amino acids sequences, amino acid segment sequences, peptide sequences, protein sequences, etc., it is understood that nucleic acids that can encode those sequences are also disclosed. This would include all degenerate sequences related to a specific amino acid sequence, i.e. all nucleic acids having a sequence that encodes one particular amino acid sequence as well as all nucleic acids, including degenerate nucleic acids, encoding the disclosed variants and derivatives of the amino acid sequences. Thus, while each particular nucleic acid sequence may not be written out herein, it is understood that each and every sequence is in fact disclosed and described herein through the disclosed amino acid sequences.

Also disclosed are bifunctional peptides, which contain a TT1 Peptide fused to a second peptide having a separate function. Such bifunctional peptides have at least two functions conferred by different portions of the full-length molecule and can, for example, display anti-angiogenic activity or pro-apoptotic activity in addition to the ability to selectively interact with gC1qR/p32.

Also disclosed are isolated multivalent peptides that include at least two subsequences each independently containing a peptide (for example, the amino acid sequence of SEQ ID NO: 1, SEQ ID NO: 2, or SEQ ID NO: 3, or a conservative variant or peptidomimetic thereof). The multivalent peptide can have, for example, at least three, at least five, or at least ten of such subsequences each independently containing a peptide. In particular embodiments, the multivalent peptide can have two, three, four, five, six, seven, eight, nine, ten, fifteen, or twenty identical or non-identical subsequences. In a further embodiment, the multivalent peptide can contain identical subsequences, such as repeats of SEQ ID NO: 1, SEQ ID NO: 2, and/or SEQ ID NO: 3. In a further embodiment, the multivalent peptide contains contiguous identical or non-identical subsequences, which are not separated by any intervening amino acids. In yet further embodiments, the multivalent peptide can be cyclic or otherwise conformationally constrained. In one example, the peptide can be circularized or cyclized via a disulfide bond.

As used herein, the term "peptide" is used broadly to mean peptides, proteins, fragments of proteins and the like. The term "peptidomimetic", as used herein, means a peptide-like molecule that has the activity of the peptide upon which it is structurally based. Such peptidomimetics include chemically modified peptides, peptide-like molecules containing non-naturally occurring amino acids, and peptoids and have an activity such as selective interaction with a target of the peptide upon which the peptidomimetic is derived (see e.g., Goodman & Ro, 1995.

A variety of peptidomimetics are known in the art including, for example, peptide-like molecules which contain a constrained amino acid, a non-peptide component that mimics peptide secondary structure, or an amide bond isostere. A peptidomimetic that contains a constrained, non-naturally occurring amino acid can include, for example, an $\alpha$-methylated amino acid; $\alpha,\alpha$-dialkylglycine or $\alpha$-aminocycloalkane carboxylic acid; an $N^\alpha$-$C^\alpha$ cyclized amino acid; an $N^\alpha$-methylated amino acid; $\beta$- or $\gamma$-amino cycloalkane carboxylic acid; an $\alpha,\beta$-unsaturated amino acid; a $\beta,\beta$-dimethyl or $\beta$-methyl amino acid; a $\beta$-substituted-2,3-methano amino acid; an N—$C^{\delta}$ or $C^\alpha$-$C^\Delta$ cyclized amino acid; a substituted proline or another amino acid mimetic. A peptidomimetic which mimics peptide secondary structure can contain, for example, a non-peptidic $\beta$-turn mimic; $\gamma$-turn mimic; mimic of f-sheet structure; or mimic of helical structure, each of which is well known in the art. A peptidomimetic also can be a peptide-like molecule which contains, for example, an amide bond isostere such as a retro-inverso modification; reduced amide bond; methylenethioether or methylenesulfoxide bond; methylene ether bond; ethylene bond; thioamide bond; trans-olefin or fluoroolefin bond; 1,5-disubstituted tetrazole ring; ketomethylene or fluoroketomethylene bond or another amide isostere. One skilled in the art understands that these and other peptidomimetics are encompassed within the meaning of the term "peptidomimetic" as used herein.

Methods for identifying a peptidomimetic are well known in the art and include, for example, the screening of databases that contain libraries of potential peptidomimetics. As an example, the Cambridge Structural Database contains a collection of greater than 300,000 compounds that have known crystal structures (see Allen et al., 1979). This structural depository is continually updated as new crystal structures are determined and can be screened for compounds having suitable shapes, for example, the same shape as a disclosed peptide, as well as potential geometrical and chemical complementarity to a target molecule. Where no crystal structure of a peptide or a target molecule that binds the peptide is available, a structure can be generated using, for example, the program CONCORD (Rusinko et al., 1989). Another database, the Available Chemicals Directory (Molecular Design Limited, Information Systems; San Leandro, Calif., United States of America), contains about 100,000 compounds that are commercially available and also can be searched to identify potential peptidomimetics of a peptide, for example, with activity in selectively interacting with cancerous cells.

Also disclosed are chimeric proteins containing a disclosed peptide fused to a heterologous protein. In some embodiments, the heterologous protein can have a therapeutic activity such as cytokine activity, cytotoxic activity or pro-apoptotic activity. In a further embodiment, the heterologous protein can be an antibody or antigen-binding fragment thereof. In other embodiments, the chimeric protein includes a peptide containing the amino acid sequence of SEQ ID NO: 1, SEQ ID NO: 2, or SEQ ID NO: 3, or a conservative variant or peptidomimetic thereof, fused to a heterologous protein. The term "heterologous," as used herein in reference to a protein fused to the disclosed peptides, means a protein derived from a source other than the gene encoding the peptide or from which the peptidomimetic is derived. The disclosed chimeric proteins can have a variety of lengths including, but not limited to, a length of less than 100 residues, less than 200 residues, less than 300 residues, less than 400 residues, less than 500 residues, less than 800 residues, less than 1000 residues, or greater than 1000 residues.

As used herein, "chimera" and "chimeric" refer to any combination of sequences derived from two or more sources. This includes, for example, from single moiety of subunit (e.g., nucleotide, amino acid) up to entire source sequences added, inserted, and/or substituted into other sequences. Chimeras can be, for example, additive, where one or more portions of one sequence are added to one or more portions of one or more other sequences; substitutional, where one or more portions of one sequence are substituted for one or more portions of one or more other sequences; or a combination. "Conservative substitutional chimeras" can be used to refer to substitutional chimeras where the source sequences for the chimera have some structural and/or functional relationship and where portions of sequences having similar or analogous structure and/or function are substituted for each other. Typical chimeric and humanized antibodies are examples of conservative substitutional chimeras.

If desired, an isolated peptide such as a TT1 Peptide can be cyclic or otherwise conformationally constrained. As used herein, a "conformationally constrained" molecule, such as a peptide, is one in which the three-dimensional structure is maintained substantially in one spatial arrangement over time. Conformationally constrained molecules can have improved properties such as increased affinity, metabolic stability, membrane permeability, or solubility. Methods of conformational constraint are well known in the art and include cyclization as discussed further elsewhere herein.

As used herein in reference to a peptide, the term "cyclic" means a structure including an intramolecular bond between two non-adjacent amino acids or amino acid analogues. The cyclization can be effected through a covalent or non-covalent bond. Intramolecular bonds include, but are not limited to, backbone to backbone, side-chain to backbone and side-chain to side-chain bonds. A preferred method of cyclization is through formation of a disulfide bond between the side-chains of non-adjacent amino acids or amino acid analogs. Residues capable of forming a disulfide bond include, for example, cysteine (Cys), penicillamine (Pen), pentamethylene cysteine (Pmc), β,β-pentamethylene-β-mercaptopropionic acid (Pmp), and functional equivalents thereof.

A peptide also can cyclize, for example, via a lactam bond, which can utilize a side-chain group of one amino acid or analog thereof to form a covalent attachment to the N-terminal amine of the amino-terminal residue. Residues capable of forming a lactam bond include aspartic acid (Asp), glutamic acid (Glu), lysine (Lys), ornithine (om), α,β-diamino-propionic acid, γ-amino-adipic acid (Adp) and M-(aminomethyl)benzoic acid (Mamb). Cyclization additionally can be effected, for example, through the formation of a lysinonorleucine bond between lysine (Lys) and leucine (Leu) residues or a dityrosine bond between two tyrosine (Tyr) residues. The skilled person understands that these and other bonds can be included in a cyclic peptide.

II.D. TT1 Peptide Compositions Comprising Moieties

The TT1 Peptide compositions disclosed herein are in some embodiments TT1 Peptide compositions comprising SEQ ID NO: 1, SEQ ID NO: 2, or SEQ ID NO: 3, which optionally can further comprise a moiety. The moiety can be any molecule. For example, disclosed are moieties containing a therapeutic agent linked to SEQ ID NO: 1, SEQ ID NO: 2, or SEQ ID NO: 3. In some embodiments, the moiety is a molecule that is usefully targeted to the gC1q/p32 receptor. For example, moieties that affect the target, such as moieties with therapeutic effect, or that facilitate detection, visualization, or imaging of the target, such as fluorescent molecule or radionuclides. The disclosed peptides, such as SEQ ID NO: 1, SEQ ID NO: 2, or SEQ ID NO: 3, that selectively interact with gC1qR/p32 can be usefully combined with, for example, moieties that can, for example, affect tumors and cancer, reduce or eliminate inflammation or infection, and/or promote wound healing. A variety of therapeutic agents are useful in the TT1 Peptide compositions disclosed herein, including, without limitation, cancer chemotherapeutic agents, cytotoxic agents, anti-angiogenic agents, polypeptides, nucleic acid molecules, and small molecules.

A TT1 Peptide composition can comprise, for example, two or more, three or more, five or more, ten or more, twenty or more, thirty or more, forty or more, fifty or more, 100 or more, 200 or more, 300 or more, 400 or more, 500 or more, or 1000 or more copies of SEQ ID NO: 1, SEQ ID NO: 2, or SEQ ID NO: 3. The TT1 Peptide composition can comprise peptides that all have an identical amino acid sequence. In some embodiments, the TT1 Peptide composition can comprise two or more non-identical amino acid sequences. For example, SEQ ID NO: 1, SEQ ID NO: 2, or SEQ ID NO: 3 and another targeting peptide can be used separately or together in a TT1 Peptide composition of the presently disclosed subject matter. Moieties useful in a TT1 Peptide composition incorporating multiple peptides include, without limitation, phage, retroviruses, adenoviruses, adeno-associated viruses and other viruses, cells, liposomes, polymeric matrices, non-polymeric matrices, particles such as gold particles, microdevices, nanodevices, and nanoscale semiconductor materials.

A TT1 Peptide composition can contain, for example, a liposome or other polymeric matrix linked to at least two peptides. If desired, the liposome or other polymeric matrix can be linked to at least ten, at least 100 or at least 1000 peptides such as SEQ ID NO: 1, SEQ ID NO: 2, or SEQ ID NO: 3. Liposomes can be useful in such conjugates; liposomes consist of phospholipids or other lipids, are nontoxic, physiologically acceptable and metabolizable carriers that are relatively simple to make and administer (see e.g., Gregoriadis, 1984). The liposome or other polymeric matrix can optionally include another component such as, without limitation, a therapeutic agent, cancer chemotherapeutic agent, cytotoxic agent, anti-angiogenic agent, and polypeptide or nucleic acid molecule.

Components of the disclosed TT1 Peptide compositions can be combined, linked, and/or coupled in any suitable manner. By way of example and not limitation, moieties and peptides can be associated covalently or non-covalently, directly or indirectly, with or without a linker moiety.

In some embodiments, one or more of the homing molecules can comprise, consist essentially of, and/or consist of the amino acid sequence KRGARST (SEQ ID NO: 1), the amino acid sequence AKRGARSTA (SEQ ID NO: 2), or a conservative derivative thereof, the amino acid sequence CKRGARSTC (SEQ ID NO: 3) or a conservative derivative thereof, or a combination. In some embodiments, one or more of the homing molecule can comprise, consist essentially of, and/or consist of the amino acid sequence KRGARST (SEQ ID NO: 1) or a conservative variant thereof. In some embodiments, one or more of the homing molecules can comprise, consist essentially of, and/or consist of the amino acid sequence KRGARST (SEQ ID NO: 1). In some embodiments, one or more of the membrane perturbing molecules can comprise, consist essentially of, and/or consist of the amino acid sequence $_D$(KLAKLAK)$_2$ (SEQ ID NO: 42) or a conservative variant thereof, (KLAKLAK)$_2$ (SEQ ID NO: 42) or a conservative variant thereof, (KLAKKLA)$_2$ (SEQ ID NO: 43) or a conservative variant thereof, (KAAKKAA)$_2$ (SEQ ID NO: 44) or a conservative variant thereof, and/or (KLGKKLG)$_3$ (SEQ ID NO: 45) or a conservative variant thereof, or a combination. In some embodiments, one or more of the membrane perturbing molecules can comprise, consist essentially of, and/or consist of the amino acid sequence $_D$(KLAKLAK)$_2$ (SEQ ID NO: 42), (KLAKLAK)$_2$ (SEQ ID NO: 42), (KLAKKLA)$_2$ (SEQ ID NO: 43), (KAAKKAA)$_2$ (SEQ ID NO: 44), (KLGKKLG)$_3$ (SEQ ID NO: 45), or a combination thereof. In some embodiments, one or more of the membrane perturbing molecules can comprise, consist essentially of, and/ or consist of the amino acid sequence $_D$(KLAKLAK)$_2$ (SEQ ID NO: 42) or a conservative variant thereof. In some embodiments, one or more of the membrane perturbing molecules can comprise, consist essentially of, and/or consist of the amino acid sequence $_D$(KLAKLAK)$_2$ (SEQ ID NO: 42).

In some embodiments, the composition can comprise a plurality of surface molecules, a plurality of homing molecules, and a plurality of cargo molecules. In some embodiments, the composition can comprise one or more surface molecules, a plurality of homing molecules and a plurality of cargo molecules. In some embodiments, the composition can comprise a plurality of surface molecules, one or more homing molecules, and a plurality of cargo molecules. In some embodiments, the composition can comprise a plurality of surface molecules, a plurality of homing molecules, and one or more cargo molecules. In some embodiments, the composition can comprise one or more surface molecules, one or more homing molecules, and a plurality of cargo molecules. In some embodiments, the composition can comprise one or more surface molecules, a plurality of homing molecules and one or more cargo molecules. In some embodiments, the composition comprises a plurality of surface molecules, one or more homing molecules, and one or more cargo molecules.

In some embodiments, the composition can comprise a surface molecule, a plurality of homing molecules and a plurality of cargo molecules, wherein one or more of the homing molecules and one or more of the cargo molecules are associated with the surface molecule. In some embodiments, the composition can comprise a surface molecule, a plurality of homing molecules, and a plurality of cargo molecules, wherein a plurality of the plurality of homing molecules and a plurality of the plurality of cargo molecules are associated with the surface molecule. In some embodiments, the composition can comprise a surface molecule, a plurality of homing molecules, and a plurality of cargo molecules, wherein the homing molecules and the cargo molecules are associated with the surface molecule.

In some embodiments, the composition can comprise a surface molecule, wherein the surface molecule is multivalent for homing molecules and cargo molecules. In some embodiments, the composition can comprise a surface molecule, wherein the surface molecule is multivalent for homing molecules and comprises one or more cargo molecules. In some embodiments, the composition can comprise a surface molecule, wherein the surface molecule is multivalent for cargo molecules and comprises one or more homing molecules. In some embodiments, the composition can comprise a surface molecule, wherein the surface molecule is multivalent for conjugates, wherein one or more of the conjugates comprise one or more homing molecules and one or more cargo molecules. In some embodiments, the composition can comprise a surface molecule, wherein the surface molecule is multivalent for conjugates, wherein one or more of the conjugates comprise a plurality of homing molecules and a plurality of cargo molecules. In some embodiments, the composition can comprise a surface molecule, wherein the surface molecule is multivalent for conjugates, wherein one or more of the conjugates comprise a homing molecule and a cargo molecule. In some embodiments, the composition can comprise a surface molecule, wherein the surface molecule is multivalent for conjugates, wherein each of the conjugates comprises a plurality of homing molecules and a plurality of cargo molecules. In some embodiments, the composition can comprise a surface molecule, wherein the surface molecule is multivalent for conjugates, wherein each of the conjugates comprises a homing molecule and a cargo molecule. As used herein, a component that is stated to be "multivalent for" one or more other components refers to a component that has a plurality of the other components associated with, conjugated to and/or covalent coupled to the first component.

In some embodiments, the composition can comprise a surface molecule, wherein the surface molecule comprises one or more conjugates, wherein one or more of the conjugates comprise one or more homing molecules and one or more cargo molecules. In some embodiments, the composition can comprise a surface molecule, wherein the surface molecule comprises one or more conjugates, wherein one or more of the conjugates comprise a plurality of homing molecules and a plurality of cargo molecules. In some embodiments, the composition can comprise a surface molecule, wherein the surface molecule comprises one or more conjugates, wherein one or more of the conjugates comprise a homing molecule and a cargo molecule. In some embodiments, the composition can comprise a surface molecule, wherein the surface molecule comprises one or more conjugates, wherein each of the conjugates comprises a plurality of homing molecules and a plurality of cargo molecules. In some embodiments, the composition can comprise a surface molecule, wherein the surface molecule comprises one or more conjugates, wherein each of the conjugates comprises a homing molecule and a cargo molecule.

In some embodiments, one or more of the membrane perturbing molecules can be conjugated to one or more of the homing molecules. In some embodiments, one or more of the conjugated membrane perturbing molecules and homing molecules can be covalently coupled. In some embodiments, one or more of the covalently coupled membrane perturbing molecules and homing molecules can comprise fusion peptides. In some embodiments, the homing molecules can be conjugated with the surface molecule. In some embodiments, one or more of the conjugated homing molecules can be directly conjugated to the surface molecule. In some embodiments, one or more of the conjugated homing molecules can be indirectly conjugated to the surface molecule. In some embodiments, one or more of the homing molecules can be covalently coupled to the surface molecule. In some embodiments, one or more of the covalently coupled homing molecules can be directly covalently coupled to the surface molecule. In some embodiments, one or more of the covalently coupled homing molecules can be indirectly covalently coupled to the surface molecule. In some embodiments, the membrane perturbing molecules can be conjugated with the surface molecule.

In some embodiments, one or more of the conjugated membrane perturbing molecules are directly conjugated to the surface molecule. In some embodiments, one or more of the conjugated membrane perturbing molecules can be indirectly conjugated to the surface molecule. In some embodiments, one or more of the membrane perturbing molecules can be covalently coupled to the surface molecule. In some embodiments, one or more of the covalently coupled membrane perturbing molecules can be directly covalently coupled to the surface molecule. In some embodiments, one or more of the covalently coupled membrane perturbing molecules can be indirectly covalently coupled to the surface molecule.

In some embodiments, the composition can further comprise one or more internalization elements. In some embodiments, one or more of the homing molecules can comprise one or more of the internalization elements. In some embodiments, one or more of the membrane perturbing molecules can comprise one or more of the internalization elements. In some embodiments, the surface molecule can comprise one or more of the internalization elements not comprised in either the homing molecules or the membrane perturbing molecules. In some embodiments, the composition can further comprise one or more tissue penetration elements. In some embodiments, one or more of the tissue penetration elements can be comprised in an internalization element. In some embodiments, the tissue penetration element can be a CendR element.

In some embodiments, the surface molecule can comprise a nanoparticle. In some embodiments, the surface molecule can comprise a nanoworm. In some embodiments, the surface molecule can comprise an iron oxide nanoworm. In some embodiments, the surface molecule can comprise an iron oxide nanoparticle. In some embodiments, the surface molecule can comprise an albumin nanoparticle. In some embodiments, the surface molecule can comprise a liposome. In some embodiments, the surface molecule can comprise a micelle. In some embodiments, the surface molecule comprises a phospholipid. In some embodiments, the surface molecule comprises a polymer. In some embodiments, the surface molecule can comprise a microparticle. In some embodiments, the surface molecule can comprise a fluorocarbon microbubble.

In some embodiments, the composition can comprise at least 100 homing molecules. In some embodiments, the composition can comprise at least 1000 homing molecules. In some embodiments, the composition can comprise at least 10,000 homing molecules. In some embodiments, the composition can comprise at least 100 membrane perturbing molecules. In some embodiments, the composition can comprise at least 1000 membrane perturbing molecules. In some embodiments, the composition can comprise at least 10,000 membrane perturbing molecules.

In some embodiments, one or more of the homing molecules can be modified homing molecules. In some embodiments, one or more of the homing molecules can comprise a methylated homing molecule. In some embodiments, one or more of the methylated homing molecules can comprise a methylated amino acid segment. In some embodiments, one or more of the membrane perturbing molecules can be modified membrane perturbing molecules. In some embodiments, one or more of the membrane perturbing molecules comprise a methylated membrane perturbing molecule. In some embodiments, one or more of the methylated membrane perturbing molecules comprise a methylated amino acid segment. In some embodiments, the amino acid sequence is N- or C-methylated in at least one position.

The disclosed components can be associated with each other (or, in some embodiments, not associated with each other) in combinations as disclosed herein. For example, homing molecules can be covalently coupled or non-covalently associated with surface molecules, homing molecules can be covalently coupled or non-covalently associated with membrane perturbing molecules, membrane perturbing molecules can be covalently coupled or non-covalently associated with surface molecules, etc. Associated components can also be referred to as being conjugated. Conjugation can be direct or indirect. Direct conjugation of components refers to covalently coupled or non-covalently associated components where there is no other molecule intervening between the conjugated components. Indirect conjugation refers to any chain of molecules and covalent bonds or non-covalent associations linking the components where the components are not directly conjugated (that is, there is a least one separate molecule other than the components intervening between the components).

Covalently coupled refers to association of components via covalent bonds. A covalent association or coupling can be either direct or indirect. A direct covalent association or coupling of components refers to a covalent bond involving atoms that are each respectively a part of the components. Thus, in a direct covalent association or coupling, there is no other molecule intervening between the associated/coupled components. An indirect covalent association or coupling refers to any chain of molecules and covalent bonds linking the components where the components are not covalently coupled (that is, there is a least one separate molecule other than the components intervening between the components via covalent bonds).

As used herein, reference to components (such as a homing molecule and a surface molecule) as being "not covalently coupled" means that the components are not connected via covalent bonds (for example, that the homing molecule and the surface molecule are not connected via covalent bonds). That is, there is no continuous chain of covalent bonds between, for example, the homing molecule and the surface molecule.

Non-covalent association refers to association of components via non-covalent bonds and interactions. A non-covalent association can be either direct or indirect. A direct non-covalent association refers to a non-covalent bond involving atoms that are each respectively connected via a chain of covalent bonds to the components. Thus, in a direct non-covalent association, there is no other molecule intervening between the associated components. An indirect non-covalent association refers to any chain of molecules and bonds linking the components where the components are not covalently coupled (that is, there is a least one separate molecule other than the components intervening between the components via non-covalent bonds).

Reference to components (such as a homing molecule and a surface molecule) as not being "non-covalently associated" means that there is no direct or indirect non-covalent association between the components. That is, for example, no atom covalently coupled to a homing molecule is involved in a non-covalent bond with an atom covalently coupled to a surface molecule. Within this meaning, a homing molecule and a surface molecule can be together in a composition where they are indirectly associated via multiple intervening non-covalent bonds while not being non-covalently associated as that term is defined herein. For example, a homing molecule and a surface molecule can be mixed together in a carrier where they are not directly non-covalently associated. A homing molecule and a surface molecule that are referred to as not indirectly non-covalently associated cannot be mixed together in a continuous composition. Reference to components (such as a homing molecule and a surface molecule) as not being "directly non-covalently associated" means that there is no direct non-covalent association between the components (an indirect non-covalent association may be present).

Reference to components (such as a homing molecule and a surface molecule) as not being "indirectly non-covalently associated" means that there is no direct or indirect non-covalent association between the components.

It is understood that components can be non-covalently associated via multiple chains and paths including both direct and indirect non-covalent associations. For the purposes of these definitions, the presence a single direct non-covalent association makes the association a direct non-covalent association even if there are also indirect non-covalent associations present. Similarly, the presence of a covalent connection between components means the components are covalently coupled even if there are also non-covalent associations present. It is also understood that covalently coupled components that happened to lack any non-covalent association with each other are not considered to fall under the definition of components that are not non-covalently associated.

Association of the components of the disclosed compositions can be aided or accomplished via molecules, conjugates, and/or compositions. Where such molecules, conjugates and/or compositions are other than surface molecules, homing molecules, or cargo molecules (such as membrane perturbing molecules, internalization elements, tissue penetration elements, and moieties), they can be referred to herein as linkers. Such linkers can be any molecule, conjugate, composition, etc. that can be used to associate components of the disclosed compositions. Generally, linkers can be used to associate components other than surface molecules to surface molecules. Useful linkers include materials that are biocompatible, have low bioactivity, have low antigenicity, etc. That is, such useful linker materials can serve the linking/association function without adding unwanted bioreactivity to the disclosed compositions. Many such materials are known and used for similar linking and association functions. Polymer materials are a particularly useful form of linker material. For example, polyethylene glycols can be used.

Linkers are useful for achieving useful numbers and densities of the components (such as homing molecules and membrane perturbing molecules) on surface molecules. For example, linkers of fibrous form are useful for increasing the number of components per surface molecule or per a given area of the surface molecule. Similarly, linkers having a branching form are useful for increasing the number of components per surface molecule or per a given area of the surface molecule. Linkers can also have a branching fibrous form.

Sufficiency of the number and composition of homing molecules in the composition can be determined by assessing homing to the target and effectively delivery of the cargo molecules in a non-human animal. The composition can comprise a sufficient number and composition of homing molecules (modified or not) such that the composition homes to the target and effectively delivers the cargo molecules. In one example, sufficiency of the number and composition of modified and/or unmodified homing molecules can be determined by assessing cargo delivery and/or therapeutic effect on the target. Sufficiency of the number and composition of membrane perturbing molecules can be determined by assessing membrane perturbing effect of the composition in a non-human animal. The composition can comprise a sufficient number and composition of membrane perturbing molecules (modified or not) such that the composition has a membrane perturbing effect on the target. In one example, sufficiency of the number and composition of modified and/or unmodified membrane perturbing molecules can be determined by assessing membrane disruption, apoptosis, and/or therapeutic effect on the target.

The composition can comprise a sufficient density and composition of homing molecules such that the composition homes to the target and effectively delivers the cargo molecules. Sufficiency of the density and composition of homing molecules can be determined by assessing cargo delivery and/or therapeutic effect on the target in a non-human animal. The composition can comprise a sufficient density and composition of membrane perturbing molecules such that the composition has a membrane perturbing effect on the target. Sufficiency of the density and composition of membrane perturbing molecules can be determined by assessing membrane disruption, apoptosis, and/or therapeutic effect on the target in a non-human animal.

The density of homing molecules and/or membrane perturbing molecules on a surface molecule can be described in any suitable manner. For example, the density can be expressed as the number of homing molecules and/or membrane perturbing molecules per, for example, a given area, surface area, volume, unit, subunit, arm, etc. of the surface molecule. The density can also be relative to, for example, the area, surface area, volume, unit, subunit, arm, etc. of the entire surface molecule or to the area, surface area, volume, unit, subunit, arm, etc. of a portion of the surface molecule. For example, a sufficient density of homing molecule and/or membrane perturbing molecule can be present in a portion of the surface molecule. The presence of this dense portion can cause clotting and amplify the accumulation of the composition. Thus, a composition having a sufficient density of homing molecules and/or membrane perturbing molecules can have a threshold density (or above) for the entire surface molecule or for just one or more portions of the surface molecule. Unless otherwise stated, densities refer to average density over the designated portion of the surface molecule. For example, a density of 1 homing molecule per square nM of the surface molecule refers to an average density of the homing molecules over the entire surface molecule. As another example, a density of 1 homing molecule per square nM of a portion of the surface molecule refers to an average density of the homing molecules over just that portion of the surface molecule.

The density can be measured or calculated in any suitable manner. For example, the number or amount of homing molecules and/or membrane perturbing molecules present on a surface molecule or group of surface molecules can be measured by, for example, detecting the level or intensity of signal produced by labeled homing molecules and/or membrane perturbing molecules and calculating the density based on the structural characteristics of the surface molecule.

The density or threshold density of homing molecules and/or membrane perturbing molecules can be, for example, at least 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, 10, 12, 14, 16, 18, 20, 25, 30, 35, 40, 45, 50, 55, 60, 65, 70, 75, 80, 85, 90, 95, 100, 110, 120, 130, 140, 150, 160, 170, 180, 190, 200, 220, 240, 260, 280, 300, 320, 340, 360, 380, 400, 420, 440, 460, 480, 500, 550, 600, 650, 700, 750, 800, 850, 900, 950, or 1000 homing molecules and/or membrane perturbing molecules per square nM of the entire or a portion of the surface molecule. The composition can also comprise any density in between those densities listed above.

The density or threshold density of homing molecules and/or membrane perturbing molecules can be, for example, at least 1, 2, 3, 4, 5, 6, 7, 8, 9, 10, 12, 14, 16, 18, 20, 25, 30, 35, 40, 45, 50, 55, 60, 65, 70, 75, 80, 85, 90, 95, 100, 110, 120, 130, 140, 150, 160, 170, 180, 190, 200, 220, 240, 260, 280, 300, 320, 340, 360, 380, 400, 420, 440, 460, 480, 500, 550, 600, 650, 700, 750, 800, 850, 900, 950, 1000, 1100, 1200, 1300, 1400, 1500, 1600, 1700, 1800, 1900, 2000, 2200, 2400, 2600, 2800, 3000, 3200, 3400, 3600, 3800, 4000, 4200, 4400, 4600, 4800, 5000, 5500, 6000, 6500, 7000, 7500, 8000, 8500, 900, 9500, 10,000 homing molecules and/or membrane perturbing molecules per square M of the entire or a portion of the surface molecule. The composition can also comprise any density in between those densities listed above.

The density or threshold density of homing molecules and/or membrane perturbing molecules can be, for example, at least 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, 10, 12, 14, 16, 18, 20, 25, 30, 35, 40, 45, 50, 55, 60, 65, 70, 75, 80, 85, 90, 95, 100, 110, 120, 130, 140, 150, 160, 170, 180, 190, 200, 220, 240, 260, 280, 300, 320, 340, 360, 380, 400, 420, 440, 460, 480, 500, 550, 600, 650, 700, 750, 800, 850, 900, 950, or 1000 homing molecules and/or membrane perturbing molecules per cubic nM of the entire or a portion of the surface molecule. The composition can also comprise any density in between those densities listed above.

The density or threshold density of homing molecules and/or membrane perturbing molecules can be, for example, at least 1, 2, 3, 4, 5, 6, 7, 8, 9, 10, 12, 14, 16, 18, 20, 25, 30, 35, 40, 45, 50, 55, 60, 65, 70, 75, 80, 85, 90, 95, 100, 110, 120, 130, 140, 150, 160, 170, 180, 190, 200, 220, 240, 260, 280, 300, 320, 340, 360, 380, 400, 420, 440, 460, 480, 500, 550, 600, 650, 700, 750, 800, 850, 900, 950, 1000, 1100, 1200, 1300, 1400, 1500, 1600, 1700, 1800, 1900, 2000, 2200, 2400, 2600, 2800, 3000, 3200, 3400, 3600, 3800, 4000, 4200, 4400, 4600, 4800, 5000, 5500, 6000, 6500, 7000, 7500, 8000, 8500, 900, 9500, 10,000 homing molecules and/or membrane perturbing molecules per cubic M of the entire or a portion of the surface molecule. The composition can also comprise any density in between those densities listed above.

The number of homing molecules and/or membrane perturbing molecules on a surface molecule can be described in any suitable manner. For example, the number can be expressed as the number of homing molecules and/or membrane perturbing molecules per, for example, a given area, surface area, volume, unit, subunit, arm, etc. of the surface molecule. The number can also be relative to, for example, the area, surface area, volume, unit, subunit, arm, etc. of the entire surface molecule or to the area, surface area, volume, unit, subunit, arm, etc. of a portion of the surface molecule. For example, a sufficient number of homing molecule and/or membrane perturbing molecule can be present in a portion of the surface molecule. The presence of this dense portion can cause clotting and amplify the accumulation of the composition. Thus, a composition having a sufficient number of homing molecules and/or membrane perturbing molecules can have a threshold number (or above) for the entire surface molecule or for just one or more portions of the surface molecule.

The number can be measured or calculated in any suitable manner. For example, the number or amount of homing molecules and/or membrane perturbing molecules present on a surface molecule or group of surface molecules can be measured by, for example, detecting the level or intensity of signal produced by labeled homing molecules and/or membrane perturbing molecules and calculating the number based on the structural characteristics of the surface molecule.

The number or threshold number of homing molecules and/or membrane perturbing molecules can be, for example, at least 1, 2, 3, 4, 5, 6, 7, 8, 9, 10, 12, 14, 16, 18, 20, 25, 30, 35, 40, 45, 50, 55, 60, 65, 70, 75, 80, 85, 90, 95, 100, 110, 120, 130, 140, 150, 160, 170, 180, 190, 200, 220, 240, 260, 280, 300, 320, 340, 360, 380, 400, 420, 440, 460, 480, 500, 550, 600, 650, 700, 750, 800, 850, 900, 950, 1000, 1100, 1200, 1300, 1400, 1500, 1600, 1700, 1800, 1900, 2000, 2200, 2400, 2600, 2800, 3000, 3200, 3400, 3600, 3800, 4000, 4200, 4400, 4600, 4800, 5000, 5500, 6000, 6500, 7000, 7500, 8000, 8500, 900, 9500, 10,000 homing molecules and/or membrane perturbing molecules on the surface molecule. The composition can also comprise any number in between those numbers listed above.

The number or threshold number of homing molecules and/or membrane perturbing molecules can be, for example, at least 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, 10, 12, 14, 16, 18, 20, 25, 30, 35, 40, 45, 50, 55, 60, 65, 70, 75, 80, 85, 90, 95, 100, 110, 120, 130, 140, 150, 160, 170, 180, 190, 200, 220, 240, 260, 280, 300, 320, 340, 360, 380, 400, 420, 440, 460, 480, 500, 550, 600, 650, 700, 750, 800, 850, 900, 950, or 1000 homing molecules and/or membrane perturbing molecules per square nM of the entire or a portion of the surface molecule. The composition can also comprise any number in between those numbers listed above.

The number or threshold number of homing molecules and/or membrane perturbing molecules can be, for example, at least 1, 2, 3, 4, 5, 6, 7, 8, 9, 10, 12, 14, 16, 18, 20, 25, 30, 35, 40, 45, 50, 55, 60, 65, 70, 75, 80, 85, 90, 95, 100, 110, 120, 130, 140, 150, 160, 170, 180, 190, 200, 220, 240, 260, 280, 300, 320, 340, 360, 380, 400, 420, 440, 460, 480, 500, 550, 600, 650, 700, 750, 800, 850, 900, 950, 1000, 1100, 1200, 1300, 1400, 1500, 1600, 1700, 1800, 1900, 2000, 2200, 2400, 2600, 2800, 3000, 3200, 3400, 3600, 3800, 4000, 4200, 4400, 4600, 4800, 5000, 5500, 6000, 6500, 7000, 7500, 8000, 8500, 900, 9500, 10,000 homing molecules and/or membrane perturbing molecules per square M of the entire or a portion of the surface molecule. The composition can also comprise any number in between those numbers listed above.

The number or threshold number of homing molecules and/or membrane perturbing molecules can be, for example, at least 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, 10, 12, 14, 16, 18, 20, 25, 30, 35, 40, 45, 50, 55, 60, 65, 70, 75, 80, 85, 90, 95, 100, 110, 120, 130, 140, 150, 160, 170, 180, 190, 200, 220, 240, 260, 280, 300, 320, 340, 360, 380, 400, 420, 440, 460, 480, 500, 550, 600, 650, 700, 750, 800, 850, 900, 950, or 1000 homing molecules and/or membrane perturbing molecules per cubic nM of the entire or a portion of the surface molecule. The composition can also comprise any number in between those numbers listed above.

The number or threshold number of homing molecules and/or membrane perturbing molecules can be, for example, at least 1, 2, 3, 4, 5, 6, 7, 8, 9, 10, 12, 14, 16, 18, 20, 25, 30, 35, 40, 45, 50, 55, 60, 65, 70, 75, 80, 85, 90, 95, 100, 110, 120, 130, 140, 150, 160, 170, 180, 190, 200, 220, 240, 260, 280, 300, 320, 340, 360, 380, 400, 420, 440, 460, 480, 500, 550, 600, 650, 700, 750, 800, 850, 900, 950, 1000, 1100, 1200, 1300, 1400, 1500, 1600, 1700, 1800, 1900, 2000, 2200, 2400, 2600, 2800, 3000, 3200, 3400, 3600, 3800, 4000, 4200, 4400, 4600, 4800, 5000, 5500, 6000, 6500, 7000, 7500, 8000, 8500, 900, 9500, 10,000 homing molecules and/or membrane perturbing molecules per cubic M of the entire or a portion of the surface molecule. The composition can also comprise any number in between those numbers listed above.

In some embodiments, the compositions not only home to tumors, but also amplify their own homing. Homing molecules can be used that are clot-binding compounds that recognize clotted plasma proteins and selectively homes to tumors, where it binds to vessel walls and tumor stroma. Surface molecules coupled with the clot-binding compounds can accumulate in tumor vessels or at wound sites, where they induce additional local clotting, thereby producing new binding sites for more particles. The system mimics platelets, which also circulate freely but accumulate at a diseased site and amplify their own accumulation at that site. The clotting-based amplification greatly enhances cargo delivery and tumor imaging.

II.D.1. Homing Molecules

Homing molecules allow the disclosed compositions to be targeted and to home to desired target sites. Homing molecules generally bind preferentially to target molecules, cells, tissues, etc., thus resulting in an accumulation of the homing molecules (and other components to which they are associated) at target sites.

The term "homing molecule" as used herein, means any molecule that selectively homes in vivo to specified target sites, such as cells or tissues, in preference to normal or other non-target sites, cells, or tissues. Similarly, the term "homing peptide" or "homing peptidomimetic" means a peptide that selectively homes in vivo to specified target sites, such as cells or tissues, in preference to normal or other non-target sites, cells, or tissues. It is understood that a homing molecule that selectively homes in vivo to, for example, tumors can home to all tumors or can exhibit preferential homing to one or a subset of tumor types.

By "selectively homes" it is meant that in vivo, the homing molecule binds preferentially to the target as compared to non-target. For example, the homing molecule can bind preferentially to certain molecules, proteins, cells, tissues, etc. as compared to other molecules, proteins, cells, tissues, etc. For example, the homing molecule can bind preferentially to tumor vasculature or one or more tumors as compared to non-tumoral tissue. Such a homing molecule can selectively home, for example, to tumors. Selective homing to, for example, certain molecules, proteins, cells, tissues, etc. generally is characterized by at least a two-fold greater localization the molecules, proteins, cells, tissues, etc. (or other target), as compared to other certain molecules, proteins, cells, tissues, etc. A homing molecule can be characterized by, for example, 5-fold, 10-fold, 20-fold or more preferential localization to the target as compared to one or more non-targets. For example, a homing molecule can be characterized by, for example, 5-fold, 10-fold, 20-fold or more preferential localization to tumor vasculature as compared to vasculature of several or many tissue types of non-tumoral tissue, or as compared to vasculature of most or all non-tumoral tissue. As another example, a homing molecule can be characterized by, for example, 5-fold, 10-fold, 20-fold or more preferential localization to tumors as compared to several or many tissue types of non-tumoral tissue, or as compared to-most or all non-tumoral tissue. Thus, it is understood that, in some cases, a homing molecule homes, in part, to one or more normal organs in addition to homing to the target tissue. Selective homing can also be referred to as targeting. The molecules, proteins, cells, tissues, etc. that are targeted by homing molecules can be referred to as targeted molecules, proteins, cells, tissues, etc.

In some embodiments, one or more of the homing molecules can comprise, consist essentially of, and/or consist of the amino acid sequence KRGARST (SEQ ID NO: 1) or a conservative derivative thereof, the amino acid sequence AKRGARSTA (SEQ ID NO: 2) or a conservative derivative thereof, and/or the amino acid sequence CKRGARSTC (SEQ ID NO: 3) or a conservative derivative thereof, or any combination thereof. In some embodiments, one or more of the homing molecule can comprise, consist essentially of, and/or consist of the amino acid sequence KRGARST (SEQ ID NO: 1) or a conservative variant thereof, and/or the amino acid sequence AKRGARSTA (SEQ ID NO: 2) or a conservative derivative thereof, or any combination thereof. In some embodiments, one or more of the homing molecules can comprise, consist essentially of, and/or consist of the amino acid sequence CKRGARSTC (SEQ ID NO: 3) or a conservative derivative thereof, or any combination thereof.

The composition can comprise a sufficient number and composition of homing molecules (modified or not) such that the composition homes to the target and effectively delivers the cargo molecules. In one example, sufficiency of the number and composition of modified and/or unmodified homing molecules can be determined by assessing cargo delivery and/or therapeutic effect on the target.

Many homing molecules and homing peptides home to the vasculature of the target tissue. However, for the sake of convenience homing is referred to in some places herein as homing to the tissue associated with the vasculature to which the homing molecule or homing peptide may actually home. Thus, for example, a homing molecule that homes to tumor vasculature can be referred to herein as homing to tumor tissue or to tumor cells. By including or associating a homing molecule or homing peptide with, for example, a protein, peptide, amino acid sequence, cargo molecules, or CendR element the protein, peptide, amino acid sequence, cargo molecules, or CendR element can be targeted or can home to the target of the homing molecule or homing peptide. In this way, the protein, peptide, amino acid sequence, cargo molecules, or CendR element can be said to home to the target of the homing molecule or homing peptide. For convenience and unless otherwise indicated, reference to homing of a protein, peptide, amino acid sequence, cargo molecules, CendR element, etc. is intended to indicate that the protein, peptide, amino acid sequence, cargo molecules, CendR element, etc. includes or is associated with an appropriate homing molecule or homing peptide.

The homing molecule can selectively home to a tumor. The homing molecule can selectively home to tumor vasculature. The homing molecule can selectively home to one or more particular types of tumor. The homing molecule can selectively home to the vasculature of one or more particular types of tumor. The homing molecule can selectively home to one or more particular stages of a tumor or cancer. The homing molecule can selectively home to the vasculature of one or more particular stages of a tumor or cancer. The homing molecule can selectively home to one or more particular stages of one or more particular types of tumor. The homing molecule can selectively home to the vasculature of one or more different stages of one or more particular types of tumor.

The composition can selectively home to a tumor. The composition can selectively home to tumor vasculature. The composition can selectively home to one or more particular types of tumor. The composition can selectively home to the vasculature of one or more particular types of tumor. The composition can selectively home to one or more particular stages of a tumor or cancer. The composition can selectively home to the vasculature of one or more particular stages of a tumor or cancer. The composition can selectively home to one or more particular stages of one or more particular types of tumor. The composition can selectively home to the vasculature of one or more different stages of one or more particular types of tumor.

The cargo molecule can selectively home to a tumor. The cargo molecule can selectively home to tumor vasculature. The cargo molecule can selectively home to one or more particular types of tumor. The cargo molecule can selectively home to the vasculature of one or more particular types of tumor. The cargo molecule can selectively home to one or more particular stages of a tumor or cancer. The cargo molecule can selectively home to the vasculature of one or more particular stages of a tumor or cancer. The cargo molecule can selectively home to one or more particular stages of one or more particular types of tumor. The cargo molecule can selectively home to the vasculature of one or more different stages of one or more particular types of tumor.

The surface molecule can selectively home to a tumor. The surface molecule can selectively home to tumor vasculature. The surface molecule can selectively home to one or more particular types of tumor. The surface molecule can selectively home to the vasculature of one or more particular types of tumor. The surface molecule can selectively home to one or more particular stages of a tumor or cancer. The surface molecule can selectively home to the vasculature of one or more particular stages of a tumor or cancer. The surface molecule can selectively home to one or more particular stages of one or more particular types of tumor. The surface molecule can selectively home to the vasculature of one or more different stages of one or more particular types of tumor.

The membrane perturbing molecule can selectively home to a tumor. The membrane perturbing molecule can selectively home to tumor vasculature. The membrane perturbing molecule can selectively home to one or more particular types of tumor. The membrane perturbing molecule can selectively home to the vasculature of one or more particular types of tumor. The membrane perturbing molecule can selectively home to one or more particular stages of a tumor or cancer. The membrane perturbing molecule can selectively home to the vasculature of one or more particular stages of a tumor or cancer. The membrane perturbing molecule can selectively home to one or more particular stages of one or more particular types of tumor. The membrane perturbing molecule can selectively home to the vasculature of one or more different stages of one or more particular types of tumor.

The disclosed compositions, surface molecules, amino acid sequences, cargo molecules, proteins or peptides can, for example, home to brain cells, brain stem cells, brain tissue, and/or brain vasculature, kidney cells, kidney stem cells, kidney tissue, and/or kidney vasculature, skin cells, skin stem cells, skin tissue, and/or skin vasculature, lung cells, lung tissue, and/or lung vasculature, pancreatic cells, pancreatic tissue, and/or pancreatic vasculature, intestinal cells, intestinal tissue, and/or intestinal vasculature, adrenal gland cells, adrenal tissue, and/or adrenal vasculature, retinal cells, retinal tissue, and/or retinal vasculature, liver cells, liver tissue, and/or liver vasculature, prostate cells, prostate tissue, and/or prostate vasculature, endometriosis cells, endometriosis tissue, and/or endometriosis vasculature, ovary cells, ovary tissue, and/or ovary vasculature, tumor cells, tumors, tumor blood vessels, and/or tumor vasculature, bone cells, bone tissue, and/or bone vasculature, bone marrow cells, bone marrow tissue, and/or bone marrow vasculature, cartilage cells, cartilage tissue, and/or cartilage vasculature, stem cells, embryonic stem cells, pluripotent stem cells, induced pluripotent stem cells, adult stem cells, hematopoietic stem cells, neural stem cells, mesenchymal stem cells, mammary stem cells, endothelial stem cells, olfactory adult stem cells, neural crest stem cells, cancer stem cells, blood cells, erythrocytes, platelets, leukocytes, granulocytes, neutrophils, eosinphils, basophils, lymphoid cells, lymphocytes, monocytes, wound vasculature, vasculature of injured tissue, vasculature of inflamed tissue, atherosclerotic plaques, or a combination.

Examples of homing molecules and homing peptides are known. Examples include brain homing peptides such as CNSRLHLRC (SEQ ID NO: 46), CENWWGDVC (SEQ ID NO: 47), WRCVLREGPAGGCAWFNRHRL (SEQ ID NO: 48), CLSSRLDAC (SEQ ID NO: 49), CVLRGGRC (SEQ ID NO: 50), CNSRLQLRC (SEQ ID NO: 51), CGVRLGC (SEQ ID NO: 52), CKDWGRIC (SEQ ID NO: 53), CLDWGRIC (SEQ ID NO: 54), CTRITESC (SEQ ID NO: 55), CETLPAC (SEQ ID NO: 56), CRTGTLFC (SEQ ID NO: 57), CGRSLDAC (SEQ ID NO: 58), CRHWFDVVC (SEQ ID NO: 59), CANAQSHC (SEQ ID NO: 60), CGNPSYRC (SEQ ID NO: 61), YPCGGEAVAGVSSVRTMCSE (SEQ ID NO: 62), LNCDYQGTNPATSVSVPCTV (SEQ ID NO: 63); kidney homing peptides such as CLPVASC (SEQ ID NO: 64), CGAREMC (SEQ ID NO: 65), CKGRSSAC (SEQ ID NO: 66), CWARAQGC (SEQ ID NO: 67), CLGRSSVC (SEQ ID NO: 68), CTSPGGSC (SEQ ID NO: 69), CMGRWRLC (SEQ ID NO: 70), CVGECGGC (SEQ ID NO: 71), CVAWLNC (SEQ ID NO: 72), CRRFQDC (SEQ ID NO: 73), CLMGVHC (SEQ ID NO: 74), CKLLSGVC (SEQ ID NO: 75), CFVGHDLC (SEQ ID NO: 76), CRCLNVC (SEQ ID NO: 77), CKLMGEC (SEQ ID NO: 78); skin homing peptides such as CARSKNKDC (SEQ ID NO: 79), CRKDKC (SEQ ID NO: 80), CVALCREACGEGC (SEQ ID NO: 81), CSSGCSKNCLEMC (SEQ ID NO: 82), CIGEVEVC (SEQ ID NO: 83), CKWSRLHSC (SEQ ID NO: 84), CWRGDRKIC (SEQ ID NO: 85), CERVVGSSC (SEQ ID NO: 86), CLAKENVVC (SEQ ID NO: 87); lung homing peptides such as CGFECVRQCPERC (SEQ ID NO: 88), CGFELETC (SEQ ID NO: 89), CTLRDRNC (SEQ ID NO: 90), CIGEVEVC (SEQ ID NO: 83), CTLRDRNC (SEQ ID NO: 90), CGKRYRNC (SEQ ID NO: 91), CLRPYLNC (SEQ ID NO: 92), CTVNEAYKTRMC (SEQ ID NO: 93), CRLRSYGTLSLC (SEQ ID NO: 94), CRPWHNQAHTEC (SEQ ID NO: 95); pancreas homing peptides such as SWCEPGWCR (SEQ ID NO: 96), CKAAKNK (SEQ ID NO: 97), CKGAKAR (SEQ ID NO: 98), VGVGEWSV (SEQ ID NO: 99); intestine homing peptides such as YSGKWGW (SEQ ID NO: 100); uterus homing peptides such as GLSGGRS (SEQ ID NO: 101); adrenal gland homing peptides such as LMLPRAD (SEQ ID NO: 102), LPRYLLS (SEQ ID NO: 103); retina homing peptides such as CSCFRDVCC (SEQ ID NO: 104), CRDVVSVIC (SEQ ID NO: 105); gut homing peptides such as YSGKWGK (SEQ ID NO: 106), GISALVLS (SEQ ID NO: 107), SRRQPLS (SEQ ID NO: 108), MSPQLAT (SEQ ID NO: 109), MRRDEQR (SEQ ID NO: 110), QVRRVPE (SEQ ID NO: 111), VRRGSPQ (SEQ ID NO: 112), GGRGSWE (SEQ ID NO: 113), FRVRGSP (SEQ ID NO: 114), RVRGPER (SEQ ID NO: 115); liver homing peptides such as VKSVCRT (SEQ ID NO: 116), WRQNMPL (SEQ ID NO: 117), SRRFVGG (SEQ ID NO: 118), ALERRSL (SEQ ID NO: 119), ARRGWTL (SEQ ID NO: 120); prostate homing peptides such as SMSIARL (SEQ ID NO: 121), VSFLEYR (SEQ ID NO: 122), RGRWLAL (SEQ ID NO: 123); ovary homing peptides such as EVRSRLS (SEQ ID NO: 124), VRARLMS (SEQ ID NO: 125), RVGLVAR (SEQ ID NO: 126), RVRLVNL (SEQ ID NO: 127); clot binding/homing peptide such as CREKA (SEQ ID NO: 128), CGLIIQKNEC (CLT1; SEQ ID NO: 129), CNAGESSKNC (CLT2; SEQ ID NO: 130); heart homing peptides such as CRPPR (SEQ ID NO: 131), CGRKSKTVC (SEQ ID NO: 132), CARPAR (SEQ ID NO: 133), CPKRPR (SEQ ID NO: 134), CKRAVR (SEQ ID NO: 135), CRNSWKPNC (SEQ ID NO: 136), RGSSS (SEQ ID NO: 137), CRSTRANPC (SEQ ID NO: 138), CPKTRRVPC (SEQ ID NO: 139), CSGMARTKC (SEQ ID NO: 140), GGGVFWQ (SEQ ID NO: 141), HGRVRPH (SEQ ID NO: 142), VVLVTSS (SEQ ID NO: 143), CLHRGNSC (SEQ ID NO: 144), CRSWNKADNRSC (SEQ ID NO: 145), CGRKSKTVC (SEQ ID NO: 132), CKRAVR (SEQ ID NO: 135), CRNSWKPNC (SEQ ID NO: 136), CPKTRRVPC (SEQ ID NO: 139), CSGMARTKC (SEQ ID NO: 140), CARPAR (SEQ ID NO: 133), CPKRPR (SEQ ID NO: 134); tumor blood vessel homing peptide such as CNGRC (SEQ ID NO: 146) and other peptides with the NGR motif (U.S. Pat. Nos. 6,177,542 and 6,576,239; U.S. Patent Application Publication No. 2009/0257951); RGD peptides, and RGR peptides. Other homing peptides include CSRPRRSEC (SEQ ID NO: 147), CSRPRRSVC (SEQ ID NO: 148), and CSRPRRSWC (SEQ ID NO: 149; Hoffman et al., 2003), F3 (KDEPQRR- SARLSAKPAPPKPEPKPKKAPAKK; SEQ ID NO: 150), PQRRSARLSA (SEQ ID NO: 151), and PKRRSARLSA (SEQ ID NO: 152; U.S. Pat. No. 7,544,767).

Homing molecules can also be defined by their targets. For example, numerous antigens and proteins are known that can be useful for targeting. Any molecule that can bind, selectively bind, home, selectively, target, selectively target, etc. such target molecules can be used as a homing molecule. For example, antibodies, nucleic acid aptamers, and compounds that can bind to target molecules can be used as homing molecules. Examples of useful target molecules for homing molecules include αv integrins, αvβ3 integrin, αvβ5 integrin, α5β1 integrin, aminopeptidase N, tumor endothelial markers (TEMs), endosialin, p32, gC1q receptor, annexin-1, nucleolin, fibronectin ED-B, fibrin-fibronectin complexes, interleukin-11 receptor a, and protease-cleaved collagen IV. These and other examples are described and referred to in Ruoslahti et al., 2010, which is hereby incorporated by reference in its entirety and specifically for its description of and references to target molecules.

The composition can comprise any number of homing molecules. By way of example, the composition can comprise at least 1, 5, 10, 15, 20, 25, 50, 75, 100, 125, 150, 175, 200, 225, 250, 275, 300, 325, 350, 375, 400, 425, 450, 475, 500, 525, 550, 575, 600, 625, 650, 675, 700, 625, 750, 775, 800, 825, 850, 875, 900, 925, 950, 975, 1000, 1100, 1200, 1300, 1400, 1500, 1600, 1700, 1800, 1900, 2000, 2250, 2500, 2750, 3000, 3500, 4000, 4500, 5000, 5500, 6000, 6500, 7000, 7500, 8000, 8500, 9000, 9500, 10,000, 15,000, 20,000, 25,000, 30,000, 35,000, 40,000, 45,000, 50,000, 75,000, or 100,000, or more homing molecules. The composition can also comprise any number in between those numbers listed above.

Homing molecules can be associated with and arranged in the compositions in a variety of configurations. In some embodiments, homing molecules can be associated with, conjugated to, and/or covalently coupled to a plurality of surface molecules. In some embodiments, homing molecules can be associated with, conjugated to, and/or covalently coupled to a plurality of cargo molecules. In some embodiments, homing molecules can be associated with, conjugated to, and/or covalently coupled to a plurality of cargo molecules, wherein the cargo molecules can be associated with, conjugated to, and/or covalently coupled to a plurality of surface molecules. Combinations of these combinations can also be used.

II.D.2.a. Tumor-Homing Molecules

The disclosed homing molecules can be tumor-homing compounds. Tumor-homing compounds are compounds that selectively home to tumors and tumor-associated tissue. Many compounds that target, bind to, and/or home to tumors are known, most of which can be used as tumor-homing compounds in the disclosed compositions. Tumor-homing compounds can each be independently selected from any known tumor-homing compounds.

Tumor-homing compounds can comprise, consist essentially of, consist of the amino acid sequence KRGARST (SEQ ID NO: 1), the amino acid sequence AKRGARSTA (SEQ ID NO: 2), or a conservative derivative thereof, the amino acid sequence CKRGARSTC (SEQ ID NO: 3) or a conservative derivative thereof, or any combination thereof, including peptidomimetics thereof. In some embodiments, one or more of the homing molecules can comprise, consist essentially of, and/or consist of the amino acid sequence KRGARST (SEQ ID NO: 1), AKRGARSTA (SEQ ID NO: 2), and/or CKRGARSTC (SEQ ID NO: 3).

Useful peptides for tumor targeting include, for example, the tumor-homing CendR peptide iRGD, LyP-1, a peptide that contains a putative CendR element and has tumor-penetrating properties, and RGR peptides. The LyP-1 peptide has a unique target within tumors; it preferentially accumulates in the hypoxic/low nutrient areas of tumors (Laakkonen et al., 2002; 2004; Karmali et al., 2009). CRGRRST (RGR; SEQ ID NO: 153; Joyce et al., 2003) is a peptide that has been successfully used in targeting a cytokine antibody combination into tumors (Hamzah et al., 2008). This peptide is linear, which simplifies the synthesis. Like LyP-1, RGR is at least to some extent tumor type-specific (Joyce et al., 2003), but the tumor types recognized by the two peptides seem to be partially different, which may be an advantage in testing combinations with the pan-tumor iRGD.

Because tumors can include clot-related proteins, some clot-binding and clot-homing compounds can also be tumor-homing compounds. Such tumor-homing clot-binding compounds can be used as tumor-homing compounds as described herein. Tumor-homing compounds can each be independently selected from, for example, an amino acid segment comprising the amino acid sequence REK, an amino acid segment comprising the amino acid sequence CAR (such as CARSKNKDC; SEQ ID NO: 79), an amino acid segment comprising the amino acid sequence CRK (such as CRKDKC; SEQ ID NO: 80), a fibrin-binding peptide, a peptide that binds clots and not fibrin (such as CGLIIQKNEC (CLT1; SEQ ID NO: 129) and CNAGESSKNC (CLT2; SEQ ID NO: 130)), a clot-binding antibody, and a clot-binding small organic molecule. A plurality of the clot-binding compounds can each independently comprise an amino acid segment comprising the amino acid sequence REK. Such peptides are also described in U.S. Patent Application Publication No. 2008/0305101, which is hereby incorporated by reference for its description of such peptides. Peptides comprising amino acid sequences CAR or CRK are also described in U.S. Patent Application Publication No. 2009/0036349, which is hereby incorporated by reference for its description of such peptides.

LyP-1 are homing molecules that selectively home to tumor lymphatic vasculature, for example, the lymphatic vasculature of breast cancer tumors and osteosarcomas, in preference to normal lymphatic vasculature. LyP-1 can selectively home, for example, to the lymphatic vasculature of squamous carcinomas. The core LyP-1 peptide has an amino acid sequence CGNKRTRGC (SEQ ID NO: 7). LyP-1 peptides are described in U.S. Patent Application Nos. 2004/0087499, 2007/0219134, and 2008/0014143, which are hereby incorporated by reference in their entirety, an specifically for their description of such peptides.

The clot-binding compound can also comprise a fibrin-binding peptide (FBP). Examples of fibrin-binding peptides are known in the art (Van Rooijen & Sanders, 1994; Moghimi et al., 2001; U.S. Pat. No. 5,792,742, all herein incorporated by reference in their entirety for their teaching concerning fibrin binding peptides).

Clot-binding peptides can also bind to proteins other than fibrin. Example include peptides that bind to fibronectin that has become incorporated into a clot (Pilch et al., 2006, hereby incorporated in its entirety for its teaching concerning clot-binding peptides). Examples of clot-binding peptides include, but is not limited to, CGLIIQKNEC (CLT1; SEQ ID NO: 129) and CNAGESSKNC (CLT2; SEQ ID NO: 130). The amino acid segments can also be independently selected from amino acid segments comprising the amino acid sequence CLT 1 or CLT2 or a conservative variant thereof, amino acid segments comprising the amino acid sequence CLT1 or CLT2, or amino acid segments consisting of the amino acid sequence CLT1 or CLT2. The amino acid segments can each independently comprise the amino acid sequence CLT1 or CLT2 or a conservative variant thereof. The amino acid segments can also each independently comprise the amino acid sequence CLT1 or CLT2. The amino acid segment can also consist of the amino acid sequence CLT1 or CLT2.

The amino acid segments can also each independently comprise the amino acid sequence CARSKNKDC (SEQ ID NO: 79), and the amino acid sequence CRK (such as CRKDKC; SEQ ID NO: 80). Peptides comprising amino acid sequences CAR or CRK are also described in U.S. Patent Application Publication No. 2009/0036349, which is hereby incorporated by reference for its description of such peptides.

The composition can comprise any number of tumor-homing compounds. By way of example, the composition can comprise at least 1, 5, 10, 15, 20, 25, 50, 75, 100, 125, 150, 175, 200, 225, 250, 275, 300, 325, 350, 375, 400, 425, 450, 475, 500, 525, 550, 575, 600, 625, 650, 675, 700, 625, 750, 775, 800, 825, 850, 875, 900, 925, 950, 975, 1000, 1100, 1200, 1300, 1400, 1500, 1600, 1700, 1800, 1900, 2000, 2250, 2500, 2750, 3000, 3500, 4000, 4500, 5000, 5500, 6000, 6500, 7000, 7500, 8000, 8500, 9000, 9500, 10,000, 15,000, 20,000, 25,000, 30,000, 35,000, 40,000, 45,000, 50,000, 75,000, or 100,000, or more tumor-homing compounds. The composition can also comprise any number in between those numbers listed above.

Table 3 shows examples of tumor-homing CendR peptides.

have any useful modification. For example, some modifications can stabilize the homing molecule. For example, the disclosed homing molecules include methylated homing molecules. Methylated homing molecules are particularly useful when the homing molecule includes a protein, peptide, or amino acid segment. For example, a homing molecule can be a modified homing molecule, where, for example, the modified homing molecule includes a modified amino acid segment or amino acid sequence. For example, a modified homing molecule can be a methylated homing molecule, where, for example, the methylated homing molecule includes a methylated amino acid segment or amino acid sequence. Other modifications can be used, either alone or in combination. Where the homing molecule is, or includes, a protein, peptide, amino acid segment and/or amino acid sequences, the modification can be to the protein, peptide, amino acid segment, amino acid sequences, and/or any amino acids in the protein, peptide, amino acid segment, and/or amino acid sequences. Amino acid and peptide modifications are known to those of skill in the art, some of which are described below and elsewhere herein. Methylation is a particularly useful modification for the disclosed homing molecules. Using modified forms of homing molecules can increase the effectiveness of the homing and targeting, which can increase the effect on the target.

A plurality of modified and/or unmodified homing molecules can each be independently selected from, for example, an amino acid segment comprising, consisting essentially of, and/or consisting of a modified or unmodified form of the amino acid sequence of a homing peptide, an amino acid segment comprising, consisting essentially of, and/or consisting of a modified or unmodified form of the

TABLE 3

Examples of Tumor-Homing Peptides with CendR Elements

| Peptide Sequence | Reference(s) |
| --- | --- |
| CRKDKC (SEQ ID NO: 80) | Jarvinen et al., 2007 |
| CGNKRTRGC (SEQ ID NO: 7) | Laakkonen et al., 2002 |
| AKVKDEPQRRSARLSAKPAPPKPEPKPKKAPAKK (SEQ ID NO: 154) | Christian et al., 2003; U.S. Pat. No. 7,544,767 |
| CSRPRRSEC (SEQ ID NO: 147) CSRPRRSVC (SEQ ID NO: 148) CSRPRRSWC (SEQ ID NO: 149) | Hoffman et al., 2003 |
| CNRRTKAGC (SEQ ID NO: 155) | Zhang et al., 2006 |
| CRGRRST (SEQ ID NO: 153) CRSRKG (SEQ ID NO: 156) CKAAKNK (SEQ ID NO: 97) CKGAKAR (SEQ ID NO: 98) | Joyce et al, 2003 |
| PQRRSARLSA (SEQ ID NO: 157) | Porkka et al., 2002; U.S. Pat. No. 7,544,767 |
| PKRRSARLSA (SEQ ID NO: 158) | U.S. Pat. No. 7,544,767 |
| CRGDKGPDC (SEQ ID NO: 159) | iRGD, Sugahara et al. 2009; Sugahara et al., 2010; U.S. Pat. No. 8,367,621 |

Tumor-homing compounds can also be modified. Any of the modifications described herein for homing molecules can be used with the disclosed tumor-homing compounds.

II.D.2.b. Modified Homing Molecules

The disclosed homing molecules can include modified forms of homing molecules. The homing molecules can amino acid sequence KRGARST (SEQ ID NO: 1), an amino acid segment comprising, consisting essentially of, and/or consisting of a modified or unmodified form of the amino acid sequence AKRGARSTA (SEQ ID NO: 2) and an amino acid segment comprising, consisting essentially of, and/or consisting of a modified or unmodified form of the amino acid sequence CKRGARSTC (SEQ ID NO: 3). A plurality of the homing molecules can each independently comprise an amino acid segment comprising a modified or unmodified form of the amino acid sequence of a homing peptide.

The composition can comprise any number of modified and/or unmodified homing molecules. By way of example, the composition can comprise at least 1, 5, 10, 15, 20, 25, 50, 75, 100, 125, 150, 175, 200, 225, 250, 275, 300, 325, 350, 375, 400, 425, 450, 475, 500, 525, 550, 575, 600, 625, 650, 675, 700, 625, 750, 775, 800, 825, 850, 875, 900, 925, 950, 975, 1000, 1100, 1200, 1300, 1400, 1500, 1600, 1700, 1800, 1900, 2000, 2250, 2500, 2750, 3000, 3500, 4000, 4500, 5000, 5500, 6000, 6500, 7000, 7500, 8000, 8500, 9000, 9500, 10,000, 15,000, 20,000, 25,000, 30,000, 35,000, 40,000, 45,000, 50,000, 75,000, or 100,000, or more modified and/or unmodified homing molecules. The composition can also comprise any number in between those numbers listed above.

As used herein, a "methylated derivative" of a protein, peptide, amino acid segment, amino acid sequence, etc. refers to a form of the protein, peptide, amino acid segment, amino acid sequence, etc. that is methylated. Unless the context indicates otherwise, reference to a methylated derivative of a protein, peptide, amino acid segment, amino acid sequence, etc. does not include any modification to the base protein, peptide, amino acid segment, amino acid sequence, etc. other than methylation. Methylated derivatives can also have other modifications, but such modifications generally will be noted. For example, conservative variants of an amino acid sequence would include conservative amino acid substitutions of the base amino acid sequence. Thus, reference to, for example, a "methylated derivative" of a specific amino acid sequence "and conservative variants thereof" would include methylated forms of the specific amino acid sequence and methylated forms of the conservative variants of the specific amino acid sequence, but not any other modifications of derivations. As another example, reference to a methylated derivative of an amino acid segment that includes amino acid substitutions would include methylated forms of the amino acid sequence of the amino acid segment and methylated forms of the amino acid sequence of the amino acid segment include amino acid substitutions.

II.D.3. Cargo Molecules

The disclosed compositions include one or more cargo molecules. Generally, the disclosed compositions can include a plurality of cargo molecules. The disclosed compositions can include a single type of cargo molecule or a plurality of different types of cargo molecules. Thus, for example, the disclosed compositions can include a plurality of different types of cargo molecules where a plurality of one or more of the different types of cargo molecules can be present.

Cargo molecules can be any compound, molecule, conjugate, composition, etc. that is desired to be delivered using the disclosed compositions. For example, the cargo molecules can be therapeutic agents, detectable agents, or a combination. For example, the cargo molecules can be membrane perturbing molecules, pro-apoptotic molecules, pore-generating molecules, antimicrobial molecules, mitochondria-affecting molecules, mitochondria-targeted molecules, or a combination. Examples of some useful cargo molecules are described below and elsewhere herein.

Cargo molecules can be associated with and arranged in the compositions in a variety of configurations. In some embodiments, cargo molecules can be associated with, conjugated to, and/or covalently coupled to a plurality of surface molecules. In some embodiments, cargo molecules can be associated with, conjugated to, and/or covalently coupled to a plurality of homing molecules. In some embodiments, cargo molecules can be associated with, conjugated to, and/or covalently coupled to a plurality of homing molecules, wherein the homing molecules can be associated with, conjugated to, and/or covalently coupled to a plurality of surface molecules. Combinations of these combinations can also be used.

II.D4.a. Membrane Perturbing Molecules

Useful forms of cargo molecules include membrane perturbing molecules Membrane perturbing molecules include molecules that can disrupt membranes, which can form pores in membranes, which can make membranes leaky, that can be targeted to or affect intracellular membranes or organelles, such mitochondria or lysosomes. Some forms of membrane perturbing molecules can be pro-apoptotic while others can be non-apoptotic. Some forms of membrane perturbing molecules can be pro-apoptotic for only some types of cells.

In some embodiments, one or more of the homing molecules can comprise, consist essentially of, and/or consist of the amino acid sequence KRGARST (SEQ ID NO: 1), the amino acid sequence AKRGARSTA (SEQ ID NO: 2), and/or the amino acid sequence CKRGARSTC (SEQ ID NO: 3). In some embodiments, one or more of the membrane perturbing molecules can comprise the amino acid sequence $_D$(KLAKLAK)$_2$ (SEQ ID NO: 42) or a conservative variant thereof, (KLAKLAK)$_2$ (SEQ ID NO: 42) or a conservative variant thereof, (KLAKKLA)$_2$ (SEQ ID NO: 43) or a conservative variant thereof, (KAAKKAA)$_2$ (SEQ ID NO: 44) or a conservative variant thereof, (KLGKKLG) (SEQ ID NO: 45) or a conservative variant thereof, or a combination. In some embodiments, one or more of the membrane perturbing molecules can comprise, consist essentially of, and/or consist of the amino acid sequence $_D$(KLAKLAK)$_2$ (SEQ ID NO: 42), (KLAKLAK)$_2$ (SEQ ID NO: 42), (KLAKKLA)$_2$ (SEQ ID NO: 43), (KAAKKAA)$_2$ (SEQ ID NO: 44), (KLGKKILG)$_3$ (SEQ ID NO: 45), or a combination. In some embodiments, one or more of the membrane perturbing molecules can comprise, consist essentially of, and/or consist of the amino acid sequence (KLAKLAK)$_2$ (SEQ ID NO: 42) or a conservative variant thereof. In some embodiments, one or more of the membrane perturbing molecules can comprise, consist essentially of, and/or consist of the amino acid sequence $_D$(KLAKLAK)$_2$ (SEQ ID NO: 42). Membrane perturbing peptides of this type are described in Ellerby, 1999, which is hereby incorporated by reference for its description of such peptides.

A plurality of modified and/or unmodified membrane perturbing molecules can each be independently selected from, for example, an amino acid segment comprise, consist essentially of, and/or consist of a modified or unmodified form of the amino acid sequence of a homing peptide, an amino acid segment comprise, consist essentially of, and/or consist of a modified or unmodified form of the amino acid sequence $_D$(KLAKLAK)$_2$ (SEQ ID NO: 42), (KLAKLAK)$_2$ (SEQ ID NO: 42), (KLAKKLA)$_2$ (SEQ ID NO: 43), (KAAKKAA)$_2$ (SEQ ID NO: 44), (KLGKKLG)$_3$ (SEQ ID NO: 45), or any combination thereof. A plurality of the membrane perturbing molecules can each independently comprise an amino acid segment comprising a modified or unmodified form of the amino acid sequence of a homing peptide.

The composition can comprise a sufficient number and composition of membrane perturbing molecules (modified or not) such that the composition has a membrane perturbing effect on the target. In one example, sufficiency of the number and composition of modified and/or unmodified membrane perturbing molecules can be determined by assessing membrane disruption, apoptosis, and/or therapeutic effect on the target.

The composition can comprise any number of modified and/or unmodified membrane perturbing molecules. By way of example, the composition can comprise at least 1, 5, 10, 15, 20, 25, 50, 75, 100, 125, 150, 175, 200, 225, 250, 275, 300, 325, 350, 375, 400, 425, 450, 475, 500, 525, 550, 575, 600, 625, 650, 675, 700, 625, 750, 775, 800, 825, 850, 875, 900, 925, 950, 975, 1000, 1100, 1200, 1300, 1400, 1500, 1600, 1700, 1800, 1900, 2000, 2250, 2500, 2750, 3000, 3500, 4000, 4500, 5000, 5500, 6000, 6500, 7000, 7500, 8000, 8500, 9000, 9500, 10,000, 15,000, 20,000, 25,000, 30,000, 35,000, 40,000, 45,000, 50,000, 75,000, or 100,000, or more modified and/or unmodified membrane perturbing molecules. The composition can also comprise any number in between those numbers listed above.

Membrane perturbing molecules can be associated with and arranged in the compositions in a variety of configurations. In some embodiments, membrane perturbing molecules can be associated with, conjugated to, and/or covalently coupled to a plurality of surface molecules. In some embodiments, membrane perturbing molecules can be associated with, conjugated to, and/or covalently coupled to a plurality of homing molecules. In some embodiments, membrane perturbing molecules can be associated with, conjugated to, and/or covalently coupled to a plurality of homing molecules, wherein the homing molecules can be associated with, conjugated to, and/or covalently coupled to a plurality of surface molecules. Combinations of these combinations can also be used.

II.D.4.b. Modified Membrane Perturbing Molecules

The disclosed membrane perturbing molecules can include modified forms of membrane perturbing molecules. The membrane perturbing molecules can have any useful modification. For example, some modifications can stabilize the membrane perturbing molecule. For example, the disclosed membrane perturbing molecules include methylated membrane perturbing molecules.

Methylated membrane perturbing molecules are particularly useful when the membrane perturbing molecule includes a protein, peptide, or amino acid segment. For example, a membrane perturbing molecule can be a modified membrane perturbing molecule, where, for example, the modified membrane perturbing molecule includes a modified amino acid segment or amino acid sequence. For example, a modified membrane perturbing molecule can be a methylated membrane perturbing molecule, where, for example, the methylated membrane perturbing molecule includes a methylated amino acid segment or amino acid sequence. Other modifications can be used, either alone or in combination. Where the membrane perturbing molecule is, or includes, a protein, peptide, amino acid segment and/or amino acid sequences, the modification can be to the protein, peptide, amino acid segment, amino acid sequences, and/or any amino acids in the protein, peptide, amino acid segment, and/or amino acid sequences. Amino acid and peptide modifications are known to those of skill in the art, some of which are described below and elsewhere herein. Methylation is a particularly useful modification for the disclosed membrane perturbing molecules, Using modified forms of membrane perturbing molecules can increase their effectiveness.

II.E.1. Moieties Generally

Disclosed are compositions useful for directing a moiety to a target. For example, the moiety can be incorporated into a TT1 Peptide composition. As used herein, the term "moiety" is used broadly to mean a physical, chemical, or biological material that generally imparts a biologically useful function to a linked molecule. A moiety can be any natural or non-natural material including, without limitation, a biological material, such as a cell, phage or other virus; an organic chemical such as a small molecule; a radionuclide; a nucleic acid molecule or oligonucleotide; a polypeptide; or a peptide. Useful moieties include, but are not limited to, therapeutic agents such as cancer chemotherapeutic agents, cytotoxic agents, pro-apoptotic agents, and anti-angiogenic agents; detectable agents and imaging agents; and tags or other insoluble supports. Useful moieties further include, without limitation, phage and other viruses, cells, liposomes, polymeric matrices, non-polymeric matrices or particles such as gold particles, microdevices and nanodevices, and nanoscale semiconductor materials. These and other moieties known in the art can be components of a conjugate.

Thus, in some embodiments the composition can further comprise one or more moieties. In some embodiments, the moieties can be independently selected from the group consisting of an anti-angiogenic agent, a pro-angiogenic agent, a cancer chemotherapeutic agent, a cytotoxic agent, an anti-inflammatory agent, an anti-arthritic agent, a polypeptide, a nucleic acid molecule, a small molecule, an image contrast agent, a fluorophore, fluorescein, rhodamine, a radionuclide, indium-111, technetium-99, carbon-11, and carbon-13. In some embodiments, at least one of the moieties can be a therapeutic agent. In some embodiments, the therapeutic agent can be iRGD, RGD, Abraxane, paclitaxel, taxol, or a combination. In some embodiments, at least one of the moieties can be a detectable agent. In some embodiments, the detectable agent can be FAM.

II.E.2. Therapeutic Agents

In some embodiments, the composition can have a therapeutic effect. In some embodiments, the composition can reduce tumor growth. In some embodiments, the therapeutic effect can be a slowing in the increase of or a reduction of tumor burden. In some embodiments, the therapeutic effect can be a slowing of the increase of or reduction of tumor size. In some embodiments, the subject can have one or more sites targeted, wherein the composition can home to one or more of the sites targeted. In some embodiments, the subject can have a tumor, wherein the composition can have a therapeutic effect on the tumor. The moiety can be a therapeutic agent. As used herein, the term "therapeutic agent" means a molecule which has one or more biological activities in a normal or pathologic tissue. A variety of therapeutic agents can be used as a moiety.

In some embodiments, the therapeutic agent can be a cancer chemotherapeutic agent. As used herein, a "cancer chemotherapeutic agent" is a chemical agent that inhibits the proliferation, growth, life-span or metastatic activity of cancer cells. Such a cancer chemotherapeutic agent can be, without limitation, a taxane such as docetaxel; an anthracyclin such as doxorubicin; an alkylating agent; a vinca alkaloid; an anti-metabolite; a platinum agent such as cisplatin or carboplatin; a steroid such as methotrexate; an antibiotic such as adriamycin; a isofamide; or a selective estrogen receptor modulator; an antibody such as trastuzumab.

Taxanes are chemotherapeutic agents useful in Lyp-1 compositions. Useful taxanes include, without limitation, docetaxel (Taxotere; Aventis Pharmaceuticals, Inc.; Parsippany, N.J., United States of America) and paclitaxel (Taxol; Bristol-Myers Squibb; Princeton, N.J., United States of America). See e.g., Chan et al., 1999; Paridaens et al., 2000.

A cancer chemotherapeutic agent useful in a TT1 Peptide composition also can be an anthracyclin such as doxorubicin, idarubicin, or daunorubicin. Doxorubicin is a commonly used cancer chemotherapeutic agent and can be useful, for example, for treating breast cancer (Stewart & Ratain, 1997; Harris et al., 1997). In addition, doxorubicin has anti-angiogenic activity (Folkman, 1997; Steiner et al., 1992), which can contribute to its effectiveness in treating cancer.

An alkylating agent such as melphalan or chlorambucil also can be a useful cancer chemotherapeutic agent. Similarly, a vinca alkaloid such as vindesine, vinblastine, or vinorelbine; or an antimetabolite such as 5-fluorouracil, 5-fluorouridine, or a derivative thereof can be a useful cancer chemotherapeutic agent.

A platinum agent also can be a useful cancer chemotherapeutic agent. Such a platinum agent can be, for example, cisplatin or carboplatin as described, for example, in Crown (2001) Sem Oncol 28:28-37. Other useful cancer chemotherapeutic agents include, without limitation, methotrexate, mitomycin-C, adriamycin, ifosfamide, and ansamycins.

A cancer chemotherapeutic agent useful for treatment of breast cancer and other hormonally-dependent cancers also can be an agent that antagonizes the effect of estrogen, such as a selective estrogen receptor modulator or an anti-estrogen. The selective estrogen receptor modulator, tamoxifen, is a cancer chemotherapeutic agent that can be used in a conjugate for treatment of breast cancer (Fisher et al., 1998).

The therapeutic agent can be an antibody such as a humanized monoclonal antibody. As an example, the anti-epidermal growth factor receptor 2 (HER2) antibody, trastuzumab (HERCEPTIN®; Genentech, South San Francisco, Calif., United States of America) can be a therapeutic agent useful for treating HER2/neu overexpressing breast cancers (White et al., 2001).

Useful therapeutic agents also can be a cytotoxic agent, which, as used herein, can be any molecule that directly or indirectly promotes cell death. Useful cytotoxic agents include, without limitation, small molecules, polypeptides, peptides, peptidomimetics, nucleic acid-molecules, cells, and viruses. As non-limiting examples, useful cytotoxic agents include cytotoxic small molecules such as doxorubicin, docetaxel or trastuzumab; antimicrobial peptides such as those described further below; pro-apoptotic polypeptides such as caspases and toxins, for example, caspase-8; diphtheria toxin A chain, Pseudomonas exotoxin A, cholera toxin, ligand fusion toxins such as DAB(389)EGF, ncinus communis toxin (ricin); and cytotoxic cells such as cytotoxic T cells. See e.g., Martin et al., 2000; Kreitman & Pastan, 1997; Allam et al., 1997; Osborne & Coronado-Heinsohn, 1996. One skilled in the art understands that these and additional cytotoxic agents described herein or known in the art can be useful in the disclosed conjugates and methods.

In some embodiments, a therapeutic agent can be a therapeutic polypeptide. As used herein, a therapeutic polypeptide can be any polypeptide with a biologically useful function. Useful therapeutic polypeptides encompass, without limitation, cytokines, antibodies, cytotoxic polypeptides; pro-apoptotic polypeptides; and anti-angiogenic polypeptides. As non-limiting examples, useful therapeutic polypeptides can be a cytokine such as tumor necrosis factor-α (TNF-α), tumor necrosis factor-β (TNF-β), granulocyte macrophage colony stimulating factor (GM-CSF), granulocyte colony stimulating factor (G-CSF), interferon alpha (IFN-α); interferon gamma (IFN-γ), interleukin-1 (IL-1), interleukin-2 (IL-2), interleukin-3 (IL-3), interleukin-4 (IL-4), interleukin-6 (IL-6), interleukin-7 (IL-7), interleukin-10 (IL-10), interleukin-12 (IL-12), lymphotactin (LTN), or dendritic cell chemokine 1 (DC-CK1); an anti-HER2 antibody or fragment thereof, a cytotoxic polypeptide including a toxin or caspase, for example, diphtheria toxin A chain, Pseudomonas exotoxin A, cholera toxin, a ligand fusion toxin such as DAB(389)EGF (see U.S. Pat. No. 5,906,820) or ricin; or an anti-angiogenic polypeptide such as angiostatin, endostatin, thrombospondin, platelet factor 4; anastellin; or one of those described further herein or known in the art (see below). It is understood that these and other polypeptides with biological activity can be a "therapeutic polypeptide."

A therapeutic agent can also be an anti-angiogenic agent. As used herein, the term "anti-angiogenic agent" means a molecule that reduces or prevents angiogenesis, which is the growth and development of blood vessels. A variety of anti-angiogenic agents can be prepared by routine methods. Such anti-angiogenic agents include, without limitation, small molecules; proteins such as dominant negative forms of angiogenic factors, transcription factors, and antibodies; peptides; and nucleic acid molecules including ribozymes, antisense oligonucleotides, and nucleic acid molecules encoding, for example, dominant negative forms of angiogenic factors and receptors, transcription factors, and antibodies and antigen-binding fragments thereof. See e.g., Hagedorn & Bikfalvi, 2000; Kirsch et al., 2000.

Vascular endothelial growth factor (VEGF) has been shown to be important for angiogenesis in many types of cancer, including breast cancer angiogenesis in vivo (Borgstrom et al., 1999). The biological effects of VEGF include stimulation of endothelial cell proliferation, survival, migration, and tube formation, and regulation of vascular permeability. An anti-angiogenic agent can be, for example, an inhibitor or neutralizing antibody that reduces the expression or signaling of VEGF or another angiogenic factor, for example, an anti-VEGF neutralizing monoclonal antibody (Borgstrom et al., 1999). An anti-angiogenic agent also can inhibit another angiogenic factor such as a member of the fibroblast growth factor family such as FGF-1 (acidic), FGF-2 (basic), FGF-4, or FGF-5 (Slavin et al., 1995; Folkman & Shing, 1992) or an angiogenic factor such as angiopoietin-1, a factor that signals through the endothelial cell-specific Tie2 receptor tyrosine kinase (Davis et al., 1996; Suri et al., 1996), or the receptor of one of these angiogenic factors. It is understood that a variety of mechanisms can act to inhibit activity of an angiogenic factor including, without limitation, direct inhibition of receptor binding, indirect inhibition by reducing secretion of the angiogenic factor into the extracellular space, or inhibition of expression, function or signaling of the angiogenic factor.

A variety of other molecules also can function as anti-angiogenic agents including, without limitation, angiostatin; a kringle peptide of angiostatin; endostatin; anastellin, heparin-binding fragments of fibronectin; modified forms of antithrombin; collagenase inhibitors; basement membrane turnover inhibitors; angiostatic steroids; platelet factor 4 and fragments and peptides thereof, thrombospondin and fragments and peptides thereof, and doxorubicin (O'Reilly et al., 1994; O'Reilly et al., 1997; Homandberg et al., 1985; Homandberg et al., 1986; O'Reilly et al., 1999). Commercially available anti-angiogenic agents include, for example, angiostatin, endostatin, metastatin and 2ME2 (EntreMed; Rockville, Md., United States of America); anti-VEGF antibodies such as Avastin (Genentech; South San Francisco, Calif., United States of America); and VEGFR-2 inhibitors such as SU5416 (3-[(3,5-Dimethyl-1H-pyrrol-2-yl)methylene]-1,3-dihydro-2H-indol-2-one), a small molecule inhibitor of VEGFR-2 (SUGEN; South San Francisco, Calif., United States of America) and SU6668 (5-[1,2-Dihydro-2-oxo-3H-indol-3-ylidene)methyl]-2,4-dimethyl-1H-pyrrole-3-propanoic acid; SUGEN), a small molecule inhibitor of VEGFR-2, platelet derived growth factor and fibroblast growth factor I receptor. It is understood that these and other anti-angiogenic agents can be prepared by routine methods and are encompassed by the term "anti-angiogenic agent" as used herein.

The TT1 Peptide compositions disclosed herein can also be used to site of inflammation. Moieties useful for this purpose can include therapeutic agents belonging to several basic groups including anti-inflammatory agents which prevent inflammation, restenosis preventing drugs which prevent tissue growth, anti-thrombogenic drugs which inhibit or control formation of thrombus or thrombolytics, and bioactive agents which regulate tissue growth and enhance healing of the tissue. Examples of useful therapeutic agents include but are not limited to steroids, fibronectin, anticlotting drugs, anti-platelet function drugs, drugs which prevent smooth muscle cell growth on inner surface wall of vessel, heparin, heparin fragments, aspirin, coumadin, tissue plasminogen activator (TPA), urokinase, hirudin, streptokinase, antiproliferatives (methotrexate, cisplatin, fluorouracil, Adriamycin), antioxidants (ascorbic acid, beta carotene, vitamin E), antimetabolites, thromboxane inhibitors, non-steroidal and steroidal anti-inflammatory drugs, beta and calcium channel blockers, genetic materials including DNA and RNA fragments, complete expression genes, antibodies, lymphokines, growth factors, prostaglandins, leukotrienes, laminin, elastin, collagen, and integrins.

Useful therapeutic agents also can be antimicrobial peptides. This can be particularly useful to target a wound or other infected sites. Thus, for example, also disclosed are TT1 Peptide compositions comprising an antimicrobial peptide, where the TT1 Peptide composition is selectively internalized and exhibits a high toxicity to the targeted area. Useful antimicrobial peptides can have low mammalian cell toxicity when not incorporated into the TT1 Peptide composition. As used herein, the term "antimicrobial peptide" means a naturally occurring or synthetic peptide having antimicrobial activity, which is the ability to kill or slow the growth of one or more microbes. An antimicrobial peptide can, for example, kill or slow the growth of one or more strains of bacteria including a Gram-positive or Gram-negative bacteria, or a fungi or protozoa. Thus, an antimicrobial peptide can have, for example, bacteriostatic or bacteriocidal activity against, for example, one or more strains of *Escherichia coli, Pseudomonas aeruginosa*, or *Staphylococcus aureus*. While not wishing to be bound by the following, an antimicrobial peptide can have biological activity due to the ability to form ion channels through membrane bilayers as a consequence of self-aggregation.

An antimicrobial peptide is typically highly basic and can have a linear or cyclic structure. As discussed further below, an antimicrobial peptide can have an amphipathic α-helical structure (see e.g., U.S. Pat. No. 5,789,542; Javadpour et al., 1996; Blondelle & Houghten, 1992a). An antimicrobial peptide also can be, for example, a β-strand/sheet-forming peptide as described in Mancheno et al., 1998.

An antimicrobial peptide can be a naturally occurring or synthetic peptide. Naturally occurring antimicrobial peptides have been isolated from biological sources such as bacteria, insects, amphibians, and mammals and are thought to represent inducible defense proteins that can protect the host organism from bacterial infection. Naturally occurring antimicrobial peptides include the gramicidins, magainins, mellitins, defensins, and cecropins (see e.g., Maloy & Kari, 1995; Alvarez-Bravo et al., 1994; Bessalle et al., 1990; Blondelle & Houghten, 1992b). An antimicrobial peptide also can be an analog of a natural peptide, especially one that retains or enhances amphipathicity (see below).

An antimicrobial peptide incorporated into a TT1 Peptide composition can have low mammalian cell toxicity linked to a TT1 Peptide. Mammalian cell toxicity readily can be assessed using routine assays. As an example, mammalian cell toxicity can be assayed by lysis of human erythrocytes in vitro as described in Javadpour et al., 1996. An antimicrobial peptide having low mammalian cell toxicity is not lytic to human erythrocytes or requires concentrations of in some embodiments greater than 100 µM for lytic activity, and requires concentrations of greater than in some embodiments 200 µM, in some embodiments 300 µM, in some embodiments 500 µM, and in some embodiments 1000 µM.

In some embodiments, disclosed are TT1 Peptide compositions in which the antimicrobial peptide portion promotes disruption of mitochondrial membranes when internalized by eukaryotic cells. In particular, such an antimicrobial peptide preferentially disrupts mitochondrial membranes as compared to eukaryotic membranes. Mitochondrial membranes, like bacterial membranes but in contrast to eukaryotic plasma membranes, have a high content of negatively charged phospholipids. An antimicrobial peptide can be assayed for activity in disrupting mitochondrial membranes using, for example, an assay for mitochondrial swelling or another assay well known in the art. $_D$(KLAK-LAK)$_2$, for example, is an antimicrobial peptide which induces marked mitochondrial swelling at a concentration of 10 µM, significantly less than the concentration required to kill eukaryotic cells.

An antimicrobial peptide that induces significant mitochondrial swelling at, for example, 50 µM, 40 µM, 30 µM, 20 µM, 10 µM, or less, is considered a peptide that promotes disruption of mitochondrial membranes.

Antimicrobial peptides generally have random coil conformations in dilute aqueous solutions, yet high levels of helicity can be induced by helix-promoting solvents and amphipathic media such as micelles, synthetic bilayers, or cell membranes. α-Helical structures are well known in the art, with an ideal α-helix characterized by having 3.6 residues per turn and a translation of 1.5 Å per residue (5.4 Å per turn; see Creighton, 1984). In an amphipathic α-helical structure, polar and non-polar amino acid residues are aligned into an amphipathic helix, which is an α-helix in which the hydrophobic amino acid residues are predominantly on one face, with hydrophilic residues predominantly on the opposite face when the peptide is viewed along the helical axis.

Antimicrobial peptides of widely varying sequence have been isolated, sharing an amphipathic α-helical structure as a common feature (Saberwal et al., 1994). Analogs of native peptides with amino acid substitutions predicted to enhance amphipathicity and helicity typically have increased antimicrobial activity. In general, analogs with increased antimicrobial activity also have increased cytotoxicity against mammalian cells (Maloy et al., 1995).

As used herein in reference to an antimicrobial peptide, the term "amphipathic α-helical structure" refers to an α-helix with a hydrophilic face containing several polar residues at physiological pH and a hydrophobic face containing nonpolar residues. A polar residue can be, for example, a lysine or arginine residue, while a nonpolar residue can be, for example, a leucine or alanine residue. An antimicrobial peptide having an amphipathic .alpha.-helical structure generally has an equivalent number of polar and nonpolar residues within the amphipathic domain and a sufficient number of basic residues to give the peptide an overall positive charge at neutral pH (Saberwal et al., 1994). One skilled in the art understands that helix-promoting amino acids such as leucine and alanine can be advantageously included in an antimicrobial peptide (see e.g., Creighton, 1984 supra). Synthetic, antimicrobial peptides having an amphipathic α-helical structure are known in the art, for example, as described in U.S. Pat. No. 5,789,542 to McLaughlin & Becker.

It is understood by one skilled in the art of medicinal oncology that these and other agents are useful therapeutic agents, which can be used separately or together in the disclosed compositions and methods. Thus, it is understood that a TT1 Peptide composition can contain one or more of such therapeutic agents and that additional components can be included as part of the composition, if desired. As a non-limiting example, it can be desirable in some cases to utilize an oligopeptide spacer between a TT1 Peptide and the therapeutic agent (Fitzpatrick & Garnett, 1995).

Other useful agents include thrombolytics, aspirin, anticoagulants, painkillers and tranquilizers, beta-blockers, ace-inhibitors, nitrates, rhythm-stabilizing drugs, and diuretics. Agents that limit damage to the heart work best if given within a few hours of the heart attack. Thrombolytic agents that break up blood clots and enable oxygen-rich blood to flow through the blocked artery increase the patient's chance of survival if given as soon as possible after the heart attack. Thrombolytics given within a few hours after a heart attack are the most effective. Injected intravenously, these include anisoylated plasminogen streptokinase activator complex (APSAC) or anistreplase, recombinant tissue-type plasminogen activator (r-tPA), and streptokinase. The disclosed TT1 Peptide compositions can use any of these or similar agents.

Some other examples of useful therapeutic agents include nitrogen mustards, nitrosoureas, ethyleneimine, alkane sulfonates, tetrazine, platinum compounds, pyrimidine analogs, purine analogs, antimetabolites, folate analogs, anthracyclines, taxanes, vinca alkaloids, topoisomerase inhibitors and hormonal agents. Exemplary chemotherapy drugs are Actinomycin-D, Alkeran, Ara-C, Anastrozole, Asparaginase, BiCNU, Bicalutamide, Bleomycin, Busulfan, Capecitabine, Carboplatin, Carboplatinum, Carmustine, CCNU, Chlorambucil, Chlomaphazine, Cholophosphamide, Cisplatin, Cladribine, CPT-11, Cyclophosphamide, Cytarabine, Cytosine arabinoside, Cytoxan, Dacarbazine, Dactinomycin, Daunorubicin, Dexrazoxane, Docetaxel, Doxorubicin, DTIC, Epirubicin, Estramustine, Ethyleneimine, Etoposide, Floxuridine, Fludarabine, Fluorouracil, Flutamide, Fotemustine, Gemcitabine, Herceptin, Hexamethylamine, Hydroxyurea, Idarubicin, Ifosfamide, Irinotecan, Lomustine, Mechlorethamine, mechlorethamine oxide hydrochloride, Melphalan, Mercaptopurine, Methotrexate, Mitomycin, Mitotane, Mitoxantrone, Novembiehin, Oxaliplatin, Paclitaxel, Pamidronate, Pentostatin, Phenesterine, Plicamycin, Prednimustine, Procarbazine, Rituximab, Steroids, Streptozocin, STI-571, Streptozocin, Tamoxifen, Temozolomide, Teniposide, Tetrazine, Thioguanine, Thiotepa, Tomudex, Topotecan, Treosulphan, Trimetrexate, Trofosfamide, Vinblastine, Vincristine, Vindesine, Vinorelbine, VP-16, and Xeloda. Alkylating agents such as Thiotepa and; alkyl sulfonates such as Busulfan, Improsulfan and Piposulfan; aziridines such as Benzodopa, Carboquone, Meturedopa, and Uredopa; ethylenimines and methylamelamines including altretamine, triethylenemelamine, trietylenephosphoramide, triethylenethiophosphaoramide and trimethylolomelamine; nitroureas such as Cannustine, Chlorozotocin, Fotemustine, Lomustine, Nimustine, and Ranimustine; antibiotics such as Aclacinomysins, Actinomycin, Authramycin, Azaserine, Bleomycins, Cactinomycin, Calicheamicin, Carabicin, Caminomycin, Carzinophilin, Chromoinycins, Dactinomycin, Daunorubicin, Detorubicin, 6-diazo-5-oxo-L-norleucine, Doxorubicin, Epirubicin, Esorubicin, Idambicin, Marcellomycin, Mitomycins, mycophenolic acid, Nogalamycin, Olivomycins, Peplomycin, Potfiromycin, Puromycin, Quelamycin, Rodorubicin, Streptonigrin, Streptozocin, Tubercidin, Ubenimex, Zinostatin, and Zorubicin; anti-metabolites such as Methotrexate and 5-fluorouracil (5-FU); folic acid analogues such as Denopterin, Methotrexate, Pteropterin, and Trimetrexate; purine analogs such as Fludarabine, 6-mercaptopurine, Thiamiprine, and Thioguanine; pyrimidine analogs such as Ancitabine, Azacitidine, 6-azauridine, Carmofur, Cytarabine, Dideoxyuridine, Doxifluridine, Enocitabine, Floxuridine, and 5-FU; androgens such as Calusterone, Dromostanolone Propionate, Epitiostanol, Rnepitiostane, and Testolactone; anti-adrenals such as aminoglutethimide, Mitotane, and Trilostane; folic acid replenisher such as frolinic acid; aceglatone; aldophosphamide glycoside; aminolevulinic acid; Amsacrine; Bestrabucil; Bisantrene; Edatraxate; Defofamine; Demecolcine; Diaziquone; Elfornithine; elliptinium acetate; Etoglucid; gallium nitrate; hydroxyurea; Lentinan; Lonidamine; Mitoguazone; Mitoxantrone; Mopidamol; Nitracrine; Pentostatin; Phenamet; Pirarubicin; podophyllinic acid; 2-ethylhydrazide; Procarbazine; PSK®; Razoxane; Sizofrran; Spirogermanium; tenuazonic acid; triaziquone; 2,2',2"-trichlorotriethylamine; Urethan; Vindesine; Dacarbazine; Mannomustine; Mitobronitol; Mitolactol; Pipobroman; Gacytosine; Arabinoside ("Ara-C"); cyclophosphamide; thiotEPa; taxoids, e.g., Paclitaxel (TAXOL®, Bristol-Myers Squibb Oncology, Princeton, N.J.) and Doxetaxel (TAXOTERE®, Rhone-Poulenc Rorer, Antony, France); Gemcitabine; 6-thioguanine; Mercaptopurine; Methotrexate; platinum analogs such as Cisplatin and Carboplatin; Vinblastine; platinum; etoposide (VP-16); Ifosfamide; Mitomycin C; Mitoxantrone; Vincristine; Vinorelbine; Navelbine; Novantrone; Teniposide; Daunomycin; Aminopterin; Xeloda; Ibandronate; CPT-11; topoisomerase inhibitor RFS 2000; difluoromethylornithine (DMFO); retinoic acid; Esperamicins; Capecitabine; and pharmaceutically acceptable salts, acids or derivatives of any of the above. Also included are anti-hormonal agents that act to regulate or inhibit hormone action on tumors such as anti-estrogens including for example Tamoxifen, Raloxifene, aromatase inhibiting 4(5)-imidazoles, 4 Hydroxytamoxifen, Trioxifene, Keoxifene, Onapristone, And Toremifene (Fareston); and anti-androgens such as Flutamide, Nilutamide, Bicalutamide, Leuprolide, and Goserelin; and pharmaceutically acceptable salts, acids or derivatives of any of the above. Useful cargo molecules include, for example, doxorubicin, Herceptin, and liposomal doxorubicin.

The cargo molecules can also comprise a boron containing compound. Boron containing compounds have received increasing attention as therapeutic agents over the past few years as technology in organic synthesis has expanded to include this atom (Groziak, 2001). The most notable boron containing therapeutic is the boronic acid bortezomib which was recently launched for the treatment of multiple myeloma. This breakthrough demonstrates the feasibility of using boron containing compounds as pharmaceutical agents. Boron containing compounds have been shown to have various biological activities including herbicides (German Patent Application Publication No. DE 1016978

19571003), boron neutron capture therapy (Yamamoto, 1991), serine protease inhibition (Simpelkamp & Jones, 1992); Weinand et al., 1999), acetylcholinesterase inhibition (Koehler & Hess, 1974) and as antibacterial agents (Bailey et al., 1980). The boron containing compounds with antibacterial activity can be sub-divided into two main classes, the diazaborinines, which have been known since the 1960's, and dithienylborinic acid complexes. This latter class has been expanded to include many different diarylborinic acid complexes with potent antibacterial activity (PCT International Patent Application Publication No. WO 2002/044184).

II.E.3. Detectable Agents

A moiety in the disclosed TT1 Peptide compositions can also be a detectable agent. A variety of detectable agents are useful in the disclosed methods. As used herein, the term "detectable agent" refers to any molecule which can be detected. Useful detectable agents include compounds and molecules that can be administered in vivo and subsequently detected. Detectable agents useful in the disclosed compositions and methods include yet are not limited to radiolabels and fluorescent molecules. The detectable agent can be, for example, any molecule that facilitates detection, either directly or indirectly, preferably by a non-invasive and/or in vivo visualization technique. For example, a detectable agent can be detectable by any known imaging techniques, including, for example, a radiological technique. Detectable agents can include, for example, a contrasting agent, e.g., where the contrasting agent is ionic or non-ionic. In some embodiments, for instance, the detectable agent comprises a tantalum compound and/or a barium compound, e.g., barium sulfate. In some embodiments, the detectable agent comprises iodine, such as radioactive iodine. In some embodiments, for instance, the detectable agent comprises an organic iodo acid, such as iodo carboxylic acid, triiodophenol, iodoform, and/or tetraiodoethylene. In some embodiments, the detectable agent comprises a non-radioactive detectable agent, e.g., a non-radioactive isotope. For example, Gd can be used as a non-radioactive detectable agent in certain embodiments.

Other examples of detectable agents include molecules which emit or can be caused to emit detectable radiation (e.g., fluorescence excitation, radioactive decay, spin resonance excitation, etc.), molecules which affect local electromagnetic fields (e.g., magnetic, ferromagnetic, ferromagnetic, paramagnetic, and/or superparamagnetic species), molecules which absorb or scatter radiation energy (e.g., chromophores and/or fluorophores), quantum dots, heavy elements and/or compounds thereof. See e.g., detectable agents described in U.S. Patent Application Publication No. 2004/0009122. Other examples of detectable agents include a proton-emitting molecules, a radiopaque molecules, and/or a radioactive molecules, such as a radionuclide like Tc-99m and/or Xe-13. Such molecules can be used as a radiopharmaceutical. In still other embodiments, the disclosed compositions can comprise one or more different types of detectable agents, including any combination of the detectable agents disclosed herein.

Useful fluorescent moieties include, but are not limited to fluorescein isothiocyanate (FITC), 5,6-carboxymethyl fluorescein, Texas red, nitrobenz-2-oxa-1,3-diazol-4-yl (NBD), coumarin, dansyl chloride, rhodamine, amino-methyl coumarin (AMCA), Eosin, Erythrosin, BODIPY®, CASCADE BLUE®, OREGON GREEN, pyrene, lissamine, xanthenes, acridines, oxazines, phycoerythrin, macrocyclic chelates of lanthanide ions such as QUANTUM DYE™, fluorescent energytransfer dyes, such as thiazole orange-ethidium heterodimer, and the cyanine dyes Cy3, Cy3.5, Cy5, Cy5.5 and Cy7. Non-limiting examples of other fluorescent labels include 3-Hydroxypyrene 5,8,10-Trisulfonic acid, 5-Hydroxytryptamine (5-HT), Acid Fuchsin, Alizarin Complexone, Alizarin Red, Allophycocyanin, Aminocoumarin, Anthroyl Stearate, Astrazon Brilliant Red 4G, Astrazon Orange R, Astrazon Red 6B, Astrazon Yellow 7 GLL, Atabrine, Auramine, Aurophosphine, Aurophosphine G, BAO 9 (Bisaminophenyloxadiazole), BCECF, Berberine Sulfate, Bisbenzamide, Blancophor FFG Solution, Blancophor SV, BODIPY® F1, Brilliant Sulfoflavin FF, Calcien Blue, Calcium Green, Calcofluor RW Solution, Calcofluor White, Calcophor White ABT Solution, Calcophor White Standard Solution, Carbostyryl, Cascade Yellow, Catecholamine, Chinacrine, Coriphosphine O, Coumarin-Phalloidin, CY3.1 8, CY5.1 8, CY7, Dans (1-Dimethyl-aminonaphthalene-5-sulfonate), Dansa (Diamino Naphtyl Sulfonic Acid), Dansyl NH—CH3, Diamino Phenyl Oxydiazole (DAO), Dimethylamino-5-Sulfonic acid, Dipyrromethenboron Difluoride, Diphenyl Brilliant Flavine 7GFF, Dopamine, Erythrosin ITC, Euchrysin, FIF (Formaldehyde Induced Fluorescence), Flazo Orange, Fluo 3, Fluorescamine, Fura-2, Genacryl Brilliant Red B, Genacryl Brilliant Yellow 10GF, Genacryl Pink 3G, Genacryl Yellow 5GF, Gloxalic Acid, Granular Blue, Haematoporphyrin, Indo-1, Intrawhite Cf Liquid, Leucophor PAF, Leucophor SF, Leucophor WS, Lissamine Rhodamine B200 (RD200), Lucifer Yellow CH, Lucifer Yellow VS, Magdala Red, Marina Blue, Maxilon Brilliant Flavin 10 GFF, Maxilon Brilliant Flavin 8 GFF, MPS (Methyl Green Pyronine Stilbene), Mithramycin, NBD Amine, Nitrobenzoxadidole, Noradrenaline, Nuclear Fast Red, Nuclear Yellow, Nylosan Brilliant Flavin E8G, Oxadiazole, Pacific Blue, Pararosaniline (Feulgen), Phorwite AR Solution, Phorwite BKL, Phorwite Rev, Phorwite RPA, Phosphine 3R, Phthalocyanine, Phycoerythrin R, Polyazaindacene Pontochrome Blue Black, Porphyrin, Primuline, Procion Yellow, Pyronine, Pyronine B, Pyrozal Brilliant Flavin 7GF, Quinacrine Mustard, Rhodamine 123, Rhodamine 5 GLD, Rhodamine 6G, Rhodamine B, Rhodamine B 200, Rhodamine B Extra, Rhodamine BB, Rhodamine BG, Rhodamine WT, Serotonin, Sevron Brilliant Red 2B, Sevron Brilliant Red 4G, Sevron Brilliant Red B, Sevron Orange, Sevron Yellow L, SITS (Primuline), SITS (Stilbene Isothiosulfonic acid), Stilbene, Snarf 1, sulfoRhodamine B Can C, Sulfo Rhodamine G Extra, Tetracycline, Thiazine Red R, Thioflavin S, Thioflavin TCN, Thioflavin 5, Thiolyte, Thiozol Orange, Tinopol CBS, True Blue, Ultralite, Uranine B, Uvitex SFC, Xylene Orange, and XRITC.

Particularly useful fluorescent labels include fluorescein (5-carboxyfluorescein-N-hydroxysuccinimide ester), rhodamine (5,6-tetramethyl rhodamine), and the cyanine dyes Cy3, Cy3.5, Cy5, Cy5.5 and Cy7. The absorption and emission maxima, respectively, for these fluors are: FITC (490 nm; 520 nm), Cy3 (554 nm; 568 nm), Cy3.5 (581 nm; 588 nm), Cy5 (652 nm: 672 nm), Cy5.5 (682 nm; 703 nm) and Cy7 (755 nm; 778 nm), thus allowing their simultaneous detection. Other examples of fluorescein dyes include 6-carboxyfluorescein (6-FAM), 2',4',1,4,-tetrachlorofluorescein (TET), 2',4',5',7',1,4-hexachlorofluorescein (HEX), 2',7'-dimethoxy-4',5'-dichloro-6-carboxyrhodamine (JOE), 2'-chloro-5'-fluoro-7',8'-fused phenyl-1,4-dichloro-6-carboxyfluorescein (NED), and 2'-chloro-7'-phenyl-1,4-dichloro-6-carboxyfluorescein (VIC). Fluorescent labels can be obtained from a variety of commercial sources, including Amersham Pharmacia Biotech, Piscataway, N.J., United States of America; Molecular Probes, Eugene, Oreg., United States of America; and Research Organics, Cleveland, Ohio, United States of America. Fluorescent probes and there use are also described in Haugland, 2002.

Further examples of radioactive detectable agents include gamma emitters (e.g., the gamma emitters In-111, I-125, and I-131; Rhenium-186 and 188; and Br-77; see e.g., Thakur et al., 1976; Powers et al., 1982; U.S. Pat. No. 5,011,686); positron emitters, such as but not limited to Cu-64, C-11, and O-15; as well as Co-57, Cu-67, Ga-67, Ga-68, Ru-97, Tc-99m, In-113m, Hg-197, Au-198, and Pb-203. Other radioactive detectable agents can include, for example tritium, C-14 and/or thallium, as well as Rh-105, 1-123, Nd-147, Pm-151, Sm-153, Gd-159, Tb-161, Er-171, and/or Tl-201.

In some embodiments, Technitium-99m (Tc-99m) is employed as has been described in other applications (see e.g., U.S. Pat. Nos. 4,418,052 and 5,024,829). Tc-99m is a gamma emitter with single photon energy of 140 keV and a half-life of about 6 hours, and can readily be obtained from a Mo-99/Tc-99 generator.

In some embodiments, compositions comprising a radioactive detectable agent can be prepared by coupling a targeting moiety with radioisotopes suitable for detection. Coupling can occur via a chelating agent such as diethylenetriaminepentaacetic acid (DTPA), 1,4,7,10-tetraazacyclododecane-1,4,7,10-tetraacetic acid (DOTA) and/or metallothionein, any of which can be covalently attached to the targeting moiety. In some embodiments, an aqueous mixture of Tc-99m, a reducing agent, and a water-soluble ligand can be prepared and then allowed to react with a disclosed targeting moiety. Such methods are known in the art (see e.g., PCT International Patent Application Publication No. WO 99/64446). In some embodiments, compositions comprising radioactive iodine can be prepared using an exchange reaction. For example, exchange of hot iodine for cold iodine is well known in the art. Alternatively, a radioiodine-labeled compound can be prepared from the corresponding bromo compound via a tributylstannyl intermediate.

Magnetic detectable agents include paramagnetic contrasting agents, for example gadolinium diethylenetriaminepentaacetic acid, which can be used, for example, in magnetic resonance imaging (MRI; see e.g., De Roos et al., 1991). Exemplary, non-limiting embodiments of the presently disclosed subject matter can use as the detectable agent paramagnetic atoms that are divalent or trivalent ions of elements with an atomic number 21, 22, 23, 24, 25, 26, 27, 28, 29, 42, 44, 58, 59, 60, 61, 62, 63, 64, 65, 66, 67, 68, 69, or 70. Suitable ions include, but are not limited to, chromium (III), manganese(II), iron(II), iron(III), cobalt(II), nickel(II), copper(II), praseodymium(III), neodymium(III), samarium (III) and ytterbium(III), as well as gadolinium(III), terbium (III), dysoprosium(III), holmium(III), and erbium(III). In some embodiments, a magnetic detectable agent employs atoms with strong magnetic moments, e.g., gadolinium(III).

In some embodiments, compositions comprising magnetic detectable agents can be prepared by coupling a targeting moiety with a paramagnetic atom. For example, the metal oxide or a metal salt, such as a nitrate, chloride or sulfate salt, of a suitable paramagnetic atom can be dissolved or suspended in a water/alcohol medium, such as methyl, ethyl, and/or isopropyl alcohol. The mixture can be added to a solution of an equimolar amount of the targeting moiety in a similar water/alcohol medium and stirred. The mixture can be heated moderately until the reaction is complete or nearly complete. Insoluble compositions formed can be obtained by filtering, while soluble compositions can be obtained by evaporating the solvent. If acid groups on the chelating moieties remain in the disclosed compositions, inorganic bases (e.g., hydroxides, carbonates and/or bicarbonates of sodium, potassium and/or lithium), organic bases, and/or basic amino acids can be used to neutralize acidic groups, e.g., to facilitate isolation or purification of the composition.

In some embodiments, the detectable agent can be coupled to a TT1 Peptide in such a way so as not to interfere with the ability of the TT1 Peptide to interact with gC1qR/p32. In some embodiments, the detectable agent can be chemically bound to the TT1 Peptide. In some embodiments, the detectable agent can be chemically bound to a moiety that is itself chemically bound to the De Roos et al., 1991, indirectly linking the imaging and targeting moieties.

II.F. Internalization Elements and Tissue Penetration Elements

The disclosed compositions, surface molecules, cargo molecules, peptides, proteins, amino acid sequences, etc. can comprise one or more internalization elements, tissue penetration elements, or both. Internalization elements and tissue penetration elements can be incorporated into or fused with other peptide components of the composition, such as peptide homing molecules and peptide cargo molecules. Internalization elements are molecules, often peptides or amino acid sequences, that allow the internalization element and components with which it is associated, to pass through biological membranes. Tissue penetration elements are molecules, often peptides or amino acid sequences, that allow the tissue penetration element and components with which it is associated to passage into and through tissue. “Internalization” refers to passage through a plasma membrane or other biological barrier. “Penetration” refers to passage into and through a membrane, cell, tissue, or other biological barrier. Penetration generally involves and includes internalization. Some molecules, such as CendR elements, function as both internalization elements and tissue penetration elements.

Internalization elements include, for example, cell-penetrating peptides (CPPs) and CendR peptides. Peptides that are internalized into cells are commonly referred to as cell-penetrating peptides. There are two main classes of such peptides: hydrophobic and cationic (Zorko and Langel, 2005). The cationic peptides, which are commonly used to introduce nucleic acids, proteins into cells, include the prototypic cell-penetrating peptides (CPP), Tat, and penetratin (Derossi et al., 1998; Meade and Dowdy, 2007). A herpes virus protein, VP22, is capable of both entering and exiting cells and carrying a payload with it (Elliott and O’Hare, 1997; Brewis et al., 2003).

II.F.1. CendR Elements

Useful forms of internalization elements and tissue penetration elements are CendR elements. CendR elements are amino acid sequences with a C-terminal element as a defining feature that signals highly efficient internalization of phage and free peptides into cells. This internalization phenomenon has been named the “C-end rule” or “CendR”. The CendR pathway can also be used for passage of compositions of interest from the vasculature and their spread into tissue. The C-terminal element can cause spread of compositions from the vasculature (and thus can be spread into tumor tissue from an intravenous injection, for example). CendR elements can also be used to mediate passage of compositions of interest through other CendR-capable membranes, such as mucous membranes and the blood-brain barrier. As used herein, “tissue penetration” and “penetration of tissue” refer to passage into or through a tissue beyond or through the outer or a first layer of cells or through a tissue membrane. Such passage or penetration through tissue (which can also be referred to as extravasation and tissue penetration) can be a function of, for example, cell internalization and passage between cells in the tissue. Throughout this application, when the term "tissue penetration" is used, it is understood that such penetration can also extend to other barriers and CendR-capable membranes found throughout the body, such as the blood brain barrier.

Unlike the known cell-penetrating peptides, the CendR internalizing element is position-dependent—it is inactive when present in positions other than the C-terminus of the peptide. Another distinguishing feature is that the CendR element is stereo-specific, that is, CendR elements composed of D-amino acids are inactive. A latent CendR peptide can be activated by cleavage by, for example, the appropriate proteolytic enzyme to expose, for example, a C-terminal arginine, lysine, or lysine-glycine. Throughout the application, when the term "CendR element" or "C-terminal element" is used, it is used to describe a C-terminal arginine, a C-terminal lysine, or a C-terminal lysine-glycine pair, where glycine is at the furthest C-terminal position. In other words, in the case where a lysine is on the C terminus end, the CendR element can remain functional with a glycine on the C terminus side of the lysine. However, it is not necessary to have glycine on the end in order for the lysine residue to be functional as a C-terminal element, so that lysine can be present without glycine and still be functional. The converse is not true, however, in that glycine cannot function as a C-terminal element without the presence of lysine adjacent to it. Arginine does not require either lysine or glycine to function as a C-terminal element, as long as it remains in the furthest C-terminal position. Such CendR elements can be referred to as type 1 CendR elements.

The term "CendR element" or "C-terminal element" can also be used to describe a C-terminal histidine and amino acid sequences having the sequence $X_1X_2X_3X_4$, where $X_1$ can be R, K or H, where $X_4$ can be R, K, H, or KG, and where $X_2$ and $X_3$ can each be, independently, any amino acid. Such CendR elements can be referred to as type 2 CendR elements. The $X_2$ and $X_3$ amino acids can be selected for specific purposes. For example, $X_2$, $X_3$, or both can be chosen to form all or a portion of a protease recognition sequence. This would be useful, for example, to specify or enable cleavage of a peptide having the CendR element as a latent or cryptic CendR element that is activated by cleavage following the $X_4$ amino acid. Examples of such amino acid choices are shown in Tables 3 and 4. The $X_1$, $X_2$, and $X_3$ amino acids can also be selected, for example, to recruit additional proteins to NRP-1 molecules at the cell surface. This can be applied, for example, to modulate the selectivity and internalization and/or tissue penetration potency of CendR elements (and the compositions, conjugates, proteins, and peptides containing CendR elements). The $X_2$ and $X_3$ amino acids can also be selected to prevent protease cleavage within the $X_1$-$X_4$ motif. Optionally, certain amino acids can also be excluded from use for $X_2$, $X_3$, or both. For example, if desired, G and D can be excluded from simultaneous use as $X_2$ and $X_3$, respectively. Some type 2 CendR elements can also be described as R/K/HXXR/K/H and R/K/HXXKG.

Examples of CendR elements include XXR/K/H, XXR/K, XXR/H, XXK/H, XXR, XXK, XXH, XXKG, RXXR/K/H, RXXR/K, RXXR/H, RXXK/H, RXXR, RXXK, RXH, RXXKG, KXXR/K/H, KXXR/K, KXXR/H, KXXK/H, KXXR, KXXK, KXXH, KXXKG, HXXR/K/H, HXXR/K, HXXR/H, HXXK/H, HXXR, HXXK, HXXH, HXXKG, R/K/HXXR, R/KXXR, R/HXXR, K/HXXR, RXXR, KXXR, HXXR, R/K/HXXK, R/KXXK, R/HXXK, K/HXXK, RXXK, KXXK, HXXK, R/K/HXXH, R/KXXH, R/HXXH, K/HXXH, RXXH, KXXH, HXXH, R/K/HXXKG, R/KXXKG, R/HXXKG, K/HXXKG, RXXKG, KXXKG, and HXXKG. A CendR element that can be internalized into a cell can be referred to as an internalization CendR element. A CendR element that can penetrate tissue can be referred to as a penetrating CendR element. A CendR element that can be internalized into a cell and that can penetrate tissue can be referred to as an internalization and penetrating CendR element. Unless the context clearly indicates otherwise, reference to "CendR element" refers to any of these, either individually, collectively, or in any combination.

As used herein, "CendR composition" refers to a composition that comprises a CendR element. The CendR element can be, for example, active, activatable, or blocked. For example, the CendR composition can comprise a protein or peptide comprising an amino acid sequence that comprises a CendR element where the amino acid sequence is at the C-terminal end of the protein or peptide.

As used herein, "activatable CendR element" refers to a CendR element having a molecule, moiety, nanoparticle, compound or other composition covalently coupled to the CendR element, such as to the terminal carboxyl group of the C-terminal element, where the molecule, moiety, nanoparticle, compound or other composition can block internalization and/or tissue penetration of the CendR composition, conjugate, molecule, protein, peptide, etc. and where the molecule, moiety, nanoparticle, compound or other composition can be removed (to expose the terminal carboxy group, for example). For example, the activatable CendR element can be on the C-terminal end of the peptide, and can prevent the CendR element from being internalized and/or from penetrating tissue. The molecule, nanoparticle, moiety, compound or other composition covalently coupled to the CendR element can be referred to as the "blocking group." For example, the blocking group can be coupled to the terminal carboxyl group of the C-terminal arginine or lysine or other C-terminal amino acid of the CendR element, to the C-terminal amino acid of the CendR element, or to an amino acid of the CendR element other than the C-terminal amino acid. The blocking group can also be coupled, or associated with a part of a CendR composition, conjugate, molecule, protein, peptide, etc. other than the CendR element so long as it can prevent the CendR element from being internalized and/or from penetrating tissue. A CendR composition comprising an activatable CendR element can be referred to as an activatable CendR composition. A CendR molecule comprising an activatable CendR element can be referred to as an activatable CendR molecule. A CendR conjugate comprising an activatable CendR element can be referred to as an activatable CendR conjugate. A CendR protein comprising an activatable CendR element can be referred to as an activatable CendR protein. A CendR peptide comprising an activatable CendR element can be referred to as an activatable CendR peptide.

An activatable CendR element can be blocked from internalization into a cell, from tissue penetration, or both. Generally, an activatable CendR element will be blocked from both internalization into a cell and penetration of tissue. Such activatable CendR elements can be referred to as activatable internalization and penetrating CendR elements. However, some activatable CendR elements could be blocked only from tissue penetration or only from internalization into a cell. Such activatable CendR elements can be referred to as activatable internalization CendR elements (for CendR elements that are blocked only from internalization into a cell) or as activatable internalization and penetrating CendR elements (for CendR elements that are blocked only from penetration of tissue). Generally, internalization CendR elements that are activatable will be activatable internalization CendR elements. Similarly, penetrating CendR elements that are activatable generally will be activatable penetrating CendR elements. Internalization and penetrating CendR elements that are activatable will be activatable internalization and penetrating CendR elements. Removal of the blocking group will allow the CendR element to be internalized into a cell, penetrate tissue, or both.

The cleavable bond of an activatable CendR element can be cleaved in any suitable way. For example, the cleavable bond can be cleaved enzymatically or non-enzymatically. For enzymatic cleavage, the cleaving enzyme can be supplied or can be present at a site where the CendR element is delivered, homes, travels or accumulates. For example, the enzyme can be present in proximity to a cell to which the CendR element is delivered, homes, travels, or accumulates. For non-enzymatic cleavage, the CendR element can be brought into contact with a cleaving agent, can be placed in cleaving conditions, or both. A cleaving agent is any substance that can mediate or stimulate cleavage of the cleavable bond. A non-enzymatic cleaving agent is any cleaving agent except enzymes. Cleaving conditions can be any solution or environmental conditions that can mediate or stimulate cleavage of the cleavable bond. For example, some labile bonds can be cleaved in acid conditions, alkaline conditions, in the presence of a reactive group, etc. Non-enzymatic cleaving conditions are any cleaving conditions except the presence of enzymes. Non-agent cleaving conditions are any cleaving conditions except the presence of cleaving agents.

A "protease-activatable CendR element" (or "protease-activated CendR element") refers to an activatable CendR element where the blocking group is coupled to the CendR element via a peptide bond and where the peptide bond can be cleaved by a protease. Cleavage of this peptide bond in a protease-activatable CendR element makes the CendR element capable of internalization into a cell and/or of tissue penetration. In one example, the blocking group can be coupled to the CendR element via a cleavable or labile bond. The cleavable bond can be cleaved by, for example, an enzyme or a chemical compound. Cleavage or 'labilization' bond in an activatable CendR element makes the CendR element capable of internalization into a cell and/or of tissue penetration. Such cleavage or 'labilization' can be referred to as activation of the CendR element. A protease-activatable CendR element is a form of activatable CendR element.

Proteolysis that uncovers a C-terminal element can serve as a switch that triggers the internalization signal. Various compositions can be internalized through this mechanism. For example, homing molecule-mediated accumulation can occur at a target site with cell type-specific proteolysis that exposes a C-terminal element which allows for highly specific homing systems with target-triggered internalization. This protease-controllable internalization system can be useful in engineering compositions with functions such as cell type-specific and/or tissue type-specific uptake and the ability to spread the compositions in tissues.

CendR elements are further described in U.S. Patent Application Publication Nos. 2009/0226372 and 2010/0322862, which are hereby incorporated by reference in their entirety, and specifically for their description of the form, structure, and use of CendR elements and peptides.

II.G. Surface Molecules

The surface molecules, alternatively referred to as a surface particles, disclosed herein can be conjugated with homing molecules and cargo molecules in such a way that the composition is delivered to a target. The surface molecule can be any substance that can be used with the homing molecules and cargo molecules, and is not restricted by size or substance. Examples include, but are not limited to, nanoparticles (such as iron oxide nanoparticles or albumin nanoparticles), liposomes, small organic molecules, microparticles, or microbubbles, such as fluorocarbon microbubbles. The term surface molecule is used to identify a component of the disclosed composition but is not intended to be limiting. In particular, the disclosed surface molecules are not limited to substances, compounds, compositions, particles or other materials composed of a single molecule. Rather, the disclosed surface molecules are any substance(s), compound(s), composition(s), particle(s) and/or other material(s) that can be conjugated with a plurality of homing molecules and cargo molecules such that at least some of the homing molecules and/or cargo molecules are presented and/or accessible on the surface of the surface molecule. A variety of examples of suitable surface molecules are described and disclosed herein.

The surface molecule can be detectable, or can be a therapeutic agent such as iRGD, RGD, or Abraxane™. The section herein which discusses cargo molecules and moieties that can be detectable or therapeutic also applies to the surface molecule.

Surface molecules can be associated with and arranged in the compositions in a variety of configurations. In some embodiments, surface molecules can be associated with, conjugated to, and/or covalently coupled to a plurality of homing molecules, a plurality of cargo molecules, or both. In some embodiments, surface molecules can be associated with, conjugated to, and/or covalently coupled to a plurality of homing molecules, wherein the homing molecules can be associated with, conjugated to, and/or covalently coupled to a plurality of cargo molecules. In some embodiments, surface molecules can be associated with, conjugated to, and/or covalently coupled to a plurality of cargo molecules, wherein the cargo molecules can be associated with, conjugated to, and/or covalently coupled to a plurality of homing molecules. Combinations of these combinations can also be used.

II.G.1. Nanoparticles, Microparticles, and Microbubbles

The term "nanoparticle" refers to a nanoscale particle with a size that is measured in nanometers, for example, a nanoscopic particle that has at least one dimension of less than about 100 nm. Examples of nanoparticles include paramagnetic nanoparticles, superparamagnetic nanoparticles, metal nanoparticles, nanoworms, fullerene-like materials, inorganic nanotubes, dendrimers (such as with covalently attached metal chelates), nanofibers, nanohorns, nano-onions, nanorods, nanoropes and quantum dots. A nanoparticle can produce a detectable signal, for example, through absorption and/or emission of photons (including radio frequency and visible photons) and plasmon resonance.

Microspheres (or microbubbles) can also be used with the methods disclosed herein. Microspheres containing chromophores have been utilized in an extensive variety of applications, including photonic crystals, biological labeling, and flow visualization in microfluidic channels. See e.g., Lin et al., 2002; Wang et al., 2003; Gao et al., 2002; Han et al., 2001; Pai et al., 1999, each of which is incorporated by reference in its entirety. Both the photostability of the chromophores and the monodispersity of the microspheres can be important.

Nanoparticles, such as, for example, metal nanoparticles, metal oxide nanoparticles, or semiconductor nanocrystals can be incorporated into microspheres. The optical, magnetic, and electronic properties of the nanoparticles can allow them to be observed while associated with the microspheres and can allow the microspheres to be identified and spatially monitored. For example, the high photostability, good fluorescence efficiency and wide emission tunability of colloidally synthesized semiconductor nanocrystals can make them an excellent choice of chromophore. Unlike organic dyes, nanocrystals that emit different colors (i.e. different wavelengths) can be excited simultaneously with a single light source. Colloidally synthesized semiconductor nanocrystals (such as, for example, core-shell CdSe/ZnS and CdS/ZnS nanocrystals) can be incorporated into microspheres. The microspheres can be monodisperse silica microspheres.

The nanoparticle can be a metal nanoparticle, a metal oxide nanoparticle, or a semiconductor nanocrystal. The metal of the metal nanoparticle or the metal oxide nanoparticle can include titanium, zirconium, hafnium, vanadium, niobium, tantalum, chromium, molybdenum, tungsten, manganese, technetium, rhenium, iron, ruthenium, osmium, cobalt, rhodium, iridium, nickel, palladium, platinum, copper, silver, gold, zinc, cadmium, scandium, yttrium, lanthanum, a lanthanide series or actinide series element (e.g., cerium, praseodymium, neodymium, promethium, samarium, europium, gadolinium, terbium, dysprosium, holmium, erbium, thulium, ytterbium, lutetium, thorium, protactinium, and uranium), boron, aluminum, gallium, indium, thallium, silicon, germanium, tin, lead, antimony, bismuth, polonium, magnesium, calcium, strontium, and barium. In certain embodiments, the metal can be iron, ruthenium, cobalt, rhodium, nickel, palladium, platinum, silver, gold, cerium or samarium. The metal oxide can be an oxide of any of these materials or combination of materials. For example, the metal can be gold, or the metal oxide can be an iron oxide, a cobalt oxide, a zinc oxide, a cerium oxide, or a titanium oxide. Preparation of metal and metal oxide nanoparticles is described, for example, in U.S. Pat. Nos. 5,897,945 and 6,759,199, each of which is incorporated by reference in its entirety.

The nanoparticles can be comprised of cargo molecules and a carrier protein (such as albumin). Such nanoparticles are useful, for example, to deliver hydrophobic or poorly soluble compounds. Nanoparticles of poorly water soluble drugs (such as taxane) have been disclosed in, for example, U.S. Pat. Nos. 5,916,596; 6,506,405; and 6,537,579; and also U.S. Patent Application Publication No. 2005/0004002.

In forms, the nanoparticles can have an average or mean diameter of no greater than about 1000 nanometers (nm), such as no greater than about any of 900, 800, 700, 600, 500, 400, 300, 200, and 100 nm. In some embodiments, the average or mean diameters of the nanoparticles can be no greater than about 200 nm. In some embodiments, the average or mean diameters of the nanoparticles can be no greater than about 150 nm. In some embodiments, the average or mean diameters of the nanoparticles can be no greater than about 100 nm. In some embodiments, the average or mean diameter of the nanoparticles can be about 20 to about 400 nm. In some embodiments, the average or mean diameter of the nanoparticles can be about 40 to about 200 nm. In some embodiments, the nanoparticles are sterile-filterable.

The nanoparticles can be present in a dry formulation (such as lyophilized composition) or suspended in a biocompatible medium. Suitable biocompatible media include, but are not limited to, water, buffered aqueous media, saline, buffered saline, optionally buffered solutions of amino acids, optionally buffered solutions of proteins, optionally buffered solutions of sugars, optionally buffered solutions of vitamins, optionally buffered solutions of synthetic polymers, lipid-containing emulsions, and the like.

Examples of suitable carrier proteins include proteins normally found in blood or plasma, which include, but are not limited to, albumin, immunoglobulin including IgA, lipoproteins, apolipoprotein B, alpha-acid glycoprotein, beta-2-macroglobulin, thyroglobulin, transferin, fibronectin, factor VII, factor VIII, factor IX, factor X, and the like. In some embodiments, the carrier protein is non-blood protein, such as casein, α-lactalbumin, and β-lactoglobulin. The carrier proteins may either be natural in origin or synthetically prepared. In some embodiments, the pharmaceutically acceptable carrier comprises albumin, such as human serum albumin. Human serum albumin (HSA) is a highly soluble globular protein of Mr 65K and consists of 585 amino acids. HSA is the most abundant protein in the plasma and accounts for 70-80% of the colloid osmotic pressure of human plasma. The amino acid sequence of HSA contains a total of 17 disulfide bridges, one free thiol (Cys 34), and a single tryptophan (Trp 214). Intravenous use of HSA solution has been indicated for the prevention and treatment of hypovolumic shock (see e.g., Tullis, 1977; Houser et al., 1980) and in conjunction with exchange transfusion in the treatment of neonatal hyperbilirubinemia (see e.g., Finlayson, 1980). Other albumins are contemplated, such as bovine serum albumin. Use of such non-human albumins could be appropriate, for example, in the context of use of these compositions in non-human mammals, such as the veterinary (including domestic pets and agricultural context).

Carrier proteins (such as albumin) in the composition generally serve as a carrier for the hydrophobic cargo molecules, i.e., the carrier protein in the composition makes the cargo molecules more readily suspendable in an aqueous medium or helps maintain the suspension as compared to compositions not comprising a carrier protein. This can avoid the use of toxic solvents (or surfactants) for solubilizing the cargo molecules, and thereby can reduce one or more side effects of administration of the cargo molecules into an individual (such as a human). Thus, in some embodiments, the composition described herein can be substantially free (such as free) of surfactants, such as Cremophor (including CREMOPHOR EL® (BASF)). In some embodiments, the composition can be substantially free (such as free) of surfactants. A composition is "substantially free of Cremophor" or "substantially free of surfactant" if the amount of Cremophor or surfactant in the composition is not sufficient to cause one or more side effect(s) in an individual when the composition is administered to the individual.

The amount of carrier protein in the composition described herein will vary depending on other components in the composition. In some embodiments, the composition comprises a carrier protein in an amount that is sufficient to stabilize the cargo molecules in an aqueous suspension, for example, in the form of a stable colloidal suspension (such as a stable suspension of nanoparticles). In some embodiments, the carrier protein is in an amount that reduces the sedimentation rate of the cargo molecules in an aqueous medium. For particle-containing compositions, the amount of the carrier protein also depends on the size and density of nanoparticles of the cargo molecules.

Methods of making nanoparticle compositions are known in the art. For example, nanoparticles containing cargo molecules and carrier protein (such as albumin) can be prepared under conditions of high shear forces (e.g., sonication, high pressure homogenization, or the like). These methods are disclosed in, for example, U.S. Pat. Nos. 5,916,596; 6,506,405; 6,537,579; see also U.S. Patent Application Publication No. 2005/0004002.

Briefly, the hydrophobic carrier molecules can be dissolved in an organic solvent, and the solution can be added to a human serum albumin solution. The mixture is subjected to high pressure homogenization. The organic solvent can then be removed by evaporation. The dispersion obtained can be further lyophilized. Suitable organic solvent include, for example, ketones, esters, ethers, chlorinated solvents, and other solvents known in the art. For example, the organic solvent can be methylene chloride and chloroform/ethanol (for example with a ratio of 1:9, 1:8, 1:7, 1:6, 1:5, 1:4, 1:3, 1:2, 1:1, 2:1, 3:1, 4:1, 5:1, 6:1, 7:1, 8:1, or 9:1).

The nanoparticle can also be, for example, a heat generating nanoshell. As used herein, "nanoshell" is a nanoparticle having a discrete dielectric or semi-conducting core section surrounded by one or more conducting shell layers. U.S. Pat. No. 6,530,944 is hereby incorporated by reference herein in its entirety for its teaching of the methods of making and using metal nanoshells. Targeting molecules can be attached to the disclosed compositions and/or carriers. For example, the targeting molecules can be antibodies or fragments thereof, ligands for specific receptors, or other proteins specifically binding to the surface of the cells to be targeted.

II.G.2. Liposomes

"Liposome" as the term is used herein refers to a structure comprising an outer lipid bi- or multi-layer membrane surrounding an internal aqueous space. Liposomes can be used to package any biologically active agent for delivery to cells.

Materials and procedures for forming liposomes are well-known to those skilled in the art. Upon dispersion in an appropriate medium, a wide variety of phospholipids swell, hydrate and form multilamellar concentric bilayer vesicles with layers of aqueous media separating the lipid bilayers. These systems are referred to as multilamellar liposomes or multilamellar lipid vesicles ("MLVs") and have diameters within the range of 10 nm to 100 m. These MLVs were first described by Bangham et al., 1965. In general, lipids or lipophilic substances are dissolved in an organic solvent. When the solvent is removed, such as under vacuum by rotary evaporation, the lipid residue forms a film on the wall of the container. An aqueous solution that typically contains electrolytes or hydrophilic biologically active materials is then added to the film. Large MLVs are produced upon agitation. When smaller MLVs are desired, the larger vesicles are subjected to sonication, sequential filtration through filters with decreasing pore size or reduced by other forms of mechanical shearing. There are also techniques by which MLVs can be reduced both in size and in number of lamellae, for example, by pressurized extrusion (Barenholz et al., 1979).

Liposomes can also take the form of unilamnellar vesicles, which are prepared by more extensive sonication of MLVs, and consist of a single spherical lipid bilayer surrounding an aqueous solution. Unilamellar vesicles ("ULVs") can be small, having diameters within the range of 20 to 200 nm, while larger ULVs can have diameters within the range of 200 nm to 2 m. There are several well-known techniques for making unilamellar vesicles. In Papahadjopoulos et al., 1968, sonication of an aqueous dispersion of phospholipids produces small ULVs having a lipid bilayer surrounding an aqueous solution. Schneider, U.S. Pat. No. 4,089,801 describes the formation of liposome precursors by ultrasonication, followed by the addition of an aqueous medium containing amphiphilic compounds and centrifugation to form a biomolecular lipid layer system.

Small ULVs can also be prepared by the ethanol injection technique described by Batzri et al., 1973 and the ether injection technique of Deamer et al., 1976. These methods involve the rapid injection of an organic solution of lipids into a buffer solution, which results in the rapid formation of unilamellar liposomes. Another technique for making ULVs is taught by Weder et al., 1984. This detergent removal method involves solubilizing the lipids and additives with detergents by agitation or sonication to produce the desired vesicles.

U.S. Pat. No. 4,235,871 describes the preparation of large ULVs by a reverse phase evaporation technique that involves the formation of a water-in-oil emulsion of lipids in an organic solvent and the drug to be encapsulated in an aqueous buffer solution. The organic solvent is removed under pressure to yield a mixture which, upon agitation or dispersion in an aqueous media, is converted to large ULVs. U.S. Pat. No. 4,016,100 describes another method of encapsulating agents in unilamellar vesicles by freezing/thawing an aqueous phospholipid dispersion of the agent and lipids.

In addition to the MLVs and ULVs, liposomes can also be multivesicular. Described in Kim et al., 1983, these multivesicular liposomes are spherical and contain internal granular structures. The outer membrane is a lipid bilayer and the internal region contains small compartments separated by bilayer septum. Still yet another type of liposomes are oligolamellar vesicles ("OLVs"), which have a large center compartment surrounded by several peripheral lipid layers. These vesicles, having a diameter of 2-15 μm, are described in Callo et al., 1985.

U.S. Pat. Nos. 4,485,054 and 4,761,288 also describe methods of preparing lipid vesicles. More recently, Hsu, U.S. Pat. No. 5,653,996 describes A method for preparing liposomes utilizing aerosolization and U.S. Pat. No. 5,013,497 describes a method for preparing liposomes utilizing a high velocity-shear mixing chamber. Methods are also described that use specific starting materials to produce ULVs (U.S. Pat. No. 4,853,228) or OLVs (Wallach, U.S. Pat. Nos. 5,474,848 and 5,628,936).

A comprehensive review of all the aforementioned lipid vesicles and methods for their preparation are described in Gregoriadis, 1984. This and the aforementioned references describing various lipid vesicles suitable for use in the invention are incorporated herein by reference.

II.G.3. Micelles

"Micelle" as used herein refers to a structure comprising an outer lipid monolayer. Micelles can be formed in an aqueous medium when the Critical Micelle Concentration (CMC) is exceeded. Small micelles in dilute solution at approximately the critical micelle concentration (CMC) are generally believed to be spherical. However, under other conditions, they may be in the shape of distorted spheres, disks, rods, lamellae, and the like. Micelles formed from relatively low molecular weight amphiphile molecules can have a high CMC so that the formed micelles dissociate rather rapidly upon dilution. If this is undesired, amphiphile molecules with large hydrophobic regions can be used. For example, lipids with a long fatty acid chain or two fatty acid chains, such as phospholipids and sphingolipids, or polymers, specifically block copolymers, can be used.

Polymeric micelles have been prepared that exhibit CMCs as low as $10^{-6}$ M (molar). Thus, they tend to be very stable while at the same time showing the same beneficial characterics as amphiphile micelles. Any micelle-forming polymer presently known in the art or as such may become known in the future may be used in the disclosed compositions and methods. Examples of micelle-forming polymers include, without limitation, methoxy poly(ethylene glycol)-b-poly(ε-caprolactone), conjugates of poly(ethylene glycol) with phosphatidyl-ethanolamine, poly(ethylene glycol)-b-polyesters, poly(ethylene glycol)-b-poly(L-aminoacids), poly(N-vinylpyrrolidone)-bl-poly(orthoesters), poly(N-vinylpyrrolidone)-b-polyanhydrides and poly(N-vinylpyrrolidone)-b-poly(alkyl acrylates).

Micelles can be produced by processes conventional in the art. Examples of such are described in, for example, Liggins & Burt, 2002; Zhang et al., 1996; U.S. Pat. No. 4,745,160. In one such method, polyether-polyester block copolymers, which are amphipathic polymers having hydrophilic (polyether) and hydrophobic (polyester) segments, are used as micelle forming carriers.

Another type of micelle can be formed using, for example, AB-type block copolymers having both hydrophilic and hydrophobic segments, as described in, for example, Tuzar & Kratochvil, 1976; Wilhelm et al., 1991. These polymeric micelles are able to maintain satisfactory aqueous stability. These micelles, in the range of approximately <200 nm in size, are effective in reducing non-selective RES scavenging and show enhanced permeability and retention.

Further, U.S. Pat. No. 5,929,177 to Kataoka et al. describes a polymeric molecule which is usable as, inter alia, a drug delivery carrier. The micelle is formed from a block copolymer having functional groups on both of its ends and which comprises hydrophilic/hydrophobic segments. The polymer functional groups on the ends of the block copolymer include amino, carboxyl and mercapto groups on the .alpha.-terminal and hydroxyl, carboxyl group, aldehyde group and vinyl group on the omega.-terminal. The hydrophilic segment comprises polyethylene oxide, while the hydrophobic segment is derived from lactide, lactone or (meth)acrylic acid ester.

Further, for example, poly(D,L-lactide)-b-methoxypolyethylene glycol (MePEG:PDLLA) diblock copolymers can be made using MePEG 1900 and 5000. The reaction can be allowed to proceed for 3 hr at 160° C., using stannous octoate (0.25%) as a catalyst. However, a temperature as low as 130° C. can be used if the reaction is allowed to proceed for about 6 hr, or a temperature as high as 190° C. can be used if the reaction is carried out for only about 2 hr.

As another example, N-isopropylacrylamide (IPAAm; Kohjin, Tokyo, Japan) and dimethylacrylamide (DMAAm; Wako Pure Chemicals, Tokyo, Japan) can be used to make hydroxyl-terminated poly(IPAAm-co-DMAAm) in a radical polymerization process, using the method of Kohori et al., 1998. The obtained copolymer can be dissolved in cold water and filtered through two ultrafiltration membranes with a 10,000 and 20,000 molecular weight cut-off. The polymer solution is first filtered through a 20,000 molecular weight cut-off membrane. Then the filtrate was filtered again through a 10,000 molecular weight cut-off membrane. Three molecular weight fractions can be obtained as a result, a low molecular weight, a middle molecular weight, and a high molecular weight fraction. A block copolymer can then be synthesized by a ring opening polymerization of D,L-lactide from the terminal hydroxyl group of the poly(IPAAm-co-DMAAm) of the middle molecular weight fraction. The resulting poly(IPAAm-co-DMAAm)-b-poly(D,L-lactide) copolymer can be purified as described in Kohori et al., 1999.

Examples of block copolymers from which micelles can be prepared which can be used to coat a support surface are found in U.S. Pat. No. 5,925,720 to Kataoka et al.; U.S. Pat. No. 5,412,072 to Sakarai et al.; U.S. Pat. No. 5,410,016 to Kataoka et al.; U.S. Pat. No. 5,929,177 to Kataoka et al.; U.S. Pat. No. 5,693,751 to Sakurai et al.; U.S. Pat. No. 5,449,513 to Yokoyama et al; PCT International Patent Application Publication Nos. WO 96/32434; WO 96/33233; WO 97/0623, the contents of all of which are incorporated by reference. Modifications thereof which are prepared by introducing thereon a suitable functional group (including an ethyleneically unsaturated polymerizable group) are also examples of block copolymers from which micelles of the present invention are preferably prepared. Preferable block copolymers are those disclosed in the above-mentioned patents and or international patent publications. If the block copolymer has a sugar residue on one end of the hydrophilic polymer segment, as in the block copolymer of WO 96/32434, the sugar residue should preferably be subjected to Malaprade oxidation so that a corresponding aldehyde group may be formed.

II.G.4. Lipids

Lipids are synthetically or naturally-occurring molecules which includes fats, waxes, sterols, prenol lipids, fat-soluble vitamins (such as vitamins A, D, E and K), glycerolipids, monoglycerides, diglycerides, triglycerides, glycerophospholipids, sphingolipids, phospholipids, fatty acids monoglycerides, saccharolipids and others. Lipids can be hydrophobic or amphiphilic small molecules; the amphiphilic nature of some lipids allows them to form structures such as monolayers, vesicles, micelles, liposomes, bi-layers or membranes in an appropriate environment i.e. aqueous environment. Any of a number of lipids can be used as amphiphile molecules, including amphipathic, neutral, cationic, and anionic lipids. Such lipids can be used alone or in combination, and can also include bilayer stabilizing components such as polyamide oligomers (see e.g., U.S. Pat. No. 6,320,017), peptides, proteins, detergents, lipid-derivatives, such as PEG coupled to phosphatidylethanolamine and PEG conjugated to ceramides (see e.g., U.S. Pat. No. 5,885,613). In some embodiments, cloaking agents, which reduce elimination of liposomes by the host immune system, can also be included, such as polyamide-oligomer conjugates, e.g., *ATTA*-lipids, (see e.g., U.S. patent application Ser. No. 08/996,783, filed Feb. 2, 1998) and PEG-lipid conjugates (see e.g., U.S. Pat. Nos. 5,820,873; 5,534,499; and 5,885, 613).

Any of a number of neutral lipids can be included, referring to any of a number of lipid species which exist either in an uncharged or neutral zwitterionic form at physiological pH, including diacylphosphatidylcholine, diacylphosphatidylethanolamine, ceramide, sphingomyelin, cephalin, cholesterol, cerebrosides, and diacylglycerols.

Cationic lipids, carry a net positive charge at physiological pH, can readily be used as amphiphile molecules. Such lipids include, but are not limited to, N,N-dioleyl-N,N-dimethylammonium chloride ("DODAC"); N-(2,3-dioleyloxy) propyl-N,N—N-triethylammonium chloride ("DOTMA"); N,N-distearyl-N,N-dimethylammonium bromide ("DDAB"); N-(2,3-dioleoyloxy)propyl)-N,N,N-trimethylammonium chloride ("DOTAP"); 3.beta.-(N—(N',N'-dimethylaminoethane)-carbamoyl)cholesterol ("DC-Chol"), N-(1-(2,3-dioleyloxy)propyl)-N-2-(sperminecarboxamido) ethyl)-N,N-dimethyl-ammonium trifluoracetate ("DOSPA"), dioctadecylamidoglycyl carboxyspermine ("DOGS"), 1,2-dileoyl-sn-3-phosphoethanolamine ("DOPE"), 1,2-dioleoyl-3-dimethylammonium propane ("DODAP"), and N-(1,2-dimyristyloxyprop-3-yl)-N,N-dimethyl-N-hydroxyethyl ammonium bromide ("DMRIE"). Additionally, a number of commercial preparations of cationic lipids can be used, such as LIPOFECTIN (including DOTMA and DOPE, available from GIBCO/BRL), LIPOFECTAMINE (comprising DOSPA and DOPE, available from GIBCO/BRL), and TRANSFECTAM (comprising DOGS, in ethanol, from Promega Corp.).

Anionic lipids can be used as amphiphile molecules and include, but are not limited to, phosphatidylglycerol, cardiolipin, diacylphosphatidylserine, diacylphosphatidic acid, N-dodecanoyl phosphatidylethanoloamine, N-succinyl phosphatidylethanolamine, N-glutaryl phosphatidylethanolamine, lysylphosphatidylglycerol, and other anionic modifying groups joined to neutral lipids.

Amphiphatic lipids can also be suitable amphiphile molecules. "Amphipathic lipids" refer to any suitable material, wherein the hydrophobic portion of the lipid material orients into a hydrophobic phase, while the hydrophilic portion orients toward the aqueous phase. Such compounds include, but are not limited to, fatty acids, phospholipids, aminolipids, and sphingolipids. Representative phospholipids include sphingomyelin, phosphatidylcholine, phosphatidylethanolamine, phosphatidylserine, phosphatidylinositol, phosphatidic acid, palmitoyloleoyl phosphatdylcholine, lysophosphatidylcholine, lysophosphatidylethanolamine, dipalmitoylphosphatidylcholine, dioleoylphosphatidylcholine, distearoylphosphatidylcholine, or dilinoleoylphosphatidylcholine. Other phosphorus-lacking compounds, such as sphingolipids, glycosphingolipid families, diacylglycerols, and β-acyloxyacids, can also be used. Additionally, such amphipathic lipids can be readily mixed with other lipids, such as triglycerides and sterols. Zwitterionic lipids are a form of amphiphatic lipid.

Sphingolipids are fatty acids conjugated to the aliphatic amino alcohol sphingosine. The fatty acid can be covalently bond to sphingosine via an amide bond. Any amino acid as described above can be covalently bond to sphingosine to form a sphingolipid. A sphingolipid can be further modified by covalent bonding through the α-hydroxyl group. The modification can include alkyl groups, alkenyl groups, alkynyl groups, aromatic groups, heteroaromatic groups, cyclyl groups, heterocyclyl groups, phosphonic acid groups. Non-limiting examples of shingolipids are N-acylsphingosine, N-Acylsphingomyelin, Forssman antigen.

Saccharolipids are compounds that contain both fatty acids and sugars. The fatty acids are covalently bonded to a sugar backbone. The sugar backbone can contain one or more sugars. The fatty acids can bond to the sugars via either amide or ester bonds. The sugar can be any sugar base. The fatty acid can be any fatty acid as described elsewhere herein. The provided compositions can comprise either natural or synthetic saccharolipids. Non-limiting saccharolipids are UDP-3-O-(D-hydroxymyristoyl)-GcNAc, lipid IV A, Kdo2-lipid A.

II.H. Linkers

Disclosed are linkers for associating components of the disclosed compositions. Such linkers can be any molecule, conjugate, composition, etc. that can be used to associate components of the disclosed compositions. Generally, linkers can be used to associate components other than surface molecules to surface molecules. Useful linkers include materials that are biocompatible, have low bioactivity, have low antigenicity, etc. That is, such useful linker materials can serve the linking/association function without adding unwanted bioreactivity to the disclosed compositions. Many such materials are known and used for similar linking and association functions. Polymer materials are a particularly useful form of linker material. For example, polyethylene glycols can be used.

Linkers are useful for achieving useful numbers and densities of the components (such as homing molecules and membrane perturbing molecules) on surface molecules. For example, linkers of fibrous form are useful for increasing the number of components per surface molecule or per a given area of the surface molecule. Similarly, linkers having a branching form are useful for increasing the number of components per surface molecule or per a given area of the surface molecule. Linkers can also have a branching fibrous form.

Linkers of different lengths can be used to bind the disclosed components to surface molecules and to each other. A flexible linker can function well even if relatively short, while a stiffer linker may can be longer to allow effective exposure and density. The length of a linker can refer to the number of atoms in a continuous covalent chain between the attachment points on the components being linked or to the length (in nanometers, for example) of a continuous covalent chain between the attachment points on the components being linked. Unless the context clearly indicates otherwise, the length refers to the shortest continuous covalent chain between the attachment points on the components being linked not accounting for side chains, branches, or loops. Due to flexibility of the linker, all of the linkers may not have same distance from the surface molecule. Thus linkers with different chain lengths can make the resulting composition more effective (by increasing density, for example). Branched linkers bearing multiple components also allow attachment of more than one component at a given site of the surface molecule. Useful lengths for linkers include at least, up to, about, exactly, or between 10, 15, 20, 25, 30, 35, 40, 45, 50, 60, 70, 80, 90, 100, 120, 140, 150, 160, 180, 200, 250, 300, 350, 400, 450, 500, 550, 600, 650, 700, 750, 800, 850, 900, 950, 1,000, 2,000, 3,000, 4,000, 5,000, 6,000, 7,000, 8,000, 9,000, and 10,000 atoms. Useful lengths for linkers include at least, up to, about, exactly, or between 10, 15, 20, 25, 30, 35, 40, 45, 50, 60, 70, 80, 90, 100, 120, 140, 150, 160, 180, 200, 250, 300, 350, 400, 450, 500, 550, 600, 650, 700, 750, 800, 850, 900, 950, 1,000, 2,000, 3,000, 4,000, 5,000, 6,000, 7,000, 8,000, 9,000, and 10,000 nanometers. Any range of these lengths and all lengths between the listed lengths are specifically contemplated.

Hydrophilic or water-solubility linkers can increase the mobility of the attached components. Examples of water-soluble, biocompatible polymers which can serve as linkers include, but are not limited to polymers such polyethylene glycol (PEG), polyethylene oxide (PEO), polyvinyl alcohol, polyhydroxyethyl methacrylate, polyacrylamide, and natural polymers such as hyaluronic acid, chondroitin sulfate, carboxymethylcellulose, and starch. Useful forms of branched tethers include star PEO and comb PEO. Star PEO can be formed of many PEO "arms" emanating from a common core.

Polyethylene glycols (PEGs) are simple, neutral polyethers which have been given much attention in biotechnical and biomedical applications (Harris, 1992). PEGs are soluble in most solvents, including water, and are highly hydrated in aqueous environments, with two or three water molecules bound to each ethylene glycol segment; this hydration phenomenon has the effect of preventing adsorption either of other polymers or of proteins onto PEG-modified surfaces. Furthermore, PEGs may readily be modified and bound to other molecules with only little effect on their chemistry. Their advantageous solubility and biological properties are apparent from the many possible uses of PEGs and copolymers thereof, including block copolymers such as PEG-polyurethanes and PEG-polypropylenes. Appropriate molecular weights for PEG linkers used in the disclosed compositions can be from about 120 daltons (Da) to about 20 kilodaltons (kDa). For example, PEGs can be at least, up to, about, exactly, or between 100, 150, 200, 250, 300, 350, 400, 450, 500, 600, 700, 800, 900, 1000, 1200, 1400, 1500, 1600, 1800, 2000, 2500, 3000, 3500, 4000, 4500, 5000, 5500, 6000, 6500, 7000, 7500, 8000, 8500, 9000, 9500, 10,000, 20,000, 30,000, 40,000, and 50,000 daltons. Any range of these masses and all masses between the listed masses are specifically contemplated. PEGs are usually available as mixtures of somewhat heterogeneous masses with a stated average mass (PEG-5000, for example).

The disclosed compositions can be produced using any suitable techniques. Many techniques, reactive groups, chemistries, etc. for linking components of the types disclosed herein are known and can be used with the disclosed components and compositions. Examples of some techniques for producing the disclosed compositions are described in the examples.

Protein crosslinkers that can be used to crosslink other molecules, elements, moieties, etc. to the disclosed compositions, surface molecules, homing molecules, membrane perturbing molecules, internalization elements, tissue penetration elements, cargo compositions, CendR elements, compositions, proteins, peptides, amino acid sequences, etc. are known in the art and are defined based on utility and structure and include DSS (Disuccinimidylsuberate), DSP (Dithiobis(succinimidylpropionate)), DTSSP(3,3'-Dithiobis (sulfosuccinimidylpropionate)), SULFO BSOCOES (Bis[2-(sulfosuccinimdooxycarbonyloxy) ethyl]sulfone), BSOCOES (Bis[2-(succinimdooxycarbonyloxy)ethyl]sulfone), SULFO DST (Disulfosuccinimdyltartrate), DST (Disuccinimdyltartrate), SULFO EGS (Ethylene glycolbis(succinimidylsuccinate)), EGS (Ethylene glycolbis(sulfosuccinimidylsuccinate)), DPDPB (1,2-Di[3'-(2'-pyridyldithio) propionamido]butane), BSSS (Bis(sulfosuccinimdyl) suberate), SMPB (Succinimidyl-4-(p-maleimidophenyl) butyrate), SULFO SMPB (Sulfosuccinimdyl-4-(p-maleimidophenyl) butyrate), MBS (3-Maleimidobenzoyl-N-hydroxysuccinimide ester), SULFO MBS (3-Maleimidobenzoyl-N-hydroxysulfosuccinimide ester), SIAB (N-Succinimidyl(4-iodoacetyl) aminobenzoate), SULFO SIAB (N-Sulfosuccinimidyl(4-iodoacetyl)aminobenzoate), SMCC (Succinimidyl-4-(N-maleimidomethyl)cyclohexane-1-carboxylate), SULFO SMCC(Sulfosuccinimidyl-4-(N-maleimidomethyl)cyclohexane-1-carboxylate), NHS LC SPDP (Succinimidyl-6-[3-(2-pyridyldithio) propionamido) hexanoate), SULFO NHS LC SPDP (Sulfosuccinimidyl-6-[3-(2-pyridyldithio) propionamido) hexanoate), SPDP(N-Succinimdyl-3-(2-pyridyldithio) propionate), NHS BROMOACETATE (N-Hydroxysuccinimidylbromoacetate), NHS IODOACETATE (N-Hydroxysuccinimidyliodoacetate), MPBH (4-(N-Maleimidophenyl) butyric acid hydrazide hydrochloride), MCCH (4-(N-Maleimidomethyl)cyclohexane-1-carboxylic acid hydrazide hydrochloride), MBH (m-Maleimidobenzoic acid hydrazidehydrochloride), SULFO EMCS(N-(epsilon-Maleimidocaproyloxy) sulfosuccinimide), EMCS(N-(epsilon-Maleimidocaproyloxy) succinimide), PMPI (N-(p-Maleimidophenyl) isocyanate), KMUH (N-(kappa-Maleimidoundecanoic acid) hydrazide), LC SMCC (Succinimidyl-4-(N-maleimidomethyl)-cyclohexane-1-carboxy(6-amidocaproate)), SULFO GMBS (N-(gamma-Maleimidobutryloxy) sulfosuccinimide ester), SMPH (Succinimidyl-6-(beta-maleimidopropionamidohexanoate)), SULFO KMUS (N-(kappa-maleimidoundecanoyloxy) sulfosuccinimide ester), GMBS (N-(gamma-Maleimidobutyrloxy) succinimide), DMP (Dimethylpimelimidate hydrochloride), DMS (Dimethylsuberimidate hydrochloride), MHBH (Wood's Reagent; Methyl-p-hydroxybenzimidate hydrochloride, 98%), DMA (Dimethyladipimidate hydrochloride).

Components of the disclosed compositions, such as surface molecules, homing molecules, membrane perturbing molecules, internalization elements, tissue penetration elements, etc., can also be coupled using, for example, maleimide coupling. By way of illustration, components can be coupled to lipids by coupling to, for example, 1,2-distearoyl-sn-glycero-3-phosphoethanolamine-N-[maleimide(polyethylene glycol)2000; DSPE-PEG2000-maleimide] (Avanti Polar Lipids) by making use of a free cysteine sulfhydryl group on the component. The reaction can be performed, for example, in aqueous solution at room temperature for 4 hours. This coupling chemistry can be used to couple components of co-compositions and cargo compositions.

Components of the disclosed compositions, such as surface molecules, homing molecules, membrane perturbing molecules, internalization elements, tissue penetration elements, etc., can also be coupled using, for example, amino group-functionalized dextran chemistry. Particles, such as, for example, nanoparticles, nanoworms, and micelles, can be coated with amino group functionalized dextran. Attachment of PEG to aminated particles increases the circulation time, presumably by reducing the binding of plasma proteins involved in opsonization (Moghimi et al., 2001). The particles can have surface modifications, for example, for reticuloendothelial system avoidance (PEG) and homing (homing molecules), endosome escape (pH-sensitive peptide; for example, Pirollo et al., 2007), a detectable agent, a therapeutic compound, or a combination. To accommodate all these functions on one particle, optimization studies can be conducted to determine what proportion of the available linking sites at the surface of the particles any one of these elements should occupy to give the best combination of targeting and payload delivery. The cell internalization and/or tissue penetration of such compositions can be mediated by the disclosed CendR elements, amino acid sequences, peptides, proteins, molecules, conjugates, and compositions.

The provided peptides and polypeptides can have additional N-terminal, C-terminal, or intermediate amino acid sequences, e.g., amino acid linkers or tags. The term "amino acid linker" refers to an amino acid sequences or insertions that can be used to connect or separate two distinct peptides, polypeptides, or polypeptide fragments, where the linker does not otherwise contribute to the essential function of the composition. The term "amino acid tag" refers to a distinct amino acid sequence that can be used to detect or purify the provided polypeptide, wherein the tag does not otherwise contribute to the essential function of the composition. The provided peptides and polypeptides can further have deleted N-terminal, C-terminal or intermediate amino acids that do not contribute to the essential activity of the peptides and polypeptides.

Components can be directly or indirectly covalently bound to surface molecules or each other by any functional group (e.g., amine, carbonyl, carboxyl, aldehyde, alcohol).

For example, one or more amine, alcohol or thiol groups on the components can be reacted directly with isothiocyanate, acyl azide, N-hydroxysuccinimide ester, aldehyde, epoxide, anhydride, lactone, or other functional groups incorporated onto the surface molecules or other components. Schiff bases formed between the amine groups on the components and aldehyde groups on the surface molecule or other components can be reduced with agents such as sodium cyanoborohydride to form hydrolytically stable amine links (Ferreira et al., 2003). Components can be coupled to surface molecules and other components by, for example, the use of a heterobifunctional silane linker reagent, or by other reactions that activate functional groups on either the surface molecule or the components.

Useful modes for linking components to surface molecules and to other components include heterobifunctional linkers or spacers. Such linkers can have both terminal amine and thiol reactive functional groups for reacting amines on components with sulfhydryl groups, thereby coupling the components in an oriented way. These linkers can contain a variable number of atoms. Examples of such linkers include, but are not limited to, N-Succinimidyl 3-(2-pyridyldithio)propionate (SPDP, 3- and 7-atom spacer), long-chain-SPDP (12-atom spacer), (Succinimidyloxycarbonyl-a-methyl-2-(2-pyridyldithio) toluene) (SMPT, 8-atom spacer), Succinimidyl-4-(N-maleimidomethyl)cyclohexane-1-carboxylate) (SMCC, 11-atom spacer) and Sulfosuccinimidyl-4-(N-maleimidomethyl)cyclohexane-1-carboxylate, (sulfo-SMCC, 11-atom spacer), m-Maleimidobenzoyl-N hydroxysuccinimide ester (MBS, 9-atom spacer), N-(g-maleimidobutyryloxy)succinimide ester (GMBS, 8-atom spacer), N-(g-maleimidobutyryloxy) sulfosuccinimide ester (sulfo-GMBS, 8-atom spacer), Succinimidyl 6-((iodoacetyl) amino) hexanoate (SIAX, 9-atom spacer), Succinimidyl 6-(6-(((4-iodoacetyl)amino)hexanoyl)amino)hexanoate (SI-AXX, 16-atom spacer), and p-nitrophenyl iodoacetate (NPIA, 2-atom spacer). One ordinarily skilled in the art also will recognize that a number of other coupling agents or links, with different number of atoms, may be used.

Hydrophilic spacer atoms can be incorporated into linkers to increase the distance between the reactive functional groups. For example, polyethylene glycol (PEG) can be incorporated into sulfo-GMBS. Hydrophilic molecules such as PEG have also been shown to decrease non-specific binding (NSB) and increase hydrophilicity of surfaces when covalently coupled. PEG can also be used as the primary linker material.

Free amine groups of components can also be attached to surface molecules or other components containing reactive amine groups via homobifunctional linkers. Linkers such as dithiobis(succinimidylpropionate) (DSP, 8-atom spacer), disuccinimidyl suberate (DSS, 8-atom spacer), glutaraldehyde (4-atom spacer), Bis[2-(succinimidyloxycarbonyloxy) ethyl]sulfone (BSOCOES, 9-atom spacer), all requiring high pH, can be used for this purpose. Examples of homobifunctional sulfhydryl-reactive linkers include, but are not limited to, 1,4-Di-[3"-2"-pyridyldithio)propion-amido]butane (DPDPB, 16-atom spacer) and Bismaleimidohexane (BMH, 14-atom spacer). For example, these homobifunctional linkers are first reacted with a thiolated surface in aqueous solution (for example PBS, pH 7.4), and then in a second step, the thiolated antibody or protein is joined by the link. Homo- and heteromultifunctional linkers can also be used.

Direct binding of components to thiol, amine, or carboxylic acid functional groups on surface molecules and other components be used to produce compositions which exhibit viral binding (due to increased density of components, for example), resulting in enhanced sensitivity.

As an example, when necessary to achieve high peptide coupling density, additional amino groups can be added to the surface molecules (such as commercially obtained SPIO) as follows: First, to crosslink the particles before the amination step, 3 ml of the colloid (~10 mgFe/ml in double-distilled water) was added to 5 ml of 5M NaOH and 2 ml of epichlorohydrin (Sigma, St. Louis, Mo.). The mixture was agitated for 24 hours at room temperature to promote interaction between the organic phase (epichlorohydrin) and aqueous phase (dextran-coated particle colloid). In order to remove excess epichlorohydrin, the reacted mixture was dialyzed against double-distilled water for 24 hours using a dialysis cassette (10,000 Da cutoff, Pierce, Rockford Ill.). Amino groups were added to the surface of the particles as follows: 0.02 ml of concentrated ammonium hydroxide (30%) was added to 1 ml of colloid (~10 mg Fe/ml). The mixture was agitated at room temperature for 24 hours. The reacted mixture was dialyzed against double-distilled water for 24 hours. To further rinse the particles, the colloid was trapped on a MACS® Midi magnetic separation column (Miltenyi Biotec, Auburn Calif.), rinsed with PBS three times, and eluted from the column with 1 ml PBS.

To conjugate peptides to SPIO, the particles can be re-suspended at a concentration of 1 mg Fe/ml, and heterobifunctional linker N-[a-maleimidoacetoxy]succinimide ester (AMAS; Pierce) can be added (2.5 mg linker per 2 mg Fe) under vortexing. After incubation at room temperature for 40 minutes, the particles can be washed 3 times with 10 ml PBS on a MACS column. The peptide with free terminal cysteine can then be added (100 g peptide per 2 mg Fe). After incubation overnight at 4° C., the particles can be washed again and re-suspended in PBS at a concentration of 0.35 mg/ml of Fe. To quantify the number of peptide molecules conjugated to the particles, a known amount of stock or AMAS-activated particles can be incubated with varying amounts of the peptide. After completion of the incubation the particles can be pelleted at 100,000×g using Beckman TLA 100.3 ultracentrifuge rotor (30 minutes) and the amount of the unbound peptide can be quantified by fluorescence. To cleave the conjugated peptide from the particles, the particles can be incubated at 37° C. overnight at pH 10. The concentration of free peptide in the supernatant can tehn be determined by reading fluorescence and by using the calibration curve obtained for the same peptide. The fluorescence intensity of known amounts of particles can be plotted as a function of peptide conjugation density, and the slope equation can be used to determine conjugation density in different batches.

II.I. Pharmaceutical Compositions and Carriers

The disclosed compositions can be administered in vivo in a pharmaceutically acceptable carrier. By "pharmaceutically acceptable" is meant a material that is not biologically or otherwise undesirable, i.e., the material can be administered to a subject, along with the TT1 Peptide composition, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art. The materials can be in solution, suspension (for example, incorporated into microparticles, liposomes, and/or cells.

The TT1 Peptide compositions of the presently disclosed subject matter can be used therapeutically in combination with one or more pharmaceutically acceptable carriers.

Suitable carriers and their formulations are described in Remington, 1995. Typically, an appropriate amount of a pharmaceutically acceptable salt is used in the formulation to render the formulation isotonic. Examples of the pharmaceutically acceptable carrier include, but are not limited to, saline, Ringer's solution, and dextrose solution. The pH of the solution is in some embodiments from about 5 to about 8, and in some embodiments from about 7 to about 7.5. Further carriers include sustained release preparations such as semipermeable matrices of solid hydrophobic polymers containing the TT1 Peptide composition, which matrices are in the form of shaped articles, e.g., films, liposomes, or microparticles. It will be apparent to those persons skilled in the art that certain carriers can be selected depending upon, for instance, the route of administration and/or concentration of composition being administered.

Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds will be administered according to standard procedures used by those skilled in the art.

Pharmaceutical compositions can include carriers, thickeners, diluents, buffers, preservatives, surface active agents, and the like, in addition to the molecule of choice. Pharmaceutical compositions can also include one or more active ingredients such as antimicrobial agents, antiinflammatory agents, anesthetics, and the like.

The pharmaceutical composition can be administered in a number of ways depending on whether local or systemic treatment is desired, and on the area to be treated. Administration can topically (including ophthalmically, vaginally, rectally, intranasally), orally, by inhalation, or parenterally, for example by intravenous drip, subcutaneous, intraperitoneal or intramuscular injection. The disclosed TT1 Peptide compositions can be administered intravenously, intraperitoneally, intramuscularly, subcutaneously, intracavity, or transdermally.

Preparations for parenteral administration can include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions, or suspensions, including saline and buffered media. Parenteral vehicles include sodium chloride solution, Ringer's dextrose, dextrose, and sodium chloride, lactated Ringer's, or fixed oils. Intravenous vehicles include fluid and nutrient replenishers, electrolyte replenishers (such as those based on Ringer's dextrose), and the like. Preservatives and other additives can also be present such as, for example, antimicrobials, antioxidants, chelating agents, and inert gases and the like.

Formulations for topical administration can include ointments, lotions, creams, gels, drops, suppositories, sprays, liquids, and powders. Conventional pharmaceutical carriers, aqueous, powder or oily bases, thickeners, and the like can also be employed, as desired.

Compositions for oral administration include powders or granules, suspensions or solutions in water or non-aqueous media, capsules, sachets, or tablets. Thickeners, flavorings, diluents, emulsifiers, dispersing aids, or binders can in some embodiments also be desirable.

Some of the compositions can be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, or phosphoric acid and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl, and aryl amines and substituted ethanolamines.

III. Combinatorial Chemistry/Screening Methods

The disclosed compositions can be used as targets for any combinatorial technique to identify molecules or macromolecular molecules that interact with the disclosed compositions in a desired way. Also disclosed are the compositions that are identified through combinatorial techniques or screening techniques in which the compositions comprising SEQ ID NO: 1, SEQ ID NO: 2, or SEQ ID NO: 3 or portions thereof, are used as the target in a combinatorial or screening protocol.

It is understood that when using the disclosed compositions in combinatorial techniques or screening methods, molecules, such as macromolecular molecules, will be identified that have particular desired properties, such as interaction with gC1qR/p32. The molecules identified and isolated when using the disclosed compositions, such as a TT1 Peptide, are also disclosed. Thus, the products produced using the combinatorial or screening approaches that involve the disclosed compositions, such as a TT1 Peptide, are also considered herein disclosed.

Disclosed herein are methods of screening for a compound that interacts with a gC1q/p32 receptor, comprising: bringing into contact a test compound, a TT1 Peptide composition, and a gC1q receptor, wherein the TT1 Peptide composition comprises SEQ ID NO: 1, SEQ ID NO: 2, or SEQ ID NO: 3; and detecting unbound TT1 Peptide composition, wherein a given amount of unbound TT1 Peptide composition indicates a compound that interacts with gC1q/p32 receptor.

Also disclosed is a method of screening for a test compound that modulates gC1q/p32 receptor activity, comprising: contacting a cell that comprises the gC1q/p32 receptor with a test compound; and detecting altered gC1q/p32 receptor activity; wherein altered levels of gC1q/p32 receptor activity indicate a compound that modulates gC1q/p32 receptor activity.

By "altered levels of activity" is meant that the gC1q/p32 receptor can display an increase or decrease in activity. The increase in activity can be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% increase, or a 1 2, 3, 4, 5, 6, 7, 8, 9, 10, 20, 25, 30, 35, 40, 45, 50, 75, or 100 fold or more increase in activity, as compared to a standard, control, or basal level. The decrease in activity can be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% decrease in activity as compared to a standard, control, or basal level. For example, a test compound can interact with the gC1q/p32 receptor in such a way as to decrease the ability of the gC1q/p32 receptor to interact with another compound, thereby decreasing its activity. In another example, a test compound can prevent the synthesis of the gC1q/p32 receptor, thereby decreasing its activity in that way.

Disclosed is a method of screening for a test compound that interacts with the gC1q/p32 receptor, comprising contacting a cell that comprises the gC1q/p32 receptor with a test compound; and detecting interaction between the gC1q/p32 receptor and the test compound. After the test compound has been shown to interact with the gC1q/p32 receptor, it can further be tested for its ability to modulate gC1q/p32 receptor activity, including the ability to treat a gC1q/p32 receptor-related disorder.

Further disclosed is a method of screening for a test compound that can be used to treat a gC1q/p32 receptor-related disorder, such as cancer, comprising: contacting a cell that comprises the gC1q/p32 receptor with a test compound; and detecting altered gC1q/p32 receptor activity; wherein altered levels of gC1q/p32 receptor activity indicate a compound that can modulate gC1q/p32 receptor activity. After the test compound has been shown to modulate gC1q/p32 receptor activity, the test compound can then be tested for its ability to treat a gC1q/p32 receptor-related disorder.

The modulation can comprise a decrease in gC1q/p32 receptor activity, expression, or the ability to treat a gC1q/p32 receptor-related disease. By a "decrease" is meant that the activity is less in the presence of the test compound than not in the presence of the test compound. The modulation can comprise an increase in gC1q/p32 receptor activity or related activity. By an "increase" is meant that the activity is greater in the presence of the test compound than not in the presence of the test compound.

The response of the gC1q/p32 receptor can be measured in the presence of various concentrations of test compound. The measuring steps can also comprise measuring the response at various concentrations of the test compound. For example, the concentration of the test compound can range from 1 nM to 1000 µM.

Assays contemplated by the invention include both binding assays and activity assays; these assays may be performed in conventional or high throughput formats. Modulator screens are designed to identify stimulatory and inhibitory agents. The sources for potential agents to be screened include natural sources, such as a cell extract (e.g., invertebrate cells including, but not limited to, bacterial, fungal, algal, and plant cells) and synthetic sources, such as chemical compound libraries or biological libraries such as antibody substance or peptide libraries. Agents are screened for the ability to either stimulate or inhibit the activity. Binding assays are used to detect activity levels. Both functional and binding assays of activity are readily adapted to screens for modulators such as agonist (stimulatory) and antagonist (inhibitory) compounds.

Contemplated herein are a multitude of assays to screen and identify modulators, such as agonists and antagonists, of the gC1q/p32 receptor (and downstream activity). In some embodiments, the cell is immobilized and interaction with a candidate modulator is detected. In some embodiments, the test compound is immobilized. In yet another example, interaction between gC1q/p32 receptor and the test compound is assessed in a solution assay. Another contemplated assay involves a variation of the di-hybrid assay wherein a modulator of protein/protein interactions is identified by detection of a positive signal in a transformed or transfected host cell.

Candidate modulators for screening according to contemplated by the invention include any chemical compounds, including libraries of chemical compounds. There are a number of different libraries used for the identification of small molecule modulators, including: (1) chemical libraries, (2) natural product libraries, and (3) combinatorial libraries comprised of random peptides, oligonucleotides or organic molecules. Chemical libraries consist of random chemical structures, or analogs of known compounds, or analogs of compounds that have been identified as "hits" or "leads" in prior drug discovery screens, some of which may be derived from natural products or from non-directed synthetic organic chemistry. Natural product libraries are collections of microorganisms, animals, plants, or marine organisms which are used to create mixtures for screening by: (1) fermentation and extraction of broths from soil, plant or marine microorganisms or (2) extraction of plants or marine organisms. Natural product libraries include polyketides, non-ribosomal peptides, and variants (non-naturally occurring) thereof. For a review, see e.g., Cane et al., 1998. Combinatorial libraries are composed of large numbers of peptides, oligonucleotides, or organic compounds as a mixture. These libraries are relatively easy to prepare by traditional automated synthesis methods, PCR, cloning, or synthetic methods. of particular interest are non-peptide combinatorial libraries. Still other libraries of interest include peptide, protein, peptidomimetic, multiparallel synthetic collection, recombinatorial, and polypeptide libraries. For a review of combinatorial chemistry and libraries created therefrom, see Myers, 1997. Identification of modulators through use of the various libraries described herein permits modification of the candidate "hit" (or "lead") to optimize the capacity of the "hit" to modulate activity.

Candidate modulators contemplated by the invention can be designed and include soluble forms of binding partners, as well as chimeric, or fusion, proteins thereof. A "binding partner" as used herein broadly encompasses non-peptide modulators, peptide modulators (e.g., neuropeptide variants), antibodies (including monoclonal and polyclonal antibodies, single chain antibodies, chimeric antibodies, bifunctional/bispecific antibodies, humanized antibodies, human antibodies, and complementary determining region (CDR)-grafted antibodies, including compounds which include CDR and/or antigen-binding sequences, which specifically recognize a polypeptide as disclosed herein), antibody fragments, and modified compounds comprising antibody domains that are immunospecific for the expression product.

Assays that measure binding or interaction of compounds with target proteins include assays that identify compounds that inhibit unfolding or denaturation of a target protein, assays that separate compounds that bind to target proteins through affinity ultrafiltration followed by ion spray mass spectroscopy/HPLC methods or other physical and analytical methods, capillary electrophoresis assays and two-hybrid assays.

One such screening method to identify direct binding of test ligands to a target protein is described in U.S. Pat. No. 5,585,277, incorporated herein by reference. This method relies on the principle that proteins generally exist as a mixture of folded and unfolded states, and continually alternate between the two states. When a test ligand binds to the folded form of a target protein (i.e., when the test ligand is a ligand of the target protein), the target protein molecule bound by the ligand remains in its folded state. Thus, the folded target protein is present to a greater extent in the presence of a test ligand which binds the target protein, than in the absence of a ligand. Binding of the ligand to the target protein can be determined by any method which distinguishes between the folded and unfolded states of the target protein. The function of the target protein need not be known in order for this assay to be performed. Virtually any agent can be assessed by this method as a test ligand, including, but not limited to, metals, polypeptides, proteins, lipids, polysaccharides, polynucleotides and small organic molecules.

Another method for identifying ligands of a target protein is described in Wieboldt et al., 1997, incorporated herein by reference. This technique screens combinatorial libraries of 20-30 agents at a time in solution phase for binding to the target protein. Agents that bind to the target protein are separated from other library components by simple membrane washing. The specifically selected molecules that are retained on the filter are subsequently liberated from the target protein and analyzed by HPLC and pneumatically assisted electrospray (ion spray) ionization mass spectroscopy. This procedure selects library components with the greatest affinity for the target protein, and is particularly useful for small molecule libraries.

Alternatively, such binding interactions are evaluated indirectly using the yeast two-hybrid system described in Fields et al., 1989 and Fields et al., 1994, both of which are incorporated herein by reference. The two-hybrid system is a genetic assay for detecting interactions between two proteins or polypeptides. It can be used to identify proteins that bind to a known protein of interest, or to delineate domains or residues critical for an interaction. Variations on this methodology have been developed to clone genes that encode DNA binding proteins, to identify peptides that bind to a protein, and to screen for drugs. The two-hybrid system exploits the ability of a pair of interacting proteins to bring a transcription activation domain into close proximity with a DNA binding domain that binds to an upstream activation sequence (UAS) of a reporter gene, and is generally performed in yeast. The assay requires the construction of two hybrid genes encoding (1) a DNA-binding domain that is fused to a first protein and (2) an activation domain fused to a second protein. The DNA-binding domain targets the first hybrid protein to the UAS of the reporter gene; however, because most proteins lack an activation domain, this DNA-binding hybrid protein does not activate transcription of the reporter gene. The second hybrid protein, which contains the activation domain, cannot by itself activate expression of the reporter gene because it does not bind the UAS. However, when both hybrid proteins are present, the noncovalent interaction of the first and second proteins tethers the activation domain to the UAS, activating transcription of the reporter gene.

The literature is replete with examples of the use of radiolabeled ligands in HTS binding assays for drug discovery (see Williams, 1991 and Sweetnam et al., 1993, each of which is herein incorporated by reference in its entirety for their teaching concerning high throughput screens). It is also possible to screen for novel neuroregeneration compounds with radiolabeled ligands in HTS binding screens. Other reasons that recombinant receptors are preferred for HTS binding assays include better specificity (higher relative purity) and ability to generate large amounts of receptor material (see Hodgson, 1992).

A variety of heterologous systems are available for expression of recombinant proteins and are well known to those skilled in the art. Such systems include bacteria (Strosberg et al., 1992), yeast (Pausch, 1997), several kinds of insect cells (Vanden Broeck, 1996), amphibian cells (Jayawickreme et al., 1997), and several mammalian cell lines (CHO, HEK293, COS, etc.; see Gerhardt et al., 1997; Wilson et al., 1998). These examples do not preclude the use of other possible cell expression systems, including cell lines obtained from nematodes (PCT International Patent Application Publication No. WO 98/37177).

Inhibition of gC1qR/p32, or downstream products or genes related thereto, can result in a variety of biological responses, which are typically mediated by proteins expressed in the host cells. The proteins can be native constituents of the host cell or can be introduced through well-known recombinant technology. They can be mutants of native varieties as well. The proteins can be intact or chimeric.

Fluorescence changes can also be used to monitor ligand-induced changes in membrane potential or intracellular pH; an automated system suitable for HTS has been described for these purposes (Schroeder et al., 1996). Among the modulators that can be identified by these assays are natural ligand compounds; synthetic analogs and derivatives of natural ligands; antibodies, antibody fragments, and/or antibody-like compounds derived from natural antibodies or from antibody-like combinatorial libraries; and/or synthetic compounds identified by high throughput screening of libraries; and other libraries known in the art. All modulators that interact with gC1qR/p32 are useful for identifying TT1 Peptide-like polypeptides (e.g., for diagnostic purposes, pathological purposes, and other purposes known in the art). Agonist and antagonist modulators are useful for up-regulating and down-regulating gC1qR/p32 activity, respectively, for purposes described herein.

The assays may be performed using single putative modulators; they may also be performed using a known agonist in combination with candidate antagonists (or vice versa). Detectable molecules that may be used include, but are not limited to, molecules that are detectable by spectroscopic, photochemical, biochemical, immunochemical, electrical, radioactive, and optical means, including but not limited to bioluminescence, phosphorescence, and fluorescence. These detectable molecules should be a biologically compatible molecule and should not compromise the biological function of the molecule and must not compromise the ability of the detectable molecule to be detected. Exemplary detectable molecules are optically detectable molecules, including optically detectable proteins, such that they may be excited chemically, mechanically, electrically, or radioactively to emit fluorescence, phosphorescence, or bioluminescence. Other exemplary detectable molecules are inherently fluorescent molecules, such as fluorescent proteins, including, for example, Green Fluorescent Protein (GFP). The detectable molecule can be conjugated to the composition by methods as described in U.S. Pat. Nos. 5,891,646 and 6,110,693, both to Barak et al.). The detectable molecule can be conjugated at the front-end, at the back-end, or in the middle.

IV. Computer Assisted Drug Design

The disclosed compositions can be used as targets for any molecular modeling technique to identify either the structure of the disclosed compositions or to identify potential or actual molecules, such as small molecules, which interact in a desired way with the disclosed compositions.

It is understood that when using the disclosed compositions in modeling techniques, molecules, such as macromolecular molecules, will be identified that have particular desired properties such as inhibition or stimulation or the target molecule's function. The molecules identified and isolated when using the disclosed compositions, such as a TT1 Peptide, are also disclosed. Thus, the products produced using the molecular modeling approaches that involve the disclosed compositions, such as a TT1 Peptide, are also considered herein disclosed.

Thus, one way to isolate molecules that bind a molecule of choice is through rational design. This can be achieved through structural information and computer modeling. Computer modeling technology allows visualization of the three-dimensional atomic structure of a selected molecule and the rational design of new compounds that will interact with the molecule. The three-dimensional construct typically depends on data from x-ray crystallographic analyses or NMR imaging of the selected molecule. The molecular dynamics require force field data. The computer graphics systems enable prediction of how a new compound will link to the target molecule and allow experimental manipulation of the structures of the compound and target molecule to perfect binding specificity. Prediction of what the molecule-compound interaction will be when small changes are made in one or both requires molecular mechanics software and computationally intensive computers, usually coupled with user-friendly, menu-driven interfaces between the molecular design program and the user.

Examples of molecular modeling systems are the CHARMm and QUANTA programs (Polygen Corporation, Waltham, Mass., United States of America). CHARMm performs the energy minimization and molecular dynamics functions. QUANTA performs the construction, graphic modeling and analysis of molecular structure. QUANTA allows interactive construction, modification, visualization, and analysis of the behavior of molecules with each other.

A number of publications review computer modeling of drugs interactive with specific proteins, such as Rotivinen et al., 1988; Ripka, 1988; McKinaly & Rossmann, 1989; Perry & Davies, 1989; Lewis & Dean, 1989; and, with respect to a model enzyme for nucleic acid components, Askew et al., 1989. Other computer programs that screen and graphically depict chemicals are available from companies such as BioDesign, Inc., Pasadena, Calif., United States of America; Allelix, Inc., Mississauga, Ontario, Canada; and Hypercube, Inc., Cambridge, Ontario, Canada. Although these are primarily designed for application to drugs specific to particular proteins, they can be adapted to design of molecules specifically interacting with specific regions of DNA or RNA, once that region is identified.

Although described above with reference to design and generation of compounds which could alter binding, one could also screen libraries of known compounds, including natural products or synthetic chemicals, and biologically active materials, including proteins, for compounds which alter substrate binding or enzymatic activity.

V. Compositions with Similar Functions

It is understood that the compositions disclosed herein have certain functions, such as interacting with gC1qR/p32. Disclosed herein are certain structural requirements for performing the disclosed functions, and it is understood that there are a variety of structures which can perform the same function which are related to the disclosed structures, and that these structures will ultimately achieve the same result, for example stimulation or inhibition.

VI. Kits

Disclosed herein are kits that are drawn to reagents that can be used in practicing the methods disclosed herein. The kits can include any reagent or combination of reagent discussed herein or that would be understood to be required or beneficial in the practice of the disclosed methods. For example, the kits could include a TT1 Peptide and/or gC1q/p32 receptors.

VII. Mixtures

Whenever A method for the presently disclosed subject matter involves mixing or bringing into contact compositions or components or reagents, performing the method creates a number of different mixtures. For example, if the method includes 3 mixing steps, after each one of these steps a unique mixture is formed if the steps are performed separately. In addition, a mixture is formed at the completion of all of the steps regardless of how the steps were performed. The present disclosure contemplates these mixtures, obtained by the performance of the disclosed methods as well as mixtures containing any disclosed reagent, composition, or component, for example, disclosed herein.

VIII. Systems

Disclosed are systems useful for performing, or aiding in the performance of, the disclosed method. Systems generally comprise combinations of articles of manufacture such as structures, machines, devices, and the like, and compositions, compounds, materials, and the like. Such combinations that are disclosed or that are apparent from the disclosure are contemplated.

IX. Computer Readable Media

It is understood that the disclosed nucleic acids and proteins can be represented as a sequence consisting of the nucleotides of amino acids. There are a variety of ways to display these sequences, for example the nucleotide guanosine can be represented by G or g. Likewise the amino acid valine can be represented by Val or V. Those of skill in the art understand how to display and express any nucleic acid or protein sequence in any of the variety of ways that exist, each of which is considered herein disclosed. Specifically contemplated herein is the display of these sequences on computer readable mediums, such as, commercially available floppy disks, tapes, chips, hard drives, compact disks, and video disks, or other computer readable mediums. Also disclosed are the binary code representations of the disclosed sequences. Those of skill in the art understand what computer readable mediums. Thus, computer readable mediums on which the nucleic acids or protein sequences are recorded, stored, or saved.

X. Peptide Synthesis

The compositions disclosed herein and the compositions necessary to perform the disclosed methods can be made using any method known to those of skill in the art for that particular reagent or compound unless otherwise specifically noted.

One method of producing the disclosed proteins, such as a TT1 Peptide or a conjugate thereof, is to link two or more peptides or polypeptides together by protein chemistry techniques. For example, peptides or polypeptides can be chemically synthesized using currently available laboratory equipment using either Fmoc (9-fluorenylmethyloxycarbonyl) or Boc (tert-butyloxycarbonoyl) chemistry. (Applied Biosystems, Inc., Foster City, Calif., United States of America). One skilled in the art can readily appreciate that a peptide or polypeptide corresponding to the disclosed proteins, for example, can be synthesized by standard chemical reactions. For example, a peptide or polypeptide can be synthesized and not cleaved from its synthesis resin whereas the other fragment of a peptide or protein can be synthesized and subsequently cleaved from the resin, thereby exposing a terminal group which is functionally blocked on the other fragment. The peptide or polypeptide is independently synthesized in vivo as described herein. Once isolated, these independent peptides or polypeptides can be linked to form a peptide or fragment thereof via similar peptide condensation reactions.

For example, enzymatic ligation of cloned or synthetic peptide segments allow relatively short peptide fragments to be joined to produce larger peptide fragments, polypeptides, or whole protein domains (Abrahmsen et al., 1991). Alternatively, native chemical ligation of synthetic peptides can be utilized to synthetically construct large peptides or polypeptides from shorter peptide fragments. This method consists of a two step chemical reaction (Dawson et al., 1994). The first step is the chemoselective reaction of an unprotected synthetic peptide-thioester with another unprotected peptide segment containing an amino-terminal Cys residue to give a thioester-linked intermediate as the initial covalent product. Without a change in the reaction conditions, this intermediate undergoes spontaneous, rapid intramolecular reaction to form a native peptide bond at the ligation site (Baggiolini al., 1992; Clark-Lewis et al., 1994; Clark-Lewis et al., 1991; Rajarathnam et al., 1994).

Alternatively, unprotected peptide segments are chemically linked where the bond formed between the peptide segments as a result of the chemical ligation is an unnatural (non-peptide) bond (Schnolzer et al., 1992). This technique has been used to synthesize analogs of protein domains as well as large amounts of relatively pure proteins with full biological activity (deLisle et al., 1992).

XI. Methods

Disclosed herein are methods of interacting compositions with gC1qR/p32. Such interactions can be, for example, selective, targeted, or homing. Interaction with gC1qR/p32 can be mediated by a TT1 Peptide and can involve any TT1 Peptide or TT1 peptide composition as described herein. Interaction with gC1qR/p32 can be useful for detecting and/or treating diseases and conditions, such as diseases and/or conditions associated with gC1qR/p32.

Disclosed herein are methods of treating a disease associated with gC1q/p32 receptor comprising identifying a subject having a disease associated with the gC1q/p32 receptor; and administering to the subject a composition comprising SEQ ID NO: 1, SEQ ID NO: 2, or SEQ ID NO: 3 (i.e., a TT1 Peptide).

Also disclosed are methods of treating a disease associated with gC1q/p32 receptor comprising identifying a subject having a disease associated with the gC1q/p32 receptor; and administering to the subject a composition that interacts with the gC1q/p32 receptor in the same location as a TT1 Peptide, thereby treating a disease associated with the gC1q/p32 receptor. The composition that interacts with the gC1q/p32 receptor can be, for example, an antibody, protein, or chemical.

Disclosed are methods of delivering a TT1 Peptide composition to a gC1q/p32 receptor, wherein the TT1 Peptide composition comprises a moiety linked to a composition comprising SEQ ID NO: 1, SEQ ID NO: 2, or SEQ ID NO: 3; wherein the method comprises bringing into contact the TT1 Peptide composition and a cell, thereby delivering the TT1 Peptide composition to the gC1q/p32 receptor.

In some embodiments, the cell is in a subject. When the cell is in a subject, the cell can be selected for its potential to comprise a gC1q/p32 receptor by detecting the presence of gC1q/p32 receptor on another cell of the subject.

Also disclosed are methods of delivering a TT1 Peptide composition to a gC1q/p32 receptor, wherein the TT1 Peptide composition comprises a moiety linked to a composition comprising SEQ ID NO: 1, SEQ ID NO: 2, or SEQ ID NO: 3; comprising: selecting a cell for its potential to comprise a gC1q/p32 receptor; and bringing into contact the TT1 Peptide composition and the cell, thereby delivering the TT1 Peptide composition to the gC1q/p32 receptor.

Also disclosed are methods of detecting interaction between a gC1q/p32 receptor and a TT1 Peptide composition, wherein the TT1 Peptide composition comprises a moiety linked to a composition comprising SEQ ID NO: 1, SEQ ID NO: 2, or SEQ ID NO: 3, the method comprising: selecting a cell for its potential to comprise a gC1q/p32 receptor; bringing into contact the TT1 Peptide composition and the cell; and detecting interaction between the gC1q/p32 receptor and the TT1 Peptide composition.

Disclosed are methods of determining and/or assessing gC1q/p32 receptor level in a cell of a subject, comprising: bringing into contact a cell of the subject and a TT1 Peptide composition comprising a detectable agent linked to a composition comprising SEQ ID NO: 1, SEQ ID NO: 2, or SEQ ID NO: 3; and detecting the level of TT1 Peptide composition interacting with gC1q/p32 receptor, thereby determining and/or assessing gC1q/p32 receptor level in the cell. The level of gC1q/p32 receptor in the subject is compared to a previous measurement in the same subject, or can be compared to a control level or standard level.

Also disclosed are methods of identifying a subject having a disease associated with gC1q/p32 receptor, the method comprising bringing into contact a cell of the subject and a TT1 Peptide composition, wherein the TT1 Peptide composition comprises a moiety linked to a composition comprising SEQ ID NO: 1, SEQ ID NO: 2, or SEQ ID NO: 3; and detecting interaction between gC1q/p32 receptor and the TT1 Peptide composition, thereby detecting the presence or level of gC1q/p32 on the cell, wherein the presence or level of gC1q/p32 receptor on the cell identifies the subject as having a disease associated with a gC1q/p32 receptor.

Also disclosed are methods of screening for a compound that interacts with a gC1q/p32 receptor, comprising bringing into contact a test compound, a TT1 Peptide composition, and a gC1q/p32 receptor, wherein the TT1 Peptide composition comprises SEQ ID NO: 1, SEQ ID NO: 2, or SEQ ID NO: 3; and detecting unbound TT1 Peptide composition, wherein a given amount of unbound TT1 Peptide composition indicates a composition that interacts with gC1q/p32 receptor. The TT1 Peptide composition can comprise a moiety, wherein the moiety comprises SEQ ID NO: 1, SEQ ID NO: 2, or SEQ ID NO: 3. In some embodiments, the moiety can be a detectable agent. Methods of screening are discussed in more detail below.

Further disclosed herein is a method of treating or preventing a disease in a subject associated with gC1q/p32 receptor, the method comprising administering to the subject a composition that modulates gC1q/p32 receptor expression or activity, thereby treating a disease in a subject associated with the gC1q/p32 receptor. The subject can have cancer. The composition can have a therapeutic effect on the cancer. The size of a tumor can be reduced. The growth of a tumor can be reduced, stopped or reversed.

Expression or activity of the gC1q/p32 receptor can be inhibited. This can occur by the use of interfering nucleic acid, such as shRNA or siRNA. Activity of the gC1q/p32 receptor can be inhibited by a TT1 Peptide, an antibody, or a small molecule mimic of a TT1 Peptide. The methods of treating or preventing cancer disclosed herein can be used in conjunction with other treatment therapies as well.

The therapeutic effect of the compositions disclosed herein can be a slowing in the increase of or a reduction of tumor burden. This slowing in the increase of, or reduction in the tumor burden, can be 1%, 5%, 10%, 15%, 20%, 25%, 30%, 35%, 40%, 45%, 50%, 55%, 60%, 65%, 70%, 75%, 80%, 85%, 90%, 95%, 100%, 150%, 200%, 300%, 400%, 500%, 600%, 700%, 800%, 900%, or 1000% or more improvement in the increase of, or reduction in the tumor burden of, compared with a non-treated tumor, or a tumor treated by a different method.

The gC1q/p32 receptor involved in the disclosed methods can be, for example, on or in a cell. The cell can be in any context, such as in an organism, in situ, ex vivo, in culture, and/or in vitro.

The disclosed compositions can be used to treat any disease where uncontrolled cellular proliferation occurs such as cancers. A non-limiting list of different types of cancers can be as follows: lymphomas (Hodgkins and non-Hodgkins), leukemias, carcinomas, carcinomas of solid tissues, squamous cell carcinomas, adenocarcinomas, sarcomas, gliomas, high grade gliomas, blastomas, neuroblastomas, plasmacytomas, histiocytomas, melanomas, adenomas, hypoxic tumors, myelomas, AIDS-related lymphomas or sarcomas, metastatic cancers, or cancers in general.

A representative but non-limiting list of cancers that the disclosed compositions can be used to treat is the following: lymphoma, B cell lymphoma, T cell lymphoma, mycosis fungoides, Hodgkin's Disease, myeloid leukemia, bladder cancer, brain cancer, nervous system cancer, head and neck cancer, squamous cell carcinoma of head and neck, kidney cancer, lung cancers such as small cell lung cancer and non-small cell lung cancer, neuroblastoma/glioblastoma, ovarian cancer, pancreatic cancer, prostate cancer, skin cancer, liver cancer, melanoma, squamous cell carcinomas of the mouth, throat, larynx, and lung, colon cancer, cervical cancer, cervical carcinoma, breast cancer, and epithelial cancer, renal cancer, genitourinary cancer, pulmonary cancer, esophageal carcinoma, head and neck carcinoma, large bowel cancer, hematopoietic cancers; testicular cancer; colon and rectal cancers, prostatic cancer, or pancreatic cancer.

EXAMPLES

The following examples are put forth so as to provide those of ordinary skill in the art with a complete disclosure and description of how to make and use the presently disclosed subject matter, and are not intended to limit the scope of what the inventors regard as their invention nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric.

Example 1

Purification and Oligomerization Analysis of the p32 Protein and Biopanning

Figure 1B:
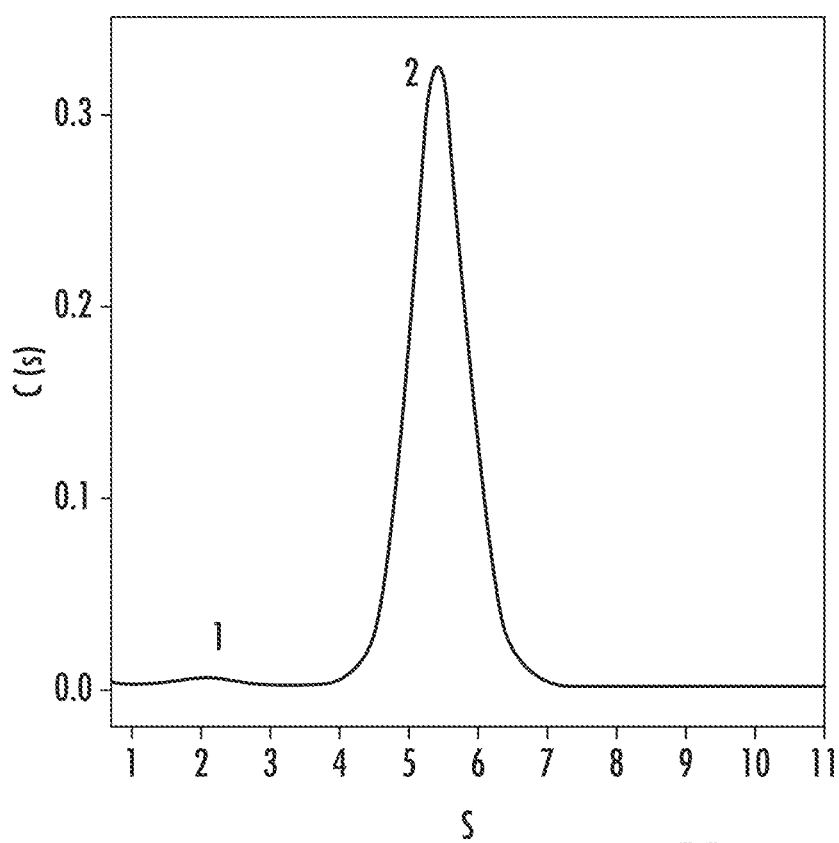

6×-His-Tagged P32 was expressed in Rosetta-gami-2 cells (Novagen). The protein was purified by IMAC using HIS-select resin (Sigma) with an imidizole gradient from 20-300 mM and eluted fractions were analyzed on analytical SDS-PAGE (see FIG. 1A). A sedimentation velocity assay that allowed determination of the multimeric state of proteins was performed, and the results are summarized in FIG. 1B and in Table 4. As shown therein, the sedimentation velocity assay demonstrated that similarly to the native p32 protein, recombinant p32 is present predominantly (>97%) as a trimer with sedimentation coefficient of 5.447 and apparent molecular weight for the complex of 79.2 kDa (see FIG. 1B).

TABLE 4

Sedimentation Velocity Assay Results

| Sample | S | S(20 w) | % | Apparent Mw |
|---|---|---|---|---|
| 1 | 2.117 | 2.201 | 2.7 | 19.2 kDa |
| 2 | 53447 | 5.663 | 97.3 | 79.2 kDa |

Figure 2A:
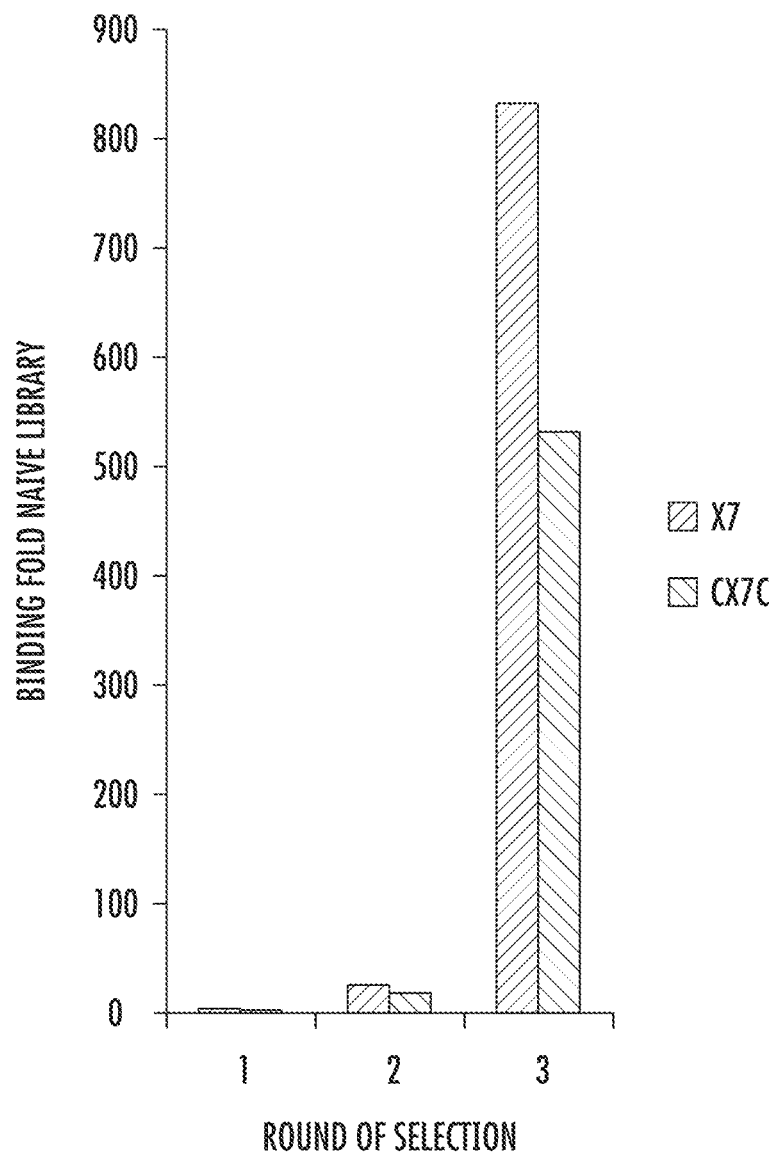

Milligram quantities of recombinant His-tagged p32 protein were expressed in *E. coli* and coated onto Ni-NTA magnetic beads, and biopanning was performed using two T7 bacteriophage peptide libraries (cyclic Cx7C and linear X7 library). After three rounds of selection, a 500-800 fold increase in binding to recombinant p32 was seen for both libraries (see FIG. 2A).

Figure 3:
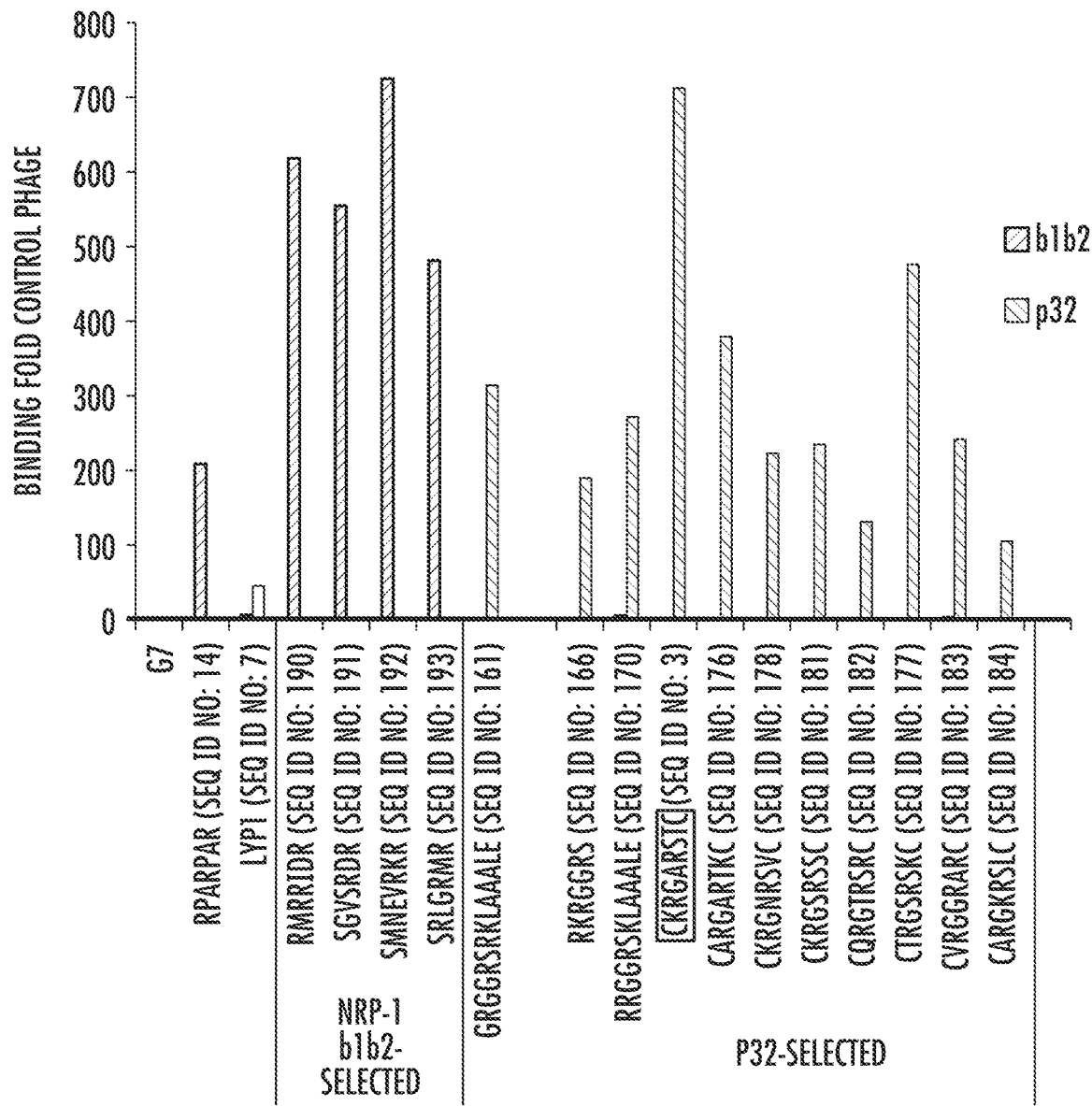
FIG. 3 is a bar graph of binding of individual RGXRS (SEQ ID NO: 4)-displaying phage clones to immobilized p32 and NRP-1 b1b2 domain. In vitro binding experiments were performed using phage clones displaying p32-selected RGRS (SEQ ID NO: 13)-containing peptides or phage clones selected on NRP-1 b1b2 domain. Note the lack of cross-binding of the phage to different target proteins. LyP-1 (a known p32 binder; SEQ ID NO: 7) and RPARPAR (a prototypic CendR peptide that binds to NRP-1 b1b2 domain; SEQ ID NO: 14) served as controls. The data are representative of three (3) independent binding experiments. An exemplary P32-binding CKRGARSTC peptide (TT1; SEQ ID NO: 3) is highlighted by a box. Peptides from left to right in FIG. 3 are a control polyglycine heptapeptide (G7), RPARPAR (SEQ ID NO: 14), LYP1 (SEQ ID NO: 7), RMRRIDR (SEQ ID NO: 190), SGVSRDR (SEQ ID NO: 191), SMNEVRKR (SEQ ID NO: (192), SRLGRMR (SEQ ID NO: 193), GRGGRSRKLAAALE (SEQ ID NO: 161), RKRGGRS (SEQ ID NO: 166), RRGGRSKLAAALE (SEQ ID NO: 170), CKRGARSTC (SEQ ID NO: 3), CARGARTKC (SEQ ID NO: 176), CKRGNRSVC (SEQ ID NO: 178), CKRGSRSSC (SEQ ID NO: 181), CQRGTRSRC (SEQ ID NO: 182), CTRGSRSKC (SEQ ID NO: 177), CVRGGRARC (SEQ ID NO: 183), and CARGKRSLC (SEQ ID NO: 184).

Variant peptide-encoding genomic DNA of phage was sequenced and analyzed for the presence of consensus motifs. After two rounds of selection, both linear and cyclic libraries converged to contain an RGXRS (SEQ ID NO: 4) pentapeptide motif (see FIG. 2B). The binding of RGXRS (SEQ ID NO: 4)-displaying phage to p32 was specific, as these phage bound to magnetic beads coated with p32 protein and not to beads coated with ligand-binding b1b2 domain of the cell and tissue penetration receptor NRP-1 or BSA (see FIG. 3).

Figure 4A:
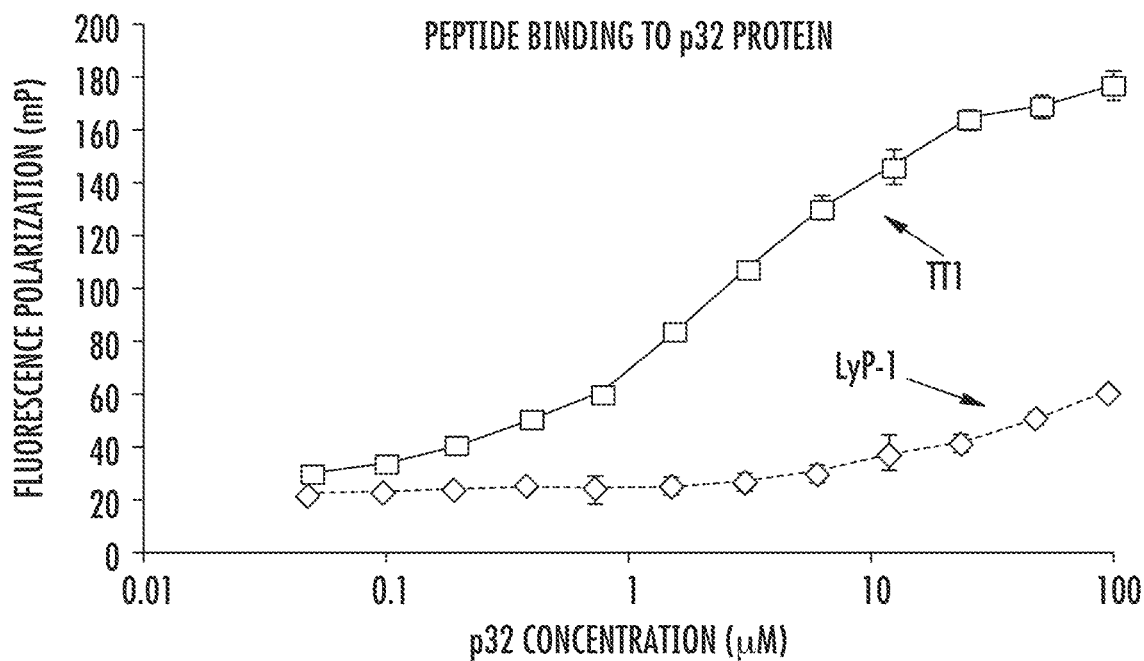
FIGS. 4A and 4B are plots showing a comparison of the binding of LyP-1 (SEQ ID NO: 7; diamonds) and TT1 (SEQ ID NO: 3; squares) to p32 in a fluorescence polarization assay.
Figure 4B:
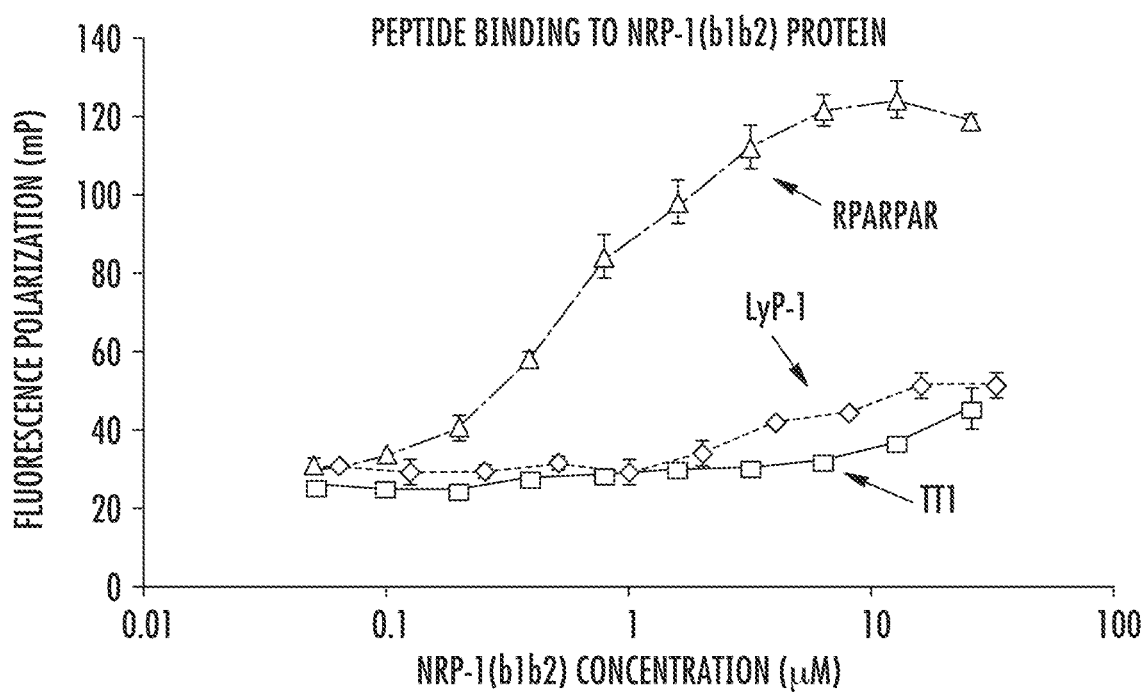
Figure 5:
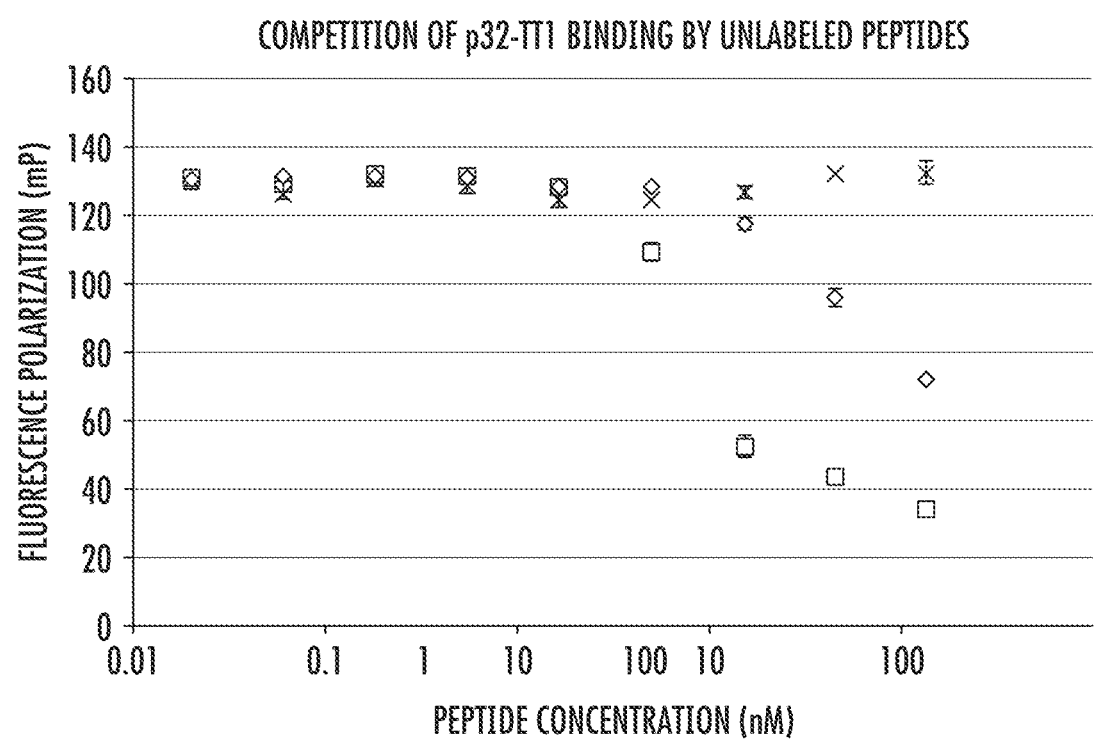
FIG. 5 is a plot showing that P32-TT1 (CKRGARSTC; SEQ ID NO: 3) and LyP-1 (SEQ ID NO: 7) peptides competed for binding to the P32 protein. The results were derived from a fluorescence polarization assay that demonstrated that binding of labeled TT1 (SEQ ID NO: 3) to P32 could be inhibited by unlabeled TT1 (SEQ ID NO: 3) and LyP-1 (SEQ ID NO: 7) but not by RPARPAR peptide (SEQ ID NO: 14). Squares: p32-TT1; Diamonds: LyP-1; X: RPARPAR peptide (SEQ ID NO: 14).
Figure 6A:
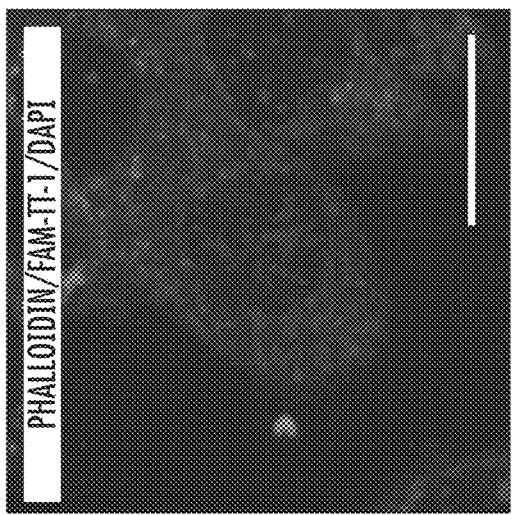
FIGS. 6A and 6B are fluorescence micrographs showing internalization of CKRGARSTC (TT1; SEQ ID NO: 3) peptide in breast tumor cells in vitro. 100 µM FAM-labeled peptides were incubated with 4T1 (FIG. 6A) or MCF10 (FIG. 6B) breast cancer cells for 1 hour at 37° C. in DMEM high glucose/10% serum medium. Cells were washed, fixed, stained with anti-FITC antibody, and MITOTRACKER® (Life Technologies) or phalloidin as indicated. Scale bars: 20 m.
Figure 6A:
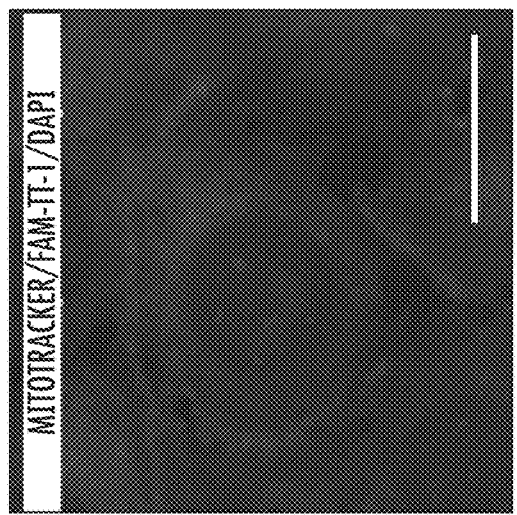
Figure 6A:
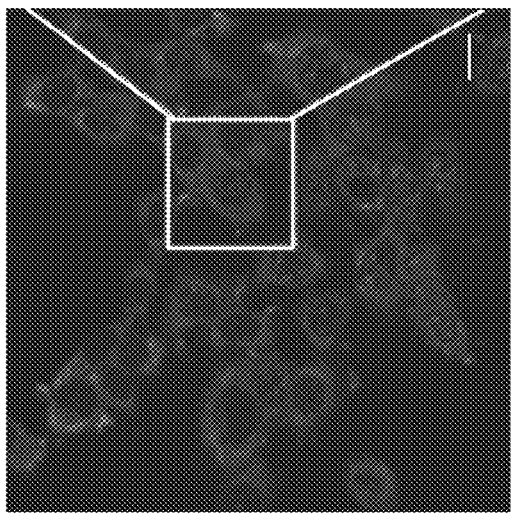
Figure 6A:
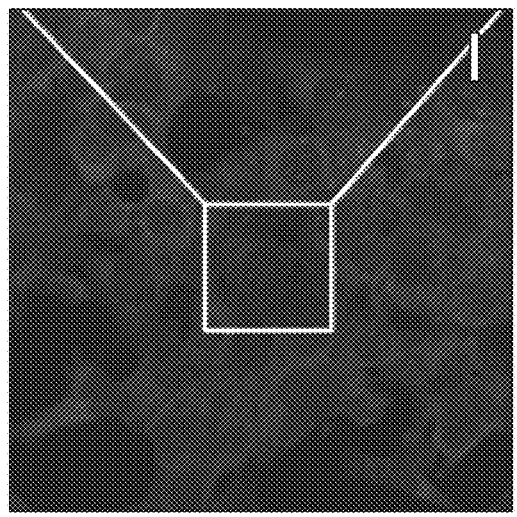
Figure 6A:
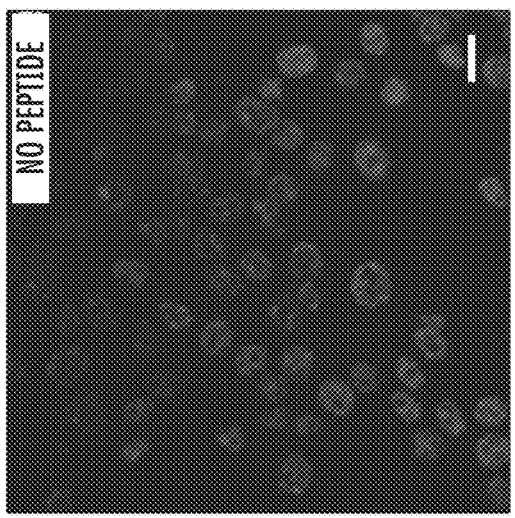
Figure 6A:
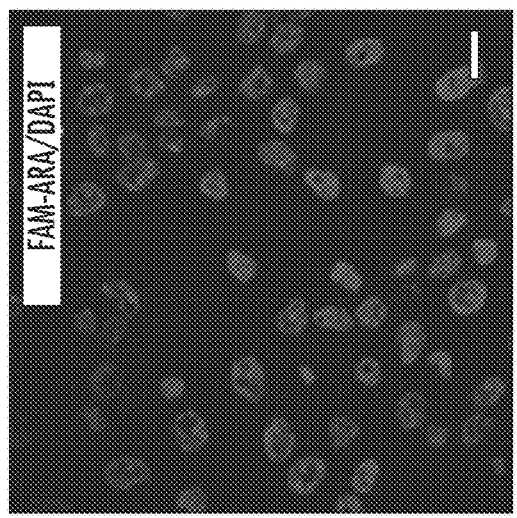
Figure 6B:
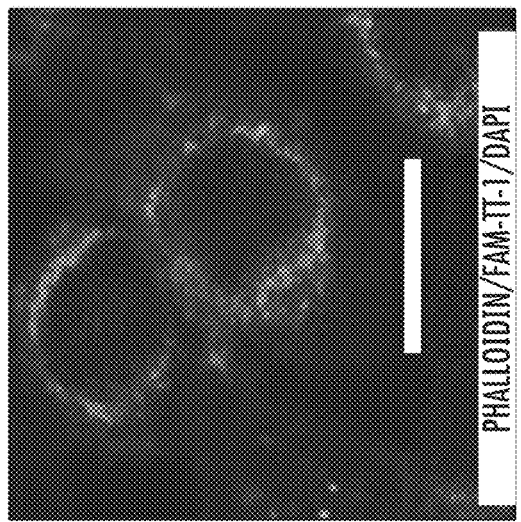
Figure 6B:
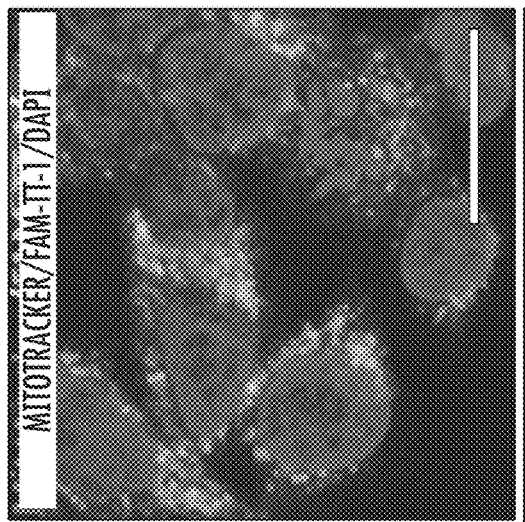
Figure 6B:
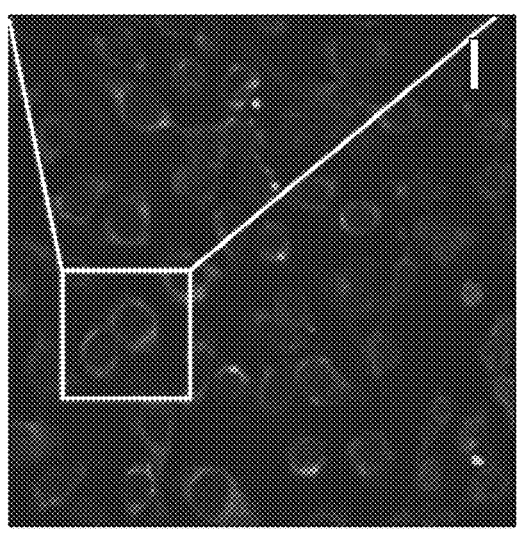
Figure 6B:
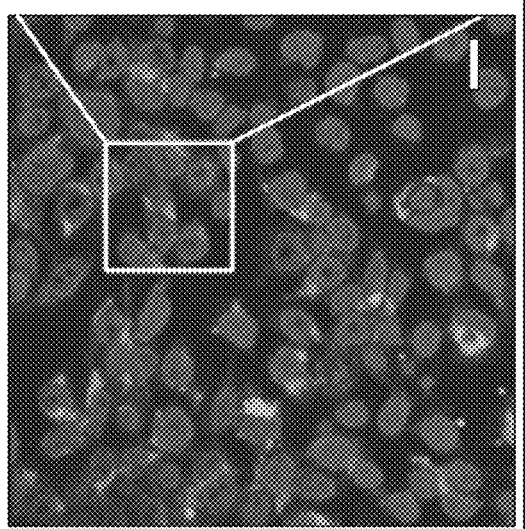
Figure 6B:
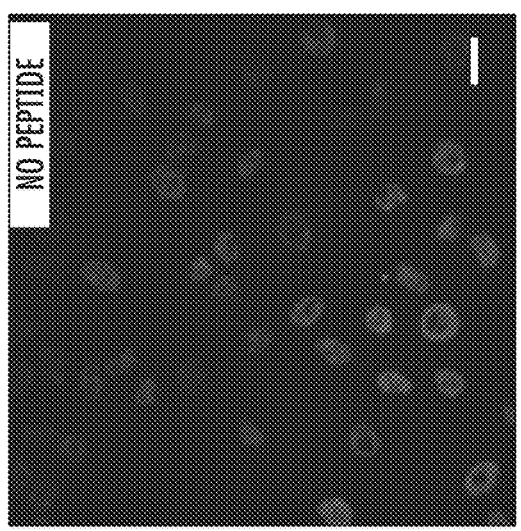
Figure 6B:
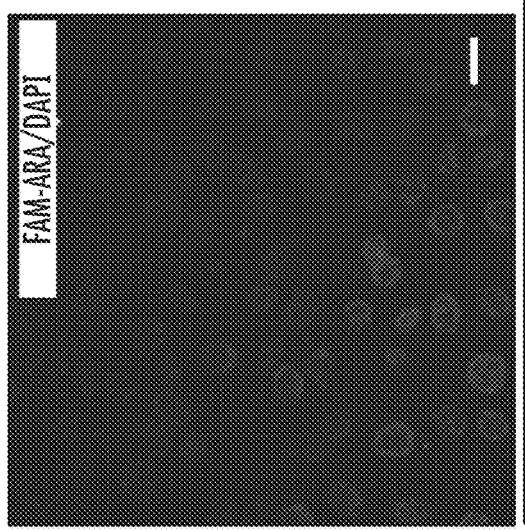

An exemplary RGXRS (SEQ ID NO: 4) pentapeptide motif-containing peptide with the sequence CKRGARSTC (SEQ ID NO: 3) was designated as the "TT1 Peptide" and used it for further studies. Mutating any amino acid in the consensus motif of TT1 abolished the phage binding to p32. This new peptide conferred about 15-fold stronger phage binding to immobilized p32 protein than did the canonical LyP-1 peptide. Fluorescence polarization assays with the synthetic peptides confirmed that the TT1 Peptide binding to p32 was specific and that the TT1 Peptide shared the binding site on p32 with the LyP-1 peptide (see FIGS. 4 and 5).

Example 2

In Vitro Internalization and In Vivo Homing of the TT1 Peptide

The ability of the TT1 Peptide to bind to cultured breast tumor cells was tested in vitro. Exemplary results are shown in FIG. 6. It appeared that the synthetic fluorophore-labeled TT1 Peptide rapidly bound to the surface of 4T1 and MCF10 breast cancer cells and was internalized over time.

Figure 7B:
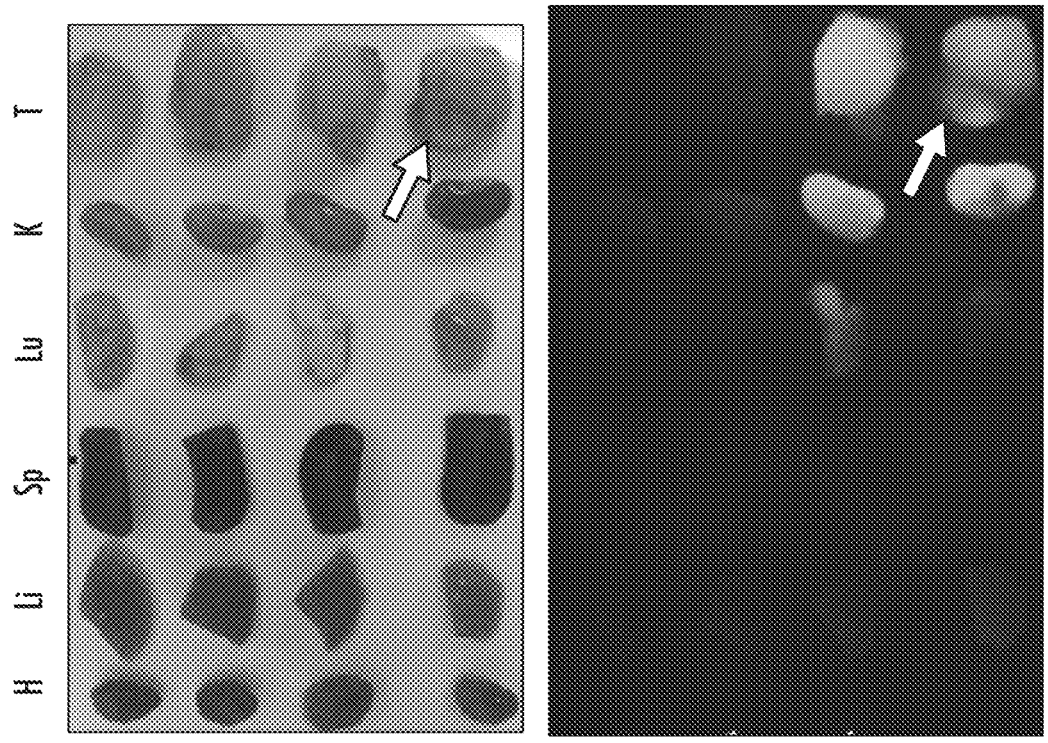
FIGS. 7A and 7B are photographs depicting in vivo homing of an exemplary TT1 peptide. 200 µg of FAM-labeled TT1 (SEQ ID NO: 3) peptide or control peptide in PBS was intravenously injected to mice bearing orthotopic 4T1 (FIG. 7A) or MCF7 (FIG. 7B) breast tumors. The peptides were allowed to circulate for 2 hours and organs were collected and photographed under white (top panels) or UV (bottom panels) light. Arrows point to the tumors of TT1 (SEQ ID NO: 3)-injected mice. Note robust signal (white in black and white versions and green in color versions of the Figures) indicating homing of TT1 (SEQ ID NO: 3) peptide to the tumor in both models. H: heart; Lu: lung; Li: liver; Ki: kidney; Sp: spleen; T: tumor.
Figure 7A:
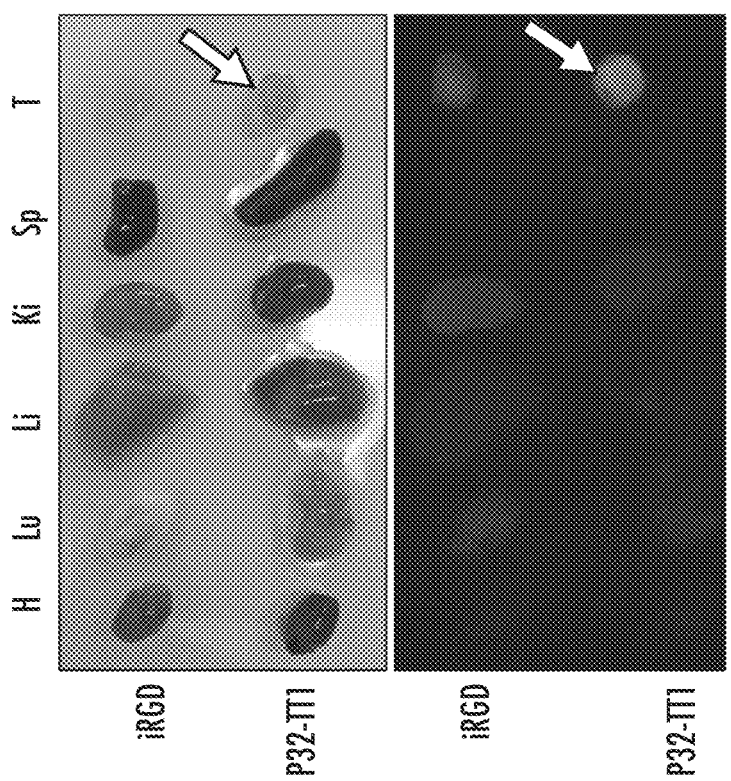

Systemically administered LyP-1 and iRGD tumor-penetrating peptides efficiently home to and penetrate orthotopic breast tumors in vivo. Intravenously administered TT1 Peptide had similar activity, and it homed to breast tumors in mice bearing 4T1 syngeneic (see FIG. 7A) tumors, as well as MCF7 (see FIG. 7B) and MDA-MB-231 xenografts.

Figure 8:
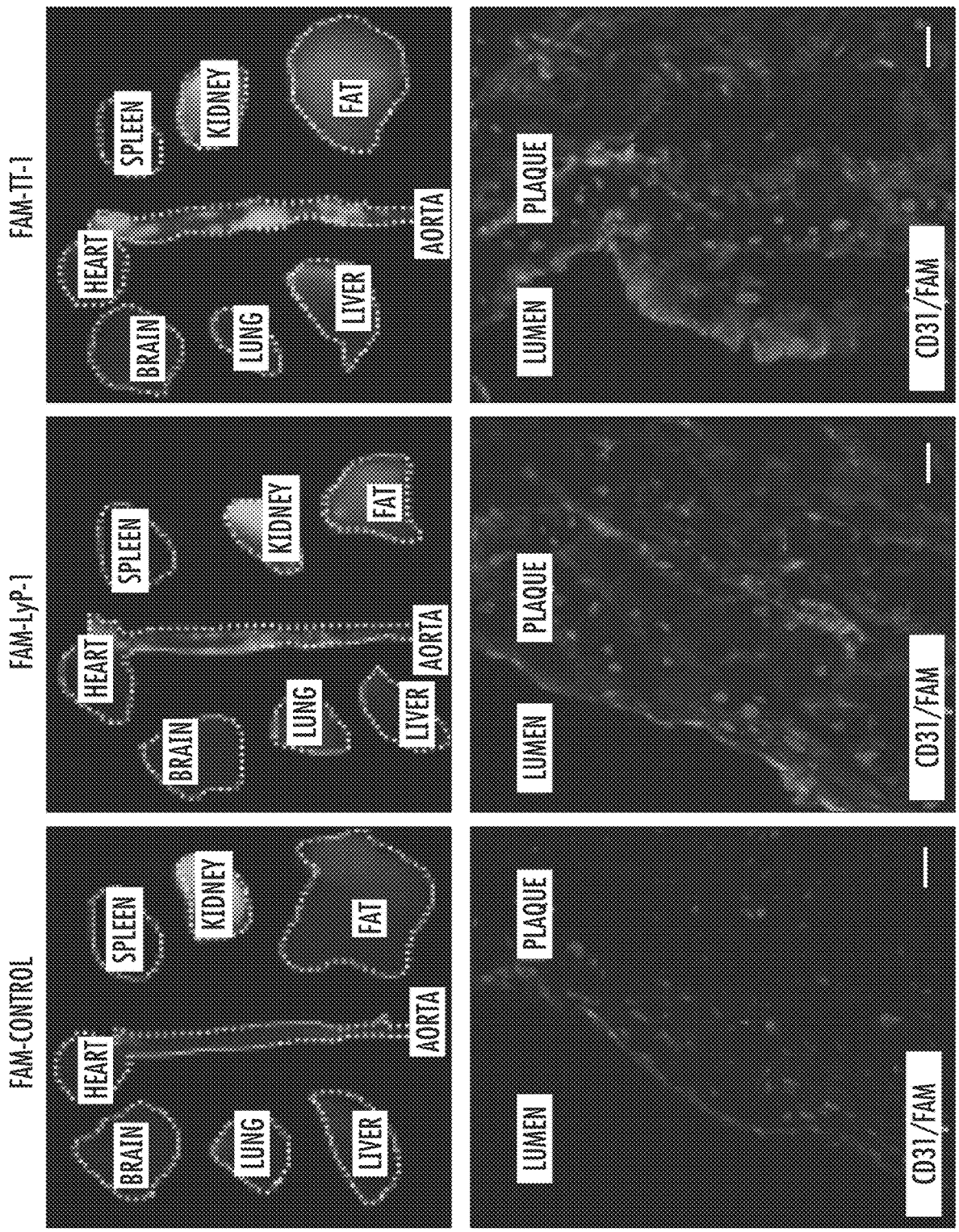
FIG. 8 is a series of fluorescence micrographs showing TT1 (SEQ ID NO: 3) peptide homed to and penetrated into plaque tissue as well as or better than LyP-1 (SEQ ID NO: 7). ApoE null mice that had been kept on a high-fat diet were intravenously injected with 100 mg of the FAM labeled peptides. One hour later, the mice were perfused through the heart under anesthesia, and tissues were collected. The panels show accumulation of FAM labeled peptides visualized with UV excitation. The center two and right two panels show atherosclerotic aortas that were sectioned at the aortic root level and examined by confocal microscopy. LyP-1 (SEQ ID NO: 7) signal (center two panels) and a stronger TT1 (SEQ ID NO: 3) signal (right two panels) were seen inside plaques, whereas a control peptide (left two panels) did not accumulate in the plaques.

In a different model, the TT1 Peptide homed to and penetrated atherosclerotic lesions in ApoE null mice maintained on high-fat diet. The homing appeared to be more robust than seen with the LyP-1 peptide (see FIG. 8).

Example 3

The Cryptic CendR Element in the TT1 Peptide can be Activated by Proteolytic Cleavage The cryptic (internal) R/KXXR/K C-end Rule (CendR) element is the key determinant of the ability of tumor-penetrating and tissue-penetrating peptides to reach deep into parenchymal extravascular tumor tissue. In these peptides, the CendR motif is exposed at the C-terminus by endogenous cell-surface proteases to trigger interaction of the peptide with cell penetration and tissue penetration receptor NRP-1. Upregulation of extracellular proteolysis machinery is one of the hallmarks common to tumors and atherosclerotic lesions. Urokinase-type plasminogen activator (uPA) and matrix metalloproteinases are thought to be of central importance for tumor invasion and metastasis, and extracellular matrix remodeling.

Figure 9:
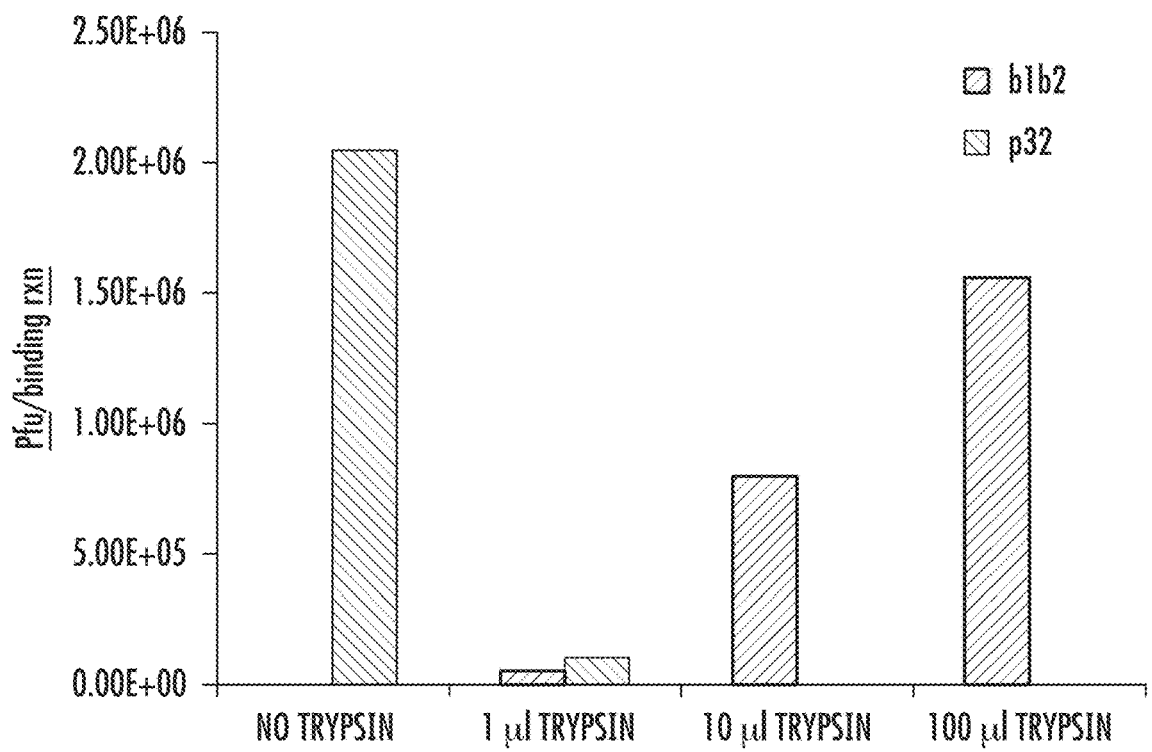
FIG. 9 is a bar graph showing proteolytic switching of binding specificity of an exemplary TT1 peptide (SEQ ID NO: 3). T7 phage displaying an exemplary TT1 peptide (SEQ ID NO: 3) were exposed to increasing concentrations of crystalline trypsin and incubated for 30 minutes at 37° C. After treatment, phage were incubated with magnetic beads coated with either p32 (decending hatching left to right) or NRP-1 b1b2 (ascending hatching left to right) protein, followed by washes to remove unbound phage and quantitation of specifically bound phage.

The p32 binding motif with consensus sequence RGXRS (SEQ ID NO: 4; i.e., the RGXRS (SEQ ID NO: 4) pentapeptide motif) contains a cryptic RGXR CendR element that can be unmasked by a tryptic cleavage. Indeed, exposure of the TT1 Peptide to trypsin resulted in affinity switching from p32 to NRP-1 b1b2 (see FIG. 9). In addition, exposure of TT phage to recombinant urokinase-type plasminogen activator (uPA) led to 180-fold enhancement of the NRP-1 b1b2 binding.

Thus, the TT1 Peptide had a dual, protelytically switchable target specificity. The peptide was first recruited to the p32 protein present on the surface of tumor macrophages, tumor lymphatic cells, and cancer cells in hypoxic areas of tumors, followed by its processing by uPA (and potentially other proteases) in the tumor extracellular milieu. Processed peptide with free C-terminal CendR motif bound to cell and tissue penetration receptor NRP-1 to trigger tumor penetration of conjugated and co-administered payloads. As both determinants of the TT1 Peptide's specificity, p32 and proteases like uPA, are expressed predominantly in tumor tissue, the generation of the CendR fragment capable of triggering cell- and tissue-penetration appeared to be limited to tumors. A similar process likely accounts for the homing and penetration of the TT1 Peptide in atherosclerotic plaques.

Example 4

Figure 10:
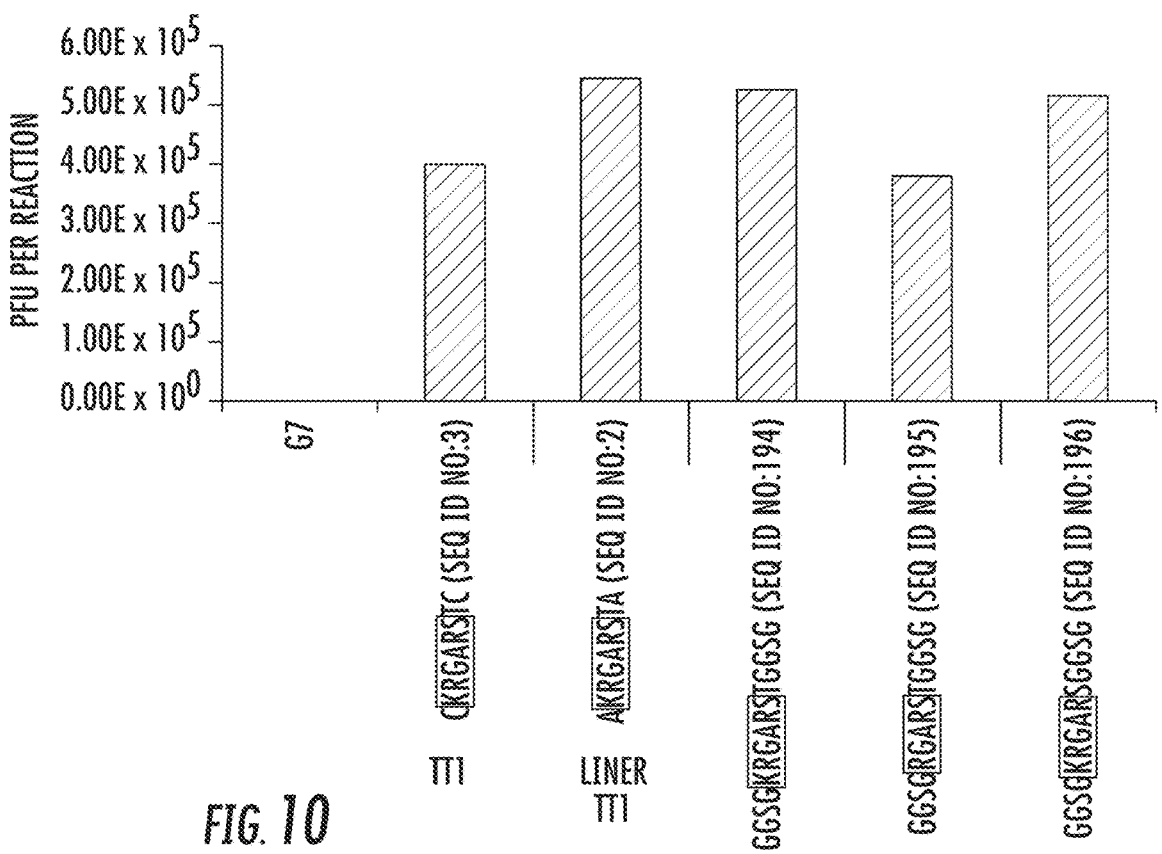
FIG. 10 is a bar graph showing that the p32 binding of the RGXR(S/T) motif (SEQ ID NOs: 4 and 5) in the exemplary TT1 peptide (SEQ ID NO: 3) was not dependent on the cyclic structure and compatible with flanking sequences. Phage clones displaying the indicated peptides were incubated in p32-coated magnetic microbeads. After washing to remove non-bound phage, specifically bound phage were quantified. Note that a TT1 variant (SEQ ID NO: 2) with cysteines replaced by alanines retained the binding activity and that the binding was not reduced by flanking (T)GGSG linkers (SEQ ID NOs: 15 and 16).

Binding of the RGXR(S/T) (SEQ ID NOs: 4 and 5) Motif to p32 is Conformation and Position Independent The cyclic structure of the LyP-1 Peptide is required for its binding to p32 and for its biological activities. In contrast, the p32-binding RGARS (SEQ ID NO: 4) motif of the TT1 Peptide did not require the motif to be in a cyclic context. A TT1 Peptide variant with cysteine residues replaced by alanine residues retains the binding activity (see FIG. 10). Of note, it is possible that in vivo, the cyclic structure of the TT1 Peptide could be beneficial and increase the stability of the peptide. Importantly, the p32 binding activity of the RGARS (SEQ ID NO: 4) motif was not adversely affected by flanking GGSG (SEQ ID NO: 16) linkers. These features render the TT1 family of peptides particularly suitable for design of modular targeting peptides.

Materials and Methods for Examples 5-7

Peptide and NW conjugation. Peptides were synthesized with an automatic microwave-assisted peptide synthesizer (Liberty; CEM) using standard solid-phase Fmoc/tBu chemistry with 2-(1H-azabenzotriazol-1-yl)-1,1,3,3-tetramethyluronium hexafluoro-phosphate (AnaSpec) as the coupling reagent. An extra cysteine residue was added to the N-terminus of the cyclic peptides (LyP-1 and cTT1) as described (Sugahara et al., 2009). During the synthesis, the peptides were labeled with 5(6)-carboxyfluorescein (FAM; Sigma-Aldrich) with a 6-aminohexanoic acid spacer to separate the dye from the sequence. The peptides were cleaved from the resin with 95% trifluoroacetic acid (Sigma-Aldrich) with 2.5% water and triisopropylsilane (Sigma-Aldrich). Subsequent purification by high-performance liquid chromatography (Gilson) yielded peptides with >90% purity. For NW coupling, aminated NWs were pegylated with maleimide-5KPEG-NHS (JenKem Technology) and peptides were conjugated to the nanoparticles through a thioether bond between the cysteine thiol in the peptide and the maleimide on the functionalized particles.

Cell lines and tumors. MCF10CA1a human tumor cells were obtained from the Barbara Ann Karmanos Cancer Institute (Detroit, Mich.). Cells were maintained in Dulbecco's Modified Eagle Medium supplemented with 10% fetal bovine serum, 1% Glutamine-Pen-Strep and 100 ng/ml of human epidermal growth factor (Sigma-Aldrich, St. Louis, Mo., United States of America).

To produce MCF10CA1a tumors, athymic nude mice were orthotopically injected into the mammary fat pad with $2 \times 10^6$ cells suspended in 100 of PBS. Animal experimentation was performed according to the procedures approved by the Animal Research Committee at the Sanford-Burnham Medical Research Institute.

In vivo peptide homing. Orthotopic breast tumor xenografts were used when they reached 0.5-1 cm in size. NWs conjugated peptides were injected into the tail vein (7.5 mg of iron per kilogram of body weight). After 5-6 hours of NW circulation the mice were euthanized by cardiac perfusion with PBS under anesthesia, and tumors and organs were dissected and analyzed for particle homing.

Immunofluorescence. Tissues from mice injected with nanoparticles were fixed in 4% paraformaldehyde overnight at 4° C., cryoprotected in 30% sucrose overnight, and frozen in optimal cutting temperature (OCT) embedding medium. Subsequently, 5-7 m sections were cut and stored at −20° C.

until used. For immunostaining, tissue sections were first incubated for 1 hour at room temperature with 10% serum from the species in which the secondary antibody was generated, followed by incubation with the primary antibody overnight at 4° C. Rat monoclonal anti-mouse CD31 (10 g/mL) was from BD Pharmingen). The primary antibody was detected with Alexa 594-labeled goat anti-rat secondary antibody (1:1000; Molecular Probes). Each staining experiment included sections stained only with secondary antibodies as negative controls. Nuclei were stained with DAPI (4',6-diamidino-2-phenylindole; 5 g/mL; Molecular Probes). The sections were mounted in gel/mount mounting medium (Biomeda) and viewed under a FluoView 500 confocal microscope (Olympus America; 200 micron micrographs, 20 m magnification and 50 microns, 40 μm).

Example 5

Peptide and Nanoparticle Synthesis

Figure 11:
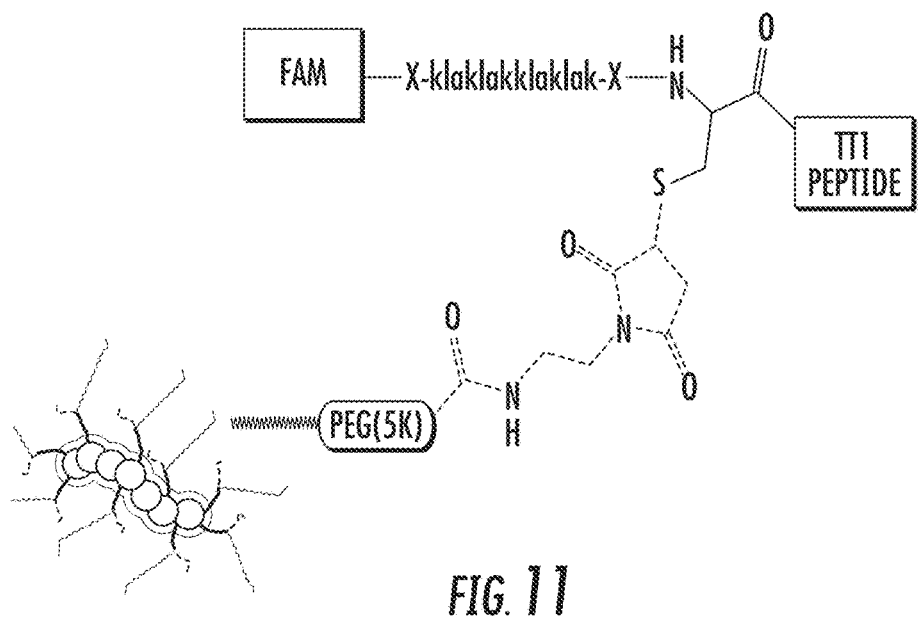
FIG. 11 depicts the design of an exemplary theranostic nanosystem. A chimeric peptide combining a tumor-homing peptide (a TT1 Peptide in this example; SEQ ID NO: 3) with a pro-apoptotic peptide (KLAKLAKKLAKLAK; SEQ ID NO: 42) was covalently coupled to iron oxide nanoworms (NWs; length 80-100 nm, width 30 nm; Park et al., 2008). An extra cysteine was added to the N-terminus of the cyclic LyP-1 (SEQ ID NO: 199) nonapeptide and used for coupling NWs. The drug peptide and the fluorophore were attached to the free N-terminus of the same cysteine residue.

Potential p32-binding peptides were synthesized as free peptides and as chimeras with $_D$(KLAKLAK)$_2$ (SEQ ID NO: 42). These included LyP-1, an exemplary cyclic TT1 Peptide (CycTT1), and an exemplary linear TT1 Peptide (LinTT1). The amino acid sequences of these peptides are shown in Table 5. The peptides were also labeled with a fluorescein (FAM) group. All peptides were successfully synthesized at >90% purity, and the structure of each peptide was confirmed by mass spectrometry analysis. The peptides were covalently conjugated onto amino group-functionalized dextran-coated superparamagnetic iron oxide nanoworms (NWs) as such or as the homing moiety in a chimeric peptide with the $_D$(KLAKLAK)$_2$ (SEQ ID NO: 42) drug peptide (see FIG. 11) for testing. Fluorescence measurement was used to compare the rate of peptide coupling. All peptides coupled at approximately the same efficiency.

TABLE 5

Amino acid Sequences of
Exemplary p32-binding Peptides

Full Length Amino Acid Sequence

CGKRK (SEQ ID NO: 6)

AKRGARSTA (LinTT1; (SEQ ID NO: 2)

CKRGARSTC (CycTT1; SEQ ID NO: 3)

CGNKRTRGC (LyP-1; SEQ ID NO: 7)

CGKRK-$_D$(KLAKLAK)$_2$ (SEQ ID NO: 8)

LyP1-$_D$(KLAKLAK)$_2$ (SEQ ID NO: 9)

LinTT1-$_D$(KLAKLAK)$_2$ (SEQ ID NO: 10)

Example 6

Tumor Homing and Tissue Penetration

The peptides were assayed for tumor homing to allow selection of the peptide with optimal homing and penetration properties on the NWs and in the context of the homing peptide-$_D$(KLAKLAK)$_2$-NW nanosystem. Mouse glioblastomas were used initially to show the efficacy of the CGKRK-$_D$(KLAKLAK)$_2$ (SEQ ID NO: 8) NWs. More recently, breast cancers were shown to respond to this nanosystem the same way as glioblastomas (see Agemy et al., 2013). This finding made it possible to use the orthotopic tumors (in the mammary fat pad), which are technically easier to produce than orthotopic glioblastomas.

Figure 12:
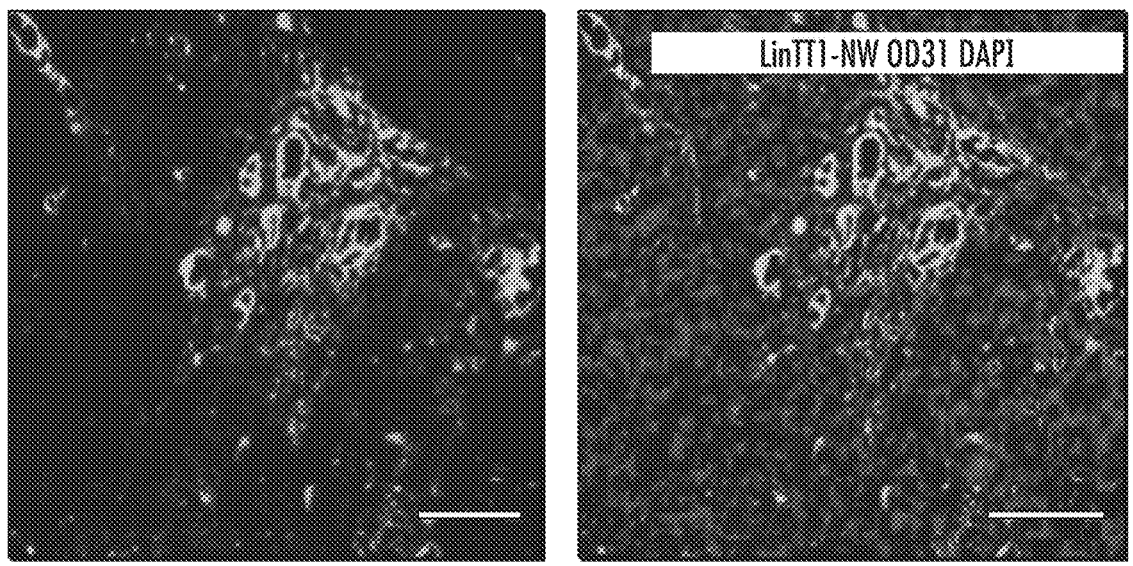
FIG. 12 is a fluorescent micrograph showing tumor homing of linear TT1-NWs. Tumor-bearing mice were intravenously injected with FAM-LinTT1-coated NWs (7.5 mg iron/kg) and allowed to circulate for 5 hours. The mice were perfused through the heart with PBS, and tumors and organs were collected and processed for fluorescence microscopy. The left panel is a representative confocal microscopy image from tumors in mice. The right panel is a merged image showing the presence of NWs (white in black and white versions and green in color versions of FIG. 12), CD31 (light gray in black and white versions and red in color versions of FIG. 12); and nuclei (dark gray in black and white versions and blue in color versions of FIG. 12). Scale bars: 100 m. The images show striking NW accumulation outside tumor blood vessels.

Tumor homing of peptide-NWs was then examined. Homing experiments showed that the new peptides were more effective in causing tumor homing of NWs than CGKRK (SEQ ID NO: 6). These included the TT1 Peptide, a cryptic CendR motif-containing p32-binding peptide. The TT1 Peptide was selected by phage library screening for binding to p32 as described herein above. A cyclic version of the TT1 Peptide had a high affinity for p32—higher than that of the LyP-1 Peptide or of a CGKRK (SEQ ID NO: 6) Peptide—but its low-affinity linear variant turned out to be the most effective peptide in the nanoparticle context (see FIG. 12).

Figure 13:
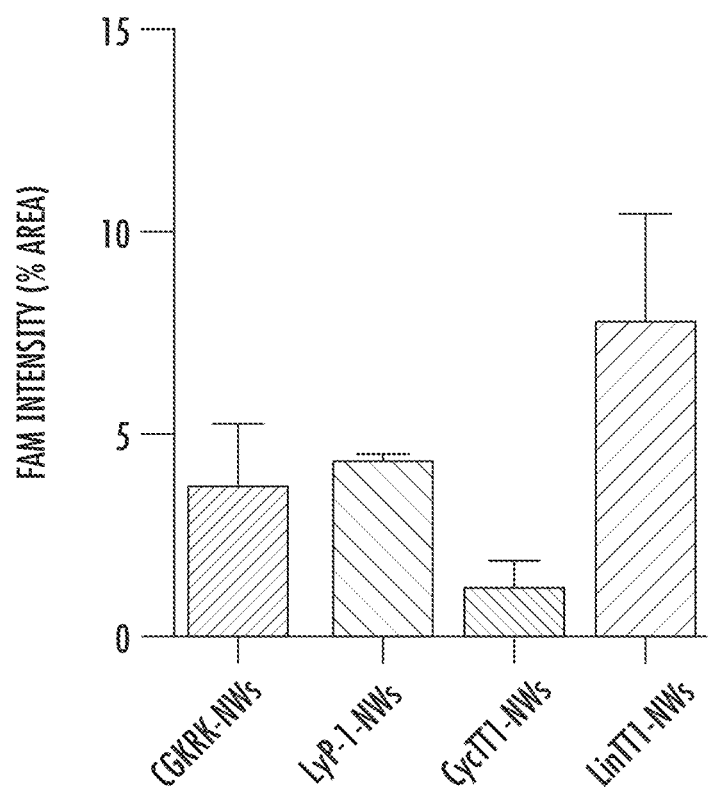
FIG. 13 is a bar graph showing quantification of the homing of various peptide-coated NWs. NWs were coated with the indicated peptides (CGKRK (SEQ ID NO: 6); LyP-1 (SEQ ID NO: 7); a cyclic TT1 peptide (SEQ ID NO: 3); or a linear TT1 peptide (SEQ ID NO: 2)) and intravenously injected into mice (n=3 per peptide) bearing orthotropic breast tumors. The dose was 7.5 mg/kg body weight of NW iron. The NWs were allowed to circulate for 5 hours, after which the mice were perfused through the heart with PBS and tumors and organs were collected. Quantification of fluorescence was done with ImageJ software (available from the website of the United States National Institutes of Health). In addition to the tumors, NWs were detected in the liver and spleen, which non-specifically capture nanoparticles regardless of their peptide coating. Other organs did not contain significant numbers of NWs, confirming the specificity of the tumor homing.

The cyclic TT1 Peptide tended to cause aggregation of the peptide-coated nanoparticles, which might explain the low activity of this peptide. The multivalent presentation of the linear TT1 Peptide likely made up for its low affinity for the receptor. A summary of the quantified peptide-NW homing results in shown in FIG. 13. The linear TT1 Peptide was selected for further study as a $_D$[KLAKLAK]$_2$ (SEQ ID NO: 42) conjugate on NWs. The CGKRK (SEQ ID NO: 6) and LyP-1 Peptides were included for comparison.

Example 7

Tumor Homing of Homing
Peptide-D[KLAKLAK]2 (SEQ ID NO: 4) NWs

Figure 14:
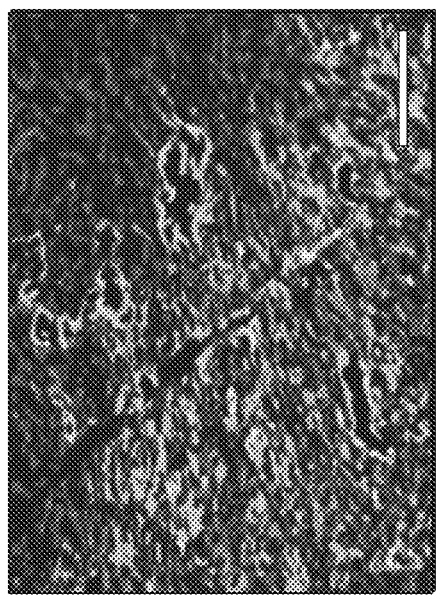
FIG. 14 is a series of fluorescent micrographs showing tumor homing of LinTT1-$_D$[KLAKLAK]$_2$-NWs (SEQ ID NO: 10). Confocal images show some co-localization of NW fluorescence (middle panel; white in black and white versions and green in color versions of FIG. 14) with blood vessels (CD31; left panel; white in black and white versions and red in color versions of FIG. 14), but most of the NWs are outside the blood vessels in the extravascular tumor tissue. The right panel is a merged image (NWs: white in black and white versions and green in color versions of FIG. 14; CD31: light gray in black and white versions and red in color versions of FIG. 14; nuclei: dark gray in black and white versions and blue in color versions of FIG. 14). Scale bars are 100 μm.
Figure 14:
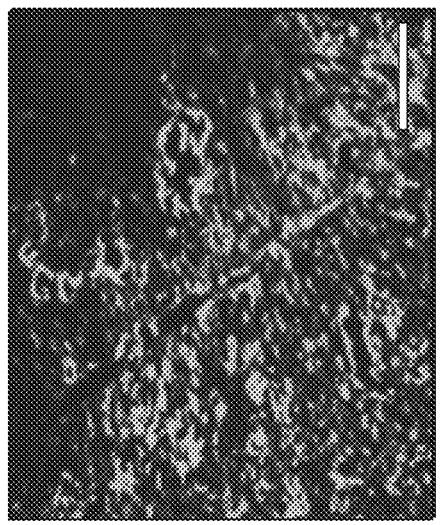
Figure 14:
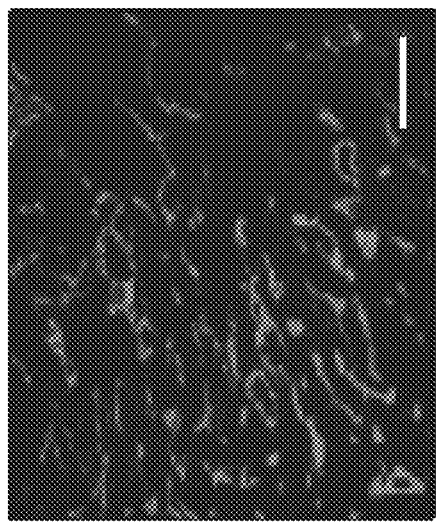
Figure 15:
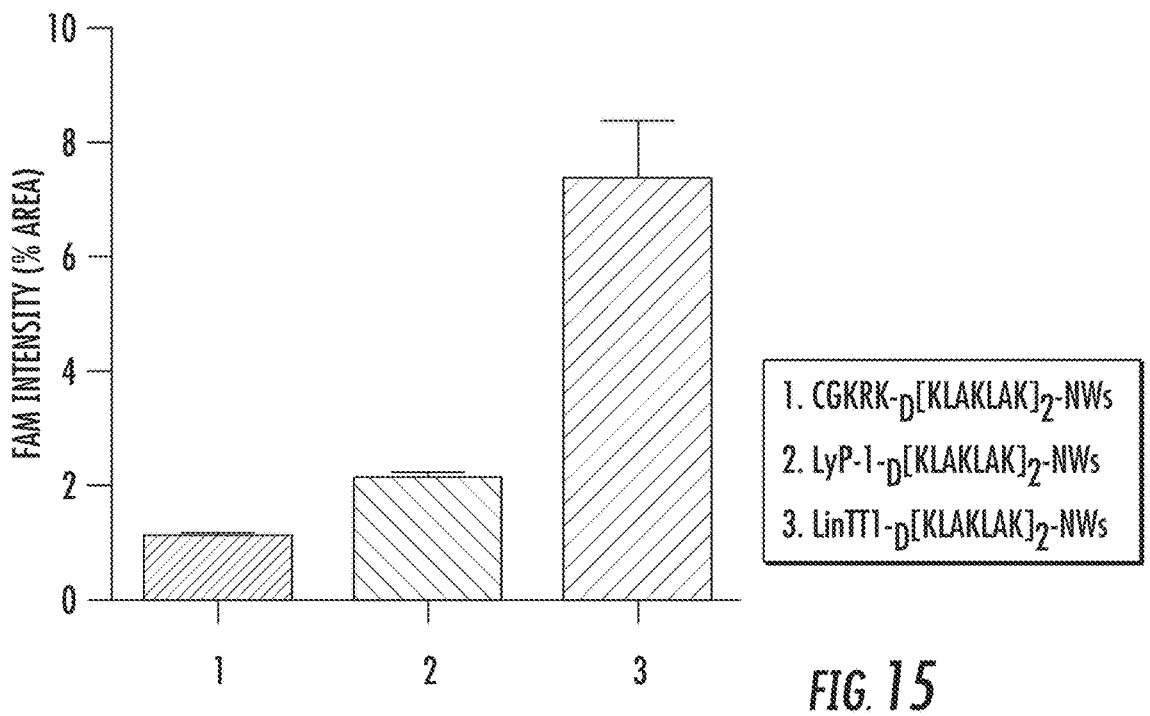
FIG. 15 is a bar graph showing tumor accumulation of NWs coated with chimeric peptides consisting of a homing peptide and pro-apoptotic peptide. Quantification of NW fluorescence was done with ImageJ software. FAM Intensity as % Area is plotted on a scale of 0-10 for the following peptide-conjugated NWs: 1—CGKRK-$_D$[KLAKLAK]$_2$-NWs (SEQ ID NO: 8); 2—LyP-1-$_D$[KLAKLAK]$_2$-NWs (SEQ ID NO: 9); 3—LinTT1-$_D$[KLAKLAK]$_2$-NWs (SEQ ID NO: 10).

CGKRK-$_D$[KLAKLAK]$_2$ (SEQ ID NO: 8) NWs have been shown previously to accumulate in tumor blood vessels without penetrating into the extravascular tumor tissue Agemy et al., 2011; 2013. The LyP-1 Peptide was more effective than the CGKRK (SEQ ID NO: 6) Peptide, but the linear TT1-$_D$[KLAKLAK]$_2$ (SEQ ID NO: 10) NWs were most effective in penetrating outside tumor vessels among the peptides tested (see FIG. 14). Quantification of the NW fluorescence in the tumors for the peptides tested is shown in FIG. 15.

Example 8

Tumor Growth Suppression Using TT1
Peptide-Conjugated Nanoworms

Tumors were induced by orthotopically inoculating immunocompromised nude mice with human MCF10-CA1a breast cancer cells. Treatment was stated 3-4 weeks after the inoculation when the tumor volume was of about 50 mm3. The mice received vehicle only (PBS; 5 mice), linear TT1-NWs without the drug peptide (5 mice), CGKRK-$_D$ (KLAKLAK)$_2$ (SEQ ID NO: 8) NWs used in previous work (see Agemy et al., 2011; 2013; 5 mice), or linear TT1-$_D$ (KLAKLAK)$_2$ (SEQ ID NO: 10) NWs (8 mice). The linear TT1 Peptide portion of the TT1-NW conjugate had the structure FAM-X-Cys-X-AKARGARSTSA (SEQ ID NO: 2)—AMIDE, where X is aminohexanoic acid. The linear TT1 Peptide portion of the linear TT1-$_D$(KLAKLAK)$_2$—NW conjugate had the structure FAM-X-KLAK-LAKKLAKLAK (SEQ ID NO: 42) X-Cys-X-AKARGA-RSTSA (SEQ ID NO: 2)—AMIDE, where X is aminohexanoic acid.

Figure 16:
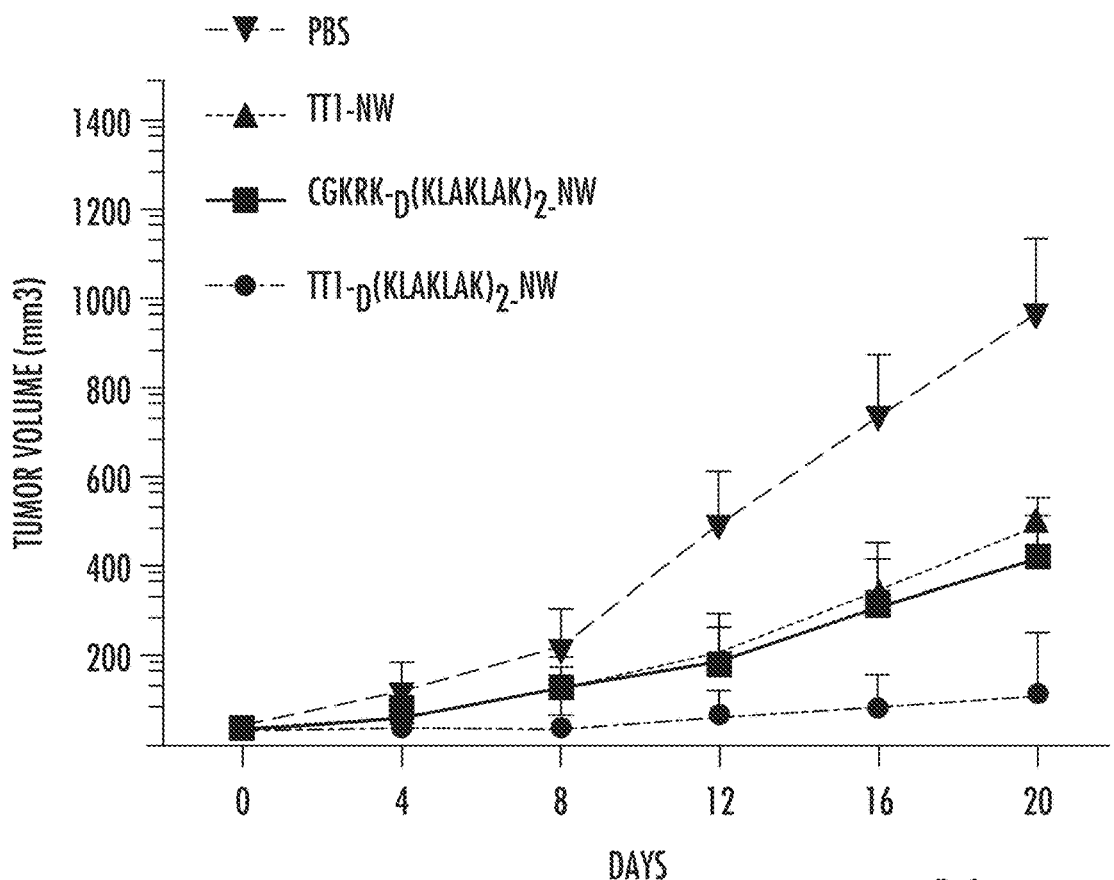
FIG. 16 is a graph of tumor volume of orthotopic MCF10-CA1a breast cancer cell tumors at days 0-20 after treatment with vehicle only (PBS; inverted triangles), linear TT1 Peptide (SEQ ID NO: 2) conjugated nanoworms without the drug peptide ((TT1-NW; triangles), CGKRK-$_D$(KLAK-LAK)$_2$—NWs (squares; SEQ ID NO: 8), or linear TT1-$_D$(KLAKLAK)$_2$—NWs (circles; SEQ ID NO: 10). Error bars relate to standard deviation as calculated by ANOVA.

The results are presented in FIG. 16. As shown in FIG. 16, a statistically significant difference between the PBS control and all 3 treatment groups was observed. The linear TT1-$_D$ (KLAKLAK)$_2$ (SEQ ID NO: 10) NW group was not statistically different from the other two treatments groups. However, this group had two long-term survivors (25%) that appeared to be complete cures. The linear TT1-coated NWs alone had a substantial effect on tumor growth. This effect is in agreement with the anti-tumor effect described for the LyP-1 peptide (Laakkonen et al., 2004). However, the linear TT1-NWs appeared to be more effective than the soluble LyP-1 peptide described in Laakkonen et al., 2004. While not wishing to be bound by any particular theory of operation, it is possible that relative to the LyP-1 Peptide conjugates described in Laakkonen et al., 2004, the presently disclosed linear TT1-$_D$(KLAKLAK)$_2$ (SEQ ID NO: 10) NW were characterized by a longer blood half-life and/or more efficient processing to the neuropilin-1-binding CendR fragment.

Example 9

Tumor Treatment with LinTT1-$_D$[KLAKLAK]$_2$ Micelles in a MCF10CA1a Breast Cancer Model Tumors were induced by orthotopically inoculating immunocompromised nude mice with human MCF10-CA1a breast cancer cells. Treatment was started 2-3 weeks after the inoculation when the tumor volume was of about 40-50 mm$^3$. The mice received vehicle only (PBS; 5 mice) or TT1-$_D$(KLAKLAK)$_2$-micelles (280 g of micelles/mouse, 5 mice; every other day for 3 weeks. The results are presented in FIG. 17.

Figure 17:
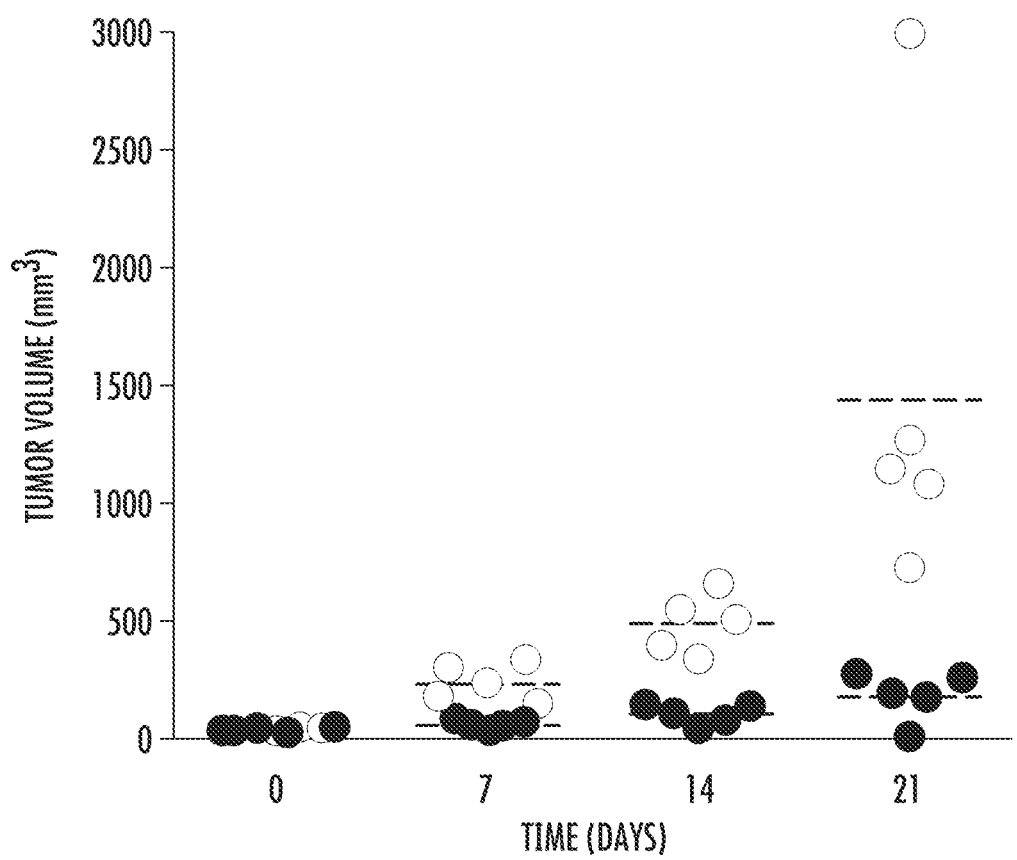
FIG. 17 is a graph depicting the results of tumor treatment with LinTT1-$_D$[KLAKLAK]$_2$ (SEQ ID NO: 10)-micelles in a MCF10CA1a breast cancer model. Black circles: PBS control; white circles: LinTT1-$_D$[KLAKLAK]$_2$ (SEQ ID NO: 10)-micelles.

The data presented in FIG. 17 showed a statistically significant difference between the PBS control and micelle treatment groups by one way ANOVA (Tukey's posthoc test, n=3 mice per group).

Discussion of the Examples

Disclosed herein is an advanced theranostic nanosystem to home active agents and other cargo to tumors. The results disclosed herein show that a new p-32-binding CendR motif peptide, referred to herein as the TT1 Peptide or the TT1 Family of Peptides, was the most effective tumor-homing peptide when tested coated onto nanoparticles, and in the context of the complete nanosystem. The TT1 Peptide-based nanosystem was eight (8) times more active in homing and penetrating into tumors than the original CGKRK-$_D$(KLAKLAK)$_2$ (SEQ ID NO: 8)-based nanosystem described in, for example, U.S. Pat. Nos. 7,723,474 and 8,598,316, PCT International Patent Application Publication No. WO 2011/127405, and U.S. Patent Application Publication No. 2011/0262347. Thus, in some embodiments the TT1 Family of Peptides represented the lead peptides going forward.

A goal of some embodiments of the methods disclosed herein was to develop a novel targeted systems for selective delivery of therapeutic and diagnostic agents to GBM and other cancers. The original nanosystem in, for example, U.S. Pat. Nos. 7,723,474 and 8,598,316, PCT International Patent Application Publication No. WO 2001/127405, and U.S. Patent Application Publication No. 2011/0262347, employed three peptides: CGKRK (SEQ ID NO: 6) as the homing peptide, a peptide known as iRGD to provide a tumor-penetrating function, and a pro-apoptotic peptide, $_D$(KLAKLAK)$_2$ (SEQ ID NO: 42), as the "drug" (see also Agemy et al., 2011; 2013). The CGKRK (SEQ ID NO: 6) peptide specifically homes to angiogenic vasculature and enters into them. When capable of accessing tumor cells, it also binds to tumor cells of various types and internalizes into them. However, CGKRK (SEQ ID NO: 6) lacks tumor-penetrating activity, which confines CGKRK (SEQ ID NO: 6)-coated nanoparticles almost entirely to the vasculature (Joyce et al., 2003, Agemy et al., 2013), findings that were confirmed as described herein.

The LyP-1 Peptide is a cyclic 9-amino acid peptide that also uses p32 as its receptor (sequence: CGNKRTRGC (SEQ ID NO: 7); Laakkonen et al., 2002). Like CGKRK (SEQ ID NO: 6), LyP-1 internalizes into its target cells, but like iRGD, LyP-1 is also capable of penetrating into tumors and accumulating in the extravascular tumor tissue (Laakkonen et al., 2004; Roth et al. 2012). LyP-1 and iRGD contain a cryptic CendR (C-end Rule) motif (R/KXXR/K), which binds to neuropilin-1 after the peptide has been cleaved by a cell surface protease (Teesalu et al., 2009; Sugahara et al., 2009; 2010). The neuropilin-1 binding activates an endocytic pathway that transports payloads through the vascular wall and through tumor tissue, endowing these peptides with the tumor penetrating ability. CGKRK (SEQ ID NO: 6) lacks the CendR function, and as a consequence, it mainly targets tumor blood vessels.

As disclosed herein, two strategies were employed to simplify the original nanosystem while also improving the homing and tumor penetration properties of the system. In particular, a tumor-penetrating (CendR) activity was introduced into the peptide to facilitate the penetration of the nanoparticles into the extracellular tumor tissue without the need of the separately injected iRGD peptide. To accomplish these objectives, peptides that bound to the same receptor as CGKRK (SEQ ID NO: 6; i.e., p32/gC1qR/HABP) and contained the CendRmotif were identified.

REFERENCES

All references listed in the instant disclosure, including but not limited to all patents, patent applications, patent application publications, scientific journal articles, and database entries (including but not limited to GENBANK® biosequence database entries and all annotations available therein) are incorporated herein by reference in their entireties to the extent not inconsistent herewith and to the extent that they supplement, explain, provide a background for, or teach methodology, techniques, and/or compositions employed herein.

Abrahmsen et al. (1991) *Biochemistry* 30:4151.
Agemy et al. (2011) *Proc Natl Acad Sci USA* 108:17450-17455.
Agemy et al. (2013) *Mol Ther* 21:2195-2204.
Alirol & Martinou (2006) *Oncogene* 25:4706-4716.
Alitalo et al. (2004) *Cancer Res* 64:9225-9229.
Allam et al. (1997) *Cancer Res* 57:2615-2618.
Allen et al. (1979) *Acta Crystallogr Section B*, 35:2331-2339.
Almquist et al. (1980) *J. Med Chem* 23:1392-1398.
Alvarez-Bravo et al. (1994) *Biochem J* 302:535-538.
Arap et al. (1998a) *Science* 279:377-380.
Arap et al. (1998b) 10:560-565.
Arap et al. (2002) *Proc Natl Acad Sci USA* 99:1527-1531.
Askew et al. (1989) *J Am Chem Soc* 111:1082-1090.
Baggiolini al. (1992) *FEBS Lett* 307:97-101.
Bailey et al. (1980) *Antimicrob Agents Chemother* 17:549-553.
Bangham et al. (1965) *J Mol Biol* 13:238-252.
Barenholz et al. (1979) *FEBS Lett* 99:210-214.
Batzri et al. (1973) *Biochim et Biophys Acta* 298:1015-1019.
Bessalle et al. (1990) *FEBS Lett* 274:151-155.
Blancato et al. (2004) *Br J Cancer* 90:1612-1619.

Blondelle & Houghten (1992a) *Biochem* 31:12688-12694.
Blondelle & Houghten (1992b) in *Annual Reports in Medicinal Chemistry*, Bristol (ed.), Academic Press, San Diego, Calif., United States of America, pages 159-168.
Bobak et al. (1987) *J Immunol* 138:1150-1156.
Bobak et al. (1988) *Eur J Immunol* 18:2001-2007.
Borgstrom et al. (1999) *Anticancer Res* 19:4213-4214.
Braun et al. (2000) *EMBO J* 19:1458-1466.
Brooks et al. (1994) *J Reprod Med* 39:755-760.
Callo et al. (1985) *Cryobiology* 22(3):251-267.
Cane et al. (1998) *Science* 282:63-68.
Chan et al. (1999) *J Clin Oncol* 17:2341-2354.
Chen et al. (1994) *J Immunol* 153:1430-1440.
Christian et al. (2003) *J Cell Biol* 163:871-878.
Clark-Lewis et al. (1991) *Biochemistry* 30:3128.
Clark-Lewis et al. (1994) *J Biol Chem* 269:16075.
Creighton (1984) Proteins: Structures and Molecular Properties, W. H Freeman, New York, N.Y., United States of America.
Crooks et al. (2004) *Genome Res* 14:1188-1190.
Davis et al. (1996) *Cell* 87:1161-1169.
Dawson et al. (1994) *Science* 266:776-779.
De Roos et al. (1991) *Intl J Card Imaging* 7:133-138.
Deamer et al. (1976) *Biochim et Biophys Acta* 443:629-634.
Deb & Datta (1996) *J Biol Chem* 271:2206-2212.
Dedio et al. (1998) *J Immunol* 160:3534-3542.
Degenhardt et al. (2006) *Cancer Cell* 10:51-64.
deLisle et al. (1992) *Techniques in Protein Chemistry IV.* Academic Press, New York, N.Y., United States of America, pp. 257-267.
Effert et al. (1996) *J Urol* 155:994-998.
Ellerby (1999) *Nature Med* 5:1032-1038.
European Patent Application Publication No. EP 0045665.
Fantin et al. (2006) *Cancer Cell* 9:425-434.
Ferrara et al. (1999) *Nat Med* 5:1359-1364.
Ferreira et al. (2003) *J Mol Catal B: Enzymatic* 21:189-199.
Fields et al. (1989) *Nature* 340:245-246.
Fields et al. (1994) *Trends Genet* 10:286-292.
Finlayson (1980) *Semin Thromb Hemost,* 6:85-120.
Fisher et al. (1998) *JNatl CancerInst* 90:1371-1388.
Fitzpatrick & Garnett (1995) *Anticancer Drug Des* 10:1-9.
Fogal et al. (2008) *Cancer Res* 68:7210-7218.
Fogal et al. (2010) *Mol Cell Biol.* 30: 1303-1318.
Folkman & Shing (1992) *J Biol Chem* 267:10931-10934.
Folkman (1997) *Nature Biotechnol* 15:510.
Gao et al. (2002) *J Biomed Opt* 7:532.
Garber (2006) *Science* 312:1158-1159.
GENBANK® Biosequence Database Accession Nos. NM_001034527; NM_001212; NM_007573; NM_019259; NP_001029699; NP_001203; NP_031599; NP_062132; XM_001100940; XM_001918118; XM_002748302; XM_002826905; XM_004058391; XM_005582637; XM_006939728; XM_546568; XP_001100940; XP_001918153; XP_002748348; XP_002826951; XP_004058439; XP_005582694; XP_006939790; XP_546568.
Gerhardt et al. (1997) *Eur J Pharmacol* 15:334:1-23.
German Patent Publication DE 1016978 19571003.
Ghebrehiwet (1989) *Behring Inst Mitt* 84:204-215.
Ghebrehiwet et al. (1994) *J Exp Med* 179:1809-1821.
Ghebrehiwet et al. (2002) *Immunobiology* 205:421-432.
Ghosh et al. (2004) *Mol Cell Biochem* 267:133-139.
Goodman & Ro (1995) Peptidomimetics for Drug Design, in *Burger's Medicinal Chemistry and Drug Discovery* Vol. 1, Wolff (ed), John Wiley & Sons, New York, N.Y., United States of America, pages 803-861.
Gregoriadis (1984) Liposome Technology, Vol. I-III, CRC Press, Boca Raton, Fla., United States of America.
Groziak (2001) *Am J Therapeut* 8:321-328.
Guarino et al. (2004) *Biotechnol Bioeng* 86, 775-787.
Guo et al. (1999) *J Lab Clin Med* 133:541-550.
Gupta et al. (1991) *Eur J Cell Biol* 56:58-67.
Hagedom & Bikfalvi (2000) *Crit Rev Oncol Hematol* 34:89-110.
Hamzah et al. (2011) *Proc Natl Acad Sci USA* 108:7154-7159.
Han et al. (2001) *Nature Biotechnol* 19:631.
Hanahan & Weinberg (2000) *Cell* 100:57-70.
Hann (1982) *J Chem Soc Perkin Trans* 1307-314.
Harris (ed) (1992) *Poly(ethylene glycol) Chemistry, Biotechnical and Biomedical Applications*, Plenum Press, New York, N.Y., United States of America.
Harris et al. (1997) in *Cancer: Principles and Practice of Oncology* (5th ed.), DeVita et al. (eds) *Lippincott Williams & Wilkins*, Philadelphia, Pa., United States of America.
Haugland (2002) *Handbook of Fluorescent Probes and Research Products* ($9^{th}$ Edition), Molecular Probes, Inc., Eugene, Oreg., United States of America.
Henikoff & Henikoff (2000) *Adv Protein Chem* 54:73-97.
Herwald et al. (1996) *J Biol Chem* 271:13040-13047.
Hirasawa et al. (2001) *Life Sci* 68:2259-2267.
Hodgson (1992) *Bio/Technol* 10:973-980.
Hofer et al. (1999) *Eur Urol* 36:31-35.
Hoffian et al. (2003) *Cancer Cell* 4:383-391.
Holladay et al. (1983) *Tetrahedron Lett* 24:4401-4404.
Homandberg et al. (1985) *Am J Path* 120:327-332.
Homandberg et al. (1986) *Biochim Biophys Acta* 874:61-71.
Houser et al. (1980) *Surg Gynecol Obstet* 150:811-816.
Hruby (1982) *Life Sci* 31:189-199.
Hruby et al. (1990) *Biochem J* 268:249-262.
Hudson et al. (1979) *Int J Pept Prot Res* 14:177-185.
Inoki et al. (2003) *Cell* 115:577-590.
Isidoro et al. (2005) *Carcinogenesis* 26:2095-2104.
Jaeger et al. (1989a) *Methods Enzymol* 183:281-306.
Jaeger et al. (1989b) *Proc Natl Acad Sci USA* 86:7706-7710.
Jain (1998) *Nat Med* 4:655-657.
Jarvinen et al. (2007) *Am J Pathol* 171:702-711.
Javadpour et al. (1996) *J Med Chem* 39:3107-3113.
Jayawickreme et al. (1997) *Curr Opin Biotechnol* 8:629-634.
Jennings-White et al. (1982) *Tetrahedron Lett* 23:2533-2534.
Jiang et al. (1999) *Proc Natl Acad Sci USA* 96:3572-3577.
Jin et al. (2007) *J Cell Sci* 120:379-383.
Jones et al. (2005) *Mol Cell* 18:283-293.
Joseph et al. (1996) *Proc Natl Acad Sci USA* 93:8552-8557.
Joyce et al. (2003) *Cancer Cell* 4:393-403.
Kaur et al. (1993) *J Immunol* 150:2046-2055.
Kerjaschki (2005) *J Clin Invest* 115:2316-2319.
Kerjaschki et al. (2006) *Nat Med* 12:230-234.
Khan et al. (1998) *Proc Natl Acad Sci USA* 95:10425-10430.
Kim et al. (1983) *Biochim et Biophys Acta* 728:339-348.
Kirsch et al. (2000) *J Neurooncol* 50:149-163.
Kittlesen et al. (2000) *J Clin Invest* 106:1239-1249.
Koehler & Hess (1974) *Biochemistry* 13:5345-5350.
Kohori et al. (1998) *J Control Rel* 55:87-98.
Kohori et al. (1999) *Colloids Surfaces B: Biointerfaces* 16:195-205.
Krainer et al. (1991) *Cell* 66:383-394.
Kreitman & Pastan (1997) *Blood* 90:252-259.
Kyte et al. (1982) *J Mol Biol* 157:105.
Laakkonen et al. (2002) *Nat Med* 8:751-755.

Laakkonen et al. (2004) *Proc Natl Acad Sci USA* 101:9381-9386.
Lee et al. (2007) *Mol Cancer Res* 5:11-19.
Leu et al. (1990) *J Immunol* 144:2281-2286.
Levine (2007) *Nature* 446:745-747.
Lewis & Dean (1989) *Proc R Soc Lond* 236:125-140 and 141-162.
Liao et al. (2000) *Endocr Relat Cancer* 7:143-164.
Liggins & Burt (2002) *Adv Drug Del Rev* 54:191-202.
Lim et al. (1996) *J Biol Chem* 271:26739-26744.
Lin et al. (2002) *Appl Phys Lett* 81:3134.
Liu (2006) *Prostate Cancer Prostatic Dis* 9:230-234.
Majumdar et al. (2002) *Biochem Biophys Res Commun* 291:829-837.
Maloy & Kari (1995) *Biopolymers* 37:105-122.
Maloy et al. (1995) *Biopolymers* 37:105-122.
Mancheno et al. (1998) *J Peptide Res* 51:142-148.
Martin et al. (2000) *Cancer Res* 60:3218-3224.
Maruyama et al. (2005) *J Clin Invest* 115:2363-2372.
Maruyama et al. (2007) *Am J Pathol* 170:1178-1191.
Matthews & Russell (1998) *J Gen Virol* 79 (Pt 7):1677-1685.
McKinaly & Rossmann (1989) *Ann Rev Pharmacol Toxiciol* 29:111-122.
Moghimi et al. (2001) *Pharm Rev* 53:283-318.
Moghimi et al. (2001) *Pharmacol Rev* 53:283-318.
Morgan and Gainor (1989) *Ann. Rep. Med. Chem.* 24:243-252.
Morley (1980) *Trends Pharmacol Sci* 1:463-468.
Muta et al. (1997) *J Biol Chem* 272:24363-24370.
Myers (1997) *Curr Opin Biotechnol* 8:701-707.
Needleman & Wunsch (1970) *J Mol Biol* 48:443.
Oh et al. (2004) *Nature* 429:629-635.
O'Reilly et al. (1994) *Cell* 79:315-328.
O'Reilly et al. (1997) *Cell* 88:277-285.
O'Reilly et al. (1999) *Science* 285:1926-1928.
Osborne & Coronado-Heinsohn (1996) *Cancer J Sci Am* 2:175-180.
Pai et al. (1999) *Mag Magnet Mater* 194:262.
Papahadjopoulos et al. (1968) *Biochim et Biophys Acta* 135:624-238.
Paridaens et al. (2000) *J Clin Oncol* 18:724-733.
Park et al. (2008) *Adv Mater* 20:1630-1635.
Parle-McDermott et al. (2000) *Br J Cancer* 83:725-728.
Pasqualini et al (2000) *Cancer Res* 60:722-727.
Pausch (1997) *Trends Biotech* 15:487-494.
PCT International Patent Application Publication Nos. WO 96/32434; WO 96/33233; WO 97/00623; WO 98/37177; WO 99/64446; WO 2002/044184; WO 2011/127405.
PCT International Patent Application Serial No. PCT/US2011/31785.
Pearson & Lipman (1988) *Proc Natl Acad Sci USA* 85:2444.
Peerschke et al. (1993) *JExpMed* 178:579-587.
Peerschke et al. (1994) *J Immunol* 152:5896-5901.
Perry & Davies (1989) QSAR: Quantitative Structure-Activity Relationships. in *Drug Design*, Alan R. Liss, Inc., New York, N.Y., United States of America, pages 189-193.
Pilch et al. (2006) *Proc Natl Acad Sci USA* 103:2800-2804.
Pirollo et al. (2007) *Cancer Res* 67:2938-2943.
Porkka et al. (2002) *Proc Natl Acad Sci USA* 99:7444-7449.
Powers et al. (1982) *Neurology* 32: 938.
Rajarathnam et al. (1994) *Biochemistry* 33:6623-6630).
Reef et al. (2007) *Oncogene* 26:6677-6683.
Remington (1995) *The Science and Practice of Pharmacy* (19th ed.) Gennaro (ed.), Mack Publishing Company, Easton, Pa., United States of America.
Ripka (1988), *New Scientist* 54-57 (Jun. 16, 1988).
Robles-Flores et al. (2002) *J Biol Chem* 277:5247-5255.
Roth et al. (2012) Transtumoral targeting enabled by a novel neuropilin-binding peptide. *Oncogene* 31:3754-3763.
Rotivinen et al. (1988) *Acta Pharmaceutica Fennica* 97:159-166.
Rozanov et al. (2002a) *J Biol Chem* 277:9318-9325.
Rozanov et al. (2002b) *FEBS Lett* 527:51-57.
Rubinstein et al. (2004) *Intl J Cancer* 110:741-750.
Rubinsztein et al. (2007) *Nat Rev Drug Discov* 6:304-312.
Ruoslahti (2002) *Nat Rev Cancer* 2:83-90.
Ruoslahti et al. (2010) *J Cell Biology* 188:759-768.
Rusinko et al. (1989) *J Chem Inf Comput Sci* 29:251-255.
Saberwal et al. (1994) *Biochim Biophys Acta* 1197:109-131.
Saharinen et al. (2004) *Trends Immunol* 25:387-395.
Schaerer et al. (2001) *J Biol Chem* 276:26597-26604.
Schledzewski et al. (2006) *J Pathol* 209:67-77.
Schneider & Stephens (1990) *Nucleic Acids Res* 18:6097-6100.
Schnolzer et al. (1992) *Science* 256:221.
Schroeder et al. (1996) *J Biomol Screening* 1:75-80.
Sengupta et al. (2004) *Biochem J* 380:837-844.
Shaw (2006) *Curr Opin Cell Biol* 18:598-608.
Shim et al. (1997) *Proc Natl Acad Sci USA* 94:6658-6663.
Sim & Reid (1991) *Immunol Today* 12:307-311.
Simberg et al. (2007) *Proc Natl Acad Sci USA* 104:932-936.
Simpelkamp & Jones (1992) *Bioorg Med Chem Lett* 2:1391-1394.
Singh et al. (1997) *Exp Cell Res* 234:205-216.
Slavin et al. (1995) *Cell Biol Intl* 19:431-444.
Smith & Waterman (1981) *Adv Appl Math* 2:482.
Soltys & Gupta (1996) *Exp Cell Res* 222:16-27.
Soltys & Gupta (1997) *Cell Biol Intl* 21:315-320.
Soltys & Gupta (1999) *Trends Biochem Sci* 24:174-177.
Soltys et al. (2000) *Histochem Cell Biol* 114:245-255.
Spatola (1983a) *Chemistry and Biochemistry of Amino Acids, Peptides, and Proteins* (Weinstein eds.), Marcel Dekker, New York, N.Y., United States of America, page 267.
Spatola (1983b) Peptide Backbone Modifications, *Vega Data* 1(3).
Spatola et al. (1986) *Life Sci* 38:1243-1249.
St. Croix et al. (2000) *Science* 289:1197-1202.
Stacker et al. (2002) *Nat Rev Cancer* 2:573-583.
Steiner et al. (eds.) (1992) in *Aniogenesis: Key Principles—Science, Technology, Medicine* Birkhäuser Verlag, Boston, Mass., United States of America, pp. 449-454.
Stewart & Ratain (1997) in *Cancer: Principles and Practice of Oncology* (5th ed.), DeVita et al. (eds) *Lippincott Williams & Wilkins*, Philadelphia, Pa., United States of America.
Storz et al. (2000) *J Biol Chem* 275:24601-24607.
Strosberg et al. (1992) *Trends Pharm Sci* 13:95-98.
Sugahara et al. (2009) *Cancer Cell* 16:510-520.
Sugahara et al. (2010) *Science* 328:1031-1035.
Suri et al. (1996) *Cell* 87:1171-1180.
Sweetnam et al. (1993) *J Nat Prod* 56:441-455.
Tange et al. (1996) *J Biol Chem* 271:10066-10072.
Teesalu et al. (2009) *Proc Natl Acad Sci USA* 106:16157-16162.
Thakur et al. (1976) *Throm Res* 9:345.
Tullis (1977) *J Am Med Assoc* 237:355-360, 460-463.
Tuzar & Kratochvil (1976) *Adv Colloid Interface Sci* 6:201-232.
U.S. Patent Application Publication No. 2004/0009122; 2004/0087499; 2005/0004002; 2007/0219134; 2008/

0014143; 2008/0305101; 2009/0036349; 2009/0226372; 2010/0322862; 2011/0262347.
U.S. patent application Ser. No. 08/996,783.
U.S. Pat. Nos. 4,016,100; 4,089,801; 4,235,871; 4,418,052; 4,485,054; 4,554,101; 4,745,160; 4,761,288; 4,853,228; 5,011,686; 5,013,497; 5,024,829; 5,410,016; 5,412,072; 5,449,513; 5,474,848; 5,534,499; 5,585,277; 5,628,936; 5,693,751; 5,789,542; 5,792,742; 5,820,873; 5,885,613; 5,891,646; 5,897,945; 5,906,820; 5,916,596; 5,925,720; 5,929,177; 6,110,693; 6,320,017; 6,506,405; 6,530,944; 6,537,579; 6,759,199; 7,544,767; 7,723,474; 8,367,621; 8,598,316.
van Leeuwen & O'Hare (2001) *J Cell Sci* 114:2115-2123.
Van Rooijen & Sanders (1994) *J Immunol Meth* 174:83-93.
Vanden Broeck (1996) *Intl Rev Cytol* 164:189-268.
Waggoner et al. (2005) *J Immunol* 175:4706-4714.
Wallace (2005) *Cold Spring Harb Symp Quant Biol* 70:363-374.
Wang et al. (2003) *Chem Mater* 15:2724.
Weder et al. (1984) in Liposome Technology, Gregoriadis (ed.), CRC Press Inc., Boca Raton, Fla., United States of America, Vol. I, Chapter 7, pages 79-107.
Weinand et al. (1999) *Bioorg Med Chem* 7:1295-1307.
White et al. (2001) *Ann Rev Med* 52:125-141.
Wieboldt et al. (1997) *Anal Chem* 69:1683-1691.
Wilhelm et al. (1991) *Macromolecules* 24:1033-1040.
Williams (1991) *Med Res Rev* 11:147-184.
Wilson et al. (1998) *Bri t JPharmacol* 125:1387-1392.
Xu et al. (1994) *Circ Res* 75:1078-1085.
Yagi et al. (2012) *Nucl. Acids Res.* 40: 9717-9737.
Yamamoto (1991) *Pure Appl Chem* 63:423-426.
Young et al. (1991) *J Immunol* 146:3356-3364.
Zhang et al. (1996) *Intl J Pharm* 132:195-206.
Zhang et al. (2006) *Cancer Res* 66:5696-5706.
Zhang et al. (2007) *Autophagy* 3:337-346.
Zuker (1989) *Science* 244:48-52.

It will be understood that various details of the presently disclosed subject matter can be changed without departing from the scope of the presently disclosed subject matter. Furthermore, the foregoing description is for the purpose of illustration only, and not for the purpose of limitation.

What is claimed is:

1. A method for treating cancer in a subject, the method comprising administering to the subject a conjugate which comprises, consists essentially of, or consists of a moiety linked to a homing molecule that selectively homes to a tumor, wherein the homing molecule comprises, consists essentially of, or consists of an isolated peptide or peptidomimetic comprising, consisting essentially of, or consisting of the amino acid sequence KRGARST (SEQ ID NO: 1) or a peptidomimetic thereof; the amino acid sequence AKRGARSTA (SEQ ID NO: 2) or a peptidomimetic thereof; the amino acid sequence CKRGARSTC (SEQ ID NO: 3) or a peptidomimetic thereof, or any combination thereof, and further wherein the conjugate has an anti-cancer biological activity in the tumor.

2. A method for treating a disease or disorder associated with gC1q/p32 receptor expression, the method comprising:
   (a) identifying a subject having a disease or disorder associated with gC1q/p32 receptor expression; and
   (b) administering to the subject an effective amount of a composition that interacts with the gC1q/p32 receptor, wherein the composition comprises, consists essentially of, or consists of one or more homing molecules comprising a TT1 Peptide comprising SEQ ID NO: 1, SEQ ID NO: 2, or SEQ ID NO: 3 linked to a therapeutic agent,
   wherein the one or more homing molecules selectively target the composition to a gC1q/p32 receptor to thereby treating the disease or disorder associated with gC1q/p32 receptor expression.

3. The method of claim 2, wherein the TT1 Peptide is cyclic or conformationally constrained.

4. The method of claim 2, wherein the TT1 Peptide has a length selected from the group consisting of less than 100 residues, less than 50 residues, and less than 20 residues.

5. The method of claim 2, wherein the therapeutic agent is selected from the group consisting of an anti-angiogenic agent, a pro-angiogenic agent, a cancer chemotherapeutic agent, a cytotoxic agent, an anti-inflammatory agent, an anti-arthritic agent, a polypeptide, a nucleic acid molecule, a small molecule, and a radionuclide, or any combination thereof.

6. The method of claim 5, wherein the therapeutic agent is selected from the group consisting of iRGD, nab-paclitaxel, paclitaxel, a taxol, cyclophosphamide, melphalan, mitomycin C, bizelesin, cisplatin, doxorubicin, etoposide, mitoxantrone, SN-38, Et-743, actinomycin D, bleomycin, geldanamycin, chlorambucil, methotrexate, and TLK286.

7. The method of claim 2, wherein the composition further comprises one or more membrane perturbing molecules.

8. The method of claim 7, wherein at least one of the one or more membrane perturbing molecules comprises the amino acid sequence $_D$(KLAKLAK)$_2$ (SEQ ID NO: 42), (KLAKLAK)$_2$ (SEQ ID NO: 42), (KLAKKLA)$_2$ (SEQ ID NO: 43), (KAAKKAA)$_2$ (SEQ ID NO: 44), (KLGKKLG)$_3$ (SEQ ID NO: 45), or any combination thereof.

9. The method of claim 7, wherein the one or more of the membrane perturbing molecules are conjugated to one or more of the one or more homing molecules.

10. The method of claim 7, wherein the one or more homing molecules, the one or more membrane perturbing molecules, or both are conjugated to a surface molecule, optionally a surface molecule selected from the group consisting of a microparticle, a nanoparticle, a nanoworm, a liposome, a micelle, a phospholipid, and a polymer, or any combination thereof.

11. The method of claim 10, wherein the surface molecule is selected from the group consisting of an iron oxide nanoworm, an iron oxide nanoparticle, an albumin nanoparticle, and a fluorocarbon microbubble.

12. The method of claim 10, wherein one or more of the conjugated homing molecules are conjugated to the surface molecule via a linker and/or wherein one or more of the conjugated membrane perturbing molecules are conjugated to the surface molecule via a linker, optionally wherein one or more of the linkers comprises a polyethylene glycol.

13. The method of claim 2, wherein the composition further comprises a detectable agent, optionally wherein the detectable agent comprises an image contrast agent, a fluorescent moiety, a radionuclide, a radiation emitter, and a magnetic detectable agent, or any combination thereof.

14. The method of claim 2, wherein the effective amount is sufficient to slow an increase of or reduce tumor burden and/or size.

15. The method of claim 1, wherein the peptide or peptidomimetic is cyclic or conformationally constrained.

16. The method of claim 1, wherein the peptide or peptidomimetic has a length selected from the group consisting of less than 100 residues, less than 50 residues, and less than 20 residues.

17. The method of claim 1, wherein the moiety is selected from the group consisting of an anti-angiogenic agent, a pro-angiogenic agent, a cancer chemotherapeutic agent, a cytotoxic agent, an anti-inflammatory agent, an anti-arthritic agent, a polypeptide, a nucleic acid molecule, a small molecule, and a radionuclide, or any combination thereof.

18. The method of claim 17, wherein the cancer chemotherapeutic agent is selected from the group consisting of iRGD, nab-paclitaxel, paclitaxel, a taxol, cyclophosphamide, melphalan, mitomycin C, bizelesin, cisplatin, doxorubicin, etoposide, mitoxantrone, SN-38, Et-743, actinomycin D, bleomycin, geldanamycin, chlorambucil, methotrexate, and TLK286.

19. The method of claim 1, wherein the composition further comprises one or more membrane perturbing molecules conjugated to one or more of the one or more homing molecules.

20. The method of claim 19, wherein at least one of the one or more membrane perturbing molecules comprises the amino acid sequence $_D$(KLAKLAK)$_2$ (SEQ ID NO: 42), (KLAKLAK)$_2$ (SEQ ID NO: 42), (KLAKKLA)$_2$ (SEQ ID NO: 43), (KAAKKAA)$_2$ (SEQ ID NO: 44), (KLGKKLG)$_3$ (SEQ ID NO: 45), or any combination thereof.

* * * * *